(12) United States Patent
Dominique et al.

(10) Patent No.: US 8,093,385 B2
(45) Date of Patent: Jan. 10, 2012

(54) LEUKOTRIENE B$_4$ INHIBITORS

(75) Inventors: Romyr Dominique, Wayne, NJ (US); Nader Fotouhi, Basking Ridge, NJ (US); Paul Gillespie, Westfield, NJ (US); Robert Alan Goodnow, Gillette, NJ (US); Agnieszka Kowalczyk, Mine Hill, NJ (US); Qi Qiao, Bloomfield, NJ (US); Achyutharao Sidduri, Livingston, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 834 days.

(21) Appl. No.: 12/180,738

(22) Filed: Jul. 28, 2008

(65) Prior Publication Data

US 2009/0054466 A1 Feb. 26, 2009

Related U.S. Application Data

(60) Provisional application No. 60/956,940, filed on Aug. 21, 2007.

(51) Int. Cl.
*C07D 403/00* (2006.01)
*C07D 231/00* (2006.01)
*C07D 239/42* (2006.01)
*C07C 59/40* (2006.01)
*A61K 31/19* (2006.01)
*A61K 31/44* (2006.01)

(52) U.S. Cl. ........ 544/296; 562/469; 546/267; 514/256; 514/570; 514/332

(58) Field of Classification Search ............... 544/296; 562/469; 546/267; 514/256, 570, 332
See application file for complete search history.

(56) References Cited

OTHER PUBLICATIONS

*Bioorganic & Medicinal Chemistry Letters* (1994), 4(24), 2883-8.
*Modern Arene Chemistry* 2002, 53-106.
J.Org.Chem.1997, 62,8215-8217.
Knochel, Chem. Rev. 1993, 93, 2117.
Klement, I., Tetrahedron 1996, 52, 7201.
Knochel, Tetrahedron 1998, 54, 8275.
Siegfried, J. Med. Chem. 2000, 43, 1670.
J. Org. Chem. 1970, 35, 244.
J. Org.Chem. 2003, 68, 8750.
Org. Lett. 2004, 6, 4587.
J. Am. Chem. Soc. 2006, 128, 2180.
J.Org.Chem. 1962, 27, 93.
Tetrahedron 2006, 62, 2357.

*Primary Examiner* — Rita Desai
*Assistant Examiner* — John Mabry
(74) *Attorney, Agent, or Firm* — George W. Johnston; Dennis P. Tramaloni; Samuel H. Megerditchian

(57) ABSTRACT

Provided herein are compounds of the formula (I):

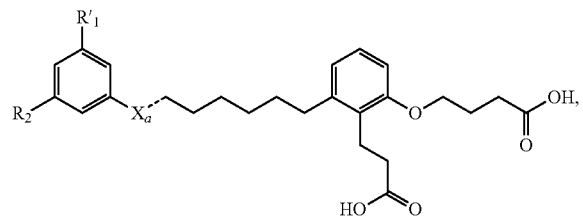

as well as pharmaceutically acceptable salts thereof, wherein the substituents are as those disclosed in the specification. These compounds, and the pharmaceutical compositions containing them, are useful for the treatment of diseases such as, for example, COPD.

16 Claims, No Drawings

LEUKOTRIENE B₄ INHIBITORS

PRIORITY TO RELATED APPLICATION(S)

This application claims the benefit of U.S. Provisional Application No. 60/956,940, filed Aug. 21, 2007, which is hereby incorporated by reference in its entirety.

FIELD OF THE INVENTION

The invention is directed to compounds of formula I:

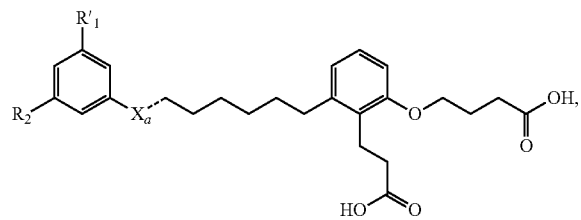

(I)

or pharmaceutically acceptable salts thereof. These compounds inhibit the interaction of leukotriene $B_4$ ($LTB_4$) pro-inflammatory lipid mediator binding to BLT-1 and BLT-2 receptors resulting in amelioration of disease states resulting from excessive inflammatory response, such as, for example, severe asthma and chronic obstructive pulmonary disease (COPD).

All documents cited or relied upon below are expressly incorporated herein by reference.

BACKGROUND OF THE INVENTION $LTB_4$ is a potent pro-inflammatory lipid mediator derived from arachidonic acid through the 5-lipoxygenase signaling pathway. $LTB_4$ is produced by multiple cell types such as neutrophils, monocytes, macrophases, keratinocytes, lymphocytes and mast cells. It functions as a chemoattractant and as an activator of neutrophil cells. It has been shown that $LTB_4$ effects its action through the agonism of G-protein coupled receptors BLT-1 and BLT-2. (Prostaglandins, Leukotrienes and Essential Fatty Acids 69, 2003, 123-134.)

$LTB_4$ is considered to be an important mediator of acute and chronic inflammatory diseases. Increased levels of $LTB_4$ have been detected in the lungs of patients with severe asthma and COPD. Thus, it is anticipated that an effective inhibitor of the action of $LTB_4$ and BLT-1 and -2 would provide effective therapy for the treatment of inflammatory conditions such as asthma and COPD.

A need exists in the art for $LTB_4$ inhibitors that have efficacy for the treatment of diseases such as COPD.

SUMMARY OF THE INVENTION

In an embodiment of the present invention, provided is a compound of formula (I):

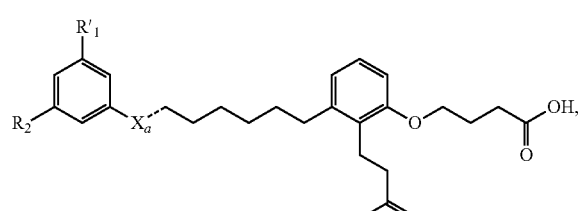

(I)

wherein:
$R_1$ and $R_2$, independently of each other, are
  halogen,
  benzo[1,3]dioxole, unsubstituted or mono- or bi-substituted with halogen,
  2,3-dihydro-benzo[1,4]dioxine, unsubstituted or mono- or bi-substituted with halogen,
  3,4-dihydro-2H-benzo[b][1,4]dioxepine, unsubstituted or mono- or bi-substituted with halogen,
  monocyclic 5- or 6-membered aryl or monocyclic 5- or 6-membered heteroaryl, unsubstituted or substituted with one to four substituents selected from the group consisting of halogen, lower alkyl, haloloweralkyl, carboxy, alkoxy, hydroxy, aminoloweralkyl and —$OCF_3$;
  bicyclic 8- to 12-membered heteroaryl, unsubstituted or substituted with one to four substituents selected from the group consisting of halogen, lower alkyl, haloloweralkyl, carboxy, alkoxy, hydroxy, aminoloweralkyl and —$OCF_3$;
X is O, C, S, or N, unsubstituted or substituted with lower alkyl; and
a is a single bond or an alkynyl bond,
and pharmaceutically acceptable salts thereof.

In an another embodiment of the present invention, provided is a pharmaceutical composition, comprising a therapeutically effective amount of a compound according to formula I or a pharmaceutically acceptable salt thereof and a pharmaceutically acceptable carrier.

In a further embodiment of the present invention, provided is a method of treating an inflammatory disease or disorder, comprising the step of administering a therapeutically effective amount of a compound according to formula I to a patient in need thereof.

DETAILED DESCRIPTION

The present invention pertains to inhibitors of $LTB_4$. In a preferred embodiment, the invention provides for pharmaceutical compounds of the formula I:

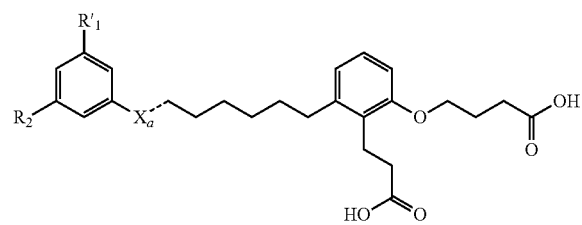

(I)

as well as pharmaceutically acceptable salts thereof, that are useful as inhibitors of $LTB_4$.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "aryl" means, for example, a monocyclic or bicyclic, substituted or unsubstituted carbocyclic aromatic group. Examples of aryl groups are phenyl, naphthyl and the like.

As used herein, the term "alkyl" means, for example, a branched or unbranched, cyclic (e.g., "cycloalkyl") or acyclic, saturated or unsaturated (e.g. alkenyl or alkynyl) hydrocarbyl radical which may be substituted or unsubstituted. Where cyclic, the alkyl group is preferably $C_3$ to $C_{12}$, more preferably $C_5$ to $C_{10}$, more preferably $C_5$ to $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl, sec-butyl or tertiary-butyl) or pentyl (including n-pentyl and isopentyl), more preferably methyl. It will be appreciated therefore that the term "alkyl" as used herein includes alkyl (branched or unbranched), substituted alkyl (branched or unbranched), alkenyl (branched or unbranched), substituted alkenyl (branched or unbranched), alkynyl (branched or unbranched), substituted alkynyl (branched or unbranched), cycloalkyl, substituted cycloalkyl, cycloalkenyl, substituted cycloalkenyl, cycloalkynyl and substituted cycloalkynyl.

As used herein, the term "lower alkyl" means, for example, a branched or unbranched, cyclic (e.g., "cycloloweralkyl") or acyclic, saturated or unsaturated (e.g. alkenyl or alkynyl) hydrocarbyl radical wherein said cyclic lower alkyl group is $C_3$, $C_4$, $C_5$, $C_6$, $C_7$, $C_8$, $C_9$ or $C_{10}$, preferably $C_3$, $C_4$, $C_5$, $C_6$ or $C_7$; and wherein said acyclic lower alkyl group is $C_1$, $C_2$, $C_3$, $C_4$, $C_5$, $C_6$ or $C_7$, preferably $C_1$, $C_2$, $C_3$, $C_4$ such as, for example, methyl, ethyl, propyl (n-propyl or isopropyl) or butyl (n-butyl, sec-butyl, isobutyl or tertiary-butyl). It will be appreciated therefore that the term "lower alkyl" as used herein includes lower alkyl (branched or unbranched), lower alkenyl (branched or unbranched), lower alkynyl (branched or unbranched), cyclo loweralkyl, cyclo loweralkenyl and cyclo loweralkynyl.

The alkyl and aryl groups may be substituted or unsubstituted. Where substituted, there will generally be, for example, 1 to 4 substituents present, preferably 1 substituent. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono-or di-alkylaminocarbonylalkyl, arylaminocarbonyl), carbamates (e.g. alkoxycarbonylamino, arloxycarbonylamino, aminocarbonyloxy, mono-or di-alkylaminocarbonyloxy, arylaminocarbonyloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl). Preferably, said aryl group is substituted with halogen, lower alkyl, haloloweralkyl, carboxy, alkoxy, hydroxy, aminoloweralkyl or —$OCF_3$.

The lower alkyl groups may be substituted or unsubstituted, preferably unsubstituted. Where substituted, there will generally be, for example, 1 to 3 substitutents present, preferably 1 substituent.

The term "heterocyclyl" refers to a saturated or partly unsaturated 5- or 6-membered ring which can comprise one, two or three atoms selected from nitrogen, oxygen and/or sulphur. Examples of heterocyclyl rings include piperidinyl, piperazinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, thiadiazolylidinyl, dihydrofuryl, tetrahydrofuryl, dihydropyranyl, tetrahydropyranyl, and thiomorpholinyl.

The term "heteroaryl", alone or in combination with other groups, means a monocyclic or bicyclic radical of 5 to 12 ring atoms having at least one aromatic ring containing one, two, or three ring heteroatoms selected from N, O, and S, the remaining ring atoms being C. One or two ring carbon atoms of the heteroaryl group may be replaced with a carbonyl group. The heteroaryl group described above may be substituted independently with one, two, three or four substituents, preferably one or two substituents such as, for example, halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, amino $C_{1-6}$ alkyl, mono- or di-substituted amino-$C_{1-6}$ alkyl, nitro, cyano, acyl, carbamoyl, mono- or di-substituted amino, aminocarbonyl, mono- or di-substituted amino-carbonyl, aminocarbonyl $C_{1-6}$ alkoxy, mono- or di-substituted aminocarbonyl-$C_{1-6}$ alkoxy, hydroxy-$C_{1-6}$ alkyl, carboxyl, $C_{1-6}$ alkoxy carbonyl, aryl $C_{1-6}$ alkoxy, heteroaryl $C_{1-6}$ alkoxy, heterocyclyl $C_{1-6}$ alkoxy, $C_{1-6}$ alkoxycarbonyl $C_{1-6}$ alkoxy, carbamoyl $C_{1-6}$ alkoxy and carboxyl $C_{1-6}$ alkoxy, preferably halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, mono-$C_{1-6}$ alkyl substituted amino, di-$C_{1-6}$ alkyl substituted amino, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl, nitro, carbamoyl, mono- or di-substituted amino-carbonyl, hydroxy-$C_{1-6}$ alkyl, carboxyl, $C_{1-6}$ alkoxy carbonyl and cyano. Preferably, said heteroaryl group is substituted with halogen, lower alkyl, haloloweralkyl, carboxy, alkoxy, hydroxy, aminoloweralkyl or —$OCF_3$.

As used herein, the term "alkoxy" means, for example, alkyl-O— and "alkoyl" means, for example, alkyl-CO—. Alkoxy substituent groups or alkoxy-containing substituent groups may be substituted by, for example, one or more alkyl groups.

As used herein, the term "halogen" is used interchangeably with the word "halo", and, unless otherwise stated, designates all four halogens, i.e. fluorine, chlorine, bromine, and iodine. As used herein, "perfluoro-lower alkyl" means any lower alkyl group wherein all of the hydrogens of the lower alkyl group are substituted or replaced by fluoro. Among the preferred perfluoro-lower alkyl groups are, for example, trifluoromethyl, pentafluoroethyl and heptafluoropropyl.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminum salts.

Compounds of formula I include pharmaceutically acceptable esters thereof. "Pharmaceutically acceptable esters" means that compounds of general formula (I) may be derivatized at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

In more detail, for example, the pharmaceutically usable esters are compounds of formula I, wherein e.g. a hydroxy group can be esterified. Examples of such esters are formate, acetate, propionate, butyrate, isobutyrate, valerate, 2-methylbutyrate, isovalerate and N,N-dimethylaminoacetate.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

The compounds of the present invention can be prepared by any conventional means. Suitable processes for synthesizing these compounds are provided in the Examples. Generally, compounds of formula I can be prepared according to the Schemes described below. The sources of the starting materials for these reactions are also described.

Scheme 1

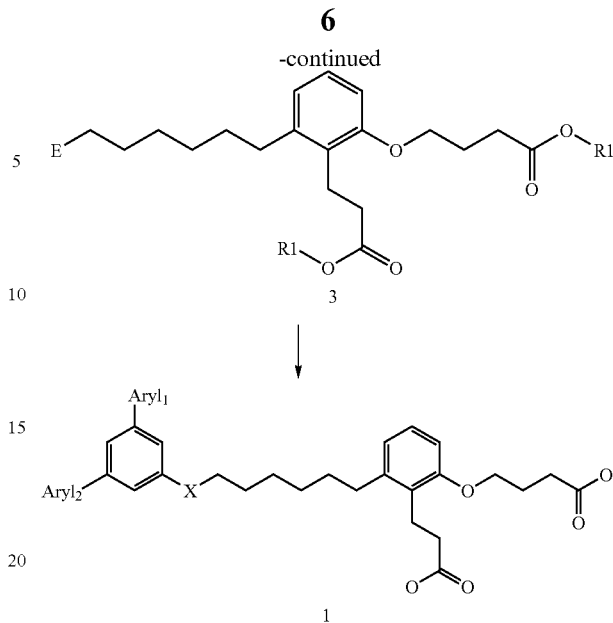

The compounds contained within this invention can be synthesized according to the following general synthetic strategies as shown in Scheme 1. The synthesis of 1 may be effected by condensation of the fragment 3, 4-[2-(2-carboxyethyl)-3-(6-E-hexyl)-phenoxy]-butyric, protected as a di-ester for R1=lower alkyl, preferably as a di-ethyl ester (R1=ethyl), and E is a leaving group, such as a halogen or mesylate with the fragment 2 wherein D is a nucleophile such as a hydroxyl or sulfhydryl group under standard conditions employed for the alkylation of phenols with primary halides or mesylates. For compounds 1 in which X is sulfur, then E as sulfur reacts with D as a leaving group is also possible to assemble target structures. Functional groups represented by symbols A and B can be together or independently halogen, nitro, and amino and can be together or independently transformed to $Aryl_1$ and $Aryl_2$ before or after coupling to 3 according to chemistry described in this invention.

A synthesis 3 for E=Br and $R_1$=Et has been described in *Bioorganic & Medicinal Chemistry Letters* (1994), 4(24), 2883-8. A synthesis 3 for E=Br and $R_1$=Et is also shown below in Schemes 2 and 3.

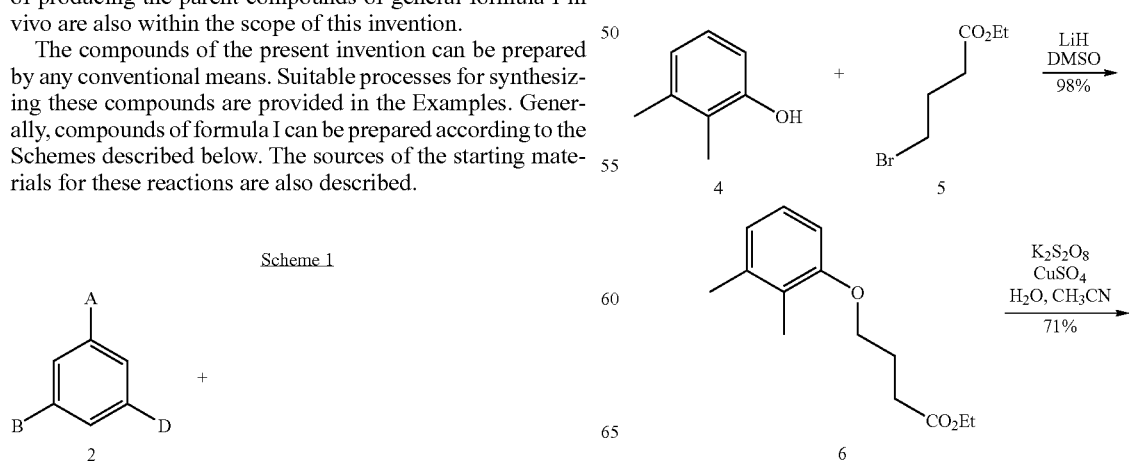

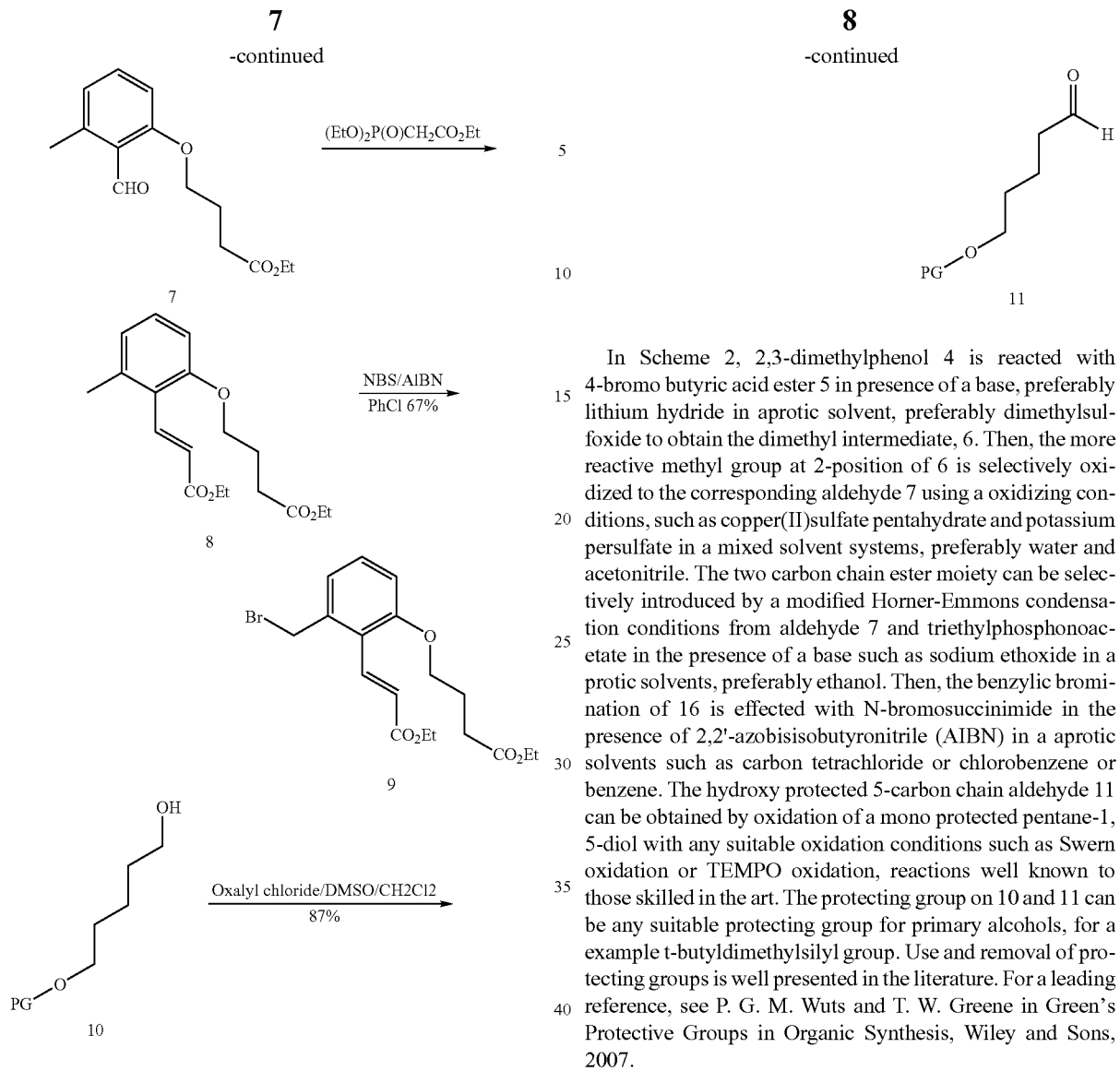

In Scheme 2, 2,3-dimethylphenol 4 is reacted with 4-bromo butyric acid ester 5 in presence of a base, preferably lithium hydride in aprotic solvent, preferably dimethylsulfoxide to obtain the dimethyl intermediate, 6. Then, the more reactive methyl group at 2-position of 6 is selectively oxidized to the corresponding aldehyde 7 using a oxidizing conditions, such as copper(II)sulfate pentahydrate and potassium persulfate in a mixed solvent systems, preferably water and acetonitrile. The two carbon chain ester moiety can be selectively introduced by a modified Horner-Emmons condensation conditions from aldehyde 7 and triethylphosphonoacetate in the presence of a base such as sodium ethoxide in a protic solvents, preferably ethanol. Then, the benzylic bromination of 16 is effected with N-bromosuccinimide in the presence of 2,2'-azobisisobutyronitrile (AIBN) in a aprotic solvents such as carbon tetrachloride or chlorobenzene or benzene. The hydroxy protected 5-carbon chain aldehyde 11 can be obtained by oxidation of a mono protected pentane-1,5-diol with any suitable oxidation conditions such as Swern oxidation or TEMPO oxidation, reactions well known to those skilled in the art. The protecting group on 10 and 11 can be any suitable protecting group for primary alcohols, for a example t-butyldimethylsilyl group. Use and removal of protecting groups is well presented in the literature. For a leading reference, see P. G. M. Wuts and T. W. Greene in Green's Protective Groups in Organic Synthesis, Wiley and Sons, 2007.

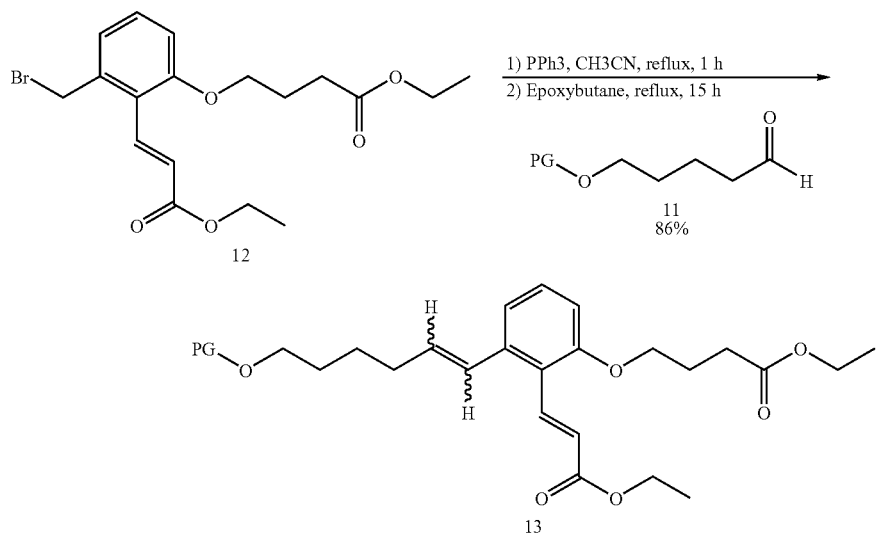

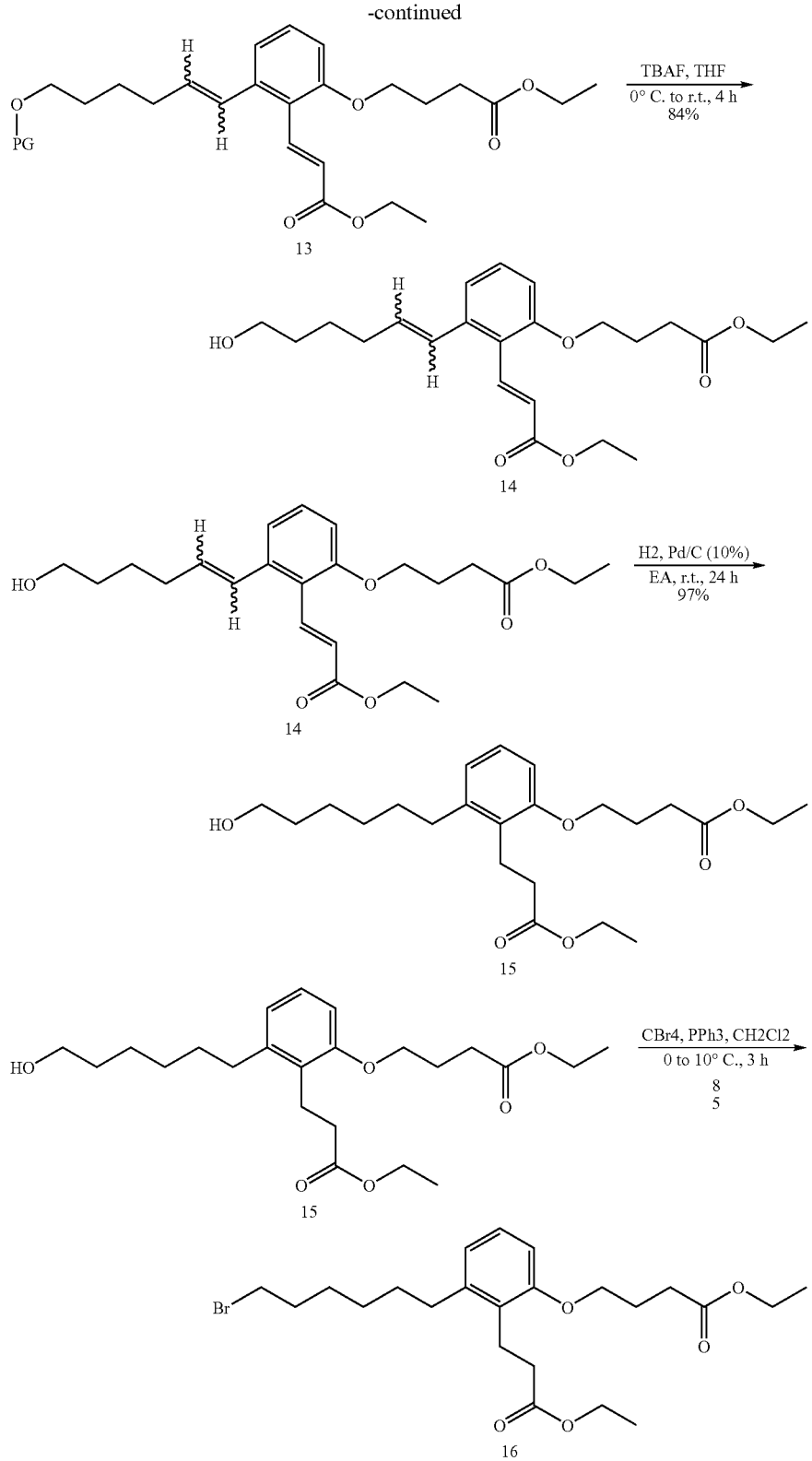

As shown in Scheme 3, a one-pot Wittig condensation reaction is conducted first by making an in situ Wittig salt from the benzylic bromide 12 and triphenylphosphine in acetonitrile and then the reaction of the resulting Wittig salt with the protected aldehyde 11 in 1,2-epoxybutane to obtain the olefinic intermediate 13 in a cis to trans ratio of ~1:3. The mixture of cis and trans compounds can be converted to the corresponding alkyl bromide intermediate 16 by removal of the protecting group, using for example tetrabutyl ammonium fluoride for the case wherein the protecting group is a t-butyldimethylsilyl group, hydrogenation of the double bonds, and conversion of the hydroxyl group to the bromide. These transformation are routine and well known to those skilled in the art.

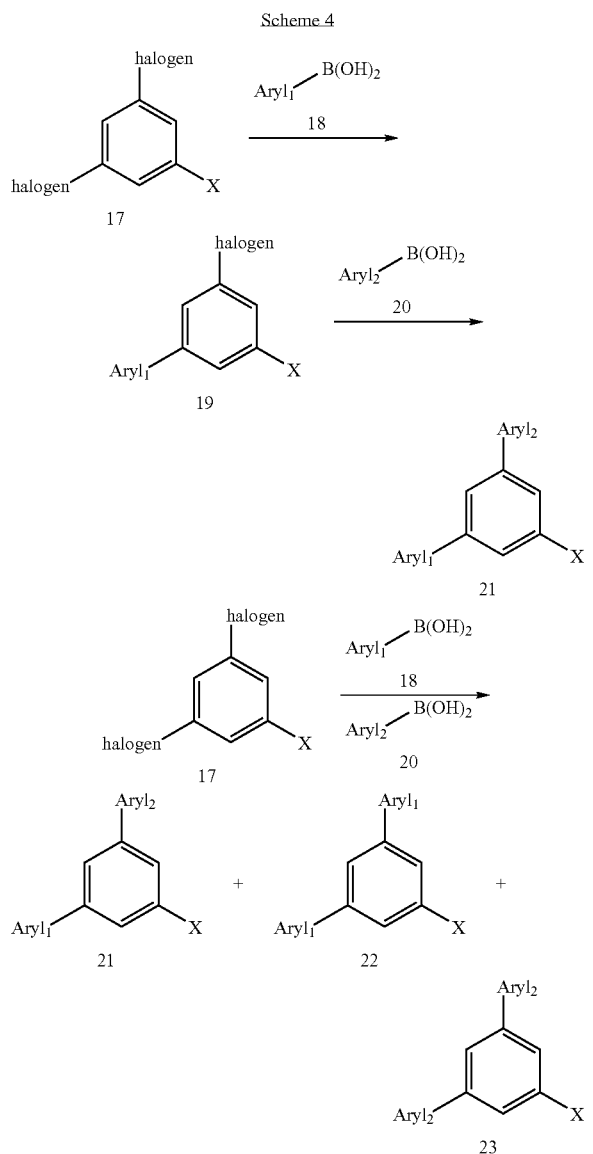

Symmetric 3,5-diaryl phenols where X equals hydroxy (22 and 23) may be synthesized from 3,5-halo phenols (17) where X equals hydroxy as shown in Scheme 4. In these reactions, halogen may be iodo, bromo and chloro, preferable bromo and iodo. In this method, halogen substitutions may be transformed to aryl substitutions using Suzuki coupling reaction conditions. The conditions of this method are disclosed in many publications which have been reviewed by A. Suzuki in an article entitled "The Suzuki reaction with arylboron compounds in arene chemistry" in *Modern Arene Chemistry* 2002, 53-106. In carrying out this reaction any of the suitable conditions conventional in a Suzuki reaction can be utilized.

The reaction in Scheme 4 can also be run in a sequential manner such that asymmetric 3,5-diaryl phenols may be synthesized in the manner as shown in Scheme 4, whether at the same time or by isolating the monoaryl substitution product; or by conducting the reaction with a mixture of aryl-substituted boronic acids. The resulting product mixtures can then be chromatographically separated and identified according to the expected molecular weights.

Generally Suzuki coupling reactions are carried out in the presence of a transition metal catalyst such as a palladium catalyst utilizing any conventional organic solvent for this reaction and a weak inorganic base. Among the preferred organic solvents are the polar aprotic solvents. Any conventional polar aprotic solvents can be utilized in preparing compounds of the invention. Suitable solvents are customary, especially higher-boiling solvents, e.g. dimethoxyethane. The weak inorganic base can be a carbonate or bicarbonate, such as potassium carbonate or cesium carbonate.

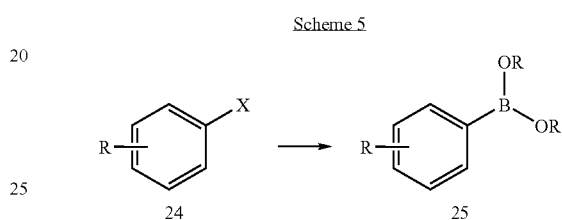

Substituted phenyl boronic acids (25, R═H) and boronic esters such as 4,4,5,5-tetramethyl-[1,3,2]dioxaborolane (25, R═—(C(CH$_3$)$_2$)$_2$—) useful in the preparation of compounds of this invention may be commercially available or they can be made by reactions that are well known in the field of organic synthesis. Aryl boronic acids and aryl boronic esters are formed by treatment of aryl halides (24) with an organometallic reagent such as n-butyl lithium followed by treatment with boron triisopropoxide or 4,4,4',4',5,5,5',5'-octamethyl-2,2'-bi-1,3,2-dioxaborolane followed by acidic work-up as is well known to those skilled in the art.

This method is also applicable where for protected phenols such as for those where X=lower alkyl, preferably methoxy. Removal of lower alkyl groups to re-generate unprotected hydroxyl groups is effected by treatment with Lewis acids such as boron tribromide and is well know to those skilled in the art.

Commercially available boronic acids used in this procedure are listed below. The Available Chemicals Database (ACD) indicates the availability of greater than seven hundred commercially available aryl boronic acids. Some boronic acids useful for the preparation of compounds of the invention are listed below.

TABLE 1

| Commercially available boronic acids Boronic acid |
|---|
| 3-CHLORO-PHENYLBORONIC ACID |
| 3-CHLORO-5-METHYLPHENYLBORONIC ACID |
| 3-CHLORO-6-METHOXYPHENYLBORONIC ACID |
| 3-CHLORO-4-FLUOROPHENYLBORONIC ACID |
| 3-CHLORO-4-METHYLPHENYLBORONIC ACID |
| 3-CHLORO-2-METHYLPHENYLBORONIC ACID |
| 4-CHLORO-3-METHYLPHENYLBORONIC ACID |
| 2,4-DI-CHLOROPHENYLBORONIC ACID |
| 4-CHLORO-2-METHYLPHENYLBORONIC ACID |
| 4-CHLORO-2-METHOXYLPHENYLBORONIC ACID |
| 4-CHLORO-2-ETHOXYLPHENYLBORONIC ACID |
| 4-CHLORO-3-AMINOPHENYLBORONIC ACID |
| 3-ISOPROPYLPHENYLBORONIC ACID |

TABLE 1-continued

Commercially available boronic acids
Boronic acid

THIOPHENE-3-BORONIC ACID
2-METHYLPHENYLBORONIC ACID
3-METHYLPHENYLBORONIC ACID
(2-HYDROXYMETHYLPHENYL)BORONIC ACID DEHYDRATE
(3-HYDROXYMETHYLPHENYL)BORONIC ACID DEHYDRATE
4-HYDROXYPHENYL)BORONIC ACID DEHYDRATE
2-METHOXYPHENYLBORONIC ACID
3-METHOXYPHENYLBORONIC ACID
2-TRIFLUOROMETHOXYPHENYLBORONIC ACID
3-TRIFLUOROMETHOXYPHENYLBORONIC ACID
6-FLUORO-2-METHOXYPHENYLBORONIC ACID
2-FLUORO-3-METHOXYPHENYLBORONIC ACID
5-FLUORO-2-METHOXYPHENYLBORONIC ACID
3,4-DIMETHOXYPHENYLBORONIC ACID
5-BENZO[1,3]DIOXOLEBORONIC ACID
2,3,4-TRIMETHOXYPHENYLBORONIC ACID
1H-INDOLE-5-BORONIC ACID
QUINOLINE-8-BORONIC ACID
4-PYRIDYL-BORONIC ACID

TABLE 2

These boronic acids are also available from other suppliers that may not necessarily be listed in the ACD.

| | | |
|---|---|---|
| 3-Fluoro-6-(4,4,5,5-tetramethyl-[1,3,2]dioxaborolan-2-yl)pyridine | ATLANTIC SCIENTIFIC CO., INC., JERSEY CITY, NJ, | 791819-04-0 |
| Quinoline-2-boronic acid | LANCASTER | 745784-12-7 |
| 3-Chloro-6-(4,4,5,5-tetramethyl-[1,3,2]dioxaborolan-2-yl)pyridine | ATLANTIC SCIENTIFIC CO., INC., JERSEY CITY, NJ, | 652148-93-1 |
| 6-Chloropyridine-2-boronic acid pinacol ester | INTERCHIM, MONTLUCON, FRANCE | 652148-92-0 |
| Boronic acid, (2-methyl-4-pyrimidinyl)- | CHEMSTEP, TALENCE, FRANCE | 647853-31-4 |
| Boronic acid, (3-methoxy-2-pyridinyl)- | CHEMSTEP, TALENCE, FRANCE | 500707-34-6 |
| Boronic acid, (6-methoxy-2-pyridinyl)- | CHEMSTEP, TALENCE, FRANCE | 372963-51-4 |
| Boronic acid, (6-methyl-2-pyridinyl)- | CHEMSTEP, TALENCE, FRANCE | 372963-50-3 |
| Boronic acid, (5-methyl-2-pyridinyl)- | CHEMSTEP, TALENCE, FRANCE | 372963-49-0 |
| Boronic acid, (4-methyl-2-pyridinyl)- | CHEMSTEP, TALENCE, FRANCE | 372963-48-9 |
| Boronic acid, 2-pyridinyl- | CHEMSTEP, TALENCE, FRANCE | 197958-29-5 |

Scheme 6

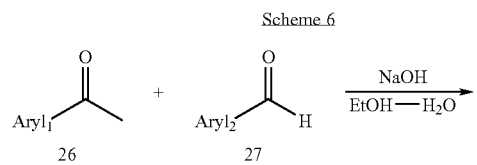

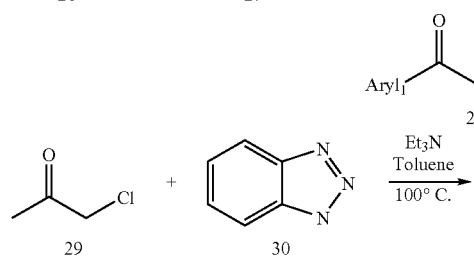

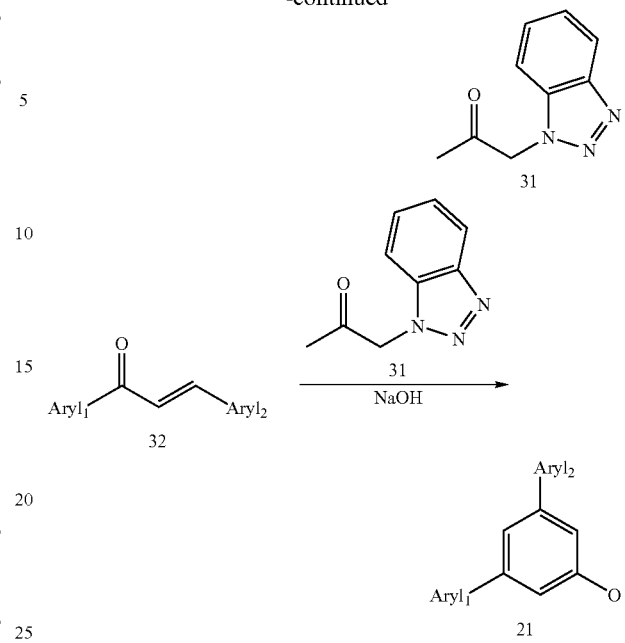

3,5-Diaryl-substituted phenols 21 can also be prepared as shown in Scheme 6 using a general methodology reported in J. Org. Chem. 1997, 62, 8215-8217. In the first step, an aryl carboxaldehyde reacted with an aryl-methyl ketone is reaction in alkaline solution to yield the corresponding α,β-unsaturated ketone, so-called chalcones. 2-Halo-acetone, preferable 2-chloro-acetone, was reacted with benzotriazole in the presence of triethylamine in aprotic solvents, preferable toluene for 1-benzotriazol-1-yl-propan-2-one. Subsequently, condensation of the α,β-unsaturated ketone with 1-benzotriazol-1-yl-propan-2-one in ethanolic aqueous base, preferable aqueous sodium hydroxide in ethanol at reflux afforded the 3,5-diaryl-substituted phenols.

Scheme 7

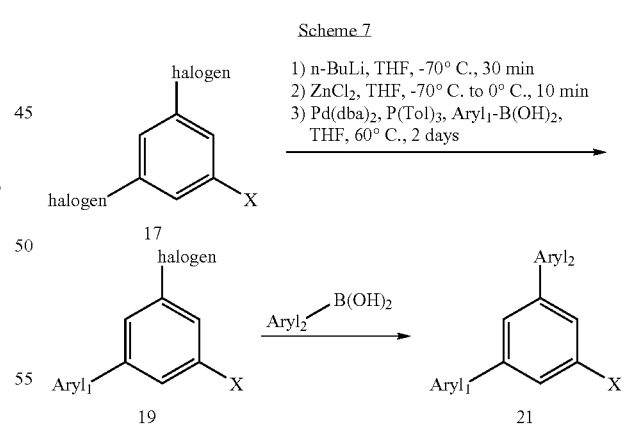

Unsymmetrical diaryl substituted compounds can also be prepared according to the synthesis shown in Scheme 7 for X=alkoxy, preferable methoxy, by preparation and application of a Zn/Li-organometallic reagent following reported procedures (see for example, Knochel, P.: Singer, R. D., Chem. Rev. 1993, 93, 2117, Klement, I., Rottlaender, M. Tucker, C. E., Majid, T. N., Knochel, P., Venegas, P., Cahiez, G. Tetrahedron 1996, 52, 7201, and Knochel, P., Perea, J. A., Jones, P. Tetrahedron 1998, 54, 8275).

Scheme 8

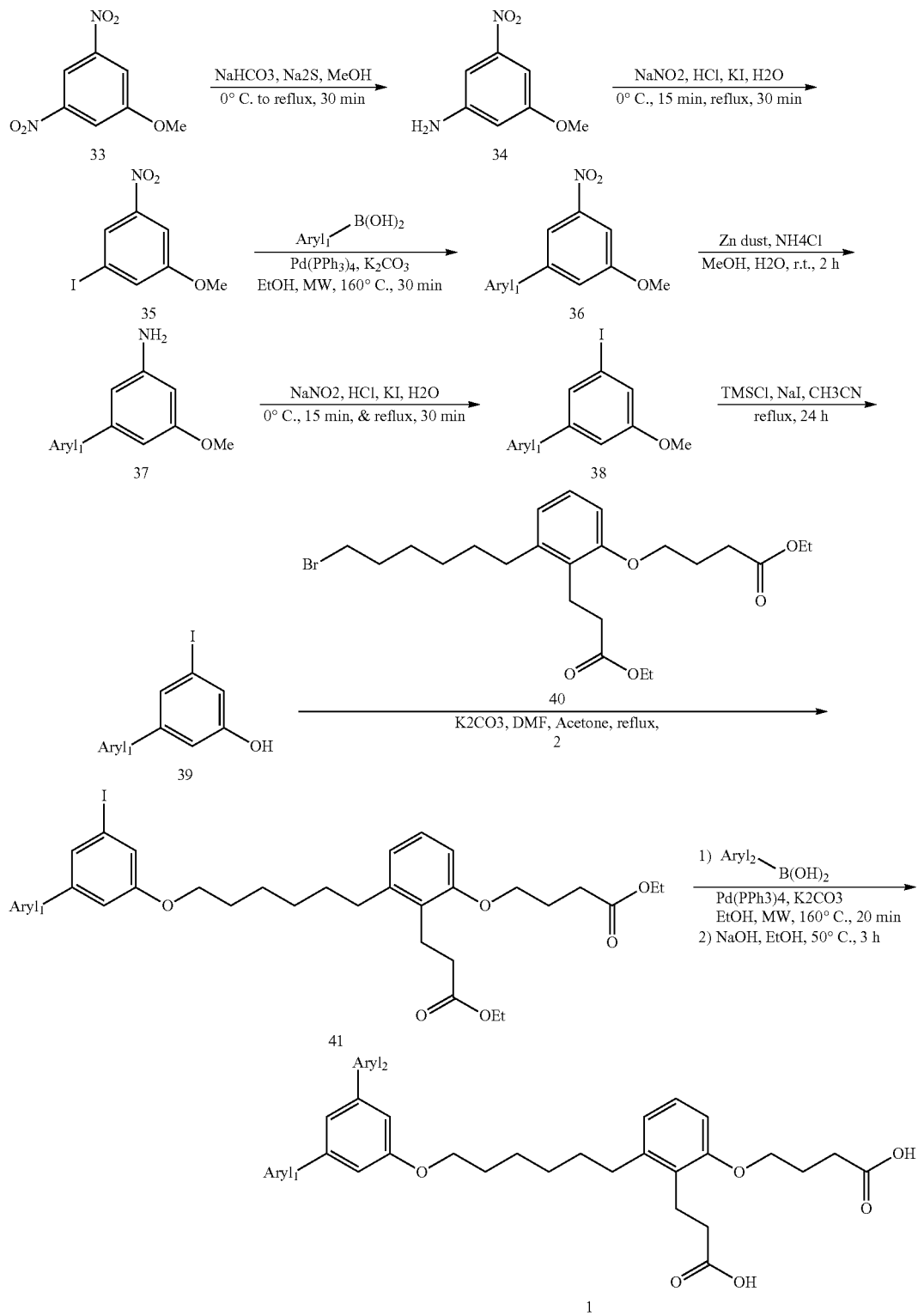

Asymmetric diaryl substituted compounds can also be prepared according to the synthesis shown in Scheme 8. In this method, commercially available dinitroanisole 33 is selectively reduced and then transformed to 3-iodo-5-nitroanisole 35 following a literature report (see for example, Siegfried, H. R., Theodore, J., Michael, B. W., Susan, E. K., Shella, A. F., Stephen, T. W., David, A. M., Thomas, F. H., For a, C., James, M., Rose, A. F., Edward, L. B., Dorothy, M. D., Amy, K. P., Susan, L. B., Clifford, E. F. J. Med. Chem. 2000, 43, 1670) and serves as a substrate for application of the Suzuki coupling reaction to produce compounds of structure 36. Structure 36 is transformed to Structure 39 according to reactions well known to those skilled in the art. Structure 39 is then reacted with alkyl bromide 40 to produce intermediate 41. Intermediate can then be transformed in two steps to compounds of general structure 1.

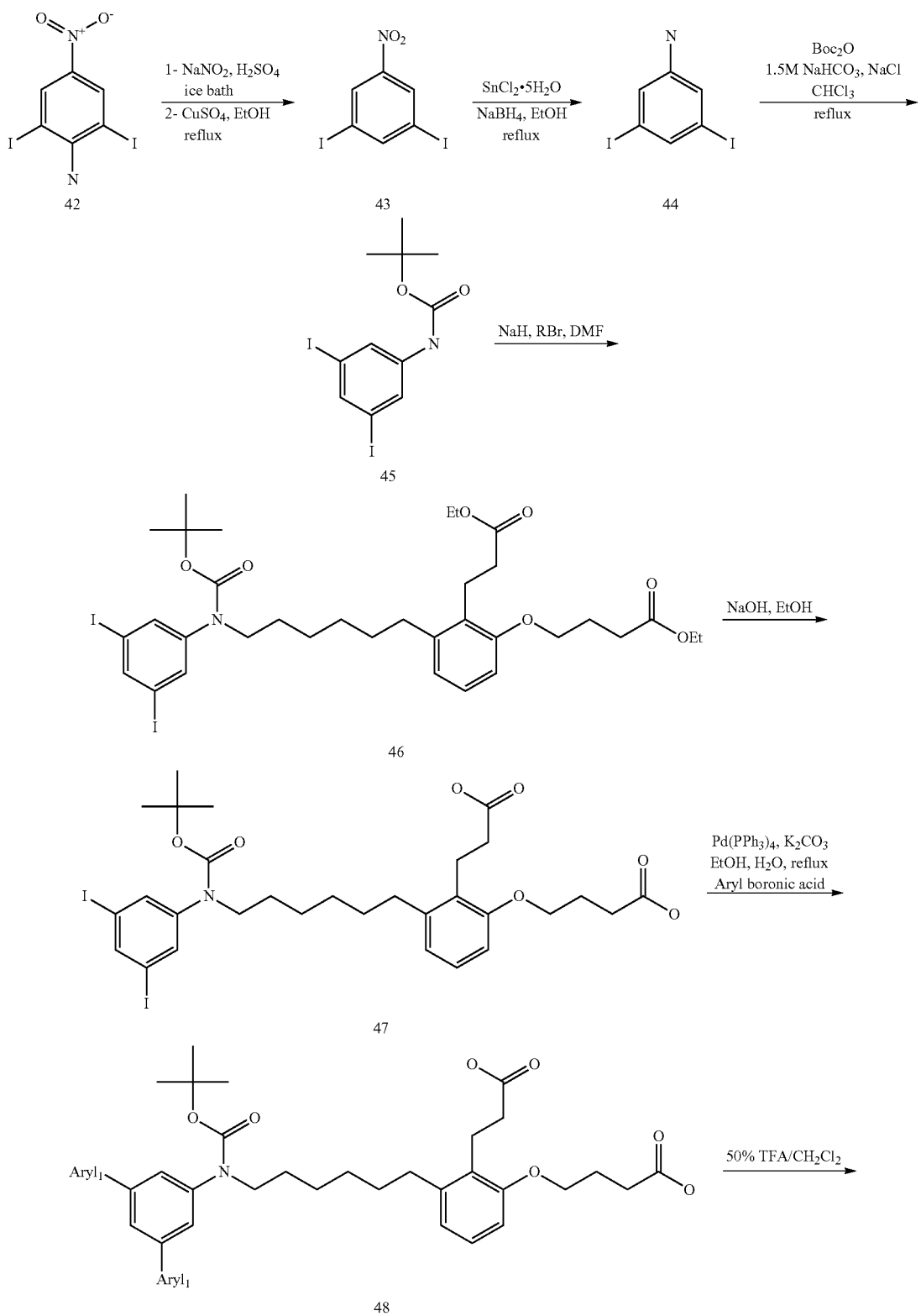

Scheme 9

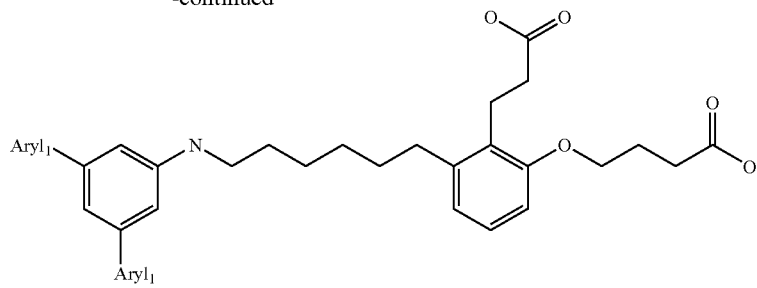

49

Target molecules 1 wherein X is nitrogen can be synthesized as shown in Scheme 9 starting with commercially available 2,6-diiodo-4-nitro-aniline. Following a literature procedure, (Org. Lett. 2004, 6, 3127), N-tert-butoxycarbonyl-3,5-diiodoaniline (45) is obtainable in 4 steps. Alkylation with compound 40 of Scheme 8 can be achieved using basic conditions, preferably NaH in DMF. Base catalyzed saponification of the diester is possible with NaOH in EtOH to afford the desired intermediate for the Suzuki coupling reaction. Standard Suzuki coupling conditions can be carried out to perform the di-aryl reaction using tetrakis(triphenylphosphine)palladium(0) and potassium carbonate in a mixture of EtOH/H$_2$O as solvent to afford the 3,5-bis-aryl-N-boc protected aniline derivatives. Finally, acid catalyzed deprotection of the tert-butoxycarbonyl group, such as by using 50% TFA/CH$_2$Cl$_2$, yielded the target molecules. It is also possible to also remove the tert-butoxycarbonyl group prior to the Suzuki reaction to obtain the target molecules.

Scheme 10

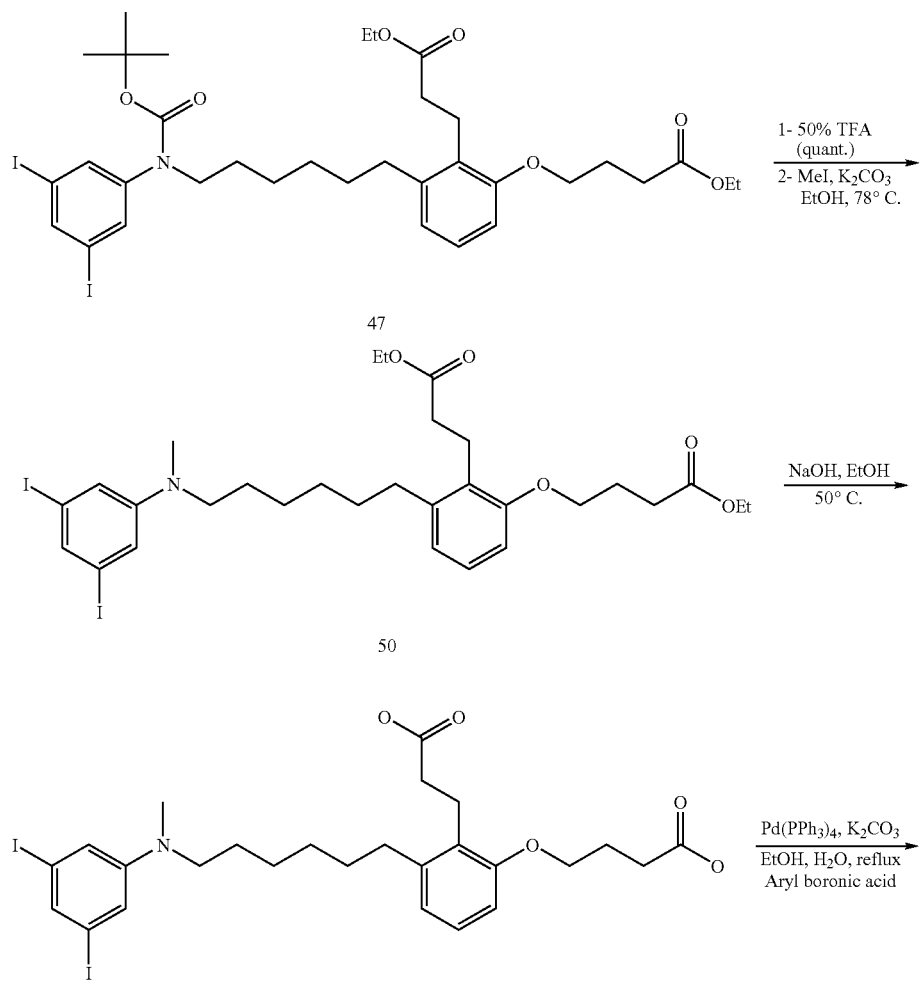

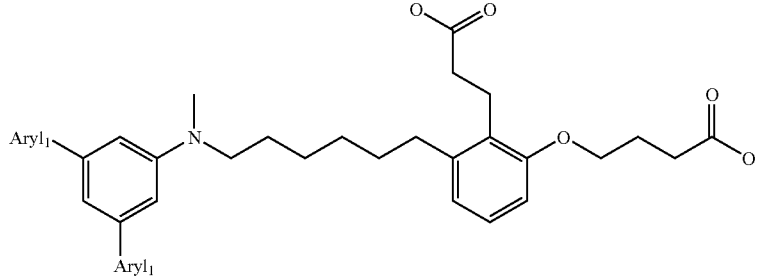

52

Target molecules wherein X is methylamino can be synthesized as shown in Scheme 10. Starting from compound 47 in Scheme 9, removal of the tert-butoxycarbonyl can be accomplished as described above and replaced with a methyl group using iodomethane and potassium carbonate. Other alkylating agents such as dimethyl sulfate are also available to perform this type of reaction (P. G. M. Wuts and T. W. Greene in Green's Protective Groups in Organic Synthesis, Wiley and Sons, 2007). Then, standard saponification can provide the required 3,5-diiodo-phenyl-methyl-amino for the Suzuki reaction. Finally, the same conditions described in Scheme 9 may be used to generate compounds such as those represented by Structure 52 of Scheme 10.

Scheme 11

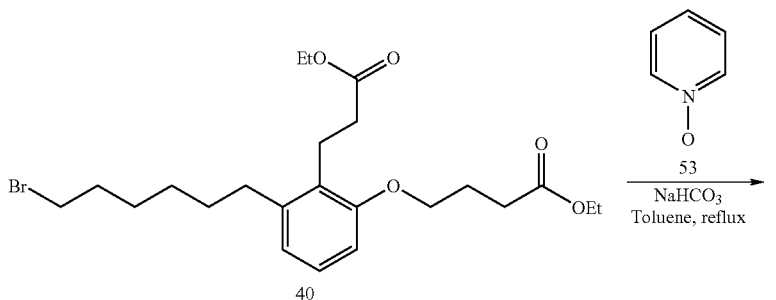

40

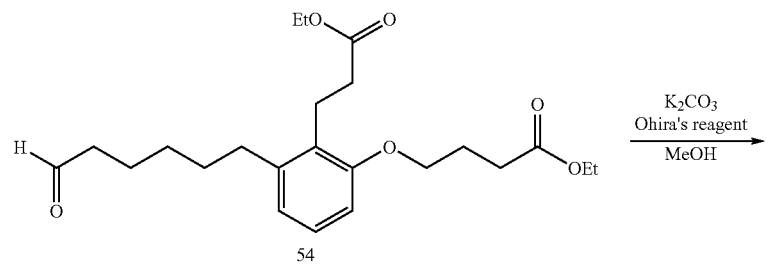

54

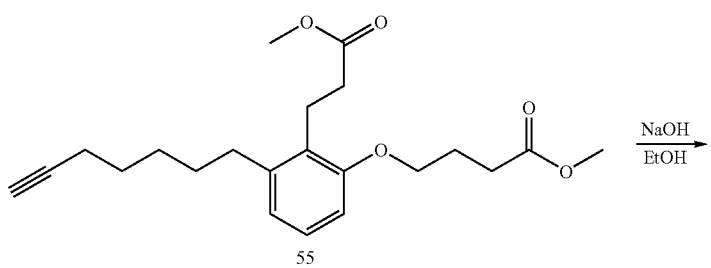

55

-continued
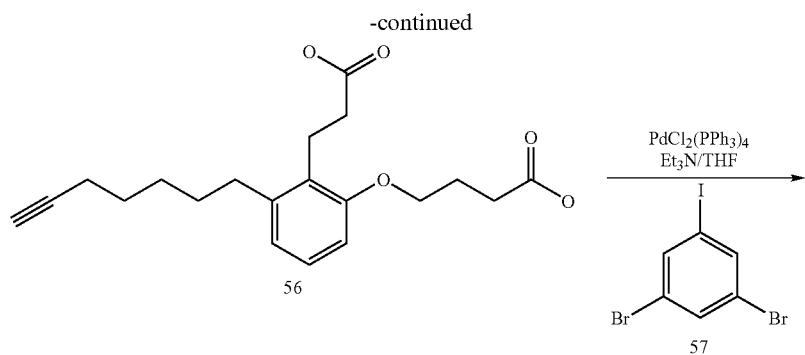
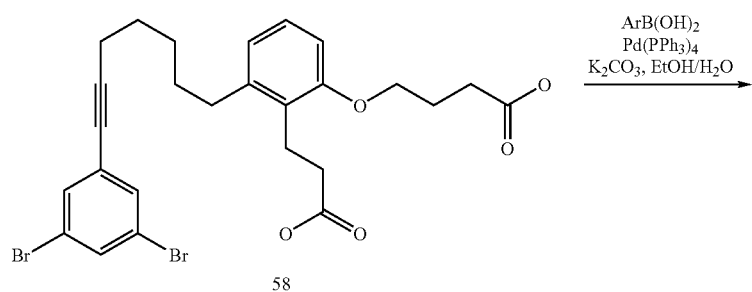
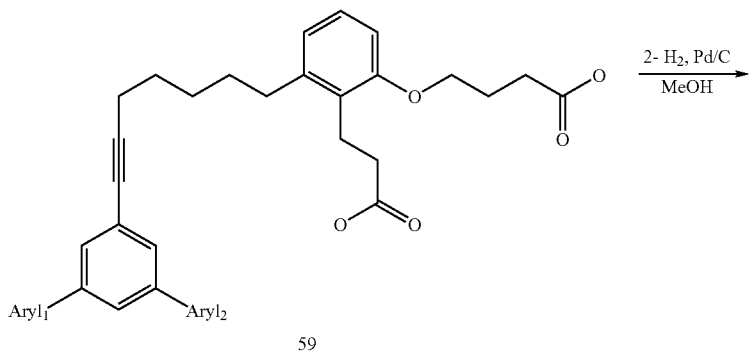
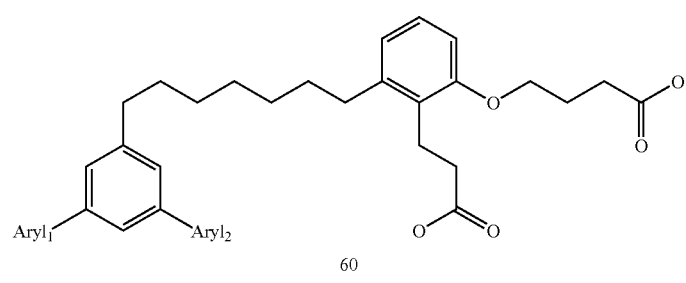

Target molecules wherein X is carbon, either saturated or doubly unsaturated, can be synthesized as shown in Scheme 11. The conversion of the bromide of 40 to aldehyde 54 can be accomplished using pyridine-N-oxide and sodium bicarbonate (J. Org. Chem. 1970, 35, 244). Other methods are also found in the literature to successfully convert an alkyl bromide to an aldehyde; use of $AgBF_4$-DMSO (Synthesis 2004, 271); trimethylamine-N-oxide-DMSO (Tet. Letters, 1990, 31, 4825); DMSO-KI—$Na_2CO_3$ (Carbohydrate. Res. 2001, 330, 295). Aldehyde 54 can then be transformed into an alkyne 55 using Ohira's reagent (Synth. Commun., 1989, 19, 561) and potassium carbonate. During the reaction, a trans- esterification may occur changing the ethyl ester to a methyl ester which can then be cleaved in the next step to generate the free diacid. Using the Sonogashira coupling reaction (Angew. Chem. Int. ed. Eng. 2000, 39, 2632), selective mono-alkynylation of 3,5-dibromoiodobenzene 57 (J. Org. Chem. 2003, 68, 8750) can be achieved. The 3,5-dibromo-phenyl derivatives 58 may then be treated under the Suzuki coupling reaction conditions described for schemes 9 and 10. Hydrogenation of the triple bond can be effected using hydrogen and Pd/C in a solvent such as methanol to provide structures such as 60.

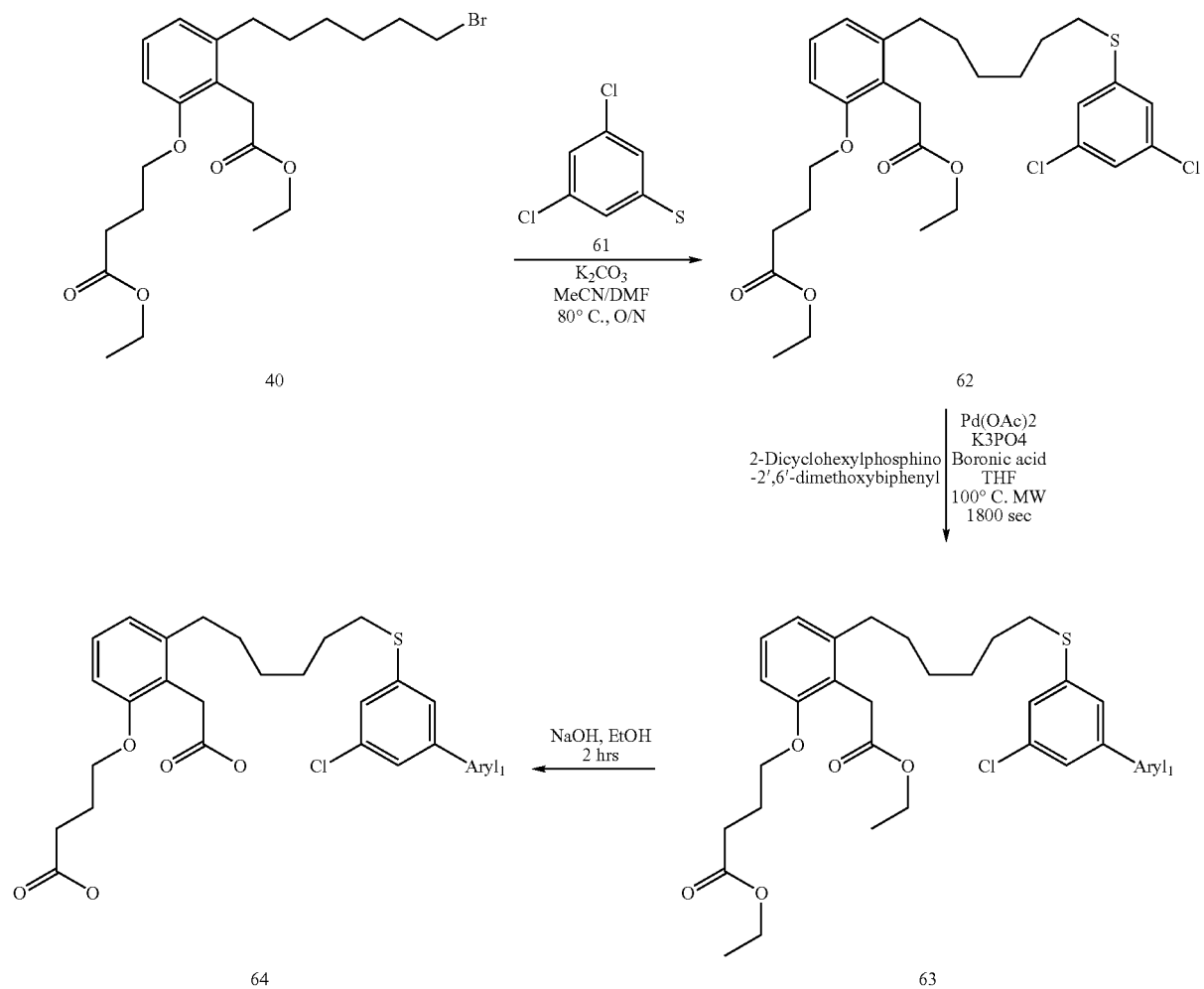

Scheme 12

Target molecules wherein X is sulfur can be synthesized as shown in Scheme 12. The precursor for the Suzuki coupling reaction can be prepared by alkylating compound 40 with 3,5-dichlorothiophenol 61 using potassium carbonate as a base. A Suzuki coupling reaction performed using a catalyst system composed of 2-(2',6'-dimethoxybiphenyl)-dicyclohexylphosphine (SPhos) and palladium acetate is effective to substitute only one chloride with an aryl group, thus producing compounds such as 63. Saponification of the ethyl ester group can then be accomplished using standard conditions to give structure 61. In the case of 3,5-dichlorothiophenyl ethers as substrates for application of the Suzuki coupling reaction, mono-aryl, mono-chloro substituted products are preferentially obtained.

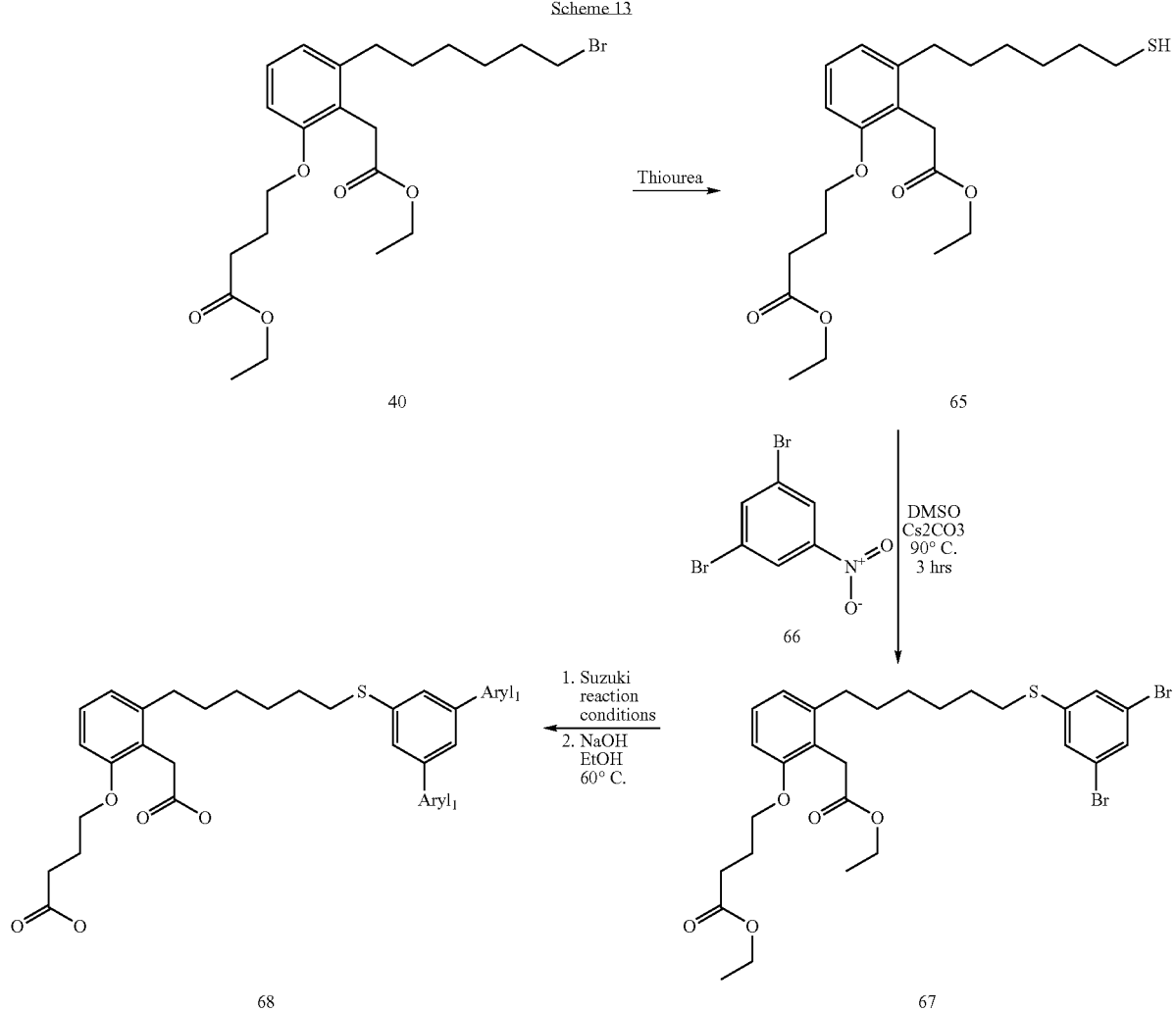

Scheme 13

Target molecules wherein X is sulfur can also be synthesized as shown in Scheme 13. The alkyl bromide 40 can be converted to a thiol in a one-pot reaction using thiourea as the first step to form an isothiuronium salt, followed by cleavage of this salt with a high-boiling amine such as tetraethylenepentamine (J. Org. Chem. 1962, 27, 93). Then, via a nucleophilic aromatic substitution on 3,5-dibromonitrobenzene (J. Org. Chem. 2003, 68, 8750), it is possible to displace the nitro group with the alkyl thiol 65 to give the thioether 67. For this transformation, the procedure reported in effective Tetrahedron 2006, 62, 2357 is effective. There are also other reported methods for the palladium catalyzed coupling of aryl halides with thiols (Org. Lett. 2004, 6, 4587.; J. Am. Chem. Soc. 2006,128, 2180). The Suzuki coupling reaction can be achieved under anhydrous conditions using $PdCl_2(dppf)$ as a catalyst and cesium carbonate as the base to introduce the two desired aryl groups. Saponification of the ethyl ester group may then accomplished using standard conditions to produce 68.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad lithium. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as an "effective amount". For example, the dose of a compound of the present invention is typically in the range of about 1 to about 1000 mg per day.

The invention will now be further described in the Examples below, which are intended as an illustration only and do not limit the scope of the invention.

EXAMPLES

Reagents were purchased from Aldrich, Sigma, Maybridge, Advanced ChemTech, and Lancaster or other suppliers as indicated below and used without further purification. Reactions using microwave irradiation for heating were conducted using either a Personal Chemistry Emrys Optimizer System or a CEM Discovery System. The purification of multi-milligram to multi-gram scale was conducted by methods known to those skilled in the art such as elution of silica gel flash column; preparative flash column purifications were also effected in some cases by use of disposal pre-packed 40 gram silica gel columns (RediSep) eluted with a CombiFlash system. Biotage and ISCO are also flash column instruments that may have been used in this invention for purification of intermediates.

For the purpose of judging compound identity and purity, LC/MS (liquid chromatography/mass spectroscopy) spectra were recorded. For measurement of mass spectra, the system consisted of a Micromass Platform II spectrometer: ES Ionization in positive mode (mass range: 150-1200 amu). The simultaneous chromatographic separation was achieved with the following HPLC system: ES Industries Chromegabond WR C-18 3u 120 Å (3.2×30 mm) column cartridge; Mobile Phase A: Water (0.02% TFA) and Phase B: Acetonitrile (0.02% TFA); gradient 10% B to 90% B in 3 minutes; equilibration time of 1 minute; flow rate of 2 mL/minute. In some cases, ammonium acetate at 20 millimolar concentration was used as a modifier for effective ionization during preparative HPLC. In such cases, the ammonium salt was isolated.

For some separations, the use of super critical fluid chromatography may also be useful. Super critical fluid chromatography separations were performed using a Mettler-Toledo Minigram system with the following typical conditions: 100 bar, 30° C., 2.0 mL/min eluting a 12 mm AD column with 40% MeOH in super critical fluid $CO_2$. In the case of analytes with basic amino groups, 0.2% isopropyl amine was added to the methanol modifier.

Many compounds of Formula 1 were also purified by reversed phased HPLC, using methods well known to those skilled in the art. In some cases, preparative HPLC purification was conducted using PE Sciex 150 EX Mass Spec controlling a Gilson 215 collector attached to a Shimadzu preparative HPLC system and a Leap autoinjector. Compounds were collected from the elution stream using LC/MS detection in the positive ion detection: The elution of compounds from C-18 columns (2.0×10 cm eluting at 20 ml/min) was effected using appropriate linear gradation mode over 10 minutes of Solvent (A) 0.05% TFA/H2O and Solvent (B) 0.035% TFA/acetyl nitrile. For injection on to HPLC systems, the crude samples were dissolved in mixtures of methanol, acetyl nitrile and DMSO Compounds were characterized either by $^1$H-NMR using a Varian Inova 400 MHz NMR Spectrometer or a Varian Mercury 300 MHz NMR Spectrometer as well as by high resolution mass spectrometry using a Bruker Apex-II high-resolution 4.7T FT-Mass Spectrometer.

LIST OF ABBREVIATIONS

DCE 1,2-dichloroethane
DCM dichloromethane
DIPEA diisopropylethylamine
DMF N,N-dimethylformamide
DMSO dimethylsulfoxide
EtOAc ethyl acetate
FCC Flash column chromatography
HPLC high pressure chromatography
HRMS high resolution mass spectra
MeOH methyl alcohol
MW microwave
NaHCO$_3$ sodium bicarbonate
NIS N-iodosuccinimide
NMP 1-methyl-2-pyrrolidinone
(PdCl$_2$(dppf)) [1,1'-Bis(diphenylphosphino)ferrocene] dichloropalladium(II)
rt room temperature
TBDMS tert-bytyl-dimethylsilyl
TEA triethylamine
TEMPO 2,2,6,6-tetra methyl-1-piperidinyloxy
THF tetrahydrofuran I. Preparation of Preferred Intermediates Preparation of 4-[3-(6-bromo-hexyl)-2-(2-ethoxycarbonyl-ethyl)-phenoxy]-butyric acid ethyl ester 1. Preparation of 4-(2,3-dimethyl-phenoxy)-butyric acid ethyl ester

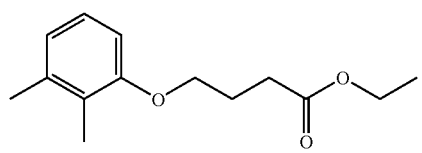

To a solution of 2,3-dimethylphenol (25 g, 204 mmol) in DMSO (205 Ml) was added 4-bromo-butyric acid ethyl ester (40.96 g, 210 mmol) and lithium hydride (2.0 g, 250 mmol) at room temperature. The resulting light brown solution was stirred for 2 days. Then, the reaction mixture was cooled to 0° C. and water (200 Ml) was added slowly. The organic compound was extracted into hexanes (2×200 Ml). The combined organic extracts were washed with brine solution (150 Ml) and the organic solution was dried over anhydrous magnesium sulfate. Filtration of the drying agent and the removal of the solvent gave light brown oil. The crude mixture was purified by using a Biotage (40L) column chromatography eluting with 5% ethyl acetate in hexanes to isolate 4-(2,3-dimethyl-phenoxy)-butyric acid ethyl ester (45.32 g, 94%) as a colorless oil: ES(+)-HRMS m/e calculated for $C_{14}H_{20}O_3$ $(M+)^+$ 236.1412, found 236.1419.

2) Preparation of 4-(2-formyl-3-methyl-phenoxy)-butyric acid ethyl ester

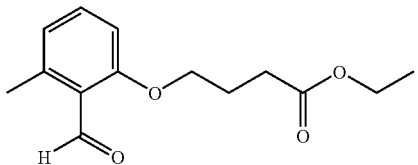

A mixture of copper(II)sulfate pentahydrate (21.98 g, 88.06 mmol) and potassium persulfate (71.42 g, 264 mmol) in water (396 mL) was heated to 63-65° C. to obtain a blue colored solution. Then, a solution of 4-(2,3-dimethyl-phenoxy)-butyric acid ethyl ester (20.81 g, 88.06 mmol) in acetonitrile (220 mL) was added at the above temperature. The resulting light green solution was refluxed for 40 minutes. Then, the reaction mixture was cooled to ~5° C. in order to precipitate most of the inorganic solids. The resulting solids were collected by filtration and the solid cake was washed with dichloromethane (1.0 L). The two layers of filtrate were separated and the aqueous layer was extracted with dichloromethane (200 mL). The combined organic extracts were washed with brine solution (150 mL) and the organic solution was dried over anhydrous magnesium sulfate. Filtration of the drying agent and the removal of the solvent gave a brown oil. The crude mixture was purified by using a Biotage (40L) column chromatography eluting with 5-10% ethyl acetate in hexanes to obtain 4-(2-formyl-3-methyl-phenoxy)-butyric acid ethyl ester (45.32 g, 94%) as a colorless oil: EI(+)-HRMS m/e calculated for $C_{14}H_{18}O_4$ $(M+)^+$ 250.1205, found 250.1202.

3) Preparation of 4-[2-((E)-2-ethoxycarbonyl-vinyl)-3-methyl-phenoxy]-butyric acid ethyl ester

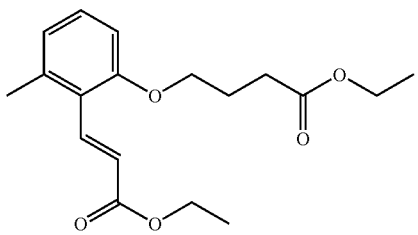

Sodium metal spheres (1.6 g, 69.6 mmol) were added to ethanol (100 mL) with stirring at room temperature under nitrogen atmosphere over 15 min. An exothermic reaction occurred and the mixture was stirred for another 15 min to form sodium ethoxide. After cooling to room temperature, triethylphosphonoacetate (14.7 mL, 73.4 mmol) and 4-(2-formyl-3-methyl-phenoxy)-butyric acid ethyl ester (13.25 g, 52.9 mmol) were added sequentially. During the addition of 4-(2-formyl-3-methyl-phenoxy)-butyric acid ethyl ester, the color of the solution turned brown and the temperature increased to ~55° C. The resulting brown solution was stirred for 2 days at room temperature. Then, the reaction mixture was diluted with water (150 mL) and stirred for 1 h. Then, the organic compound was extracted into hexanes (3×100 mL). The combined organic extracts were washed with brine solution (150 mL) and the organic solution was dried over anhydrous magnesium sulfate. Filtration of the drying agent and the removal of the solvent gave a light yellow oil. The crude oil was dissolved in hexanes (~50 mL) and treated with charcoal and heated gently with a heat gun. After cooling to room temperature, the charcoal was filtered-off and the filtrate was removed under vacuum to give 4-[2-((E)-2-ethoxycarbonyl-vinyl)-3-methyl-phenoxy]-butyric acid ethyl ester (13.25 g, 78%) as a colorless oil: EI(+)-HRMS m/e calculated for $C_{18}H_{24}O_5$ $(M+)^+$ 320.1624, found 320.1626.

4) Preparation of 4-[3-bromomethyl-2-((E)-2-ethoxycarbonyl-vinyl)-phenoxy]-butyric acid ethyl ester

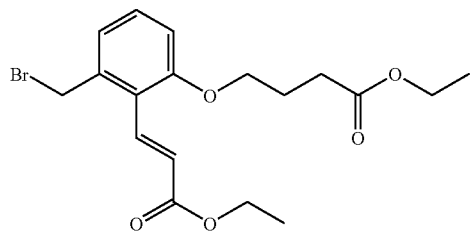

To a solution of 4-[2-((E)-2-ethoxycarbonyl-vinyl)-3-methyl-phenoxy]-butyric acid ethyl ester (8.0 g, 25.0 mmol) in chlorobenzene (190 mL) were added N-bromosuccinimide (6.67 g, 37.5 mmol) and 2,2'-azobisisobutyronitrile (AIBN) (591 mg, 3.6 mmol) at room temperature. Then, the solution was heated to 85° C. and stirred for 1 h. Then, the reaction mixture was cooled to room temperature and diluted with water (100 mL). Then, the organic compound was extracted into hexanes (3×100 mL). The combined organic extracts were washed with brine solution (150 mL) and the organic solution was dried over anhydrous magnesium sulfate. Filtration of the drying agent and the removal of the solvent gave a crude oil. The crude oil was purified by using a Biotage (40L) column eluting with 15-25% ethyl acetate in hexanes to isolate 4-[3-bromomethyl-2-((E)-2-ethoxycarbonyl-vinyl)-phenoxy]-butyric acid ethyl ester (7.11 g, 71%) as a low melting solid: ES(+)-HRMS m/e calculated for $C_{18}H_{23}BrO_5$ $(M+Na)^+$ 421.0621, found 421.0621.

5) Preparation of 5-(tert-butyl-dimethyl-silanyloxy)-pentanal

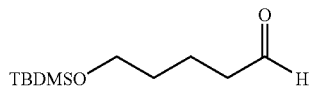

To a solution of 5-(tert-butyl-dimethyl-silanyloxy)-pentanol (16.8 mmol, 3.66 g) in dichloromethane (30 mL) were added water (5.6 mL), potassium bromide (1.7 mmol, 202 mg), n-tetrabutylammonium hydrogensulfate (0.84 mmol, 290 mg), and TEMPO (30 mg) at room temperature. The resulting light brown solution was cooled to ~5° C. and a solution of sodium hypochlorite (19.3 mmol, 30 mL, 5%) was added dropwise at this temperature. After addition of half of the sodium hypochlorite solution, solid potassium carbonate (300 mg) was added to maintain the reaction mixture basic. Then, the remaining sodium hypochlorite solution was added at 5-10° C. By this point, a precipitate had formed and the reaction mixture was stirred for another 1 h at ~10-15° C. Then, water (100 mL) was added and the resulting solution was extracted into diethyl ether (2×100 mL). The combined organic extracts were washed with brine solution (150 mL) and the organic layer was dried over anhydrous magnesium sulfate. Filtration of the drying agent and the removal of the solvent gave 5-(tert-butyl-dimethyl-silanyloxy)-pentanal (3.32 g, 91%) as a light brown oil: ES(+)-HRMS m/e calculated for $C_{11}H_{24}O_2Si$ (M+H)$^+$ 217.1619, found 217.1619.

6) Preparation of 4-[3-[6-(tert-butyl-dimethyl-silanyloxy)-hex-1-enyl]-2-((E)-2-ethoxycarbonyl-vinyl)-phenoxy]-butyric acid ethyl ester

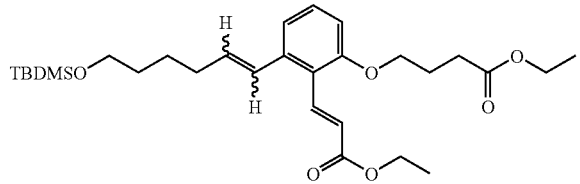

A solution of 4-[3-bromomethyl-2-((E)-2-ethoxycarbonyl-vinyl)-phenoxy]-butyric acid ethyl ester (2.0 mmol, 798 mg) and triphenylphosphine (2.2 mmol, 577 mg) in acetonitrile (12 mL) was heated to reflux for 1 h under nitrogen atmosphere. Then, it was cooled to room temperature and a solution of 5-(tert-butyl-dimethyl-silanyloxy)-pentanal (2.8 mmol, 606 mg) in 1,2-epoxybutane (22 mL) was added at room temperature and the mixture was again heated to reflux for 15 h. During this period, the mixture first turned to a brick red color and at the end of the reaction it had become a pale yellow solution. Then, the reaction mixture was cooled to room temperature and the solvent was removed under vacuum. The residue was dissolved in a solution of ethyl acetate and hexanes (1:3, 150 mL) and the resulting cloudy solution was washed with a mixture of methanol and water (2:1, 225 mL). The aqueous layer was extracted one more time with ethyl acetate and hexanes (1:3, 50 mL). The combined organic extracts were washed with brine solution (150 mL) and the organic solution was dried over anhydrous magnesium sulfate. Filtration of the drying agent and the removal of the solvent gave light brown oil. The crude mixture was purified by using a Biotage (40L) column chromatograph eluting with 5 and 15% ethyl acetate in hexanes to obtain the desired 4-[3-[6-(tert-butyl-dimethyl-silanyloxy)-hex-1-enyl]-2-((E)-2-ethoxycarbonyl-vinyl)-phenoxy]-butyric acid ethyl ester (760 mg, 74%) as a colorless oil: ES(+)-HRMS m/e calculated for $C_{29}H_{46}O_6Si$ (M+Na)$^+$ 541.2956, found 541.2953.

7) Preparation of 4-[3-[6-(tert-butyl-dimethyl-silanyloxy)-hexyl]-2-(2-ethoxycarbonyl-ethyl)-phenoxy]-butyric acid ethyl ester

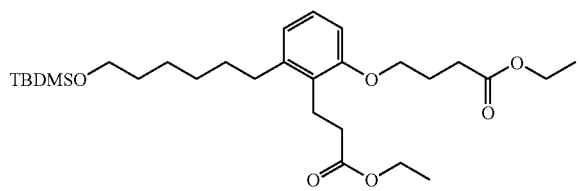

To a solution of 4-[3-[6-(tert-butyl-dimethyl-silanyloxy)-hex-1-enyl]-2-((E)-2-ethoxycarbonyl-vinyl)-phenoxy]-butyric acid ethyl ester (0.977 mmol, 507 mg) in ethyl acetate (10 mL) was added 10% palladium on carbon (350 mg) at room temperature. The resulting black mixture was stirred in the presence of atmospheric hydrogen gas in a balloon for 36 h at room temperature. Then, the catalyst was removed by filtration using a filter paper and the residue was washed with hot ethyl acetate (~60 mL). The filtrate was concentrated in vacuo and the resulting residue was dried under high vacuum to obtain 4-[3-[6-(tert-butyl-dimethyl-silanyloxy)-hexyl]-2-(2-ethoxycarbonyl-ethyl)-phenoxy]-butyric acid ethyl ester (438 mg, 86%) as a colorless oil: ES(+)-HRMS m/e calculated for $C_{29}H_{50}O_6Si$ (M+Na)$^+$ 545.3269, found 545.3267.

8) Preparation of 4-[2-(2-ethoxycarbonyl-ethyl)-3-(6-hydroxy-hexyl)-phenoxy]-butyric acid ethyl ester

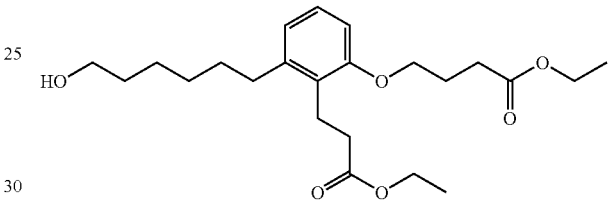

To a solution of 4-[3-[6-(tert-butyl-dimethyl-silanyloxy)-hexyl]-2-(2-ethoxycarbonyl-ethyl)-phenoxy]-butyric acid ethyl ester (0.837 mmol, 438 mg) in THF (12 mL) was added a solution of n-tetrabutyl ammonium fluoride (1.25 mmol, 1.25 mL, 1.0M) in THF at 0° C. Then, the resulting colorless solution was allowed to warm to room temperature in 2 h and the mixture was stirred for another 2 h at room temperature before being diluted with water (~50 mL). The organic compound was extracted into ethyl acetate (2×50 mL) and the combined extracts were washed with brine solution (100 mL). The organic solution was dried over anhydrous magnesium sulfate and the filtrate was removed under vacuum after filtration of the drying agent. The crude residue was dried further under high vacuum and the desired 4-[2-(2-ethoxycarbonyl-ethyl)-3-(6-hydroxy-hexyl)-phenoxy]-butyric acid ethyl ester (342 mg, 99%) was isolated as a colorless oil: ES(+)-HRMS m/e calculated for $C_{23}H_{36}O_6$ (M+Na)$^+$ 431.2404, found 431.2404.

9) Preparation of 4-[3-(6-bromo-hexyl)-2-(2-ethoxycarbonyl-ethyl)-phenoxy]-butyric acid ethyl ester

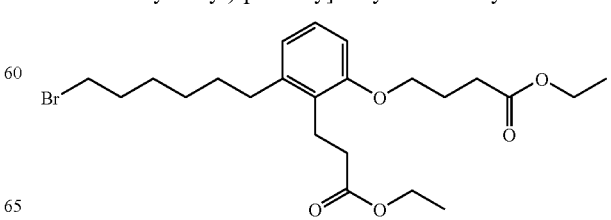

To a solution of 4-[2-(2-ethoxycarbonyl-ethyl)-3-(6-hydroxy-hexyl)-phenoxy]-butyric acid ethyl ester (0.85 mmol, 349 mg) and carbon tetrabromide (1.26 mmol, 423 mg) in dichloromethane (10 mL) was added triphenylphosphine (1.07 mmol, 281 mg) at ~0° C. The resulting colorless solution was stirred for 3 h at 5-10° C. Then, the solvent was removed under vacuum and the crude was tried to dissolve in a mixture of ethyl acetate and hexanes (1:3, 50 mL). As a result, a cloudy solution containing some precipitate was formed and the cloudy solution was transferred into a separatory funnel and was washed with a mixture of methanol and water (2:1, 150 mL). The aqueous layer was extracted one more time with ethyl acetate and hexanes (1:3, 50 mL). The combined organic extracts were washed with brine solution (100 mL) and the organic solution was dried over anhydrous magnesium sulfate. Filtration of the drying agent and the removal of the solvent gave a colorless oil which was purified by using a Biotage (40M) column chromatography eluting with 10% ethyl acetate in hexanes to obtain the desired 4-[3-(6-bromo-hexyl)-2-(2-ethoxycarbonyl-ethyl)-phenoxy]-butyric acid ethyl ester (350 mg, 87.5%) as a colorless oil: ES(+)-HRMS m/e calculated for $C_{23}H_{35}BrO_5$ $(M+Na)^+$ 493.1560, found 493.1560.

II. Preparation of Preferred Compounds

Example 1

4-{2-(2-Carboxy-ethyl)-3-[6-(3,5-di-pyridin-4-yl-phenoxy)-hexyl]-phenoxy}-butyric acid

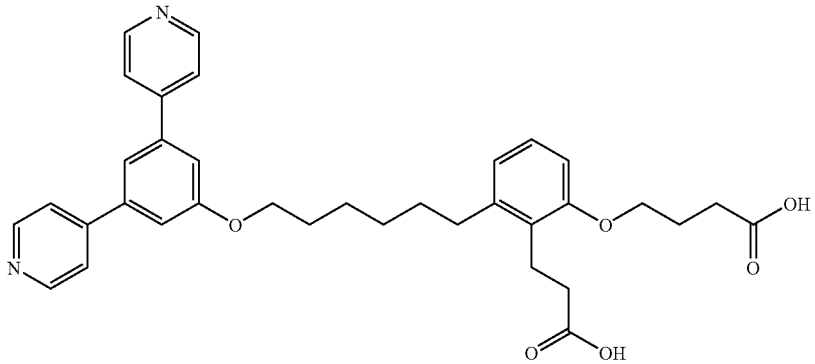

Step 1: Preparation of 4-{3-[6-(3,5-dibromo-phenoxy)-hexyl]-2-(2-ethoxycarbonyl-ethyl)-phenoxy}-butyric acid ethyl ester

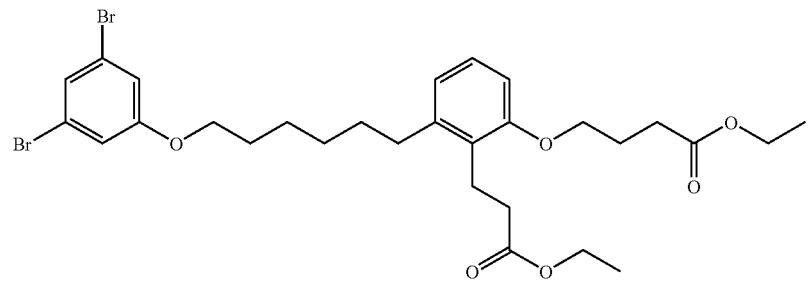

To a mixture of 4-[3-(6-bromo-hexyl)-2-(2-ethoxycarbonyl-ethyl)-phenoxy]-butyric acid ethyl ester (14.54 g, 30.84 mmol), 3,5-dibromophenol (8.55 g, 33.92 mmol), and potassium carbonate (8.53 g, 61.68 mmol) were added N,N-dimethylformamide (210 mL) and acetone (420 mL) at room temperature. The resulting suspension was heated to reflux for 2 days. Then, the reaction mixture was cooled to room temperature and diluted with water (200 mL). The organic compound was extracted into ethyl acetate (2×200 mL) and the combined organic extracts were washed with brine solution (200 mL). The organic layers were dried over anhydrous magnesium sulfate, filtered, and concentrated in vacuo to give the crude product which was purified by using a Biotage column chromatography (FLASH 40L, Silica), eluting with 10% ethyl acetate/hexanes to obtain 4-{3-[6-(3,5-dibromo-phenoxy)-hexyl]-2-(2-ethoxycarbonyl-ethyl)-phenoxy}-butyric acid ethyl ester (19.61 g, 99%) as a colorless oil: ES(+)-HRMS m/e calculated for $C_{29}H_{38}O_6Br_2$ $(M+H)^+$ 641.1108, found 641.1101.

Step 2: Preparation of 4-{3-[6-(3,5-di-pyridin-4-yl-phenoxy)-hexyl]-2-(2-ethoxycarbonyl-ethyl)-phenoxy}-butyric acid ethyl ester

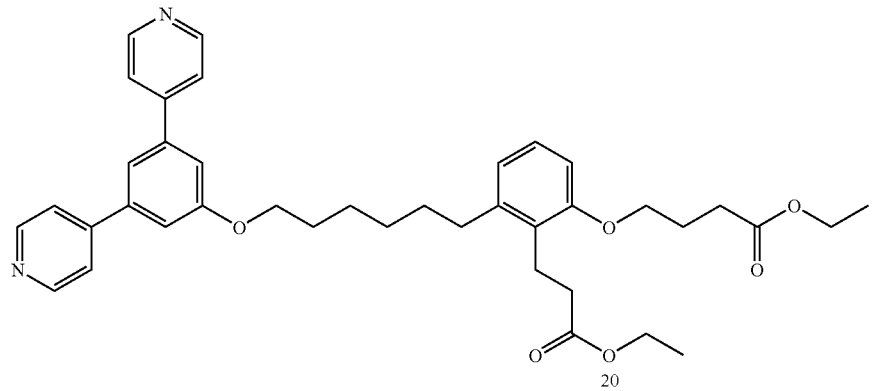

A solution of 4-{3-[6-(3,5-dibromo-phenoxy)-hexyl]-2-(2-ethoxycarbonyl-ethyl)-phenoxy}-butyric acid ethyl ester (321 mg, 0.5 mmol) in dimethoxyethane (10 mL) was stirred for 5 minutes at room temperature under a nitrogen atmosphere. Then, tetrakis(triphenylphosphine)palladium(0) (115 mg, 0.1 mmol) was added at room temperature and the resulting light yellow solution was heated to 80° C. and stirred for 5 minutes. At this point, a solution of pyridin-4-ylboronic acid (368 mg, 3.0 mmol) in ethanol (10 mL) was added followed by a solution of sodium carbonate (318 mg, 3.0 mmol) in water (1.0 mL). The resulting light yellow suspension was stirred for 24 h at reflux. Then, the reaction mixture was cooled to room temperature and diluted with water (20 mL) and ethyl acetate (50 mL). The two layers were separated and the aqueous layer was extracted with ethyl acetate (50 mL). The combined organic extracts were washed with water (100 mL), brine solution (100 mL), and dried over anhydrous magnesium sulfate. Filtration and concentration of the solvent gave the crude residue which was purified by using an ISCO 40 g column, eluting with 0-50% ethyl acetate/hexanes to afford 4-{3-[6-(3,5-di-pyridin-4-yl-phenoxy)-hexyl]-2-(2-ethoxycarbonyl-ethyl)-phenoxy}-butyric acid ethyl ester (205 mg, 64%) as a light brown oil: ES(+)-HRMS m/e calculated for $C_{39}H_{46}N_2O_6$ (M+H)$^+$ 639.3429, found 639.3426.

Step 3: Preparation of 4-{2-(2-carboxy-ethyl)-3-[6-(3,5-di-pyridin-4-yl-phenoxy)-hexyl]-phenoxy}-butyric acid

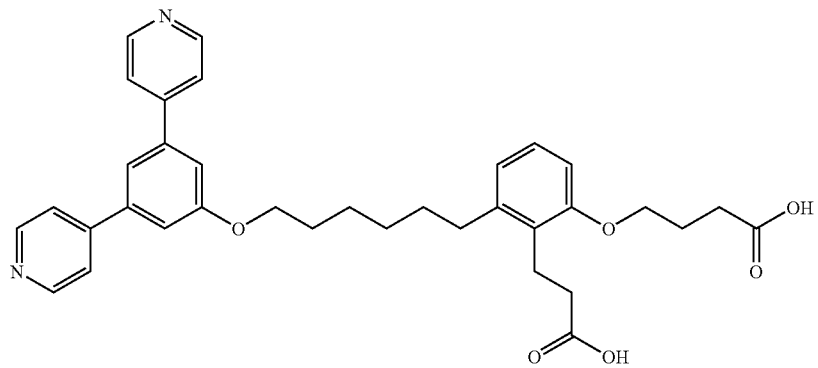

To a solution of 4-{3-[6-(3,5-di-pyridin-4-yl-phenoxy)-hexyl]-2-(2-ethoxycarbonyl-ethyl)-phenoxy}-butyric acid ethyl ester (195 mg, 0.3 mmol) in ethanol (10 mL) was added aqueous 1.0 N sodium hydroxide (8 mL) at room temperature. The mixture was heated to 50-55° C. and the resulting solution was stirred for 3 h. Then, the reaction mixture was concentrated and the residue was diluted with water (20 mL) and extracted with diethyl ether (50 mL) to remove any neutral impurities. The aqueous layer was acidified with 1 N hydrochloric acid until the solution become slightly acidic. The resulting white solids were collected by filtration and washed with water. After air-drying, 4-{2-(2-carboxy-ethyl)-3-[6-(3,5-di-pyridin-4-yl-phenoxy)-hexyl]-phenoxy}-butyric acid (176 mg, 99%) was isolated as a white solid: ES(+)-HRMS m/e calculated for $C_{35}H_{38}N_2O_6$ (M+H)$^+$ 583.2803, found 584.2805.

Example 2

4-{2-(2-Carboxy-ethyl)-3-[6-([1,1',3,1"]terphenyl-5'-yloxy)-hexyl]-phenoxy}-butyric acid

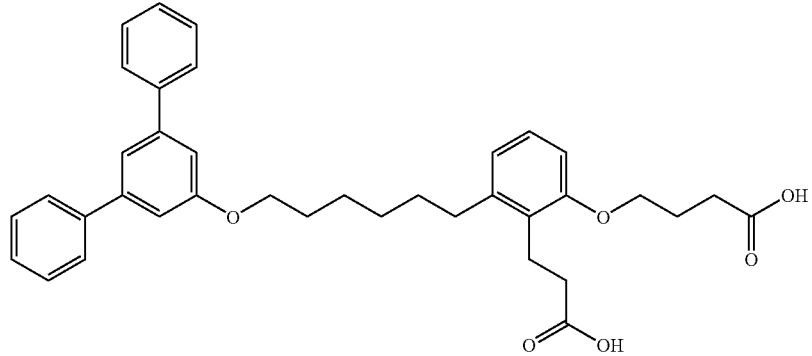

Step 1: Preparation of 4-{2-(2-ethoxycarbonyl-ethyl)-3-[6-([1,1',3,1"]terphenyl-5'-yloxy)-hexyl]-phenoxy}-butyric acid ethyl ester

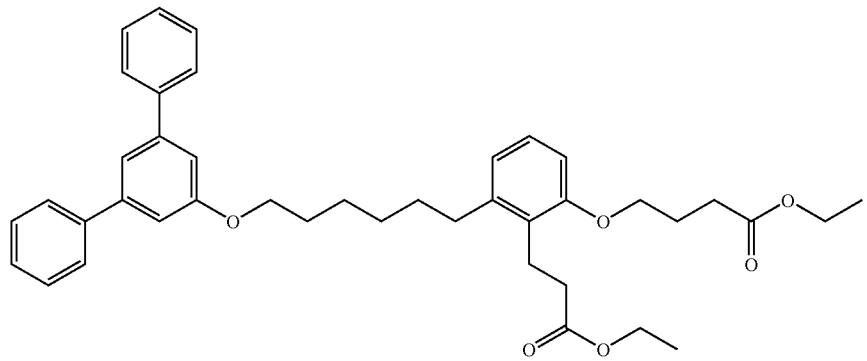

A similar procedure as described in Example 1, step 2 was used, starting from 4-{3-[6-(3,5-dibromo-phenoxy)-hexyl]-2-(2-ethoxycarbonyl-ethyl)-phenoxy}-butyric acid ethyl ester (321 mg, 0.5 mmol) and phenylboronic acid (366 mg, 3.0 mmol) to obtain 4-{2-(2-ethoxycarbonyl-ethyl)-3-[6-([1,1',3,1"]terphenyl-5'-yloxy)-hexyl]-phenoxy}-butyric acid ethyl ester (147 mg, 46%) as a colorless oil: ES(+)-HRMS m/e calculated for $C_{41}H_{48}O_6$ $(M+Na)^+$ 659.3343, found 659.3343.

Step 2: Preparation of 4-{2-(2-carboxy-ethyl)-3-[6-([1,1',3,1"]terphenyl-5'-yloxy)-hexyl]-phenoxy}-butyric acid ethyl ester

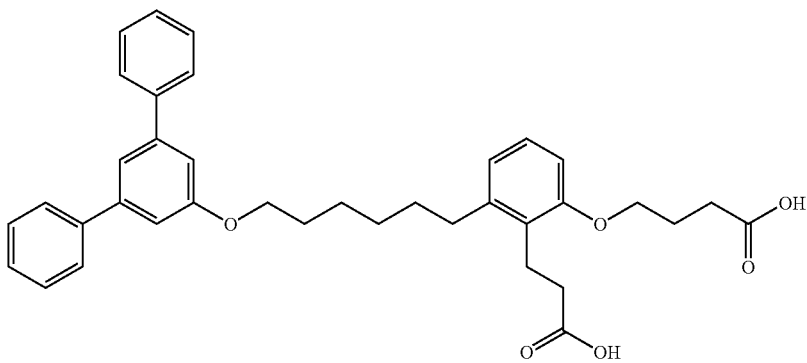

A similar procedure as described in Example 1, step 3 was used, starting from 4-{2-(2-ethoxycarbonyl-ethyl)-3-[6-([1,1',3,1"]terphenyl-5'-yloxy)-hexyl]-phenoxy}-butyric acid ethyl ester (90 mg, 0.14 mmol) and 1.0 N aqueous NaOH (10 mL) to afford 4-{2-(2-carboxy-ethyl)-3-[6-([1,1',3,1"]terphenyl-5'-yloxy)-hexyl]-phenoxy}-butyric acid (75 mg, 91%) as a white solid: ES(+)-HRMS m/e calculated for $C_{37}H_{40}O_6$ (M+Na)$^+$ 603.2717, found 603.2713.

Example 3

4-[3-{6-[3,5-Bis-(2-fluoro-pyridin-4-yl)-phenoxy]-hexyl}-2-(2-carboxy-ethyl)-phenoxy]-butyric acid

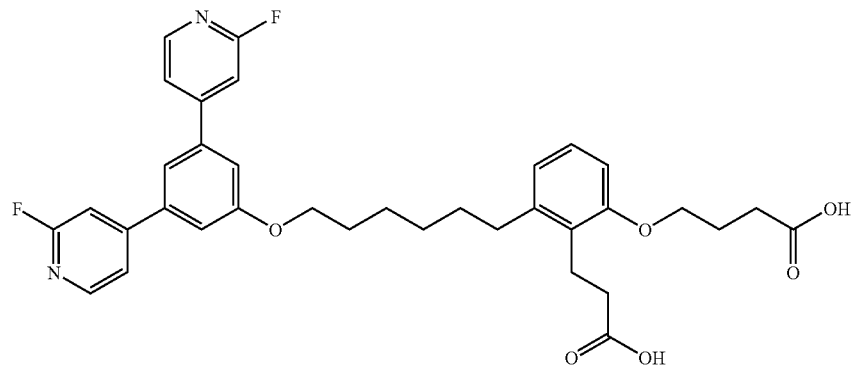

Step 1: Preparation of 4-[3-{6-[3,5-bis-(2-fluoro-pyridin-4-yl)-phenoxy]-hexyl}-2-(2-ethoxycarbonyl-ethyl)-phenoxy]-butyric acid ethyl ester

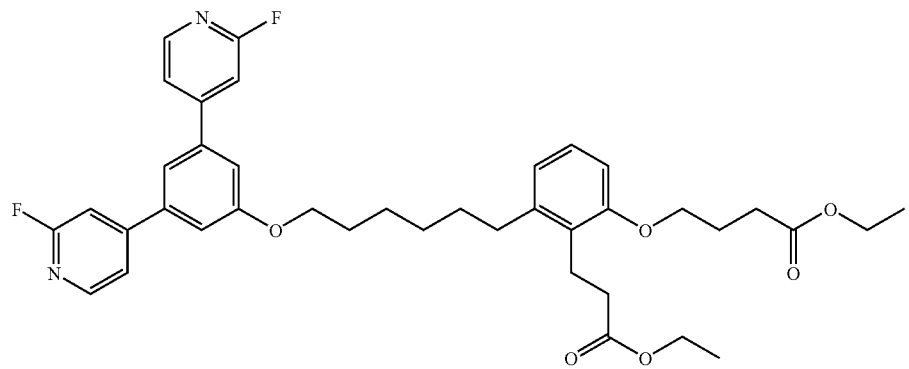

A similar procedure as described in Example 1, step 2 was used, starting from 4-{3-[6-(3,5-dibromo-phenoxy)-hexyl]-2-(2-ethoxycarbonyl-ethyl)-phenoxy}-butyric acid ethyl ester (321 mg, 0.5 mmol) and 2-fluoro-pyridin-4-ylboronic acid (422 mg, 3.0 mmol) to isolate 4-[3-{6-[3,5-bis-(2-fluoro-pyridin-4-yl)-phenoxy]-hexyl}-2-(2-ethoxycarbonyl-ethyl)-phenoxy]-butyric acid ethyl ester (225 mg, 67%) as a colorless oil: ES(+)-HRMS m/e calculated for $C_{39}H_{44}F_2N_2O_6$ (M+H)$^+$ 675.3240, found 675.3238.

Step 2: Preparation of 4-[3-{6-[3,5-bis-(2-fluoro-pyridin-4-yl)-phenoxy]-hexyl}-2-(2-carboxy-ethyl)-phenoxy]-butyric acid

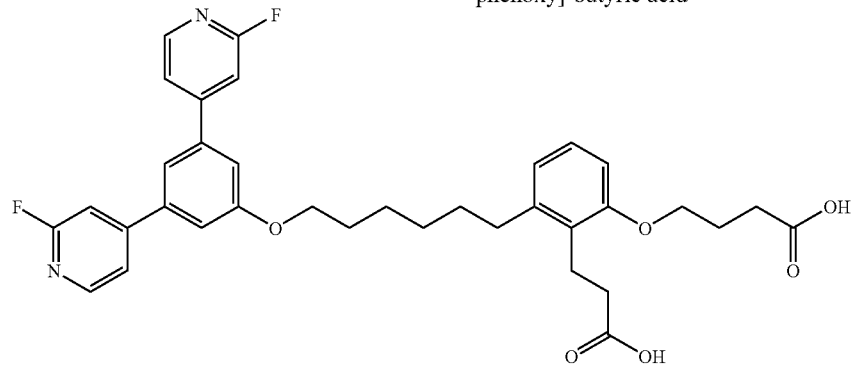

A similar procedure as described in Example 1, step 3 was used, starting from 4-[3-{6-[3,5-bis-(2-fluoro-pyridin-4-yl)-phenoxy]-hexyl}-2-(2-ethoxycarbonyl-ethyl)-phenoxy]-butyric acid ethyl ester (220 mg, 0.32 mmol) and 1.0 N aqueous NaOH (10 mL) to afford 4-[3-{6-[3,5-bis-(2-fluoro-pyridin-4-yl)-phenoxy]-hexyl}-2-(2-carboxy-ethyl)-phenoxy]-butyric acid (110 mg, 56%) as an amorphous white solid: ES(+)-HRMS m/e calculated for $C_{35}H_{36}F_2N_2O_6$ (M+H)$^+$ 619.2614, found 619.2615.

Example 4

4-{2-(2-Carboxy-ethyl)-3-[6-(3,5-di-pyridin-3-yl-phenoxy)-hexyl]-phenoxy}-butyric acid

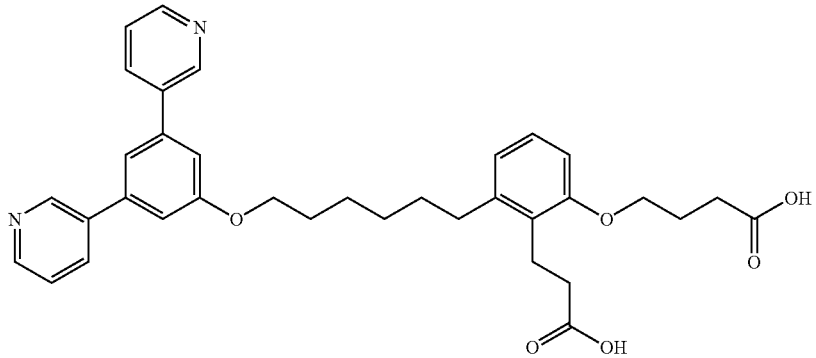

Step 1: Preparation of 4-{3-[6-(3,5-di-pyridin-3-yl-phenoxy)-hexyl]-2-(2-ethoxycarbonyl-ethyl)-phenoxy}-butyric acid ethyl ester

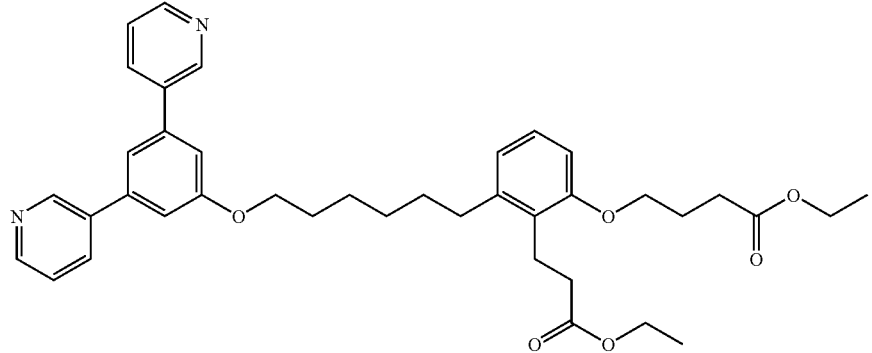

A similar procedure as described in Example 1, step 2 was used, starting from 4-{3-[6-(3,5-dibromo-phenoxy)-hexyl]-2-(2-ethoxycarbonyl-ethyl)-phenoxy}-butyric acid ethyl ester (250 mg, 0.39 mmol) and pyridin-3-ylboronic acid (201 mg, 1.55 mmol) to give 4-{3-[6-(3,5-di-pyridin-3-yl-phenoxy)-hexyl]-2-(2-ethoxycarbonyl-ethyl)-phenoxy}-butyric acid ethyl ester (155 mg, 62%) as a colorless oil: ES(+)-HRMS m/e calculated for $C_{39}H_{46}N_2O_6$ (M+H)$^+$ 639.3429, found 639.3416.

Step 2: Preparation of 4-{2-(2-carboxy-ethyl)-3-[6-(3,5-di-pyridin-3-yl-phenoxy)-hexyl]-phenoxy}-butyric acid

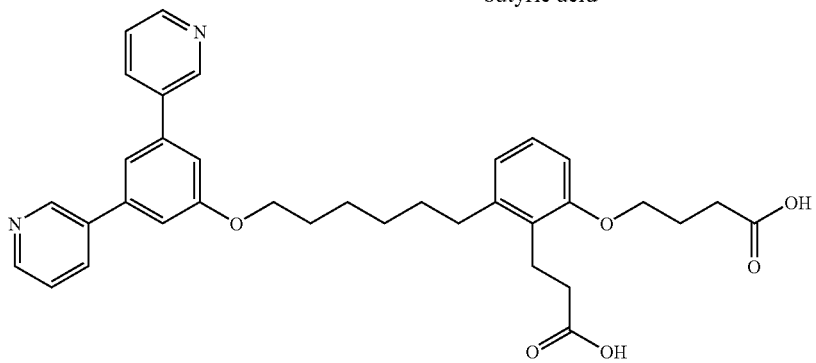

A similar procedure as described in Example 1, step 3 was used, starting from 4-{3-[6-(3,5-di-pyridin-3-yl-phenoxy)-hexyl]-2-(2-ethoxycarbonyl-ethyl)-phenoxy}-butyric acid ethyl ester (150 mg, 0.26 mmol) and 1.0 N aqueous NaOH (2.5 mL) to afford 4-{2-(2-carboxy-ethyl)-3-[6-(3,5-di-pyridin-3-yl-phenoxy)-hexyl]-phenoxy}-butyric acid (110 mg, 80%) as an amorphous white solid: ES(+)-HRMS m/e calculated for $C_{35}H_{38}N_2O_6$ $(M+H)^+$ 583.2803, found 583.2800.

Example 5

4-{2-(2-Carboxy-ethyl)-3-[6-(3,5-di-pyrimidin-5-yl-phenoxy)-hexyl]-phenoxy}-butyric acid

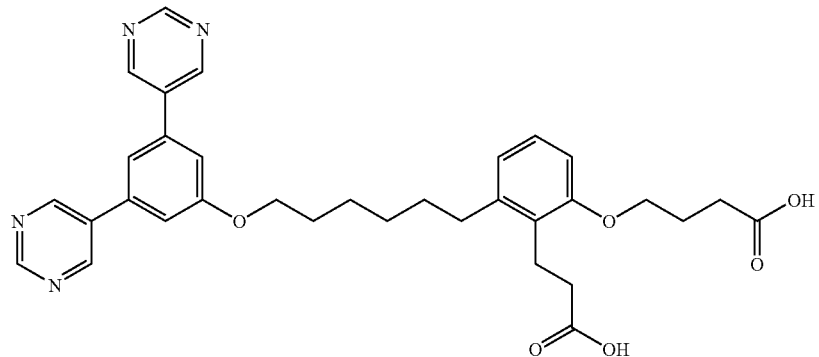

Step 1: Preparation of 4-{2-(2-carboxy-ethyl)-3-[6-(3,5-dibromo-phenoxy)-hexyl]-phenoxy}-butyric acid

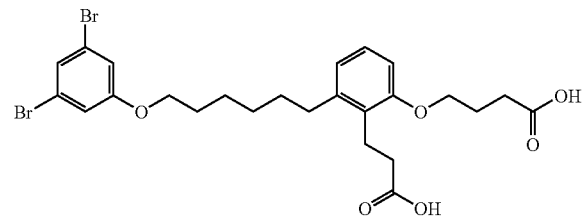

To a solution of 4-{3-[6-(3,5-dibromo-phenoxy)-hexyl]-2-(2-ethoxycarbonyl-ethyl)-phenoxy}-butyric acid ethyl ester (1.5 g, 2.33 mmol) in ethanol (30 mL) was added aqueous 1 N sodium hydroxide (25 mL) at room temperature. The resulting suspension was heated to 50-55° C. and the mixture was stirred for 3 h. Then, the reaction mixture was concentrated and the residue was diluted with water (20 mL) and extracted with diethyl ether (50 mL) to remove any neutral impurities. The aqueous layer was acidified with 1 N hydrochloric acid and the organic compound was extracted into ethyl acetate (2×50 mL). The combined ethyl acetate extracts were washed with brine solution (50 mL), dried over anhydrous magnesium sulfate, filtered, and concentrated to give the crude product which was purified by using an ISCO 40 g column, eluting with 0-100% ethyl acetate/hexanes to isolate 4-{2-(2-carboxy-ethyl)-3-[6-(3,5-dibromo-phenoxy)-hexyl]-phenoxy}-butyric acid (1.26 g, 92%) as a white solid: ES(+)-HRMS m/e calculated for $C_{25}H_{30}Br_2O_6$ $(M+Na)^+$ 607.0301, found 607.0298.

Step 2: Preparation of 4-{2-(2-carboxy-ethyl)-3-[6-(3,5-di-pyrimidin-5-yl-phenoxy)-hexyl]-phenoxy}-butyric acid

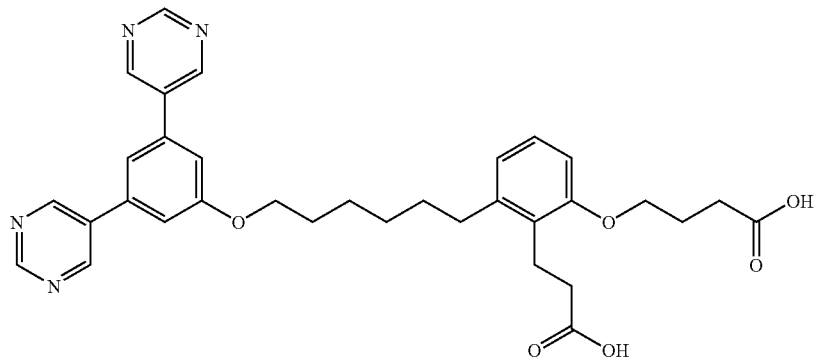

To a solution of 4-{2-(2-carboxy-ethyl)-3-[6-(3,5-dibromo-phenoxy)-hexyl]-phenoxy}-butyric acid (150 mg, 0.26 mmol) in ethanol (2 mL) in a 20 mL microwave tube were added tetrakis(triphenylphosphine)palladium(0) (29.5 mg, 0.03 mmol), pyrimidin-5-ylboronic acid (189 mg, 3.0 mmol), and potassium carbonate (212 mg, 1.53 mmol) at room temperature. The microwave tube was sealed and heated to 160° C. in a microwave oven for 30 minutes. Then, the reaction mixture was cooled to room temperature and diluted with water (20 mL) and ethyl acetate (20 mL). The two layers were separated and the ethyl acetate layer was discarded. Then, the aqueous layer was acidified with 1.0 N hydrochloric acid and the organic compound was extracted into ethyl acetate (2×20 mL). The combined organic extracts were washed with brine solution (20 mL), dried over anhydrous magnesium sulfate, filtered, and concentrated to afford 4-{2-(2-carboxy-ethyl)-3-[6-(3,5-di-pyrimidin-5-yl-phenoxy)-hexyl]-phenoxy}-butyric acid (85 mg, 57%) as a light yellow solid: ES(+)-HRMS m/e calculated for $C_{33}H_{36}N_4O_6$ (M+Na)$^+$ 607.2527, found 607.2527.

Example 6

4-[3-{6-[3,5-Bis-(4-methyl-thiophen-3-yl)-phenoxy]-hexyl}-2-(2-carboxy-ethyl)-phenoxy]-butyric acid

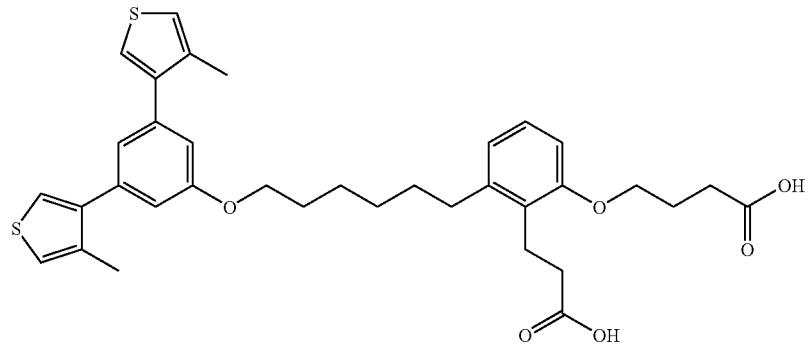

A similar procedure as described in Example 5, step 2 was used, starting from 4-{3-[6-(3,5-dibromo-phenoxy)-hexyl]-2-(2-ethoxycarbonyl-ethyl)-phenoxy}-butyric acid (150 mg, 0.25 mmol) and 4-methyl-thiophen-3-ylboronic acid (217 mg, 1.53 mmol) to afford 4-[3-{6-[3,5-bis-(4-methyl-thiophen-3-yl)-phenoxy]-hexyl}-2-(2-carboxy-ethyl)-phenoxy]-butyric acid (80 mg, 51%) as an amorphous white solid: ES(+)-HRMS m/e calculated for $C_{35}H_{40}O_6S_2$ (M+Na)$^+$ 643.2158, found 643.2158.

Example 7

4-{2-(2-Carboxy-ethyl)-3-[6-([1,1';3',1"]terphenyl-5'-ylsulfanyl)-hexyl]-pheoxy}-butyric acid

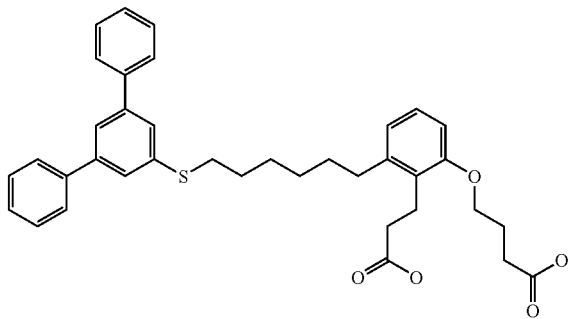

Step 1: Preparation of 4-[2-(2-Ethoxycarbonyl-ethyl)-3-(6-mercapto-hexyl)-phenoxy]-butyric acid ethyl ester

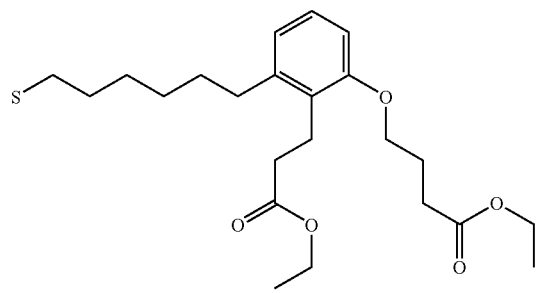

To a solution of 4-[3-(6-Bromo-hexyl)-2-(2-ethoxycarbonyl-ethyl)-phenoxy]-butyric acid ethyl ester (5g, 10.60 mmol) in THF (100 mL), thiourea (0.889 g, 11.68 mmol) was added and heated to reflux overnight. According to HPLC analysis, the starting material was completely consumed. Tetraethylenepentamine (4.02 g, 2.7 mL, 21.23 mmol) was added and the reaction mixture was heated to reflux overnight. At this time, the reaction mixture was diluted with EtOAc (500 mL), washed with 3N HCl (100 mL), water brine and dried over $Na_2SO_4$. The solvent was removed in vacuo to afford an oil. FCC (2% EtOAc/Hex) provided an oil (3.65 g, yield 81%). $^1$H NMR (CDCl$_3$): □ 7.09 (t, 1H), 6.75 (d, 1H), 6.69 (d, 1H), 4.18-4.08 (m, 4H), 3.99 (t, 2H), 2.95 (t, 2H), 2.64-2.46 (m, 8H), 2.13 (m, 2H), 1.67-1.39 (m, 8H), 1.27 (m, 6H).

Step 2: Preparation of 4-[3-[6-(3,5-dibromo-phenylsulfanyl)-hexyl]-2-(2-ethoxycarbonyl-ethyl)-phenoxy]-butyric acid ethyl ester

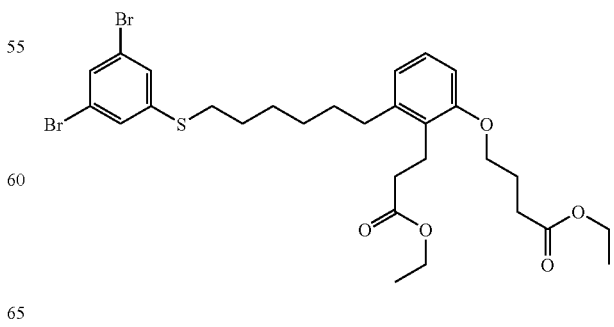

To a solution of 4-[2-(2-ethoxycarbonyl-ethyl)-3-(6-mercapto-hexyl)-phenoxy]-butyric acid ethyl ester (162 mg, 0.388 mmol) in DMSO (5 mL), 3,5-dibromonitrobenzene (129 mg, 0.46 mmol) and $Cs_2CO_3$ (150 mg, 0.46 mmol) were added and stirred at 90° C. for 3 hrs. At this time, the reaction mixture was diluted with EtOAc (200 mL) and washed with water (100 mL). The EtOAc layer was washed), brine and then dried over $Na_2SO_4$. This mixture was filtered and the filtrate was concentrated. The solvent was removed in vacuo to afford an oil. This oil was purified using FCC (15% EtOAc/Hex) to provide a colorless oil (180 mg, yield 72%). $^1$H NMR ($CDCl_3$): □ 7.42 (s, 1H), 7.32 (s, 2H), 7.09 (dd, 1H), 6.75 (d, 1H), 6.69 (d, 1H), 4.14 (m, 4H), 3.99 (t, 2H), 2.98-2.89 (m, 4H), 2.64-2.46 (m, 6H), 2.13 (m, 2H), 1.67-1.39 (m, 8H), 1.27 (m, 6H).

Step 3: General Method

To a solution of 4-[3-[6-(3,5-dibromo-phenylsulfanyl)-hexyl]-2-(2-ethoxycarbonyl-ethyl)-phenoxy]-butyric acid ethyl ester (80 mg) in DME (3 mL), was added an arylboronic acid (3 equiv.), $PdCl_2$(dppf) (10 mg), and $Cs_2CO_3$ (100 mg). This mixture was stirred under 90° C. overnight. At this time, the reaction mixture was diluted with EtOAc (5 mL), washed with water (3 mL), dried over $Na_2SO_4$. The solvent was removed in vacuo to afford an oil crude bis-aryl coupling product. The crude residue was dissolved in ethanol (5 mL) and 3N NaOH (1 mL) was added; this reaction and the mixture was stirred at 60° C. for two hours. At this time, the reaction was acidified with 3N HCl; concentration. Evaporation under vacuo of the crude reaction mixture in vacuo provided the analog of Formula 1 in crude form. HPLC purification provided the title compound of Formula 1 where X=S.

Preparation of 4-{2-(2-Carboxy-ethyl)-3-[6-([1,1';3',1"]terphenyl-5'-ylsulfanyl)-hexyl]-pheoxy}-butyric acid

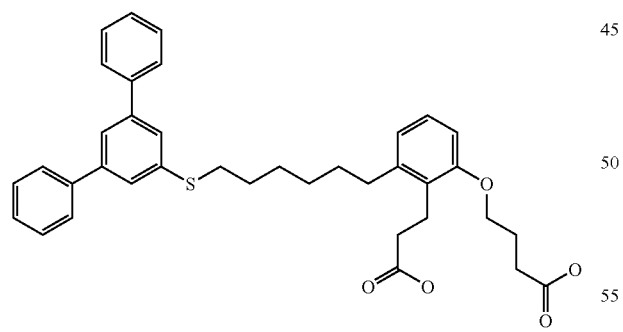

The title compound was prepared by following Step 3 with benzeneboronic acid. The compound was isolated by preparative HPLC. The expected product was characterized by LC/MS (M+Na) where the mass was observed as 619; the expected mass is 596. LC/MS indicated a purity of 100% as measured by UV 214 nM. ES(+)-HRMS m/e calcd for $C_{37}H_{40}O_5S_1$ (M+Na)$^+$ 619.2488, found 619.2488.

Example 8

4-[3-[6-(3-Benzo[1,3]dioxol-5-yl-5-chloro-phenylsulfanyl)-hexyl]-2-(2-carboxy-ethyl)-phenoxy]-butyric acid ammonium salt

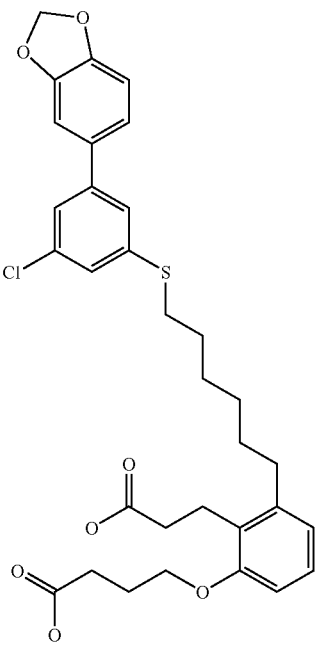

Step 1 Preparation of 4-[3-[6-(3,5-Dichloro-phenylsulfanyl)-hexyl]-2-(2-ethoxycarbonyl-ethyl)-phenoxy]-butyric acid ethyl ester To a solution of 3,5-dichlorothiophenol (1.67 g, 9.34 mmol) in MeCN (120 mL) and DMF (80 mL), 4-[3-(6-bromo-hexyl)-2-(2-ethoxycarbonyl-ethyl)-phenoxy]-butyric acid ethyl ester (4.0 g, 8.49 mmol) was added, followed by $K_2CO_3$ (3.52 g, 25.48 mmol). The reaction mixture was stirred at 80° C. overnight. At this time, after cooling, the reaction was diluted with EtOAc (300 mL), washed with water (twice with 150 mL) and brine, and dried over Na₂SO₄. Concentration under reduced pressure provided an oil. A sample (2.73 g) was purified by FCC (10% EtOAc/Hex) provide a pure sample (1.20 g) of 4-[3-[6-(3,5-Dichloro-phenylsulfanyl)-hexyl]-2-(2-ethoxycarbonyl-ethyl)-phenoxy]-butyric acid ethyl ester. ¹H NMR (CDCl₃): δ 7.26 (s, 1H), 7.12 (s, 2H), 7.09 (dd, 1H), 6.75 (d, 1H), 6.69 (d, 1H), 4.14 (m, 4H), 3.99 (t, 2H), 2.98-2.89 (m, 4H), 2.64-2.46 (m, 6H), 2.13 (m, 2H), 1.67-1.39 (m, 8H), 1.27 (m, 6H).

Step 2: General Method

To a sealable tube, 2-dicyclohexylphosphino-2',6'-dimethoxybiphenyl (0.08 equiv.), arylboronic acid (3 equiv.), Pd(OAc)2 (0.04 equiv.) and K₃PO₄ (4 equiv.) were added; the tube was then sealed with a pressure septum. The tube was purged with argon for 1 min. THF (1 mL) was then added and the mixture was stirred for 2 mins. 4-[3-[6-(3,5-Dichloro-phenylsulfanyl)-hexyl]-2-(2-ethoxycarbonyl-ethyl)-phenoxy]-butyric acid ethyl ester (1 equiv.) in THF (1.5 mL) was added and the reaction mixture was heated at 100° C. microwave for 1800 sec. At this time, the reaction was diluted with EtOAc (5 mL), washed with water (3 mL). The combined organic phases were dried over sodium sulfate and evaporation of the solvent under vacuo in vacuo provided the crude oil. The crude sample was dissolved in ethanol (5 mL) and 3N NaOH (1 mL) was added; this mixture was stirred at 60° C. for two hours. At this time, the reaction was acidified with 3N HCl. Concentration in vacuo gave a crude sample which was isolated by evaporation in vacuo of the crude reaction mixture to provide a crude sample. The desired product was isolated by preparative HPLC using an acetyl nitrile/water gradient modified with 20 millimolar ammonium acetate, pH=7.0.

Preparation of 4-[3-[6-(3-Benzo[1,3]dioxol-5-yl-5-chloro-phenylsulfanyl)-hexyl]-2-(2-carboxy-ethyl)-phenoxy]-butyric acid ammonium salt

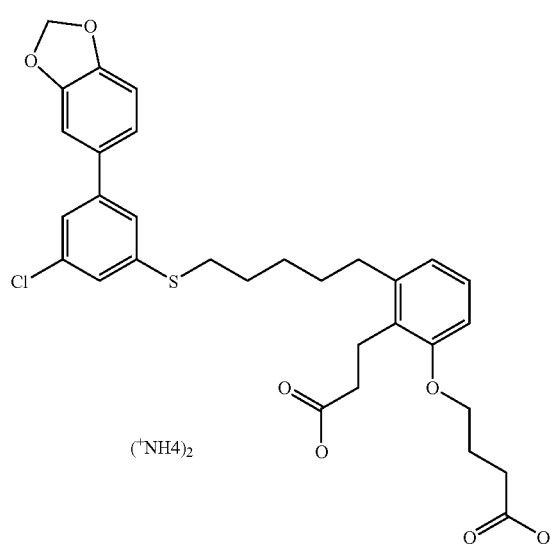

The title compound was prepared by following the general method described above in step 2 with benzo[1,3]dioxol-5-yl-boronic acid. The compound was isolated by preparative HPLC using an acetyl nitrile/water gradient modified with 20 millimolar ammonium acetate, pH=7.0. The expected product was characterized by LC/MS (M+H) where the mass was observed as 599; the expected mass is 598. LC/MS indicated a purity of 100% as measured by UV 214 nM. ES(+)-HRMS m/e calcd for $C_{32}H_{35}O_7S_1Cl_1$ (M+Na)⁺ 621.1684, found 621.1685.

Example 9

4-{2-(2-Carboxy-ethyl)-3-[6-(3-chloro-5-thiophen-3-yl-phenylsulfanyl)-hexyl]-phenoxy}-butyric acid ammonium salt

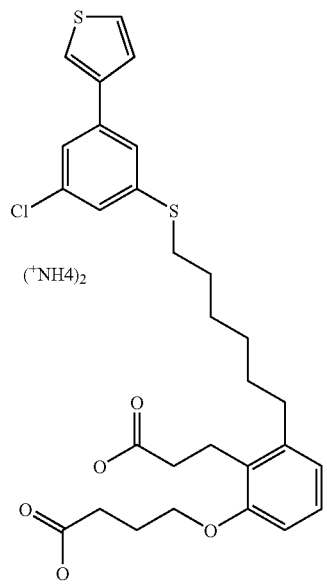

The title compound was prepared by following the general method as described in example 8 above with, step 2 3-thiopheneboronic acid. The compound was isolated by preparative HPLC using an acetyl nitrile/water gradient modified with 20 millimolar ammonium acetate, pH=7.0. The expected product was characterized by LC/MS (M+Na) where the mass was observed as 583.1; the expected mass is 560. LC/MS indicated a purity of 100% as measured by UV 214 nM.

Example 10

4-{2-(2-Carboxy-ethyl)-3-[6-(5-chloro-4'-methoxy-biphenyl-3-ylsulfanyl)-hexyl]-phenoxy}-butyric acid ammonia salt

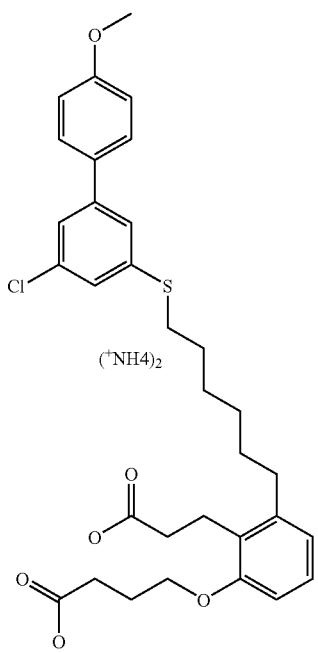

The title compound was prepared by following the general procedure in Example 8 above with, step 2 4-methoxybenzeneboronic acid. The compound was isolated by preparative HPLC using an acetyl nitrile/water gradient modified with 20 millimolar ammonium acetate, pH=7.0. The expected product was characterized by LC/MS (M+H) where the mass was observed as 585.2; the expected mass is 584. LC/MS indicated a purity of 94% as measured by UV 214 nM. ES(+)-HRMS m/e calcd for $C_{32}H_{37}O_6S_1Cl_1$ (M+Na)⁺ 607.1891, found 607.1890.

Example 11

4-{2-(2-Carboxy-ethyl)-3-[6-(2,2''-difluoro-[1,1';3',1'']terphenyl-5'-ylsulfanyl)-hexyl]-phenoxy}-butyric acid ammonia salt

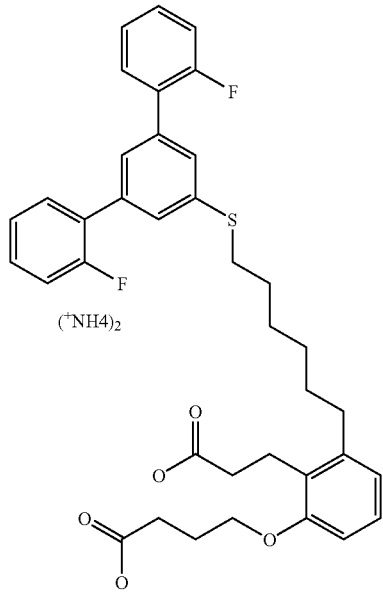

The title compound was prepared by following the general method as described for Example 8 above with procedures in Example 7, step 3 2-Fluorophenylboronic acid. The compound was isolated by preparative HPLC in which the TFA modifier was replace with 0.1% ammonium acetate. The expected product was characterized by LC/MS (M+Na) where the mass was observed as 655; the expected mass is 632. LC/MS indicated a purity of 100% as measured by UV 214 nM. ES(+)-HRMS m/e calcd for $C_{37}H_{38}O_5S_1F_2$ (M+Na)⁺ 655.2300, found 655.2300.

Example 12

4-{3-[6-(3-Benzo[1,3]dioxol-5-yl-5-thiophen-3-yl-phenoxy)-hexyl]-2-(2-carboxy-ethyl)-phenoxy}-butyric acid

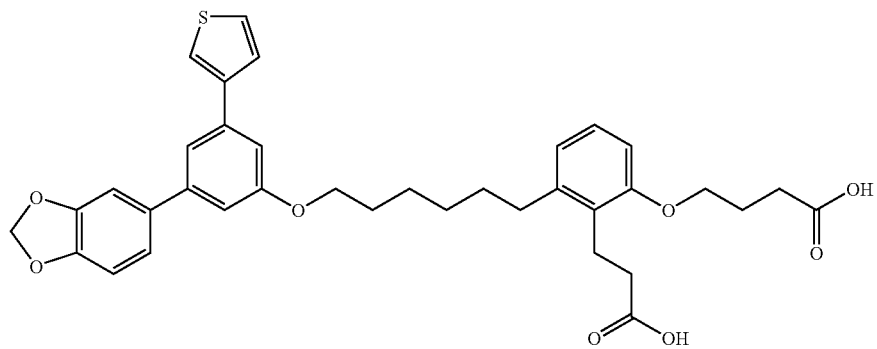

Step 1: Preparation of 3-methoxy-5-nitro-phenylamine

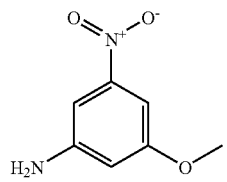

Sodium bicarbonate (5.62 g, 66.87 mmol) was added to a solution of sodium sulfide (5.5 g, 70.58 mmol) in deionized water (60 mL). When the sodium bicarbonate was completely dissolved, methanol (50 mL) was added, and the solution was cooled to 0° C. A precipitate formed, which was removed by filtration through a Celite pad. The filtered solution was added quickly to a solution of 3,5-dinitroanisole (7.36 g, 37.15 mmol) in methanol (50 mL). The resulting suspension was heated to reflux for 30 min and then the solution was concentrated in vacuo to remove methanol. The aqueous residue was poured into 200 mL of ice-water, and the resulting orange precipitate was collected by filtration. After air-drying, 3-methoxy-5-nitro-phenylamine (5.82 g, 93%) was obtained as light brown solid: ES(+)-HRMS m/e calculated for $C_7H_8N_2O_3$ (M+H)$^+$ 169.0608, found 169.0608.

Step 2: Preparation of 1-iodo-3-methoxy-5-nitro-benzene

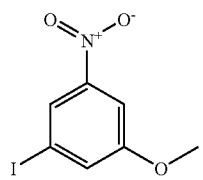

To a solution of 3-methoxy-5-nitro-phenylamine (7.5 g, 44.6 mmol) in water (20 mL) was added a concentrated hydrochloric acid (19.95 mL, 267.6 mmol, 36%) at 0° C. To this was added a chilled solution of sodium nitrite (5.62 g, 80.28 mmol) in water (28.4 mL) dropwise with a vigorous stirring. Then, the resulting colored mixture was stirred for 15 min at 0° C., and a cold solution of potassium iodide (14.81 g, 89.2 mmol) in water (28.4 mL) was added carefully. During this addition, a black brown solid was formed and after addition the ice-cold bath was removed, and the reaction mixture was heated to reflux. When the production of purple vapor ceased, the mixture was cooled to room temperature and the organic compound was extracted into dichloromethane (3×200 mL). The combined organic extracts were washed with brine solution (300 mL) and dried over anhydrous magnesium sulfate, filtered, and concentrated in vacuo. Then, the crude residue was purified by using a LC 120 column, eluting with 0-10% ethyl acetate in hexanes to obtain 1-iodo-3-methoxy-5-nitro-benzene (10 g, 80%) as a white solid: EI(+)-HRMS m/e calculated for $C_7H_6INO_3$ (M+)$^+$ 278.9392, found 278.9393.

Step 3: Preparation of 3-(3-methoxy-5-nitro-phenyl)-thiophene

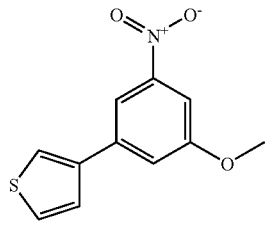

To a solution of 1-iodo-3-methoxy-5-nitro-benzene (1.0 g, 3.59 mmol) in ethanol (18 mL) in a microwave tube were added tetrakis(triphenylphosphine)palladium(0) (837 mg, 0.72 mmol), thiophen-3-ylboronic acid (748 mg, 5.55 mmol), and potassium carbonate (496 mg, 3.58 mmol) at room temperature. The mixture was heated to 160° C. under closed microwave conditions for 30 minutes. After cooling to room temperature, the colored mixture was filtered and the filter cake was washed with water. The filtrate was diluted with 1.0 N HCl and the organic compound was extracted into ethyl acetate (2×50 mL). The combined organic extracts were washed with brine solution (100 mL) and dried over anhydrous magnesium sulfate, filtered, and concentrated in vacuo. The crude mixture was purified by using an ISCO 80 g column, eluting with 0-10% ethyl acetate in hexanes to obtain 3-(3-methoxy-5-nitro-phenyl)-thiophene (776 mg, 92%) as a light yellow oil: EI(+)-HRMS m/e calculated for $C_{11}H_9NO_3S$ (M+)$^+$ 235.0303, found 235.0298.

Step 4: Preparation of 3-methoxy-5-thiophen-3-yl-phenylamine

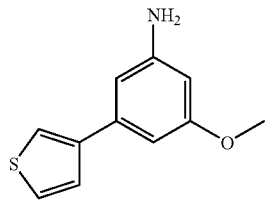

To a mixture of 3-(3-methoxy-5-nitro-phenyl)-thiophene (3.78 g, 16.07 mmol), zinc dust (10.72 g, 160.7 mmol), and ammonium chloride (12.89 g, 241.1 mmol) were added methanol (50 mL) and water (25 mL) at room temperature. After addition of water, the reaction became exothermic. The suspension was stirred for 1 h and the reaction mixture was filtered through the Celite. The filter cake was washed with water and methanol. The filtrate was concentrated to remove methanol and the residue was extracted with ethyl acetate (2×100 mL). The combined extracts were washed with brine solution (100 mL), dried over anhydrous magnesium sulfate, filtered, and concentrated in vacuo. The residue was then purified by using an ISCO 120 g column, eluting with 0-20% ethyl acetate in hexanes to afford 3-methoxy-5-thiophen-3-yl-phenylamine (3.08 g, 93%) as a light yellow solid: ES(+)-HRMS m/e calculated for $C_{11}H_{11}NOS$ (M+H)$^+$ 206.0634, found 206.0634.

Step 5: Preparation of 3-(3-iodo-5-methoxy-phenyl)-thiophene

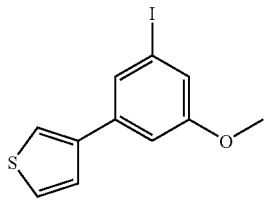

To a solution of 3-methoxy-5-thiophen-3-yl-phenylamine (2.45 g, 11.93 mmol) in water (7.2 mL) was added a concentrated hydrochloric acid (5.34 mL, 71.58 mmol, 36%) at 0° C. To this was added in a dropwise manner to a vigorously stirred, chilled solution of sodium nitrite (1.5 g, 21.47 mmol) in water (9.3 mL). Then, the resulting colored mixture was stirred for 15 min at 0° C., and a cold solution of potassium iodide (3.96 g, 23.86 mmol) in water (9.3 mL) was added carefully. During this addition, a black brown solid was formed and after addition the ice-cold bath was removed, and the reaction mixture was heated to reflux. When the production of purple vapor ceased, the mixture was cooled to room temperature and the organic compound was extracted into dichloromethane (3×100 mL). The combined organic extracts were washed with brine solution (200 mL) and dried over anhydrous magnesium sulfate, filtered, and concentrated in vacuo. Then, the crude residue was purified by using a LC 80 column, eluting with 0-10% ethyl acetate in hexanes to obtain 3-(3-iodo-5-methoxy-phenyl)-thiophene (2.19 g, 58%) as a white solid: ES(+)-HRMS m/e calculated for $C_{11}H_9IOS$ (M+)$^+$ 315.9419, found 315.9418.

Step 6: Preparation of 3-iodo-5-thiophen-3-yl-phenol

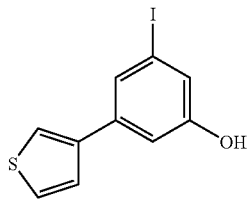

To a suspension of 3-(3-iodo-5-methoxy-phenyl)-thiophene (2.08 g, 6.7 mmol) and sodium iodide (65.73 mmol, 9.85 g) in acetonitrile (80 mL) was added trimethylsilyl chloride (32.86 mmol, 4.16 mL) at room temperature. Then, the resulting light yellow suspension was heated to reflux for 48 h. Then, it was cooled to room temperature and diluted with water (50 mL). The organic compound was extracted into ethyl acetate (2×75 mL) and the combined ethyl acetate extracts were washed with saturated sodium thiosulfate solution (100 mL) to remove the iodine color and was also washed with brine solution (100 mL). Then, the organic layer was dried over anhydrous magnesium sulfate, filtered, and concentrated in vacuo. The crude residue was purified by using an ISCO 120 g column, eluting with 0-20% ethyl acetate in hexanes to obtain 3-iodo-5-thiophen-3-yl-phenol (1.92 g, 97%) as a light brown oil: ES(+)-HRMS m/e calculated for $C_{10}H_7IOS$ (M−H)$^+$ 300.9189, found 300.9189.

Step 7: Preparation of 4-{3-[6-(3-iodo-5-thiophen-3-yl-phenoxy)-hexyl]-2-(2-ethoxycarbonyl-ethyl)-phenoxy}-butyric acid ethyl ester

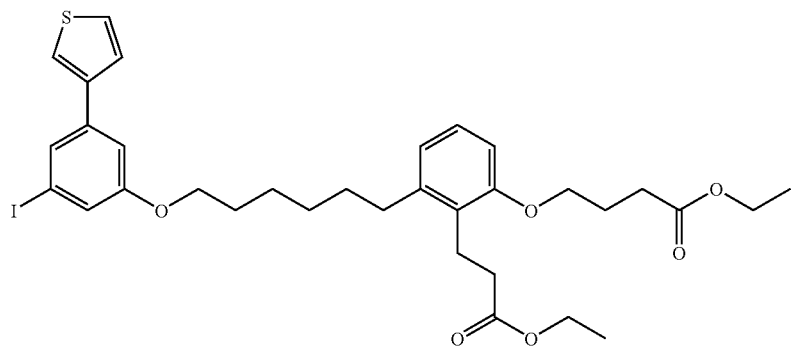

To a mixture of 4-[3-(6-bromo-hexyl)-2-(2-ethoxycarbonyl-ethyl)-phenoxy]-butyric acid ethyl ester (2.99 g, 6.35 mmol), 3-iodo-5-thiophen-3-yl-phenol (1.92 g, 6.35 mmol), and potassium carbonate (1.75 g, 12.7 mmol) were added N,N-dimethylformamide (50 mL) and acetone (100 mL) at room temperature. The resulting suspension was heated to reflux for 2 days. Then, the reaction mixture was cooled to room temperature and diluted with water (200 mL). The organic compound was extracted into ethyl acetate (3×100 mL) and the combined organic extracts were washed with water (300 mL) and brine solution (200 mL). The organic layers were dried over anhydrous magnesium sulfate and filtration of the drying agent and concentration of the solvent gave the crude product which was purified by using an ISCO 80 g column, eluting with 0-20% ethyl acetate in hexanes to afford 4-{3-[6-(3-iodo-5-thiophen-3-yl-phenoxy)-hexyl]-2-(2-ethoxycarbonyl-ethyl)-phenoxy}-butyric acid ethyl ester (4.39 g, 99%) as a colorless oil: ES(+)-HRMS m/e calculated for $C_{33}H_{41}IO_6S$ (M+Na)$^+$ 715.1561, found 715.1561.

Step 8: Preparation of 4-{3-[6-(3-benzo[1,3]dioxol-5-yl-5-thiophen-3-yl-phenoxy)-hexyl]-2-(2-ethoxy-carbonyl-ethyl)-phenoxy}-butyric acid ethyl ester

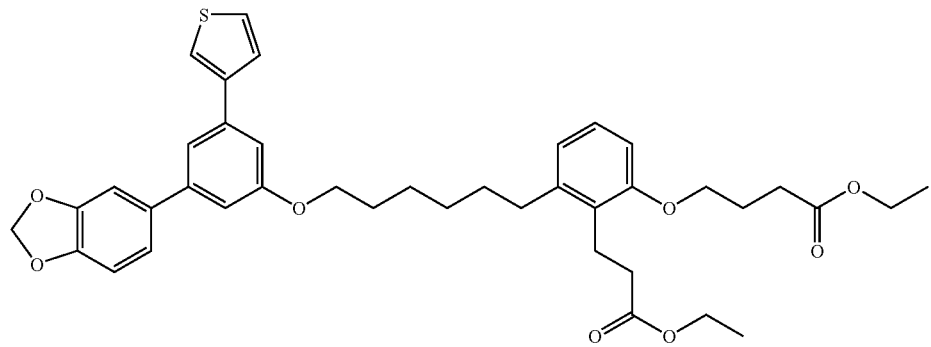

A solution of 4-{3-[6-(3-iodo-5-thiophen-3-yl-phenoxy)-hexyl]-2-(2-ethoxycarbonyl-ethyl)-phenoxy}-butyric acid ethyl ester (2.13 g, 3.06 mmol) in dimethoxyethane (75 mL) was stirred for 5 minutes at room temperature under nitrogen atmosphere. Then, tetrakis(triphenylphosphine)palladium(0) (1.06 g, 0.92 mmol) was added at room temperature and the resulting light yellow solution was heated to 80° C. and stirred for 5 minutes. At this period, a solution of benzo[1,3]dioxol-5-yl-boronic acid (1.53 g, 9.2 mmol) in ethanol (75 mL) was added followed by a solution of sodium carbonate (975 mg, 9.2 mmol) in water (6.0 mL). The resulting light yellow suspension was stirred for 24 h at reflux. Then, the reaction mixture was cooled to room temperature and diluted with water (100 mL) and ethyl acetate (100 mL). The two layers were separated and the aqueous layer was extracted with ethyl acetate (2×100 mL) and the combined organic extracts were washed with water (300 mL) and brine solution (300 mL). The organic layer was dried over anhydrous magnesium sulfate and filtration of the drying agent and removal of the solvent in vacuo gave the colored residue which was purified by using an ISCO 120 column, eluting with 0-20% ethyl acetate in hexanes to afford 4-{3-[6-(3-benzo[1,3]dioxol-5-yl-5-thiophen-3-yl-phenoxy)-hexyl]-2-(2-ethoxycarbonyl-ethyl)-phenoxy}-butyric acid ethyl ester (1.125 g, 53.5%) as a light brown viscous oil: ES(+)-HRMS m/e calculated for $C_{40}H_{46}O_8S$ (M+Na)$^+$ 709.2805, found 709.2808.

Step 9: Preparation of 4-{3-[6-(3-benzo[1,3]dioxol-5-yl-5-thiophen-3-yl-phenoxy)-hexyl]-2-(2-carboxy-ethyl)-phenoxy}-butyric acid To a solution of the 4-{3-[6-(3-benzo[1,3]dioxol-5-yl-5-thiophen-3-yl-phenoxy)-hexyl]-2-(2-ethoxycarbonyl-ethyl)-phenoxy}-butyric acid ethyl ester (649 mg, 0.944 mmol) in ethanol (40 mL) was added aqueous 1.0 N sodium hydroxide (35 mL) at room temperature. The resulting suspension was heated to 50-55° C. and the mixture was stirred for 5 h. Then, the reaction mixture was concentrated and the residue was diluted with water (20 mL) and extracted with diethyl ether (50 mL) to remove any neutral impurities. The aqueous layer was acidified with 1.0 N hydrochloric acid and the precipitated white organic compound was extracted into ethyl acetate (2×100 mL). The combined ethyl acetate extracts were washed with brine solution (100 mL) and the organic layers were dried over anhydrous magnesium sulfate. Filtration and removal of the solvent afforded the crude product which was dissolved in hot iso-propyl acetate (10 mL) and then diluted with hexanes (5 mL). The resulting light yellow solution was stored in the refrigerator for 2 days. The white solids were collected by filtration and washed with hexanes. After air-drying, 4-{3-[6-(3-benzo[1,3]dioxol-5-yl-5-thiophen-3-yl-phenoxy)-hexyl]-2-(2-carboxy-ethyl)-phenoxy}-butyric acid (404 mg, 68%) was isolated as a white solids, mp=110-112° C.: ES(+)-HRMS m/e calculated for $C_{36}H_{38}O_8S$ (M+Na)$^+$ 653.2179, found 653.2183. Elemental analysis: ($C_{36}H_{38}O_8S$): C=68.49 (calcd, 68.55), H=5.93 (6.07), S=5.15 (5.08).

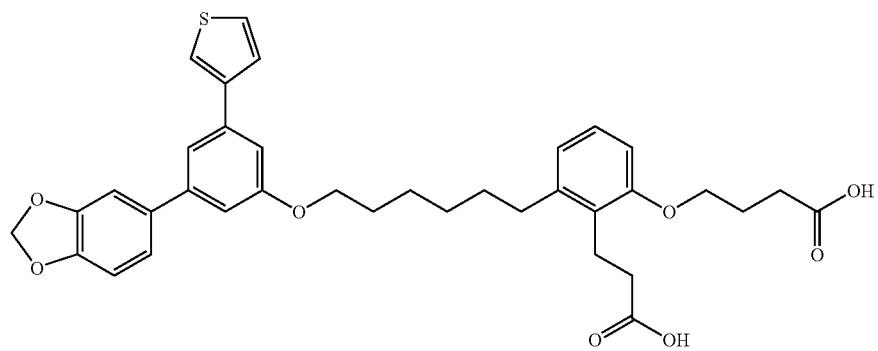

Example 12a

4-{3-[6-(3-benzo[1,3]dioxol-5-yl-5-thiophen-3-yl-phenoxy)-hexyl]-2-(2-carboxy-ethyl)-phenoxy}-butyric acid The following is an alternative method of preparing the compound of Example 12:

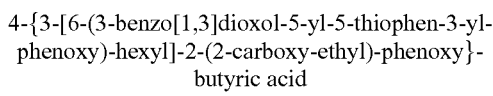

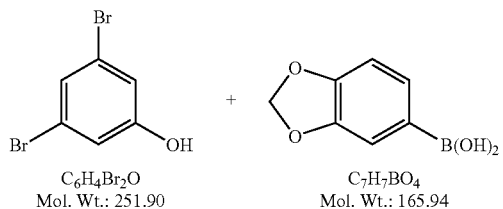

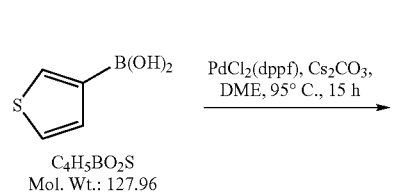

To a mixture of 3,5-dibromophenol (59.54 mmol, 15 g), 3,4-(methylenedioxy) phenylboronic acid (77.40 mmol, 12.84 g), 3-thiopheneboronic acid (62.52 mmol, 8 g), PdCl$_2$(dppf) (6.75 mmol, 4.94 g), and cesium carbonate (240 mmol, 78.19 g) was added dimethoxyethane (550 mL) at room temperature under nitrogen atmosphere. Then, the resulting light brown suspension was heated to 97° C. and stirred for 15 h. Then, the reaction mixture was cooled to room temperature and the solids were filtered-off and the cake was washed with ethyl acetate. The filtrate was diluted with water (300 mL) and the two layers were separated. The aqueous layer was extracted with ethyl acetate (2×100 mL) and the combined organic extracts were washed with brine solution (300 mL). The organic layer was dried over anhydrous magnesium sulfate and filtration of the drying agent and removal of the solvent gave the crude dark brown residue which was purified by two times using an ISCO (330 g) column chromatography eluting with 0-20% ethyl acetate in hexanes to afford the desired 3-benzo[1,3]dioxol-5-yl-5-thiophen-3-yl-phenol (7.48 g, 42.5%) as a white low melting solid. HRES(+) m/e calcd for C$_{17}$H$_{12}$O$_3$S (M+H)$^+$ 297.0580, found 297.0580

Benzo[1,3]dioxol-5-yl-5-thiophen-3-yl-phenol was prepared in the following three steps:

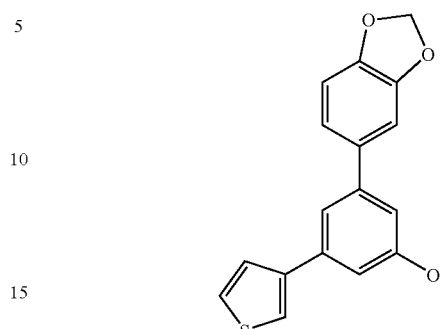

Step 1:

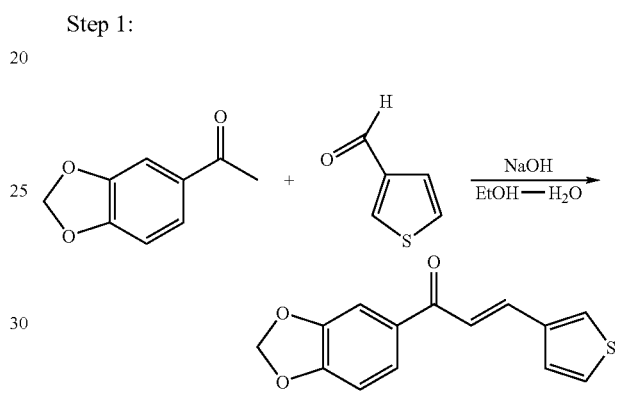

To a solution of NaOH (1.6 g; 40.1 mmoles) in 30 mL EtOH and 30 mL H$_2$O was added 3,4-methylenedioxy-acetophenone (6.0 g; 36.5 mmoles). Note: The reaction mixture was sonicated and heated to help solubilize completely 3,4-methylenedioxy-acetophenone. Once the solution was homogeneous, 3-thiophene carboxaldehyde (3.33 mL; 36.5 mmoles) was added slowly. The reaction mixture was stirred at room temperature overnight. The brown solid obtained in the reaction mixture was separated by filtration, then washed with water to provide 7.48 g of the desired chalcone (79%) as a brown solid. ES(+)-HRMS m/e calculated for C$_{14}$H$_{10}$O$_3$S$_1$ (M+H)$^+$ 259.0424, found 259.0423.

Step 2:

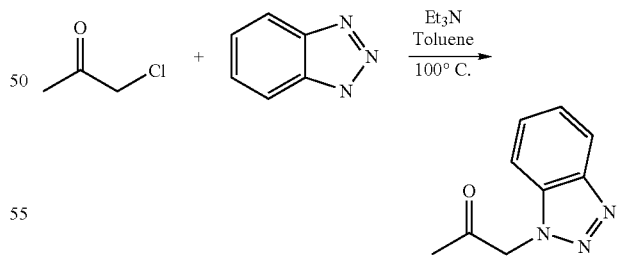

A solution of benzotriazole (6.42 g; 54.43 mmoles), chloroacetone (4.3 mL; 54.43 mmoles) and triethylamine (8.34 mL; 59.8 mL) in toluene (100 mL) was stirred at 100° C. for 5 h. The reaction mixture was cooled down and the precipitate was filtered, washed with toluene, dispersed in water, stirred for 5 min, and filtered again. The crude light brown solid was suspended in 10% NaOH solution, stirred for 5 min, filtered and washed with water to give 3.59 g of the desired ketone, 1-(benzotriazol-1-yl)propan-2-one (38%) as a light brown solid. ES(+)-HRMS m/e calculated for C$_9$H$_9$N$_3$O$_1$ (M+H)$^+$ 176.0819, found 176.0818.

Step 3:

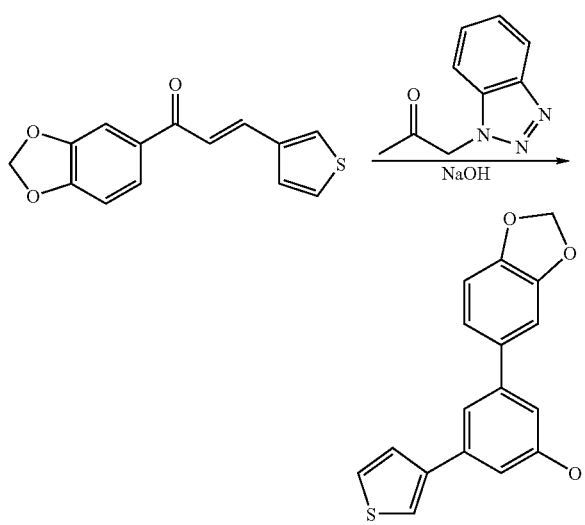

To a solution of NaOH (619 mg; 15.5 mmoles) in EtOH (30 mL) were added 1,3-diarylprop-2-enone (1.0 g; 3.87 mmoles) and 1-(benzotriazol-1-yl)propan-2-one (745 mg, 4.25 mmoles) at room temperature, and the reaction mixture was heated at 78° C. for 1 h. The reaction mixture was then acidified with conc.HCl. Formation of a precipitate which was the product still containing the benzotriazole moiety was filtered. The filtrate is then diluted with methylene chloride and water is added. The organic layer was separated, and dried over anhydrous sodium sulfate. After evaporation of the solvent, the crude brown oil was purified by column chromatography (ISCO 120 g column). The desired phenol is eluted with 20% EtOAc to afford 690 mg (83%) as a brown oil.

Step 1: 4-{3-[6-(3-benzo[1,3]dioxol-5-yl-5-thiophen-3-yl-phenoxy)-hexyl]-2-(2-ethoxycarbonyl-ethyl)-phenoxy}-butyric acid ethyl ester

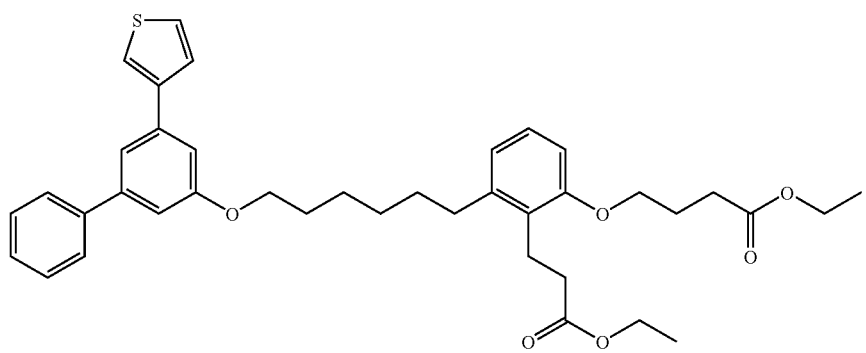

A similar procedure as described in Example 5, step 1 was used, starting from 4-[3-(6-bromo-hexyl)-2-(ethoxycarbonyl-ethyl)-phenoxy]-butyric acid ethyl ester and benzo[1,3]dioxol-5-yl-5-thiophen-3-yl-phenol to obtain 4-{2-(2-ethoxycarbonyl-ethyl)-3-[6-(5-thiophen-3-yl-biphenyl-3-yloxy)-hexyl]-phenoxy}-butyric acid ethyl ester.

Example 13

4-{2-(2-Carboxy-ethyl)-3-[6-(5-thiophen-3-yl-biphenyl-3-yloxy)-hexyl]-phenoxy}-butyric acid

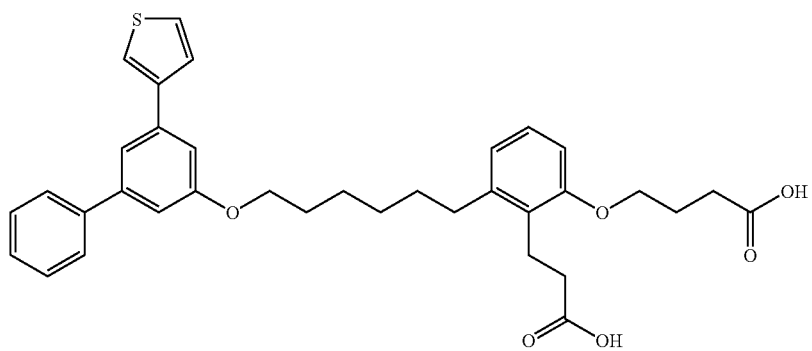

Step 1: Preparation of 4-{2-(2-ethoxycarbonyl-ethyl)-3-[6-(5-thiophen-3-yl-biphenyl-3-yloxy)-hexyl]-phenoxy}-butyric acid ethyl ester

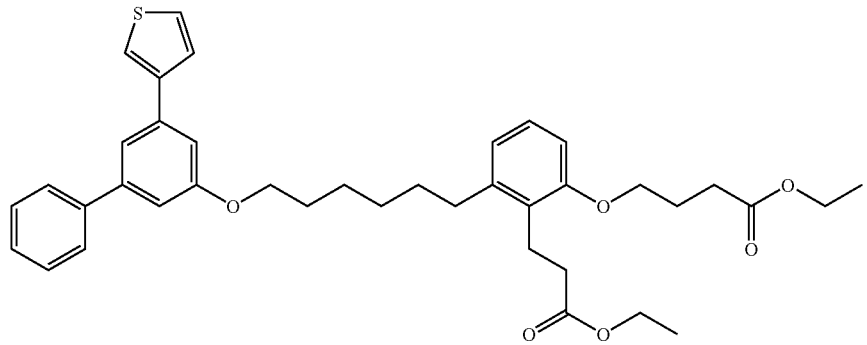

A similar procedure as described in Example 12, step 8 was used, starting from 4-{3-[6-(3-iodo-5-thiophen-3-yl-phenoxy)-hexyl]-2-(2-ethoxycarbonyl-ethyl)-phenoxy}-butyric acid ethyl ester (216 mg, 0.31 mmol) and phenylboronic acid (152 mg, 1.25 mmol) to give 4-{2-(2-ethoxycarbonyl-ethyl)-3-[6-(5-thiophen-3-yl-biphenyl-3-yloxy)-hexyl]-phenoxy}-butyric acid ethyl ester (110 mg, 55%) as a colorless oil: ES(+)-HRMS m/e calculated for $C_{39}H_{46}O_6S$ (M+Na)$^+$ 665.2907, found 665.2907.

Step 2: Preparation of 4-{2-(2-carboxy-ethyl)-3-[6-(5-thiophen-3-yl-biphenyl-3-yloxy)-hexyl]-phenoxy}-butyric acid

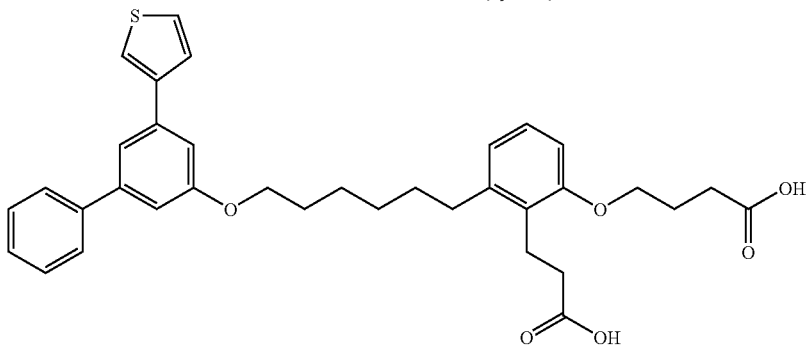

A similar procedure as described in Example 12, step 9 was used, starting from 4-{2-(2-ethoxycarbonyl-ethyl)-3-[6-(5-thiophen-3-yl-biphenyl-3-yloxy)-hexyl]-phenoxy}-butyric acid ethyl ester (85 mg, 0.13 mmol) and 1.0 N aqueous NaOH (8 mL) to afford 4-{2-(2-carboxy-ethyl)-3-[6-(5-thiophen-3-yl-biphenyl-3-yloxy)-hexyl]-phenoxy}-butyric acid (55 mg, 71%) as an amorphous white solid: ES(+)-HRMS m/e calculated for $C_{35}H_{38}O_6S$ (M+H)$^+$ 587.2462, found 587.2461.

Example 14

4-{2-(2-Carboxy-ethyl)-3-[6-(3-pyridin-4-yl-5-thiophen-3-yl-phenoxy)-hexyl]-phenoxy}-butyric acid

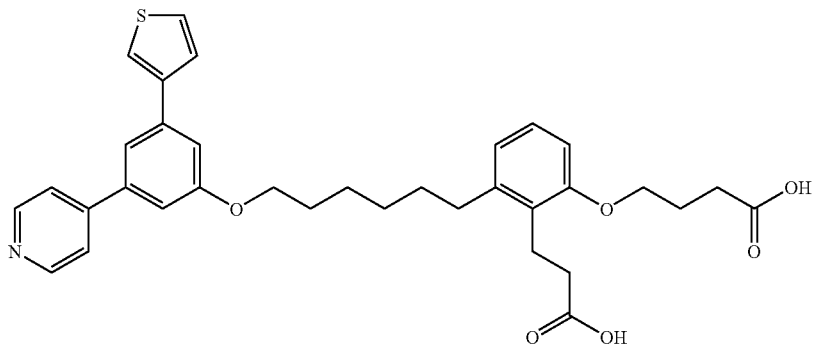

Step 1: Preparation of 4-{2-(2-ethoxycarbonyl-ethyl)-3-[6-(3-pyridin-4-yl-5-thiophen-3-yl-phenoxy)-hexyl]-phenoxy}-butyric acid ethyl ester

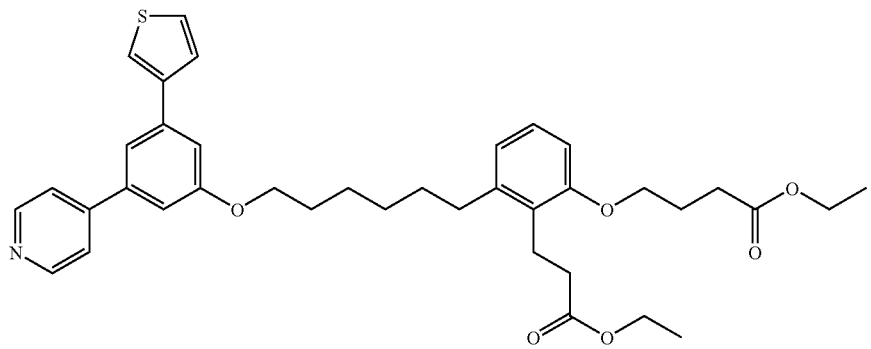

A similar procedure as described in Example 12, step 8 was used, starting from 4-{3-[6-(3-iodo-5-thiophen-3-yl-phenoxy)-hexyl]-2-(2-ethoxycarbonyl-ethyl)-phenoxy}-butyric acid ethyl ester (207 mg, 0.3 mmol) and pyridin-4-ylboronic acid (123 mg, 1.0 mmol) to obtain 4-{2-(2-ethoxycarbony-ethyl)-3-[6-(3-pyridin-4-yl-5-thiophen-3-yl-phenoxy)-hexyl]-phenoxy}-butyric acid ethyl ester (120 mg, 62%) as an yellow oil: ES(+)-HRMS m/e calculated for $C_{38}H_{45}NO_6S$ (M+H)$^+$ 644.3041, found 644.3041.

Step 2: Preparation of 4-{2-(2-carboxy-ethyl)-3-[6-(3-pyridin-4-yl-5-thiophen-3-yl-phenoxy)-hexyl]-phenoxy}-butyric acid

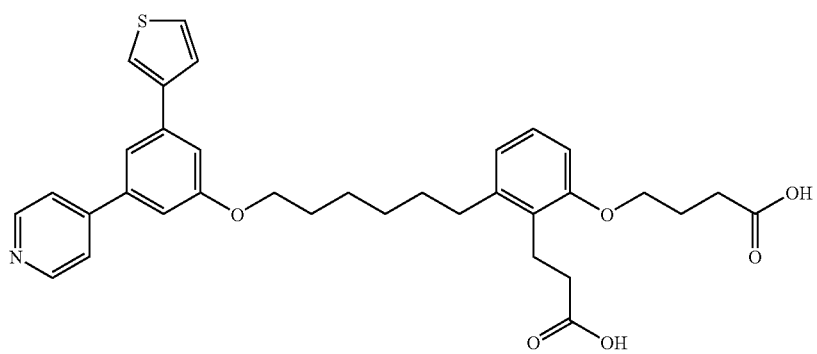

A similar procedure as described in Example 12, step 9 was used, starting from 4-{2-(2-ethoxycarbony-ethyl)-3-[6-(3-pyridin-4-yl-5-thiophen-3-yl-phenoxy)-hexyl]-phenoxy}-butyric acid ethyl ester (114 mg, 0.18 mmol) and 1.0 N aqueous NaOH (6 mL) to afford 4-{2-(2-carboxy-ethyl)-3-[6-(3-pyridin-4-yl-5-thiophen-3-yl-phenoxy)-hexyl]-phenoxy}-butyric acid (95 mg, 91%) as an amorphous white solid: ES(+)-HRMS m/e calculated for $C_{34}H_{37}NO_6S$ (M+H)$^+$ 588.2415, found 588.2414.

Example 15

4-(2-(2-Carboxy-ethyl)-3-{6-[3-(2-cholor-pyridin-4-y;-5-thiophen-3-yl-phenoxy)-hexyl]-phenoxy}-butyric acid

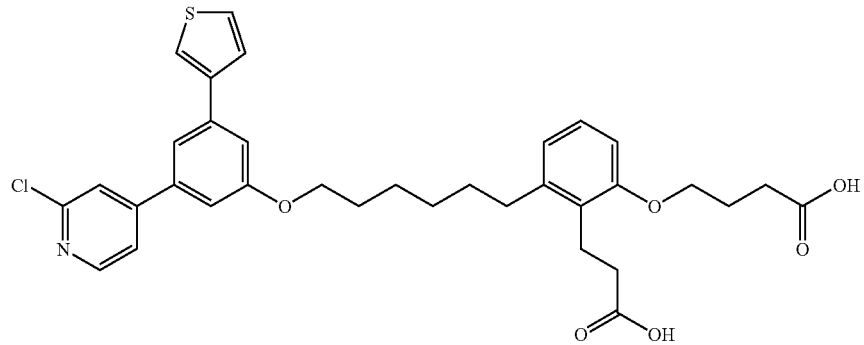

Step 1: Preparation of 4-[3-{6-[3-(2-chloro-pyridin-4-yl)-5-thiophen-3-yl-phenoxy]-hexyl}-2-(2-ethoxycarbony-ethyl)-phenoxy]-butyric acid ethyl ester

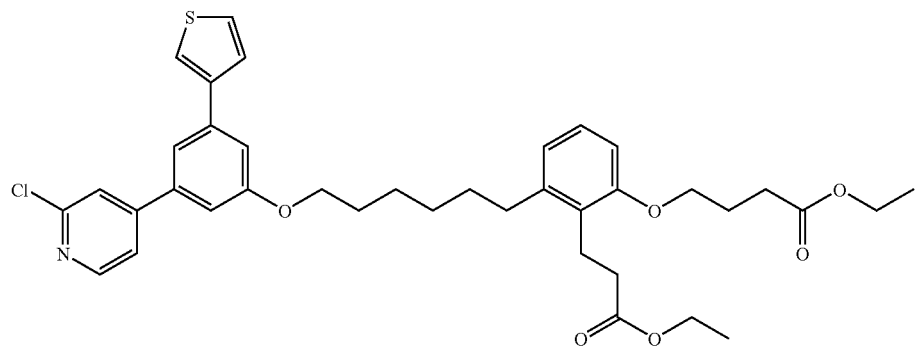

A similar procedure as described in Example 12, step 8 was used, starting from 4-{3-[6-(3-iodo-5-thiophen-3-yl-phenoxy)-hexyl]-2-(2-ethoxycarbonyl-ethyl)-phenoxy}-butyric acid ethyl ester (179 mg, 0.26 mmol) and 2-chloro-pyridin-4-ylboronic acid (126 mg, 0.8 mmol) to obtain 4-[3-{6-[3-(2-cholor-pyridin-4-yl)-5-thiophen-3-yl-phenoxy]-hexyl}-2-(2-ethoxycarbony-ethyl)-phenoxy]-butyric acid ethyl ester (52 mg, 30%) as a colorless viscous oil: ES(+)-HRMS m/e calculated for $C_{38}H_{44}ClNO_6S$ $(M+H)^+$ 678.2651, found 678.2650.

Step 2: Preparation of 4-(2-(2-carboxy-ethyl)-3-{6-[3-(2-cholor-pyridin-4-yl-5-thiophen-3-yl-phenoxy)-hexyl]-phenoxy}-butyric acid

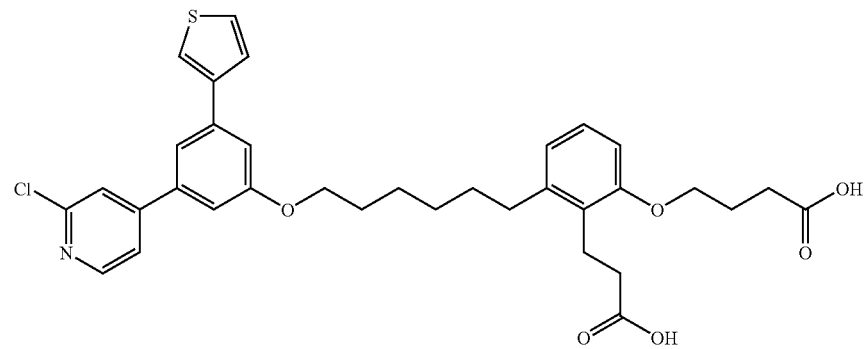

A similar procedure as described in Example 12, step 9 was used, starting from 4-[3-{6-[3-(2-cholor-pyridin-4-yl)-5-thiophen-3-yl-phenoxy]-hexyl}-2-(2-ethoxycarbony-ethyl)-phenoxy]-butyric acid ethyl ester (48 mg, 0.07 mmol) and 1.0 N aqueous NaOH (4 mL) to afford 4-(2-(2-carboxy-ethyl)-3-{6-[3-(2-cholor-pyridin-4-yl-5-thiophen-3-yl-phenoxy)-hexyl]-phenoxy}-butyric acid (32 mg, 74%) as an amorphous white solid: ES(+)-HRMS m/e calculated for $C_{34}H_{36}ClNO_6S$ (M+H)$^+$ 622.2025, found 622.2027.

Example 16

4-{2-(2-Carboxy-ethyl)-3-[6-(3-pyrimidin-5-yl-5-thiophen-3-yl-phenoxy)-hexyl]-phenoxy}-butyric acid

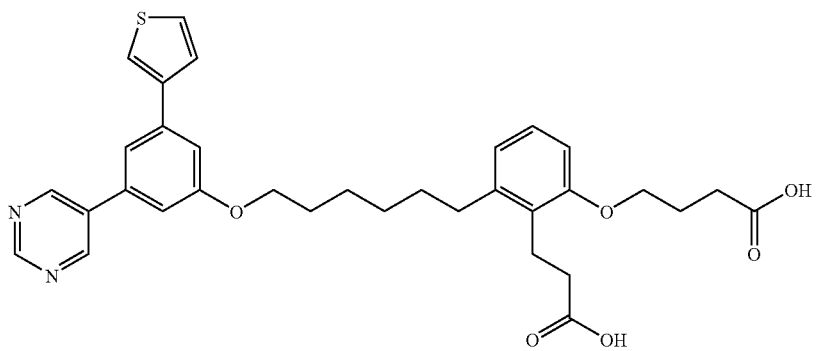

Step 1: Preparation of 4-{2-(2-ethoxycarbonyl-ethyl)-3-[6-(3-pyrimidin-5-yl-5-thiophen-3-yl-phenoxy)-hexyl]-phenoxy}-butyric acid ethyl ester

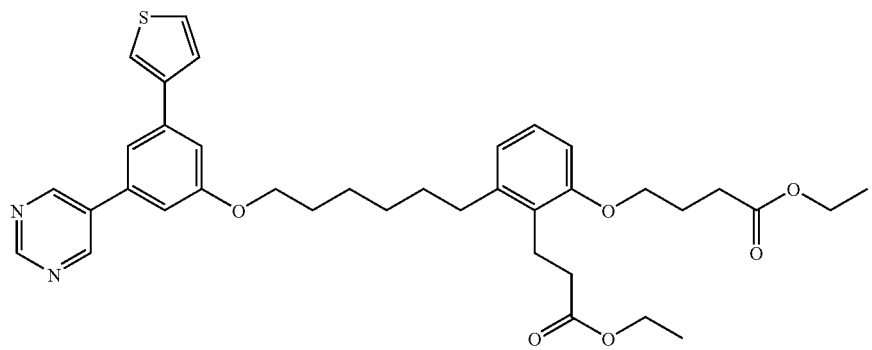

A similar procedure as described in Example 12, step 8 was used, starting from 4-{3-[6-(3-iodo-5-thiophen-3-yl-phenoxy)-hexyl]-2-(2-ethoxycarbonyl-ethyl)-phenoxy}-butyric acid ethyl ester (207 mg, 0.3 mmol) and pyrimidin-5-ylboronic acid (124 mg, 1.0 mmol) to obtain 4-{2-(2-ethoxycarbonyl-ethyl)-3-[6-(3-pyrimidin-5-yl-5-thiophen-3-yl-phenoxy)-hexyl]-phenoxy}-butyric acid ethyl ester (142 mg, 73%) as a light yellow viscous oil: ES(+)-HRMS m/e calculated for $C_{37}H_{44}N_2O_6S$ (M+H)$^+$ 645.2993, found 645.2987.

Step 2: Preparation of 4-{2-(2-carboxy-ethyl)-3-[6-(3-pyrimidin-5-yl-5-thiophen-3-yl-phenoxy)-hexyl]-phenoxy}-butyric acid

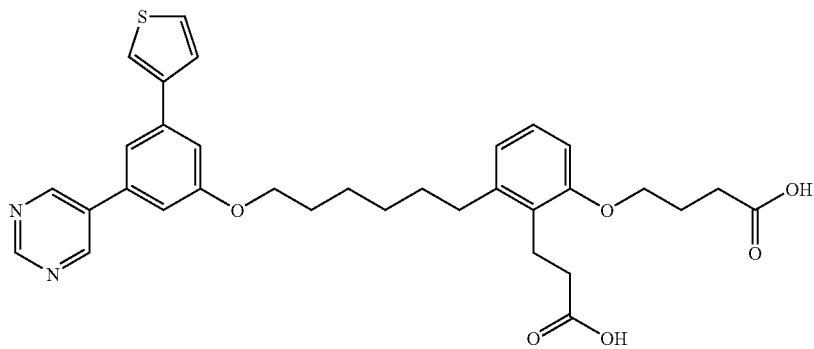

A similar procedure as described in Example 12, step 9 was used, starting from 4-{2-(2-ethoxycarbonyl-ethyl)-3-[6-(3-pyrimidin-5-yl-5-thiophen-3-yl-phenoxy)-hexyl]-phenoxy}-butyric acid ethyl ester (137 mg, 0.21 mmol) and 1.0 N aqueous NaOH (6 mL) to give 4-{2-(2-carboxy-ethyl)-3-[6-(3-pyrimidin-5-yl-5-thiophen-3-yl-phenoxy)-hexyl]-phenoxy}-butyric acid (115 mg, 93%) as an amorphous light yellow solid: ES(+)-HRMS m/e calculated for $C_{33}H_{36}N_2O_6S$ (M+H)$^+$ 589.2367, found 589.2366.

Example 17

4-{3-[6-(5-Benzo[1,3]dioxol-5-yl-3'-fluoro-biphenyl-3-yloxy)-hexyl]-2-(2-carboxy-ethyl)-phenoxy}-butyric acid bis-sodium salt

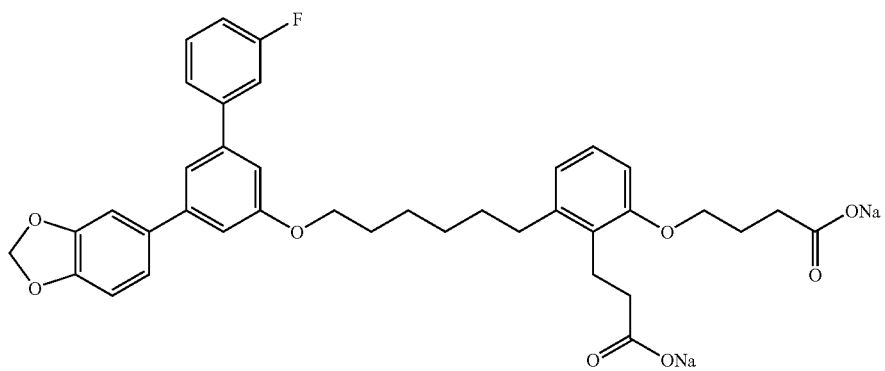

Step 1: Preparation of 3'-fluoro-5-methoxy-3-nitro-biphenyl

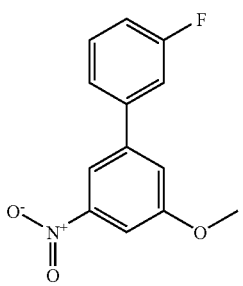

A similar procedure as described in Example 12, step 3 was used, starting from 1-iodo-3-methoxy-5-nitro-benzene (1.03 g, 3.69 mmol) and 3-fluoro-phenylboronic acid (800 mg, 5.72 mmol) to afford 3'-fluoro-5-methoxy-3-nitro-biphenyl (745 mg, 82%) as an amorphous white solid: EI(+)-HRMS m/e calculated for $C_{13}H_{10}FNO_3$ (M)$^+$ 247.0645, found 247.0645.

Step 2: Preparation of 3'-fluoro-5-methoxy-biphenyl-3-ylamine

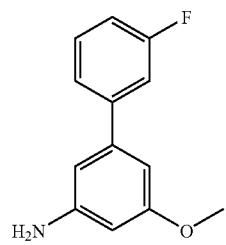

A similar procedure as described in Example 12, step 4 was used, starting from 3-fluoro-5-methoxy-3-nitro-biphenyl (738 mg, 2.98 mmol), zinc dust (1.99 mg, 29.85 mmol), and ammonium chloride (2.4 g, 44.77 mmol) to obtain 3'-fluoro-5-methoxy-biphenyl-3-ylamine (585 mg, 90%) as an amorphous light yellow solid: ES(+)-HRMS m/e calculated for $C_{13}H_{12}FNO$ (M+H)$^+$ 218.0976, found 218.0976.

Step 3: Preparation of 3'-fluoro-3-iodo-5-methoxy-biphenyl

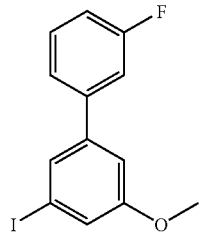

A similar procedure as described in Example 12, step 5 was used, starting from 3'-fluoro-5-methoxy-biphenyl-3-ylamine (940 mg, 4.32 mmol), sodium nitrite (545 mg, 7.79 mmol), and potassium iodide (1.44 mg, 8.65 mmol) to afford 3'-fluoro-3-iodo-5-methoxy-biphenyl (1.1 g, 78%) as an amorphous light yellow oil: ES(+)-HRMS m/e calculated for $C_{13}H_{10}FIO$ (M+H)$^+$ 329.1190, found 329.1192.

Step 4: Preparation of 3'-fluoro-5-iodo-biphenyl-3-ol

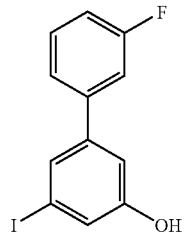

A similar procedure as described in Example 12, step 6 was used, starting from 3'-fluoro-3-iodo-5-methoxy-biphenyl (1.1 g, 3.35 mmol), sodium iodide (5.024 g, 33.52 mmol), and trimethylsilyl chloride (2.12 mL, 16.76 mmol) to give 3'-fluoro-5-iodo-biphenyl-3-ol (1.03 g, 98%) as an amorphous light brown oil: ES(+)-HRMS m/e calculated for $C_{12}H_8FIO$ (M+H)$^+$ 314.9677, found 314.9676.

Step 5: Preparation of 4-{2-(2-ethoxycarbonyl-ethyl)-3-[6-(3'-fluoro-5-iodo-biphenyl-3-yloxy)-hexyl]-phenoxy}-butyric acid ethyl ester

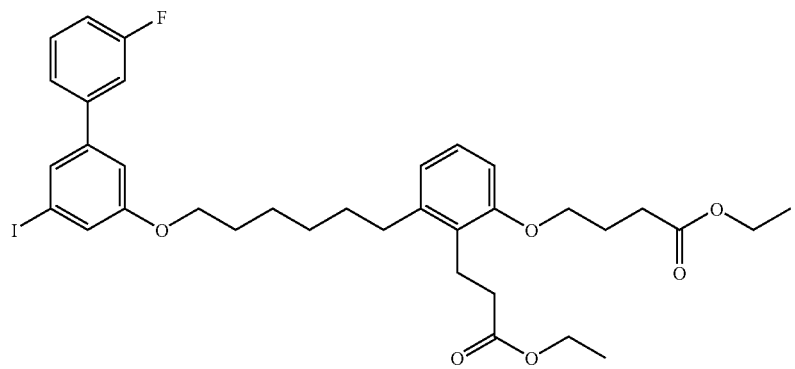

A similar procedure as described in Example 12, step 7 was used, starting from 4-[3-(6-bromo-hexyl)-2-(ethoxycarbonyl-ethyl)-phenoxy]-butyric acid ethyl ester (1.67 g, 3.54 mmol) and 3'-fluoro-5-iodo-biphenyl-3-ol (1.01 g, 3.22 mmol) to obtain 4-{2-(2-ethoxycarbonyl-ethyl)-3-[6-(3'-fluoro-5-iodo-biphenyl-3-yloxy)-hexyl]-phenoxy}-butyric acid ethyl ester (2.24 g, 99%) as a light yellow oil: ES(+)-HRMS m/e calculated for $C_{35}H_{42}FIO_6$ (M+Na)$^+$ 727.1902, found 727.1902.

Step 6: Preparation of 4-{2-(2-carboxy-ethyl)-3-[6-(3'-fluoro-5-iodo-biphenyl-3-yloxy)-hexyl]-phenoxy}-butyric acid

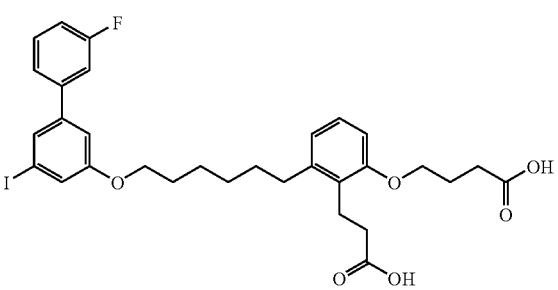

A similar procedure as described in Example 12, step 9 was used, starting from 4-{2-(2-ethoxycarbonyl-ethyl)-3-[6-(3'-fluoro-5-iodo-biphenyl-3-yloxy)-hexyl]-phenoxy}-butyric acid ethyl ester (2.23 g, 3.17 mmol) and aqueous 1.0 N sodium hydroxide (31.65 mL) to obtain 4-{2-(2-carboxy-ethyl)-3-[6-(3'-fluoro-5-iodo-biphenyl-3-yloxy)-hexyl]-phenoxy}-butyric acid (1.86 g, 91%) as a light yellow oil: ES(+)-HRMS m/e calculated for $C_{31}H_{34}FIO_6$ (M+Na)$^+$ 671.1276, found 671.1271.

Step 7: Preparation of 4-{3-[6-(5-benzo[1,3]dioxol-5-yl-3'-fluoro-biphenyl-3-yloxy)-hexyl]-2-(2-carboxy-ethyl)-phenoxy}-butyric acid

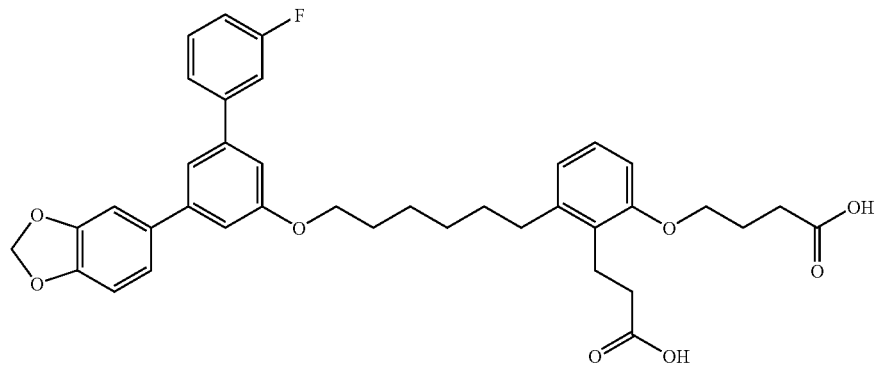

A similar procedure as described in Example 5, step 2 was used, starting from 4-{2-(2-carboxy-ethyl)-3-[6-(3'-fluoro-5-iodo-biphenyl-3-yloxy)-hexyl]-phenoxy}-butyric acid (1.2 g, 1.85 mmol) and benzo[1,3]dioxol-5-yl-boronic acid (614 mg, 3.7 mmol) to obtain 4-{3-[6-(5-benzo[1,3]dioxol-5-yl-3'-fluoro-biphenyl-3-yloxy)-hexyl]-2-(2-carboxy-ethyl)-phenoxy}-butyric acid (737 mg, 62%) as an amorphous white solid: ES(+)-HRMS m/e calculated for $C_{38}H_{39}FO_8$ (M+Na)$^+$ 665.2521, found 665.2520.

Step 8: Preparation of 4-{3-[6-(5-benzo[1,3]dioxol-5-yl-3'-fluoro-biphenyl-3-yloxy)-hexyl]-2-(2-carboxy-ethyl)-phenoxy}-butyric acid bis-sodium salt

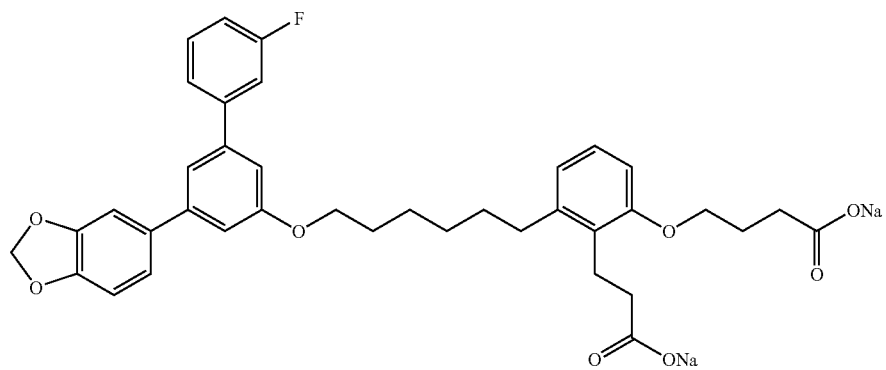

To a suspension of 4-{3-[6-(5-benzo[1,3]dioxol-5-yl-3'-fluoro-biphenyl-3-yloxy)-hexyl]-2-(2-carboxy-ethyl)-phenoxy}-butyric acid (704 mg, 1.09 mmol) in water (5.0 mL) was added an aqueous solution of 1.0 N sodium hydroxide (2.1 mL, 2.1 mmol) at room temperature. The resulting suspension was stirred until it gave a clear solution which is the indication of the complete formation of bis-sodium salt. The resulting solution was frozen and lyophilized under high vacuum to obtain 4-{3-[6-(5-benzo[1,3]dioxol-5-yl-3'-fluoro-biphenyl-3-yloxy)-hexyl]-2-(2-carboxy-ethyl)-phenoxy}-butyric acid bis-sodium salt (748 mg, 100%) as an amorphous white solid: ES(+)-HRMS m/e calculated for $C_{38}H_{37}FNa_2O_8$ (M+Na)$^+$ 686.2521, found 686.2525.

Example 18

4-{2-(2-Carboxy-ethyl)-3-[6-(3'-fluoro-5-pyridin-4-yl-biphenyl-3-yloxy)-hexyl]-phenoxy}-butyric acid

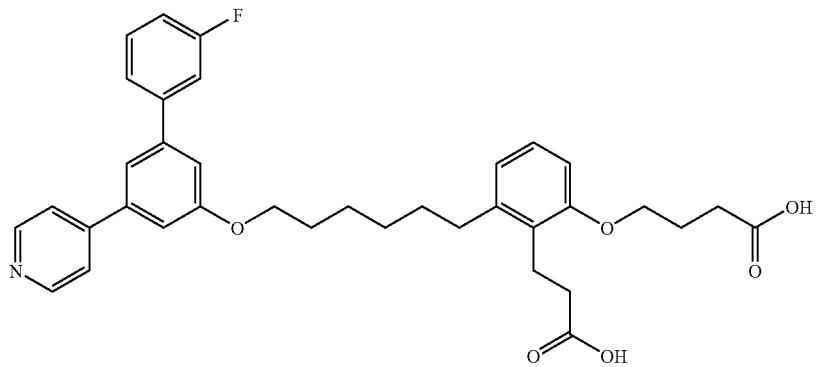

A similar procedure as described in Example 5, step 2 was used, starting from 4-{2-(2-carboxy-ethyl)-3-[6-(3'-fluoro-5-iodo-bi phenyl-3-yloxy)-hexyl]-phenoxy}-butyric acid (116 mg, 0.18 mmol) and pyridin-4-ylboronic acid (66 mg, 0.54 mmol) to obtain 4-{2-(2-carboxy-ethyl)-3-[6-(3'-fluoro-5-pyridin-4-yl-biphenyl-3-yloxy)-hexyl]-phenoxy}-butyric acid (28 mg, 26%) as an amorphous white solid: ES(+)-HRMS m/e calculated for $C_{36}H_{38}FNO_6$ (M+H)$^+$ 600.2756, found 600.2754.

Example 19

4-(2-(2-Carboxy-ethyl)-3-{6-[3'-fluoro-5-(1H-indol-5-yl)-biphenyl-3-yloxy]-hexyl}-phenoxy)-butyric acid

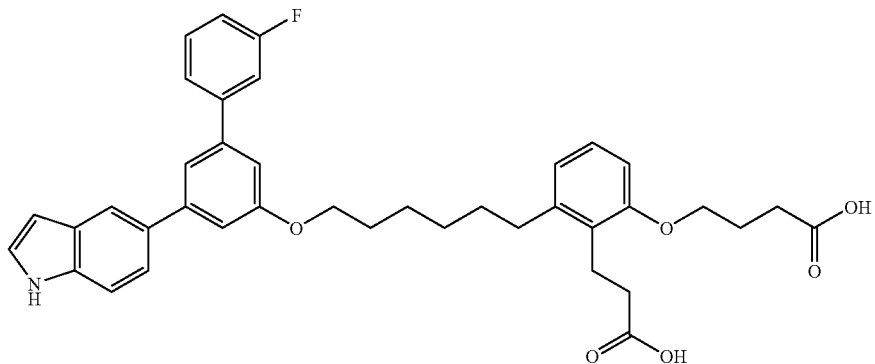

A similar procedure as described in Example 5, step 2 was used, starting from 4-{2-(2-carboxy-ethyl)-3-[6-(3'-fluoro-5-iodo-biphenyl-3-yloxy)-hexyl]-phenoxy}-butyric acid (116 mg, 0.18 mmol) and 1H-indol-5-ylboronic acid (66 mg, 0.54 mmol) to obtain 4-(2-(2-carboxy-ethyl)-3-{6-[3'fluoro-5-(1H-indol-5-yl)-biphenyl-3-yloxy]-hexyl}-phenoxy)-butyric acid (35 mg, 31%) as an amorphous light yellow solid: ES(+)-HRMS m/e calculated for $C_{39}H_{40}FNO_6$ (M+Na)$^+$ 660.2732, found 660.2735.

Example 20

4-{3-[6-(3-Benzo[1,3]dioxol-5-yl-5-pyridin-4-yl-phenoxy)-hexyl]-2-(2-carboxy-ethyl)-phenoxy}-butyric acid

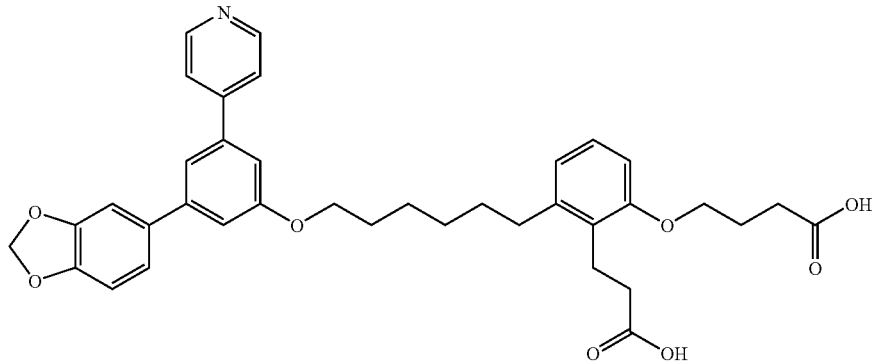

Step 1: Preparation of 3-iodo-5-nitro-phenol

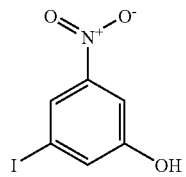

To a solution of 1-iodo-3-methoxy-5-nitro-benzene (8.2 g, 29.39 mmol) in methylene chloride (600 mL) was added 1.0 M solution of borontribromide (58.78 mL, 58.78 mmol) in methylene chloride at −78° C. The resulting solution was stirred for 30 minutes and then the cooling bath was removed to warm to room temperature. After stirring for 15 h at this temperature, the reaction mixture was heated to reflux for 4 h in order to complete the reaction. Then, it was cooled to room temperature and diluted with water (100 mL) and the methylene chloride was removed under vacuum. Then, the organic compound was extracted into diethyl ether (2×100 mL) and the combined ether extracts were washed with brine solution (200 mL). Then, the organic layer was dried over anhydrous magnesium sulfate, filtered, and concentrated in vacuo. The crude residue was purified by using an ISCO 120 g column, eluting with 0-15% ethyl acetate in hexanes to obtain 3-iodo-5-nitro-phenol (4.8 g, 62%) as a light yellow solid: ES(+)-HRMS m/e calculated for $C_6H_4INO_3$ (M−H)$^+$ 263.9163, found 263.9162.

Step 2: Preparation of 4-{2-(2-ethoxycarbonyl-ethyl)-3-[6-(3-iodo-5-nitro-phenoxy)-hexyl]-phenoxy}-butyric acid ethyl ester

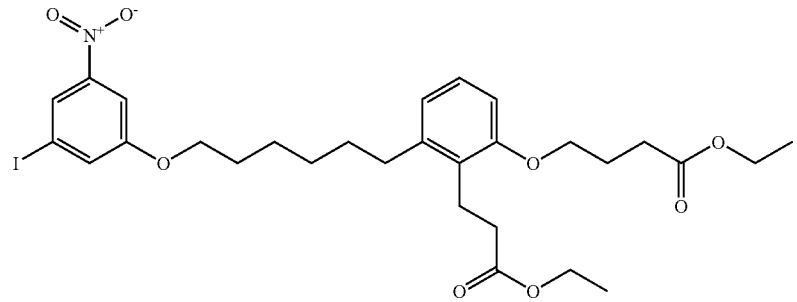

A similar procedure as described in Example 12, step 7 was used, starting from 4-[3-(6-bromo-hexyl)-2-(ethoxycarbonyl-ethyl)-phenoxy]-butyric acid ethyl ester (9.39 g, 19.92 mmol) and 3-iodo-5-nitro-phenol (4.8 g, 18.11 mmol) to afford 4-{2-(2-ethoxycarbonyl-ethyl)-3-[6-(3-iodo-5-nitro-phenoxy)-hexyl]-phenoxy}-butyric acid ethyl ester (8.7 g, 73%) as a light yellow oil: ES(+)-HRMS m/e calculated for $C_{29}H_{38}INO_8$ (M+H)$^+$ 656.1715, found 656.1721.

Step 3: Preparation of 4-{3-[6-(3-benzo[1,3]dioxol-5-yl-5-nitro-phenoxy)-hexyl]-2-(2-ethoxycarbonyl-ethyl)-phenoxy}-butyric acid ethyl ester

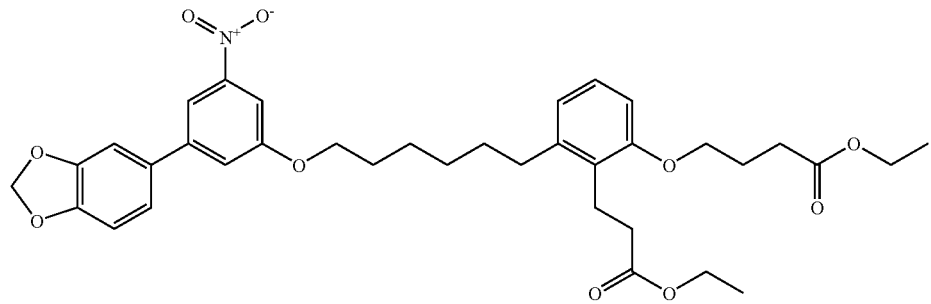

A similar procedure as described in Example 12, step 8 was used, starting from 4-{2-(2-ethoxycarbonyl-ethyl)-3-[6-(3-iodo-5-nitro-phenoxy)-hexyl]-phenoxy}-butyric acid ethyl ester (6.6 g, 10.07 mmol) and benzo[1,3]dioxol-5-yl-boronic acid (3.45 g, 20.14 mmol) to afford 4-{3-[6-(3-benzo[1,3]dioxol-5-yl-5-nitro-phenoxy)-hexyl]-2-(2-ethoxycarbonyl-ethyl)-phenoxy}-butyric acid ethyl ester (4.8 g, 73%) as a light yellow oil: EI(+)-HRMS m/e calculated for $C_{36}H_{43}NO_{10}$ (M+Na)$^+$ 672.2779, found 672.2773.

Step 4: Preparation of 4-{3-[6-(3-amino-5-benzo[1,3]dioxol-5-yl-phenoxy)-hexyl]-2-(2-ethoxycarbonyl-ethyl)-phenoxy}-butyric acid ethyl ester

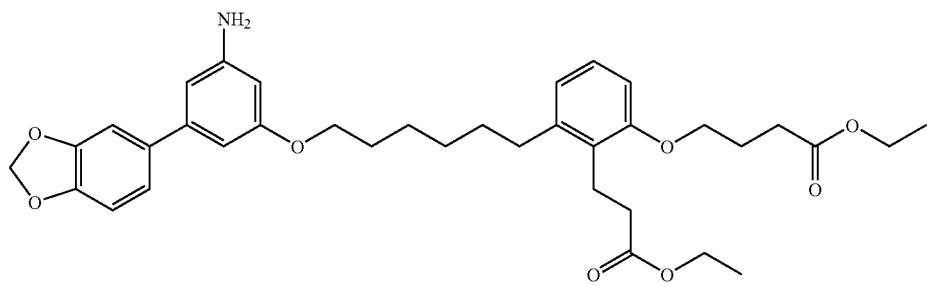

A similar procedure as described in Example 12, step 4 was used, starting from 4-{3-[6-(3-benzo[1,3]dioxol-5-yl-5-nitro-phenoxy)-hexyl]-2-(2-ethoxycarbonyl-ethyl)-phenoxy}-butyric acid ethyl ester (4.8 g, 7.38 mmol), zinc dust (2.46 g, 36.94 mmol), and ammonium chloride (3.95 g, 73.88 mmol) to obtain 4-{3-[6-(3-amino-5-benzo[1,3]dioxol-5-yl-phenoxy)-hexyl]-2-(2-ethoxycarbonyl-ethyl)-phenoxy}-butyric acid ethyl ester (3.99 g, 87%) as a light yellow oil: ES(+)-HRMS m/e calculated for $C_{36}H_{45}NO_8$ (M+H)$^+$ 619.0000, found 619.0000.

Step 5: Preparation of 4-{3-[6-(3-benzo[1,3]dioxol-5-yl-5-iodo-phenoxy)-hexyl]-2-(2-ethoxycarbonyl-ethyl)-phenoxy}-butyric acid ethyl ester

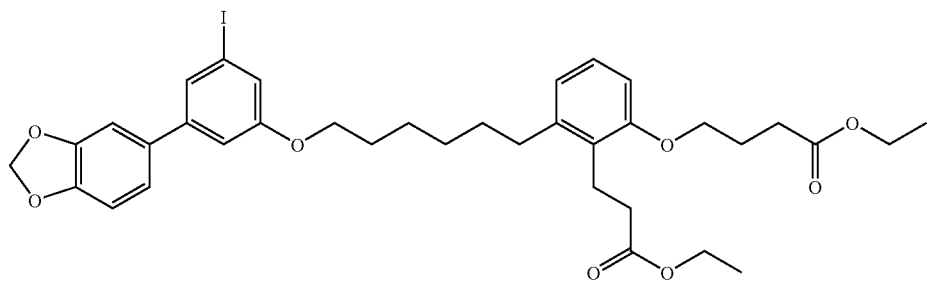

A similar procedure as described in Example 12, step 5 was used, starting from 4-{3-[6-(3-amino-5-benzo[1,3]dioxol-5-phenoxy)-hexyl]-2-(2-ethoxycarbonyl-ethyl)-phenoxy}-butyric acid ethyl ester (960 mg, 1.55 mmol), sodium nitrite (195 mg, 2.79 mmol), and potassium iodide (514 mg, 3.09 mmol) to afford 4-{3-[6-(3-benzo[1,3]dioxol-5-yl-5-iodo-phenoxy)-hexyl]-2-(2-ethoxycarbonyl-ethyl)-phenoxy}-butyric acid ethyl ester (145 mg, 13%) as a light yellow oil: ES(+)-HRMS m/e calculated for $C_{36}H_{43}IO_8$ $(M+Na)^+$ 753.1895, found 753.1894.

Step 6: Preparation of 4-{3-[6-(3-benzo[1,3]dioxol-5-yl-5-pyridin-4-yl-phenoxy)-hexyl]-2-(2-ethoxycarbonyl-ethyl)-phenoxy}-butyric acid ethyl ester

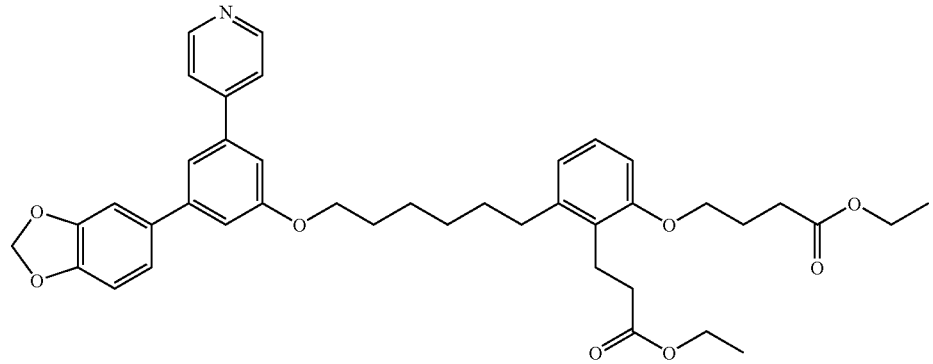

A similar procedure as described in Example 12, step 8 was used, starting from 4-{3-[6-(3-benzo[1,3]dioxol-5-yl-5-iodo-phenoxy)-hexyl]-2-(2-ethoxycarbonyl-ethyl)-phenoxy}-butyric acid ethyl ester (87 mg, 0.12 mmol) and pyridin-4-ylboronic acid (45 mg, 0.36 mmol) to afford 4-{3-[6-(3-benzo[1,3]dioxol-5-yl-5-pyridin-4-yl-phenoxy)-hexyl]-2-(2-ethoxycarbonyl-ethyl)-phenoxy-butyric acid ethyl ester (51 mg, 63%) as a light yellow oil: ES(+)-HRMS m/e calculated for $C_{41}H_{47}NO_8$ $(M+H)^+$ 682.3375, found 682.3369.

Step 7: Preparation of 4-{3-[6-(3-benzo[1,3]dioxol-5-yl-5-pyridin-4-yl-phenoxy)-hexyl]-2-(2-carboxy-ethyl)-phenoxy}-butyric acid

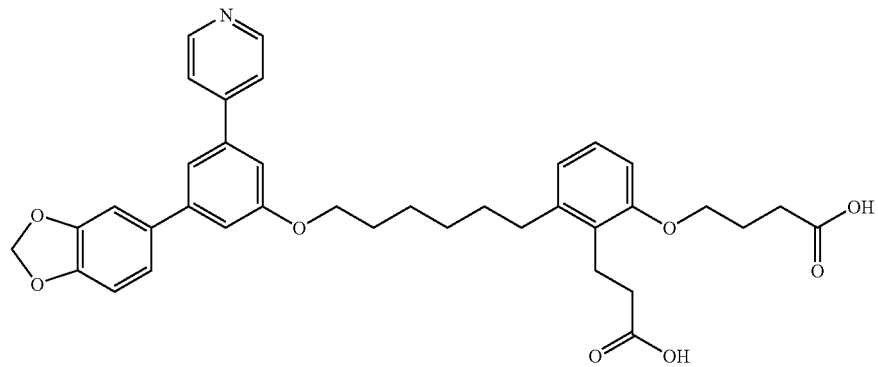

A similar procedure as described in Example 12, step 9 was used, starting from 4-{3-[6-(3-benzo[1,3]dioxol-5-yl-5-pyridin-4-yl-phenoxy)-hexyl]-2-(2-ethoxycarbonyl-ethyl)-phenoxy}-butyric acid ethyl ester (45 mg, 0.12 mmol) and 1.0 N aqueous sodium hydroxide (4 mL) to afford 4-{3-[6-(3-benzo[1,3]dioxol-5-yl-5-pyridin-4-yl-phenoxy)-hexyl]-2-(2-carboxy-ethyl)-phenoxy}-butyric acid (22 mg, 54%) as an amorphous white solid: ES(+)-HRMS m/e calculated for $C_{37}H_{39}NO_8$ $(M+H)^+$ 626.2749, found 626.2748.

Example 21

4-{3-[6-(3-Benzo[1,3]dioxol-5-yl-5-pyrimidin-4-yl-phenoxy)-hexyl]-2-(2-carboxy-ethyl)-phenoxy}-butyric acid

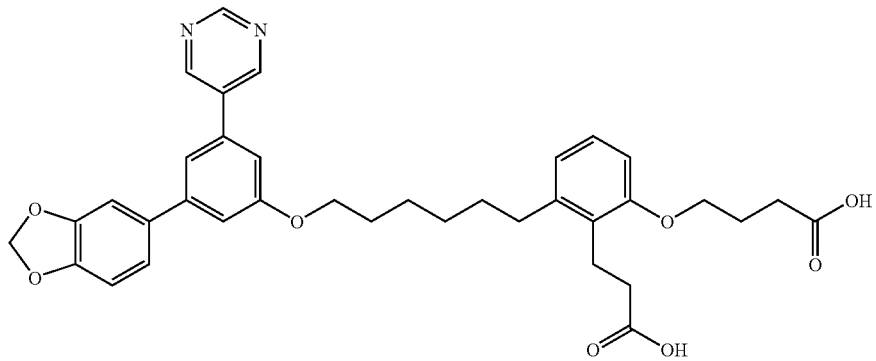

Step 1: Preparation of 4-{3-[6-(3-benzo[1,3]dioxol-5-yl-5-pyrimidin-4-yl-phenoxy)-hexyl]-2-(2-ethoxy-carbonyl-ethyl)-phenoxy}-butyric acid ethyl ester

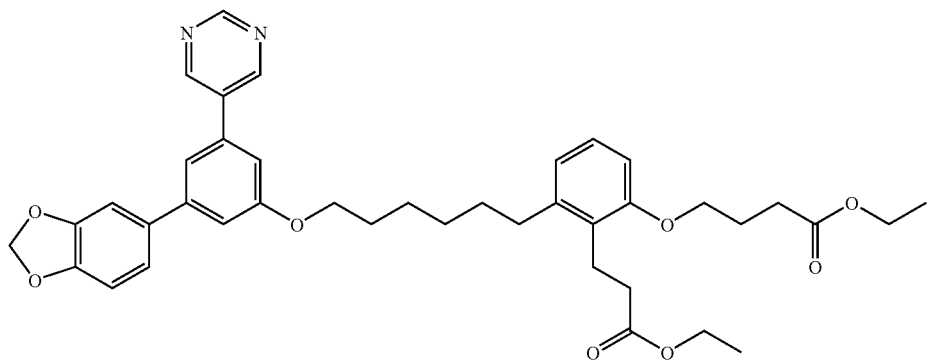

A similar procedure as described in Example 12, step 8 was used, starting from 4-{3-[6-(3-benzo[1,3]dioxol-5-yl-5-iodo-phenoxy)-hexyl]-2-(2-ethoxycarbonyl-ethyl)-phenoxy}-butyric acid ethyl ester (47 mg, 0.06 mmol) and pyrimidin-5-ylboronic acid (32 mg, 0.26 mmol) to afford 4-{3-[6-(3-benzo[1,3]dioxol-5-yl-5-pyrimidin-4-yl-phenoxy)-hexyl]-2-(2-ethoxycarbonyl-ethyl)-phenoxy-butyric acid ethyl ester (31 mg, 71%) as a light yellow oil: ES(+)-HRMS m/e calculated for $C_{40}H_{46}N_2O_8$ (M+H)$^+$ 683.3327, found 683.3327.

Step 2: Preparation of 4-{3-[6-(3-benzo[1,3]dioxol-5-yl-5-pyrimidin-4-yl-phenoxy)-hexyl]-2-(2-carboxy-ethyl)-phenoxy}-butyric acid

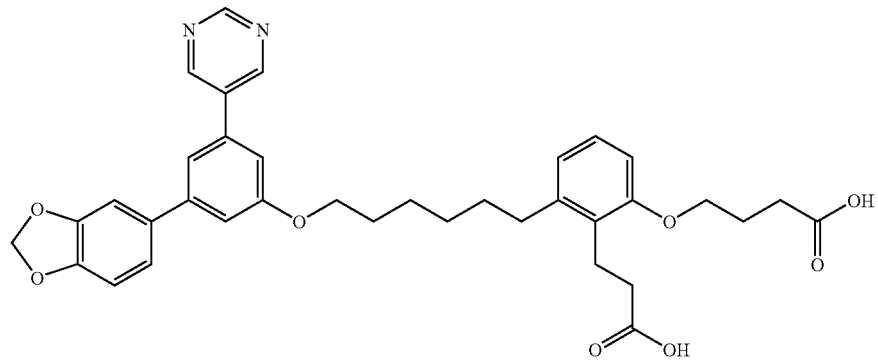

A similar procedure as described in Example 12, step 9 was used, starting from 4-{3-[6-(3-benzo[1,3]dioxol-5-yl-5-pyrimidin-4-yl-phenoxy)-hexyl]-2-(2-ethoxycarbonyl-ethyl)-phenoxy}-butyric acid ethyl ester (26 mg, 0.12 mmol) and 1.0 N aqueous sodium hydroxide (3 mL) to afford 4-{3-[6-(3-benzo[1,3]dioxol-5-yl-5-pyrimidin-4-yl-phenoxy)-hexyl]-2-(2-carboxy-ethyl)-phenoxy}-butyric acid (19 mg, 79%) as an amorphous light yellow solid: ES(+)-HRMS m/e calculated for $C_{36}H_{38}N_2O_8$ (M+H)$^+$ 627.2701, found 627.2696.

Example 22

4-(2-(2-Carboxy-ethyl)-3-{6-[5-(2,3-dihydro-benzo[1,4]dioxin-6-yl)-biphenyl-3-yloxy]-hexyl}-phenoxy)-butyric acid

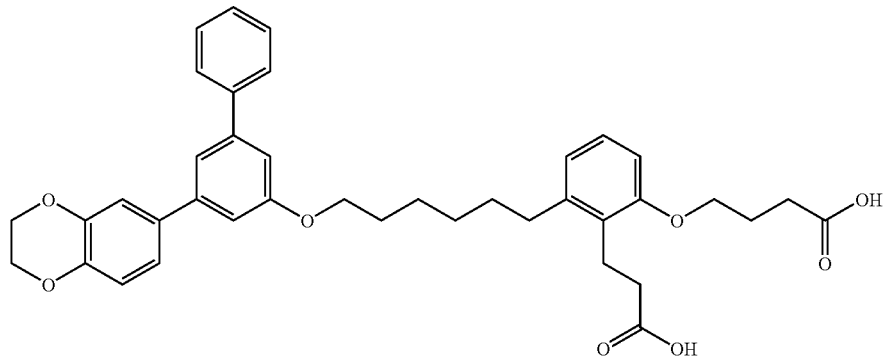

Step 1: Preparation of 4-[3-{6-[3-bromo-5-(2,3-dihydro-benzo[1,4]dioxin-6-yl)-phenoxy]-hexyl}-(2-(2-ethoxycarbonyl-ethyl)-phenoxy)-butyric acid ethyl ester

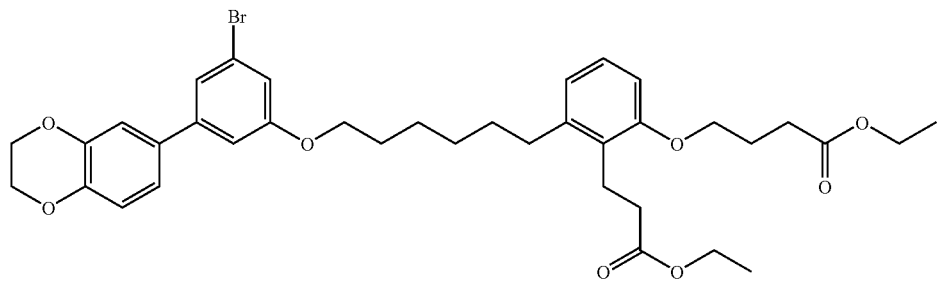

To a solution of 3,4-ethylenedioxyiodobenzene (1.31 g, 5.0 mmol) in dry tetrahydrofuran (10 mL) was added n-butyllithium (2.2 mL, 5.5 mmol, 2.5 M) in hexanes at −70° C. for 5 minutes. After addition, some white precipitate was formed and the suspension was stirred for 30 minutes at this temperature. Then, a solution of anhydrous zinc chloride (1.64 g, 12.0 mmol) (anhydrous zinc chloride can be obtained by heating commercial zinc chloride with heat gun under high vacuum until it melts and then cool down to room temperature before dissolve) in dry tetrahydrofuran (8 mL) was added at −70° C. The resulting clear solution was allowed to warm to 0° C. by removing the cooling bath. In a separate reaction flask, bis(dibenzylidene-acetone)palladium(0) (288 mg, 0.5 mmol) and tri-tolylphosphine (608 mg, 2.0 mmol) in dry tetrahydrofuran (5 mL) was stirred for 10 min under nitrogen at room temperature and then treated with 4-{3-[6-(3,5-dibromo-phenoxy)-hexyl]-2-(2-ethoxycarbonyl-ethyl)-phenoxy}-butyric acid ethyl ester (2.56 g, 4.0 mmol) in dry tetrahydrofuran (10 mL) and the above freshly prepared zinc compound in dry tetrahydrofuran at room temperature. The resulting brick red suspension was heated to 60-65° C. for 24 h. Then, the reaction mixture was cooled to room temperature and then diluted with saturated ammonium chloride solution (100 mL). The organic compound was extracted into ethyl acetate (3×75 mL) and the combined organic extracts were washed with brine solution (200 mL). The organic layers were dried over anhydrous magnesium sulfate and filtration of the drying agent and concentration of the solvent gave the crude product which was purified by using an ISCO 80 g column, eluting with 0-20% ethyl acetate in hexanes to isolate 4-[3-{6-[3-bromo-5-(2,3-dihydro-benzo[1,4]dioxin-6-yl)-phenoxy]-hexyl}-(2-(2-ethoxycarbonyl-ethyl)-phenoxy)-butyric acid ethyl ester (579 mg, 20%) as a light yellow oil: ES(+)-HRMS m/e calculated for $C_{37}H_{45}BrO_8$ (M+Na)$^+$ 719.2190, found 719.2191.

Step 2: Preparation of 4-[3-{6-[5-(2,3-dihydro-benzo[1,4]dioxin-6-yl)-biphenyl-3-yloxy]-hexyl}-(2-(2-ethoxycarbonyl-ethyl)-phenoxy)-butyric acid ethyl ester

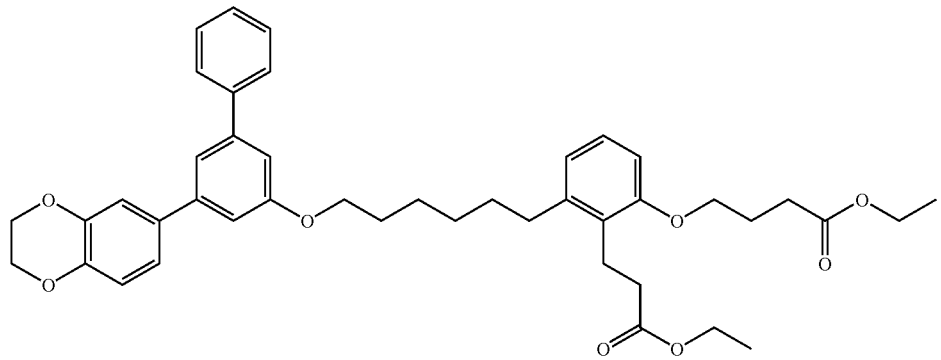

A solution of 4-[3-{6-[3-bromo-5-(2,3-dihydro-benzo[1,4]dioxin-6-yl)-phenoxy]-hexyl}-(2-(2-ethoxycarbonyl-ethyl)-phenoxy)-butyric acid ethyl ester (189 mg, 0.27 mmol) in dimethoxyethane (5 mL) was stirred for 5 minutes at room temperature under nitrogen atmosphere. Then, tetrakis(triphenylphosphine)palladium(0) (78 mg, 0.07 mmol) was added at room temperature and the resulting light yellow solution was heated to 80° C. and stirred for 5 minutes. At this period, a solution of phenylboronic acid (99 mg, 0.82 mmol) in ethanol (5 mL) was added followed by a solution of sodium carbonate (86 mg, 0.82 mmol) in water (0.5 mL). The resulting light yellow suspension was stirred for 24 h at reflux. Then, the reaction mixture was cooled to room temperature and diluted with water (20 mL) and ethyl acetate (30 mL). The two layers were separated and the aqueous layer was extracted with ethyl acetate (2×20 mL) and the combined organic extracts were washed with water (100 mL) and brine solution (100 mL). The organic layer was dried over anhydrous magnesium sulfate and filtration of the drying agent and removal of the solvent in vacuo gave the colored residue which was purified by using an ISCO 80 column, eluting with 0-30% ethyl acetate in hexanes to afford 4-[3-{6-[5-(2,3-dihydro-benzo[1,4]dioxin-6-yl)-biphenyl-3-yloxy]-hexyl}-(2-(2-ethoxycarbonyl-ethyl)-phenoxy)-butyric acid ethyl ester (85 mg, 45%) as a light brown oil: ES(+)-HRMS m/e calculated for $C_{43}H_{50}O_8$ $(M+Na)^+$ 717.3398, found 717.3405.

Step 3: Preparation of 4-(2-(2-carboxy-ethyl)-3-{6-[5-(2,3-dihydro-benzo[1,4]dioxin-6-yl)-biphenyl-3-yloxy]-hexyl}-phenoxy)-butyric acid To a solution of 4-[3-{6-[5-(2,3-dihydro-benzo[1,4]dioxin-6-yl)-biphenyl-3-yloxy]-hexyl}-(2-(2-ethoxycarbonyl-ethyl)-phenoxy)-butyric acid ethyl ester (27 mg, 0.04 mmol) in ethanol (3 mL) was added aqueous 1.0 N sodium hydroxide (2 mL) at room temperature. The resulting suspension was heated to 50-55° C. and the mixture was stirred for 5 h. Then, the reaction mixture was concentrated and the residue was diluted with water (10 mL) and extracted with diethyl ether (20 mL) to remove any neutral impurities. The aqueous layer was acidified with 1.0 N hydrochloric acid and the precipitated white organic compound was extracted into ethyl acetate (2×20 mL). The combined ethyl acetate extracts were washed with brine solution (50 mL) and the organic layers were dried over anhydrous magnesium sulfate. Filtration and removal of the solvent afforded the product which was dissolved in acetonitrile (3 mL) and diluted with water (3 mL) and lyophilized under high vacuum to obtain 4-(2-(2-carboxy-ethyl)-3-{6-[5-(2,3-dihydro-benzo[1,4]dioxin-6-yl)-biphenyl-3-yloxy]-hexyl}-phenoxy)-butyric acid (19 mg, 79%) as an amorphous white solids: ES(+)-HRMS m/e calculated for $C_{39}H_{42}O_8$ $(M+Na)^+$ 661.2772, found 661.2769.

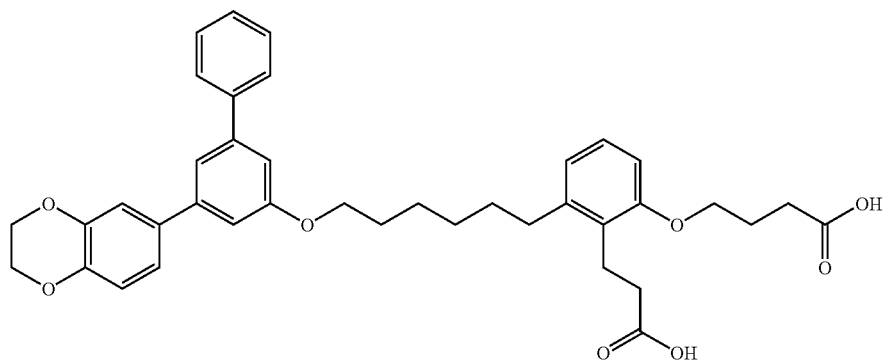

Example 23

4-(2-(2-Carboxy-ethyl)-3-{6-[5-(2,3-dihydro-benzo[1,4]dioxin-6-yl)-4'-fluoro-biphenyl-3-yloxy]-hexyl}-phenoxy)-butyric acid

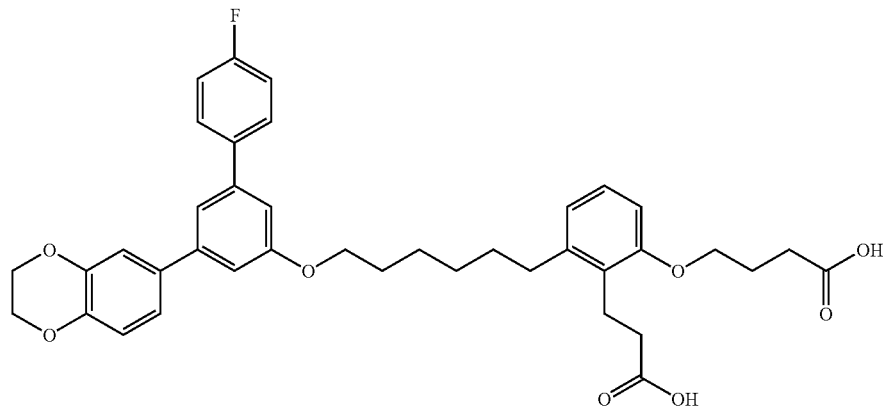

Step 1: Preparation of 4-[3-{6-[5-(2,3-dihydro-benzo[1,4]dioxin-6-yl)-4'-fluoro-biphenyl-3-yloxy]-hexyl}-(2-(2-ethoxycarbonyl-ethyl)-phenoxy)-butyric acid ethyl ester

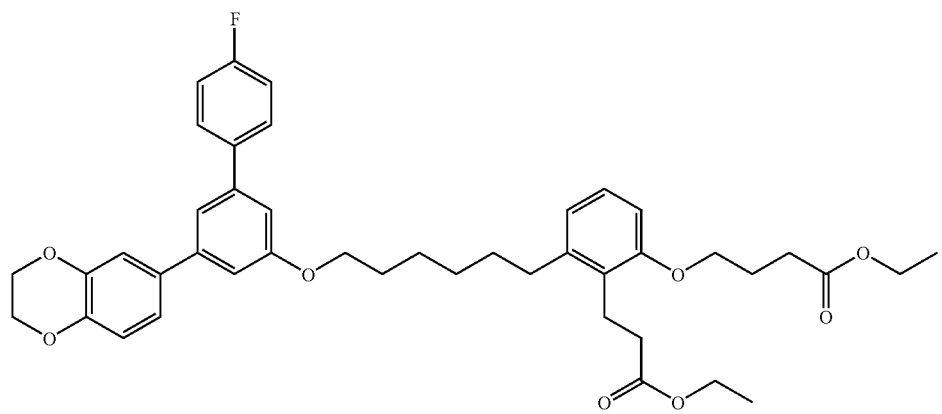

A similar procedure as described in Example 22, step 2 was used, starting from 4-[3-{6-[3-bromo-5-(2,3-dihydro-benzo[1,4]dioxin-6-yl)-phenoxy]-hexyl}-(2-(2-ethoxycarbonyl-ethyl)-phenoxy)-butyric acid ethyl ester (189 mg, 0.27 mmol) and 4-fluoro-phenylboronic acid (114 mg, 0.82 mmol) to obtain 4-[3-{6-[5-(2,3-dihydro-benzo[1,4]dioxin-6-yl)-4'-fluoro-biphenyl-3-yloxy]-hexyl}-(2-(2-ethoxycarbonyl-ethyl)-phenoxy)-butyric acid ethyl ester (65 mg, 34%) as a light yellow oil: ES(+)-HRMS m/e calculated for $C_{43}H_{49}FO_8$ (M+Na)$^+$ 735.3303, found 735.3298.

Step 2: Preparation of 4-(2-(2-carboxy-ethyl)-3-{6-[5-(2,3-dihydro-benzo[1,4]dioxin-6-yl)-4'-fluoro-biphenyl-3-yloxy]-hexyl}-phenoxy)-butyric acid

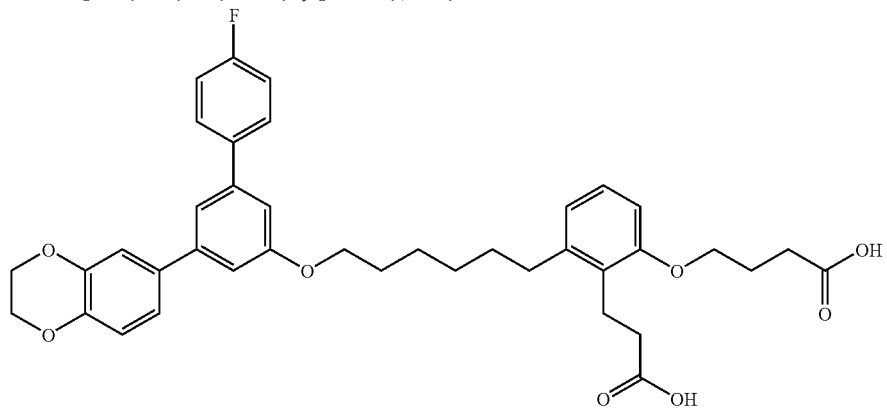

A similar procedure as described in Example 22, step 3 was used, starting from 4-[3-{6-[5-(2,3-dihydro-benzo[1,4]dioxin-6-yl)-4'-fluoro-biphenyl-3-yloxy]-hexyl}-(2-(2-ethoxycarbonyl-ethyl)-phenoxy)-butyric acid ethyl ester (50 mg, 0.07 mmol) and 1.0 N aqueous sodium hydroxide (5 mL) to afford 4-(2-(2-carboxy-ethyl)-3-{6-[5-(2,3-dihydro-benzo[1,4]dioxin-6-yl)-4'-fluoro-biphenyl-3-yloxy]-hexyl}-phenoxy)-butyric acid (25 mg, 54%) as an amorphous off-white solid: ES(+)-HRMS m/e calculated for $C_{39}H_{41}FO_8$ (M+Na)$^+$ 679.2677, found 679.2678.

Example 24

4-(2-(2-Carboxy-ethyl)-3-{6-[3-(2,3-dihydro-benzo[1,4]dioxin-6-yl)-5-pyridin-4-yl-phenoxy]-hexyl}-phenoxy)-butyric acid

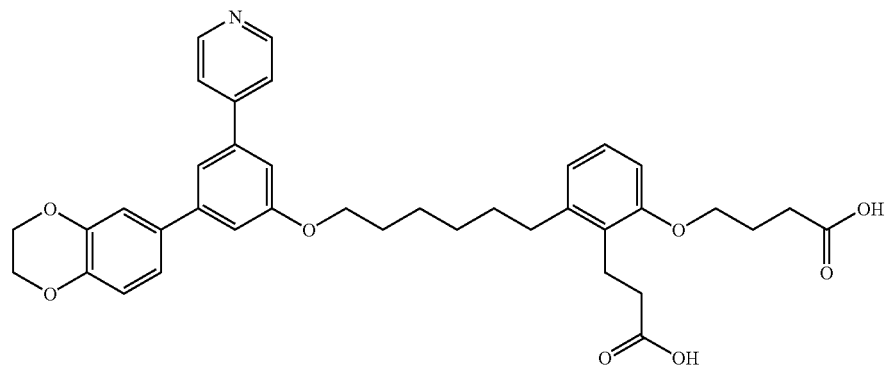

Step 1: Preparation of 4-[3-{6-[3-(2,3-dihydro-benzo[1,4]dioxin-6-yl)-5-pyridin-4-yl-phenoxy]-hexyl}-2-(2-ethoxycarbonyl-ethyl)-phenoxy)-butyric acid ethyl ester

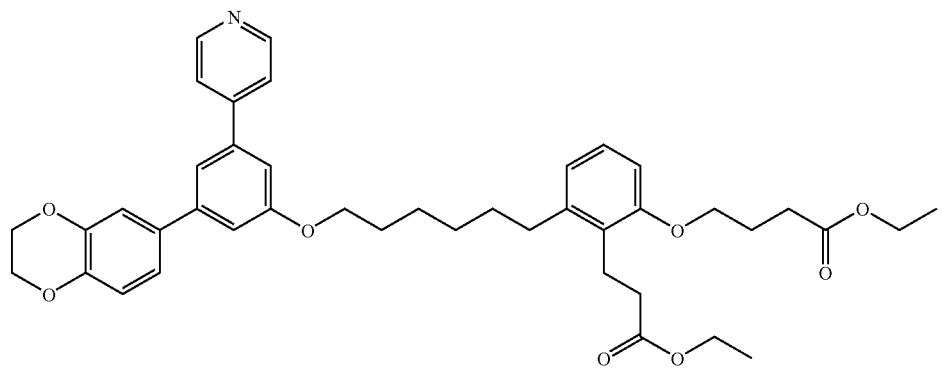

A similar procedure as described in Example 22, step 2 was used, starting from 4-[3-{6-[3-bromo-5-(2,3-dihydro-benzo[1,4]dioxin-6-yl)-phenoxy]-hexyl}-(2-(2-ethoxycarbonyl-ethyl)-phenoxy)-butyric acid ethyl ester (149 mg, 0.21 mmol) and pyridine-4-ylboronic acid (79 mg, 0.64 mmol) to obtain 4-[3-{6-[3-(2,3-dihydro-benzo[1,4]dioxin-6-yl)-5-pyridin-4-yl-phenoxy]-hexyl}-2-(2-ethoxycarbonyl-ethyl)-phenoxy)-butyric acid ethyl ester (89 mg, 60%) as a light yellow paste: ES(+)-HRMS m/e calculated for $C_{42}H_{49}NO_8$ (M+H)$^+$ 696.3531, found 696.3526.

Step 2: Preparation of 4-(2-(2-carboxy-ethyl)-3-{6-[3-(2,3-dihydro-benzo[1,4]dioxin-6-yl)-5-pyridin-4-yl-phenoxy]-hexyl}-phenoxy)-butyric acid

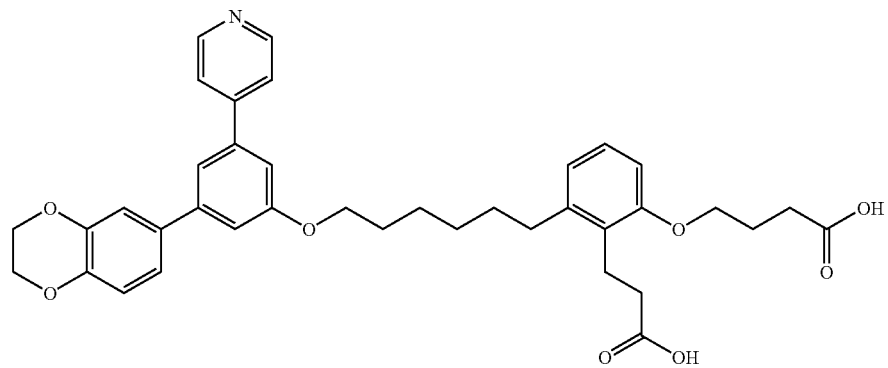

A similar procedure as described in Example 22, step 3 was used, starting from 4-[3-{6-[3-(2,3-dihydro-benzo[1,4]dioxin-6-yl)-5-pyridin-4-yl-phenoxy]-hexyl}-2-(2-ethoxycarbonyl-ethyl)-phenoxy)-butyric acid ethyl ester (75 mg, 0.1 mmol) and 1.0 N aqueous sodium hydroxide (6 mL) to afford 4-(2-(2-carboxy-ethyl)-3-{6-[3-(2,3-dihydro-benzo[1,4]dioxin-6-yl)-5-pyridin-4-yl-phenoxy]-hexyl}-phenoxy)-butyric acid (55 mg, 86%) as an amorphous off-white solid: ES(+)-HRMS m/e calculated for $C_{38}H_{41}NO_8$ (M+H)$^+$ 640.2905, found 640.2899.

Example 25

4-(2-(2-Carboxy-ethyl)-3-{6-[5-(2,3-dihydro-benzo[1,4]dioxin-6-yl)-2'-fluoro-biphenyl-3-yloxy]-hexyl}-phenoxy)-butyric acid

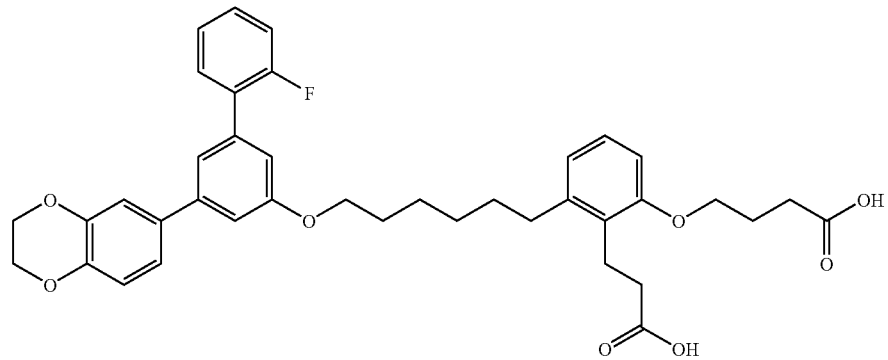

Step 1: Preparation of 4-[3-{6-[5-(2,3-dihydro-benzo[1,4]dioxin-6-yl)-2'-fluoro-biphenyl-3-yloxy]-hexyl}-(2-(2-ethoxycarbonyl-ethyl)-phenoxy)-butyric acid ethyl ester

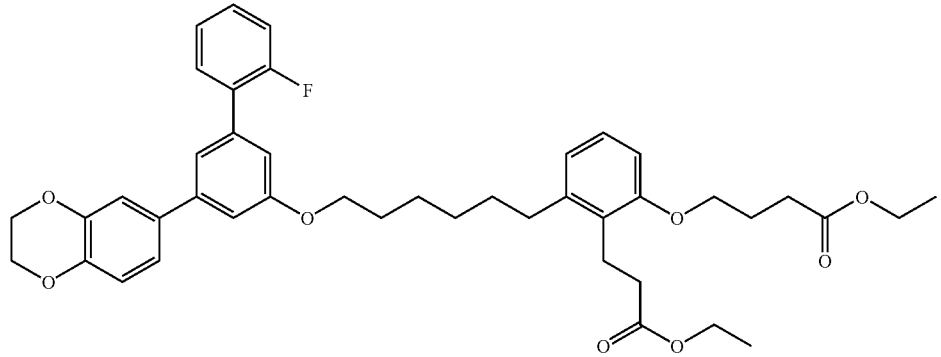

A similar procedure as described in Example 22, step 2 was used, starting from 4-[3-{6-[3-bromo-5-(2,3-dihydro-benzo[1,4]dioxin-6-yl)-phenoxy]-hexyl}-(2-(2-ethoxycarbonyl-ethyl)-phenoxy)-butyric acid ethyl ester (149 mg, 0.21 mmol) and 2-fluoro-phenylboronic acid (89 mg, 0.64 mmol) to obtain 4-[3-{6-[5-(2,3-dihydro-benzo[1,4]dioxin-6-yl)-2'-fluoro-biphenyl-3-yloxy]-hexyl}-(2-(2-ethoxycarbonyl-ethyl)-phenoxy)-butyric ethyl)-phenoxy)-butyric acid ethyl ester (89 mg, 59%) as a light yellow oil: ES(+)-HRMS m/e calculated for $C_{43}H_{49}FO_8$ $(M+Na)^+$ 735.3303, found 735.3296.

Step 2: Preparation of 4-(2-(2-carboxy-ethyl)-3-{6-[5-(2,3-dihydro-benzo[1,4]dioxin-6-yl)-2'-fluoro-biphenyl-3-yloxy]-hexyl}-phenoxy)-butyric acid

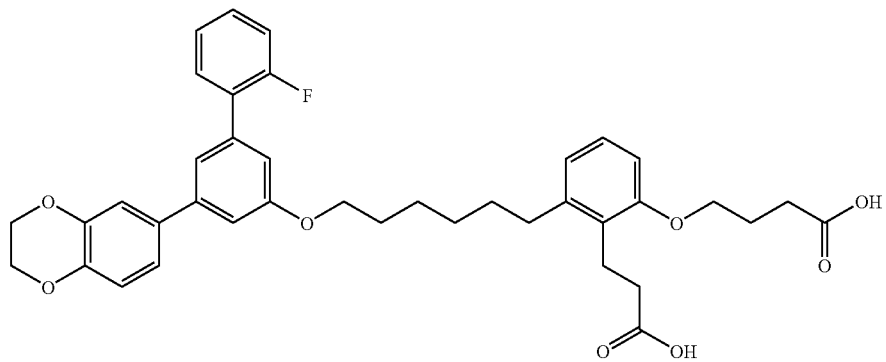

A similar procedure as described in Example 22, step 3 was used, starting from 4-[3-{6-[5-(2,3-dihydro-benzo[1,4]dioxin-6-yl)-2'-fluoro-biphenyl-3-yloxy]-hexyl}-(2-(2-ethoxycarbonyl-ethyl)-phenoxy)-butyric acid ethyl ester (78 mg, 0.11 mmol) and 1.0 N aqueous sodium hydroxide (6 mL) to afford 4-(2-(2-carboxy-ethyl)-3-{6-[5-(2,3-dihydro-benzo[1,4]dioxin-6-yl)-2'-fluoro-biphenyl-3-yloxy]-hexyl}-phenoxy)-butyric acid (18 mg, 25%) as an amorphous light yellow solid: ES(+)-HRMS m/e calculated for $C_{39}H_{41}FO_8$ $(M+Na)^+$ 679.2677, found 679.2684.

Example 26

4-(2-(2-Carboxy-ethyl)-3-{6-[3,5-di-pyridin-2-yl-phenoxy]-hexyl}-phenoxy)-butyric acid

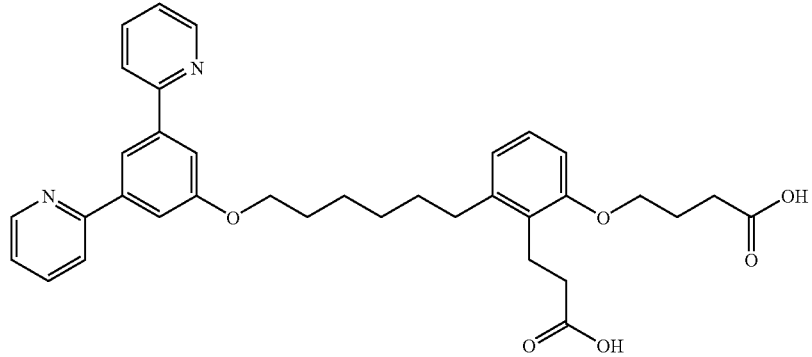

Step 1: Preparation of 4-[3-{6-(3,5-di-pyridin-2-yl-phenoxy)-hexyl}-(2-(2-ethoxycarbonyl-ethyl)-phenoxy)-butyric acid ethyl ester

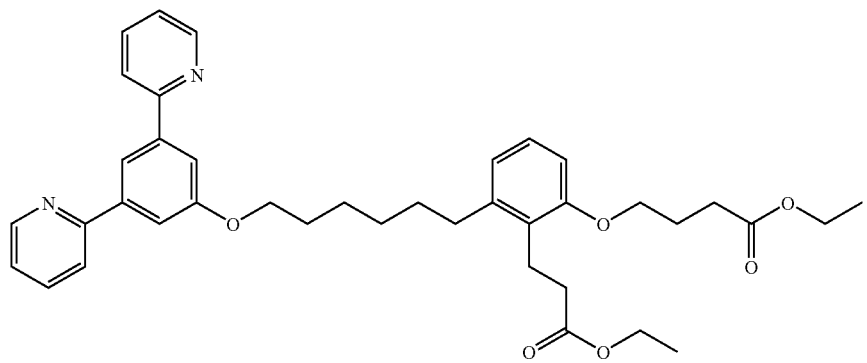

A similar procedure as described in Example 22, step 1 was used, starting from 2-bromo-pyridine (474 mg, 3.0 mmol), n-butyllithium (1.32 mL, 3.3 mmol), 2.5M), and 4-{3-[6-(3,5-dibromo-phenoxy)-hexyl]-2-(2-ethoxycarbonyl-ethyl)-phenoxy}-butyric acid ethyl ester (450 mg, 0.7 mmol) to obtain 4-[3-{6-(3,5-di-pyridin-2-yl-phenoxy)-hexyl}-(2-(2-ethoxycarbonyl-ethyl)-phenoxy)-butyric acid ethyl ester (72 mg, 16%) as a light yellow oil: ES(+)-HRMS m/e calculated for $C_{39}H_{46}N_2O_6$ (M+H)$^+$ 639.3429, found 639.3423.

Step 2: Preparation of 4-(2-(2-carboxy-ethyl)-3-{6-[3,5-di-pyridin-2-yl-phenoxy]-hexyl}-phenoxy)-butyric acid

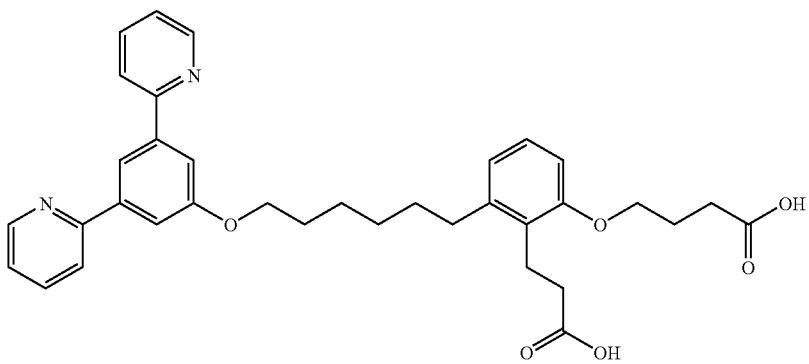

A similar procedure as described in Example 22, step 3 was used, starting from 4-[3-{6-(3,5-d i-pyridin-2-yl-phenoxy)-hexyl}-(2-(2-ethoxycarbonyl-ethyl)-phenoxy)-butyric acid ethyl ester (72 mg, 0.11 mmol) and 1.0 N aqueous sodium hydroxide (8 mL) to afford 4-(2-(2-carboxy-ethyl)-3-{6-[3,5-di-pyridin-2-yl-phenoxy]-hexyl}-phenoxy)-butyric acid (37 mg, 56%) as an amorphous white solid: ES(+)-HRMS 0m/e calculated for $C_{35}H_{38}N_2O_6$ (M+H)$^+$ 583.2803, found 583.2804.

Example 27

4-[3-{6-[3,5-Bis-(2,3-dihydro-benzo[1,4]dioxin-6-yl)-phenoxy]-hexyl}-2-(2-carboxy-ethyl)-phenoxy)-butyric acid

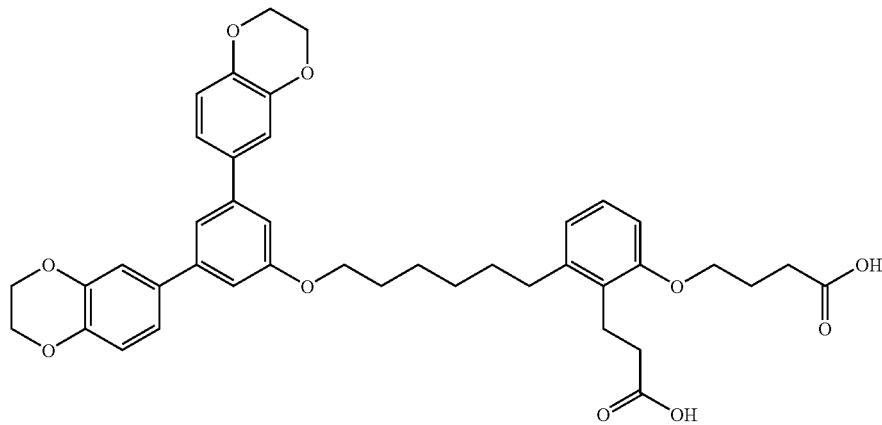

Step 1: Preparation of 3,5-bis-(2,3-dihydro-benzo[1,4]dioxin-6-yl)-phenol

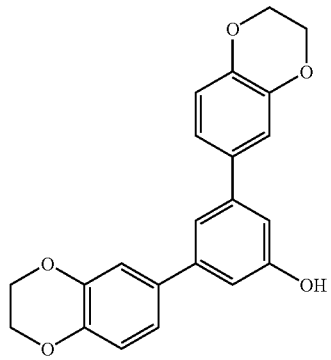

A solution of 3,5-dibromophenol (500 mg, 1.98 mmol) in dimethoxyethane (12.5 mL) was stirred for 5 minutes at room temperature under nitrogen atmosphere. Then, the solid tetrakis(triphenylphosphine)palladium(0) (496 mg, 0.43 mmol) was added at room temperature and the resulting light yellow solution was heated to 80° C. and stirred for 5 minutes. At this period, a solution of 1,4-benzodioxane-6-boronic acid (536 mg, 2.98 mmol) in ethanol (12.5 mL) was added followed by a solution of sodium carbonate (421 mg, 3.97 mmol) in water (0.5 mL). The resulting light yellow suspension was stirred for 4 h at reflux. Then, the reaction mixture was cooled to room temperature and diluted with water (20 mL) and ethyl acetate (30 mL). The two layers were separated and the aqueous layer was extracted with ethyl acetate (2×20 mL) and the combined organic extracts were washed with water (100 mL) and brine solution (100 mL). The organic layer was dried over anhydrous magnesium sulfate and filtration of the drying agent and removal of the solvent in vacuo gave the colored residue which was purified by using an ISCO 120 column, eluting with 10-30% ethyl acetate in hexanes to afford 3,5-bis-(2,3-dihydro-benzo[1,4]dioxin-6-yl)-phenol (386 mg, 54%) as an amorphous light brown solid: ES(+)-HRMS m/e calculated for $C_{22}H_{18}O_5$ (M+H)$^+$ 363.1227, found 363.1226.

Step 2: Preparation of 4-[3-{6-[3,5-bis-(2,3-dihydro-benzo[1,4]dioxin-6-yl)-phenoxy]-hexyl}-(2-(2-ethoxycarbonyl-ethyl)-phenoxy)-butyric acid ethyl ester

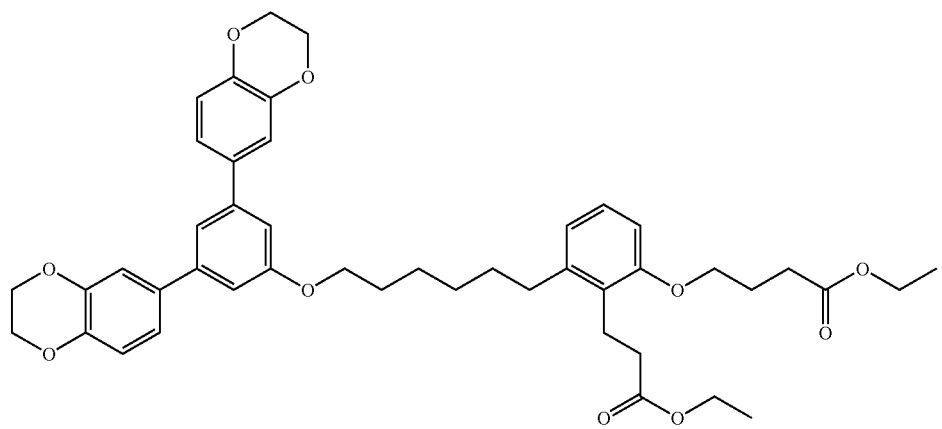

A similar procedure as described in Example 1, step 1 was used, starting from 4-[3-(6-bromo-hexyl)-2-(2-ethoxycarbonyl-ethyl)-phenoxy]-butyric acid ethyl ester (502 mg, 1.06 mmol), 3,5-bis-(2,3-dihydro-benzo[1,4]dioxin-6-yl)-phenol (386 mg, 1.06 mmol), and potassium carbonate (294 mg, 2.13 mmol) to afford 4-[3-{6-[3,5-bis-(2,3-dihydro-benzo[1,4]dioxin-6-yl)-phenoxy]-hexyl}-(2-(2-ethoxycarbonyl-ethyl)-phenoxy)-butyric acid ethyl ester (165 mg, 21%) as an amorphous white solid: ES(+)-HRMS m/e calculated for $C_{45}H_{52}O_{10}$ (M+Na)$^+$ 775.3452, found 775.3444.

Step 3: Preparation of 4-[3-{6-[3,5-bis-(2,3-dihydro-benzo[1,4]dioxin-6-yl)-phenoxy]-hexyl}-2-(2-carboxy-ethyl)-phenoxy)-butyric acid

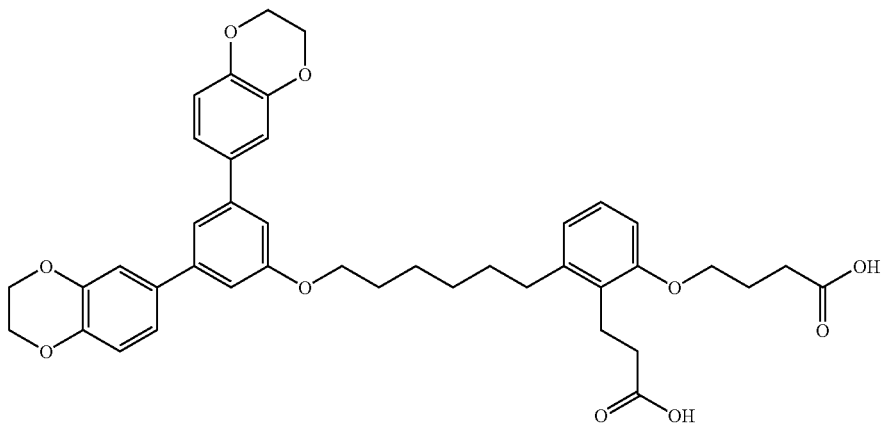

A similar procedure as described in Example 1, step 3 was used, starting from 4-[3-{6-[3,5-bis-(2,3-dihydro-benzo[1,4]dioxin-6-yl)-phenoxy]-hexyl}-(2-(2-ethoxycarbonyl-ethyl)-phenoxy)-butyric acid ethyl ester (156 mg, 0.21 mmol) and 1.0 N aqueous sodium hydroxide (2.1 mL) to give 4-[3-{6-[3,5-bis-(2,3-dihydro-benzo[1,4]dioxin-6-yl)-phenoxy]-hexyl}-2-(2-carboxy-ethyl)-phenoxy)-butyric acid (89 mg, 62%) as an amorphous white solid: ES(+)-HRMS m/e calculated for $C_{41}H_{44}O_{10}$ (M+Na)$^+$ 719.2826, found 719.2828.

Example 28

4-(2-(2-Carboxy-ethyl)-3-{6-[3-(1,6-dimethyl-2-oxo-4-trifluoromethyl-1,2-dihydro-pyridin-3-yl)-5-thiophen-3-yl-phenoxy]-hexyl}-phenoxy)-butyric acid

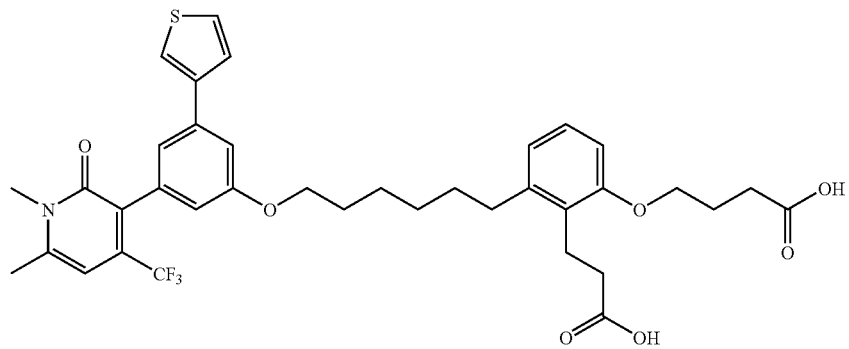

Step 1: Preparation of 4-[3-{6-[3-bromo-5-(1,6-dimethyl-2-oxo-4-trifluoromethyl-1,2-dihydro-pyridin-3-yl)-phenoxy]-hexyl}-(2-(2-ethoxycarbonyl-ethyl)-phenoxy)-butyric acid ethyl ester

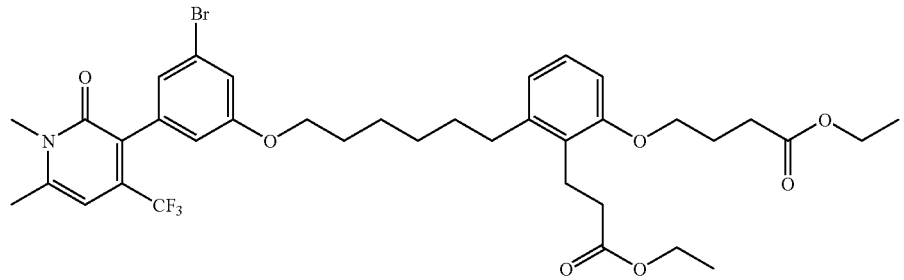

A mixture of zinc dust (1.3 g, 20 mmol) and dry tetrahydrofuran (2 mL) under nitrogen was treated with 1,2-dibromoethane (375 mg, 2.0 mmol). The zinc suspension was then heated with a heat gun to ebullition, allowed to cool, and heated again. This process was repeated three times to make sure the zinc dust was activated. The activated zinc dust was then treated with trimethylsilyl chloride (217 mg, 2.0 mmol), and the suspension was stirred for 15 min at room temperature. The reaction mixture was then treated dropwise with a solution of 1,6-dimethyl-2-oxo-4-trifluoromethyl-1,2-dihydro-3-iodo-pyridine (1.59 g, 5.0 mmol) in dry dimethylacetamide (5 mL) at ambient temperature. After the addition, the reaction mixture was stirred for 3 h at 70-75° C. and then stirred overnight at room temperature. The reaction mixture was diluted with dry tetrahydrofuran (5 mL), and the stirring was stopped to allow the excess zinc dust to settle down (~2 h). In a separate reaction flask, bis(dibenzylidene-acetone) palladium(0) (144 mg, 0.25 mmol) and tri-tolylphosphine (304 mg, 1.0 mmol) in dry tetrahydrofuran (2 mL) was stirred at room temperature under nitrogen for 10 min and then treated with 4-{3-[6-(3,5-dibromo-phenoxy)-hexyl]-2-(2-ethoxycarbonyl-ethyl)-phenoxy}-butyric acid ethyl ester (1.28 g, 2.0 mmol) in dry tetrahydrofuran (3 mL) and the above freshly prepared organozinc compound in tetrahydrofuran at room temperature. The resulting brick red suspension was heated to 60-65° C. for 24 h. Then, the reaction mixture was cooled to room temperature and then diluted with saturated ammonium chloride solution (100 mL). The organic compound was extracted into ethyl acetate (3×75 mL) and the combined organic extracts were washed with brine solution (200 mL). The organic layers were dried over anhydrous magnesium sulfate and filtration of the drying agent and concentration of the solvent gave the crude product which was purified by using an ISCO 120 g column, eluting with 0-20% ethyl acetate in hexanes to isolate 4-[3-{6-[3-bromo-5-(1,6-dimethyl-2-oxo-4-trifluoromethyl-1,2-dihydro-pyridin-3-yl)-phenoxy]-hexyl}-(2-(2-ethoxycarbonyl-ethyl)-phenoxy)-butyric acid ethyl ester (390 mg, 26%) as a light yellow oil: ES(+)-HRMS m/e calculated for $C_{37}H_{45}BrF_3NO_7$ (M+Na)$^+$ 774.2224, found 774.2215.

Step 2: Preparation of 4-[3-{6-[3-bromo-5-(1,6-dimethyl-2-oxo-4-trifluoromethyl-1,2-dihydro-pyridin-3-yl)-phenoxy]-hexyl}-(2-(2-carboxy-ethyl)-phenoxy)-butyric acid

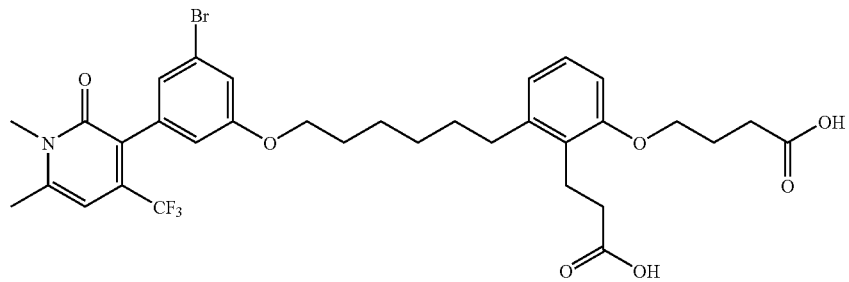

A similar procedure as described in Example 1, step 3 was used, starting from 4-[3-{6-[3-bromo-5-(1,6-dimethyl-2-oxo-4-trifluoromethyl-1,2-dihydro-pyridin-3-yl)-phenoxy]-hexyl}-(2-(2-ethoxycarbonyl-ethyl)-phenoxy)-butyric acid ethyl ester (537 mg, 0.71 mmol) and 1.0 N aqueous sodium hydroxide (7.1 mL) to give 4-[3-{6-[3-bromo-5-(1,6-dimethyl -2-oxo-4-trifluoromethyl-1,2-dihydro-pyridin-3-yl)-phenoxy]-hexyl}-(2-(2-carboxy-ethyl)-phenoxy)-butyric acid (260 mg, 52%) as an amorphous white solid: ES(+)-HRMS m/e calculated for $C_{33}H_{37}BrF_3NO_7$ (M+Na)$^+$ 718.1597, found 718.1601.

Step 3: Preparation of 4-(2-(2-carboxy-ethyl)-3-{6-[3-(1,6-dimethyl-2-oxo-4-trifluoromethyl-1,2-dihydro-pyridin-3-yl)-5-thiophen-3-yl-phenoxy]-hexyl}-phenoxy)-butyric acid

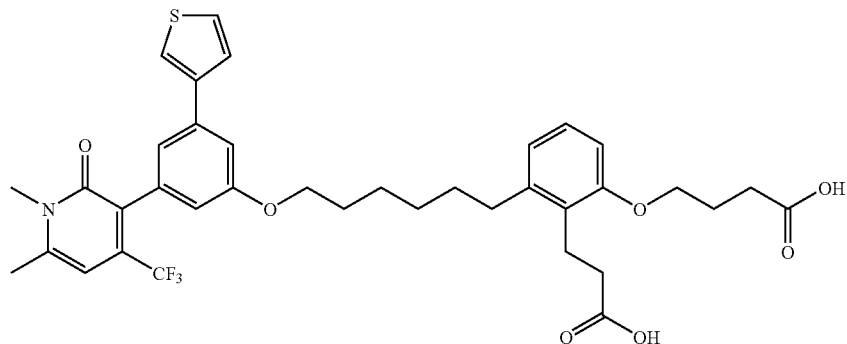

A similar procedure as described in Example 5, step 2 was used, starting from 4-[3-{6-[3-bromo-5-(1,6-dimethyl-2-oxo-4-trifluoromethyl-1,2-dihydro-pyridin-3-yl)-phenoxy]-hexyl}-(2-(2-carboxy-ethyl)-phenoxy)-butyric acid (50 mg, 0.07 mmol) and thiophen-3-ylboronic acid (19.4 mg, 0.14 mmol) to obtain 4-(2-(2-carboxy-ethyl)-3-{6-[3-(1,6-dimethyl-2-oxo-4-trifluoromethyl-1,2-dihydro-pyridin-3-yl)-5-thiophen-3-yl-phenoxy]-hexyl}-phenoxy)-butyric acid (18 mg, 36%) as an amorphous white solid: ES(+)-HRMS m/e calculated for $C_{37}H_{40}F_3NO_8S$ (M+Na)$^+$ 722.2370, found 722.2376.

Example 29

4-[3-{6-[3-Benzo[1,3]dioxol-5-yl-5-(1,6-dimethyl-2-oxo-4-trifluoromethyl-1,2-dihydro-pyridin-3-yl)-5-thiophen-3-yl-phenoxy]-hexyl}-(2-(2-carboxy-ethyl)-phenoxy)-butyric acid

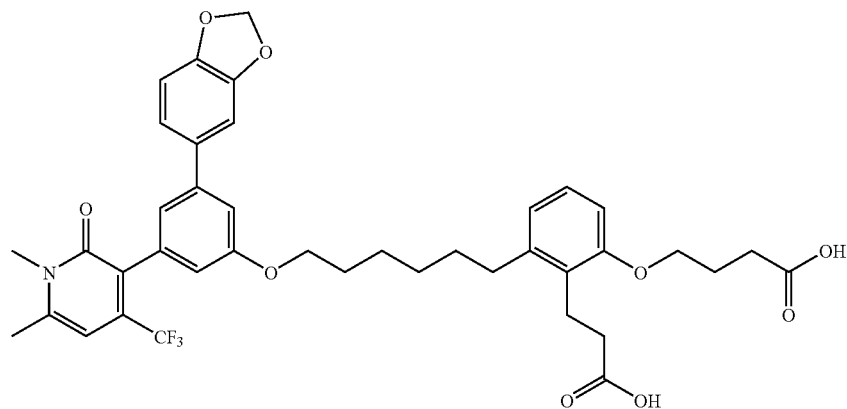

Step 1: Preparation of 4-[3-{6-[3-benzo[1,3]dioxol-5-yl-5-(1,6-dimethyl-2-oxo-4-trifluoromethyl-1,2-dihydro-pyridin-3-yl)-5-thiophen-3-yl-phenoxy]-hexyl}-(2-(2-ethoxycarbonyl-ethyl)-phenoxy)-butyric acid ethyl ester

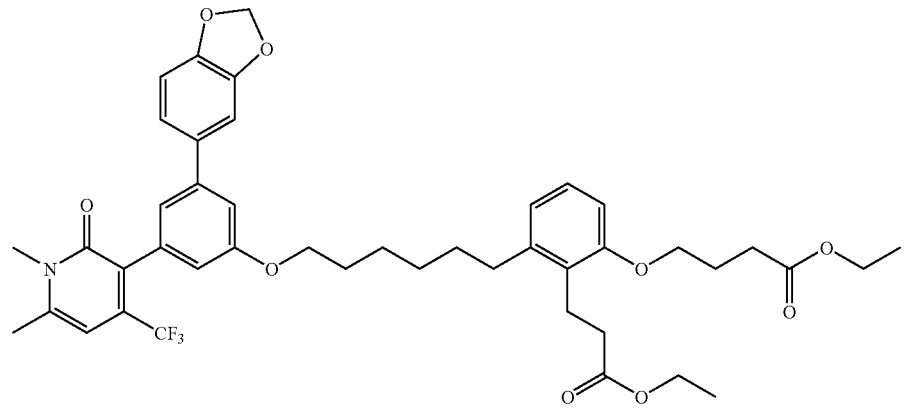

A similar procedure as described in Example 1, step 2 was used, starting from 4-[3-{6-[3-bromo-5-(1,6-dimethyl-2-oxo-4-trifluoromethyl-1,2-dihydro-pyridin-3-yl)-phenoxy]-hexyl}-(2-(2-ethoxycarbonyl-ethyl)-phenoxy)-butyric acid ethyl ester (130 mg, 0.17 mmol) and benzo[1,3]dioxol-5-yl-boronic acid (143 mg, 0.86 mmol) to obtain 4-[3-{6-[3-benzo[1,3]dioxol-5-yl-5-(1,6-dimethyl-2-oxo-4-trifluoromethyl-1,2-dihydro-pyridin-3-yl)-5-thiophen-3-yl-phenoxy]-hexyl}-(2-(2-ethoxycarbonyl-ethyl)-phenoxy)-butyric acid ethyl ester (20 mg, 15%) as a light yellow oil: ES(+)-HRMS m/e calculated for $C_{44}H_{50}F_3NO_9$ (M+Na)$^+$ 816.3330, found 816.3335.

Step 2: Preparation of 4-[3-{6-[3-benzo[1,3]dioxol-5-yl-5-(1,6-dimethyl-2-oxo-4-trifluoromethyl-1,2-dihydro-pyridin-3-yl)-5-thiophen-3-yl-phenoxy]-hexyl}-(2-(2-carboxy-ethyl)-phenoxy)-butyric acid

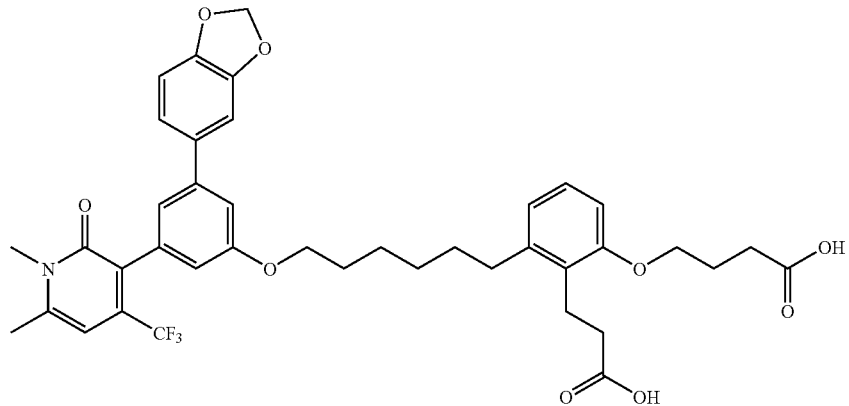

A similar procedure as described in Example 1, step 3 was used, starting from 4-[3-{6-[3-benzo[1,3]dioxol-5-yl-5-(1,6-dimethyl-2-oxo-4-trifluoromethyl-1,2-dihydro-pyridin-3-yl)-5-thiophen-3-yl-phenoxy]-hexyl}-(2-(2-ethoxycarbonyl-ethyl)-phenoxy)-butyric acid ethyl ester (15 mg, 0.018 mmol) and 1.0 N aqueous sodium hydroxide (2 mL) to afford 4-[3-{6-[3-benzo[1,3]dioxol-5-yl-5-(1,6-dimethyl-2-oxo-4-trifluoromethyl-1,2-dihydro-pyridin-3-yl)-5-thiophen-3-yl-phenoxy]-hexyl}-(2-(2-carboxy-ethyl)-phenoxy)-butyric acid (12 mg, 86%) as an amorphous off-white solid: ES(+)-HRMS m/e calculated for $C_{40}H_{42}F_3NO_9$ (M+H)$^+$ 738.2885, found 738.2884.

Example 30

4-(2-(2-Carboxy-ethyl)-3-{6-[5-(1,3-dimethyl-2,4-dioxo-1,2,3,4-tetrahydro-pyrimidin-5-yl)-4'-methoxy-biphenyl-3-yloxy]-hexyl}-phenoxy)-butyric acid

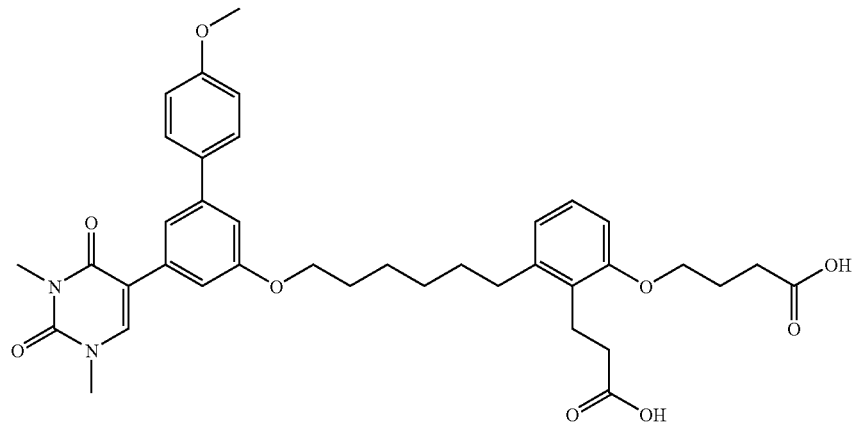

Step 1: Preparation of 4-[3-{6-[3-bromo-5-(1,3-dimethyl-2,4-dioxo-1,2,3,4-tetrahydro-pyrimidin-5-yl)-phenoxy]-hexyl}-(2-(2-ethoxycarbonyl-ethyl)-phenoxy)-butyric acid ethyl ester

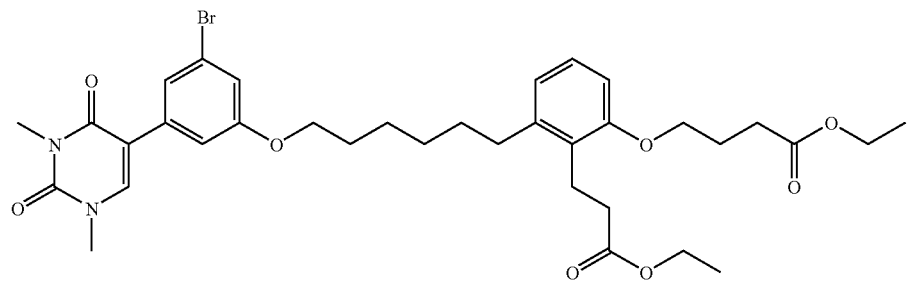

A similar procedure as described in Example 28, step 1 was used, starting from 5-iodo-1,3-dimethyl uracil (1.33 g, 5.0 mmol), zinc dust (980 mg, 15 mmol), and 4-{3-[6-(3,5-dibromo-phenoxy)-hexyl]-2-(2-ethoxycarbonyl-ethyl)-phenoxy}-butyric acid ethyl ester (1.92 g, 3.0 mmol) to obtain 4-[3-{6-[3-bromo-5-(1,3-dimethyl-2,4-dioxo-1,2,3,4-tetrahydro-pyrimidin-5-yl)-phenoxy]-hexyl}-(2-(2-ethoxycarbonyl-ethyl)-phenoxy)-butyric acid ethyl ester (280 mg, 13%) as a light yellow oil: ES(+)-HRMS m/e calculated for $C_{35}H_{45}BrN_2O_8$ $(M+Na)^+$ 723.2251, found 723.2246.

Step 2: Preparation of 4-[3-{6-[5-(1,3-dimethyl-2,4-dioxo-1,2,3,4-tetrahydro-pyrimidin-5-yl)-4'-methoxy-biphenyl-3-yloxy]-hexyl}-(2-(2-ethoxycarbonyl-ethyl)-phenoxy)-butyric acid ethyl ester

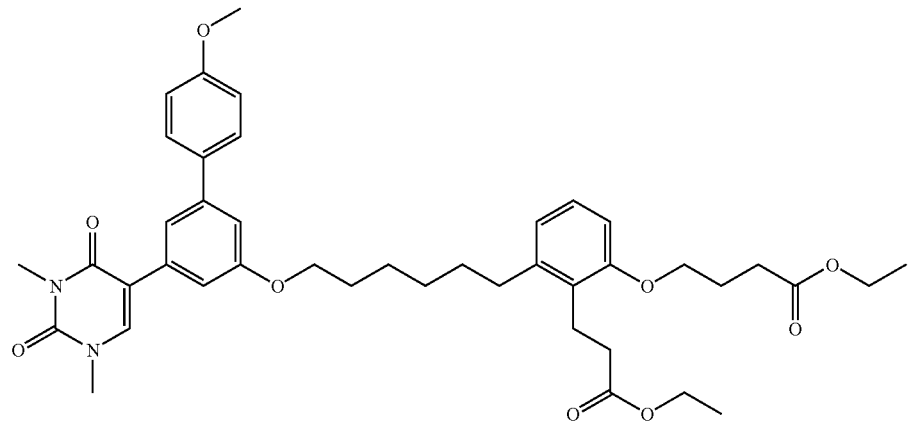

A similar procedure as described in Example 1, step 2 was used, starting from 4-[3-{6-[3-bromo-5-(1,3-dimethyl-2,4-dioxo-1,2,3,4-tetrahydro-pyrimidin-5-yl)-phenoxy]-hexyl}-(2-(2-ethoxycarbonyl-ethyl)-phenoxy)-butyric acid ethyl ester (130 mg, 0.18 mmol) and 4-methoxyphenylboronic acid (85 mg, 0.56 mmol) to obtain 4-[3-{6-[5-(1,3-dimethyl-2,4-dioxo-1,2,3,4-tetrahydro-pyrimidin-5-yl)-4'-methoxy-biphenyl-3-yloxy]-hexyl}-(2-(2-ethoxycarbonyl-ethyl)-phenoxy)-butyric acid ethyl ester (59 mg, 44%) as a light yellow oil: ES(+)-HRMS m/e calculated for $C_{42}H_{52}N_2O_9$ $(M+H)^+$ 729.3746, found 729.3742.

Step 3: Preparation of 4-(2-(2-carboxy-ethyl)-3-{6-[5-(1,3-dimethyl-2,4-dioxo-1,2,3,4-tetrahydro-pyrimidin-5-yl)-4'

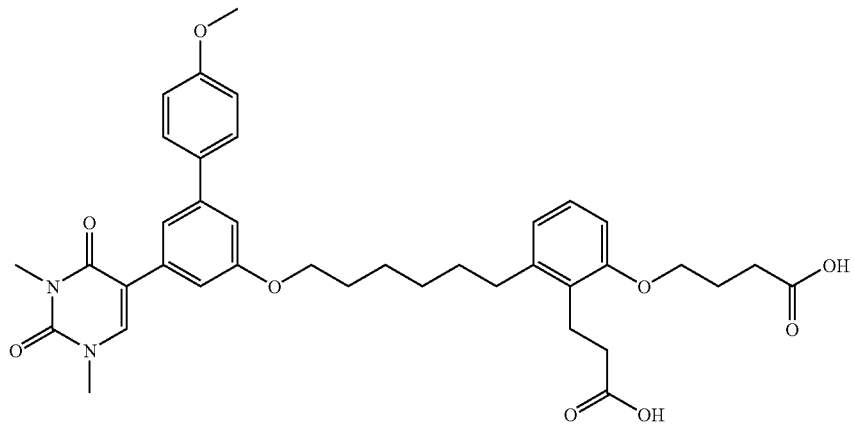

A similar procedure as described in Example 1, step 3 was used, starting from 4-[3-{6-[5-(1,3-dimethyl-2,4-dioxo-1,2,3,4-tetrahydro-pyrimidin-5-yl)-4'-methoxy-biphenyl-3-yloxy]-hexyl}-(2-(2-ethoxycarbonyl-ethyl)-phenoxy)-butyric acid ethyl ester (52 mg, 0.07 mmol) and 1.0 N aqueous sodium hydroxide (2 mL) to afford 4-(2-(2-carboxy-ethyl)-3-{6-[5-(1,3-dimethyl-2,4-dioxo-1,2,3,4-tetrahydro-pyrimidin-5-yl)-4'-methoxy-biphenyl-3-yloxy]-hexyl}-phenoxy)-butyric acid (13 mg, 28%) as an amorphous white solid:

ES(+)-HRMS m/e calculated for $C_{38}H_{44}N_2O_9$ (M+Na)$^+$ 695.2939, found 695.2928.

Example 31

4-(2-(2-Carboxy-ethyl)-3-{6-[5-(1,3-dimethyl-2,4-dioxo-1,2,3,4-tetrahydro-pyrimidin-5-yl)-biphenyl-3-yloxy]-hexyl}-phenoxy)-butyric acid

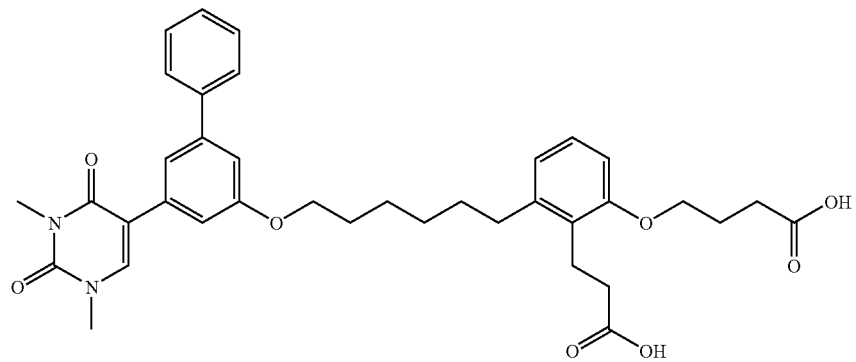

Step 1: Preparation of 4-[3-{6-[5-(1,3-dimethyl-2,4-dioxo-1,2,3,4-tetrahydro-pyrimidin-5-yl)-biphenyl-3-yloxy]-hexyl}-(2-(2-ethoxycarbonyl-ethyl)-phenoxy)-butyric acid ethyl ester

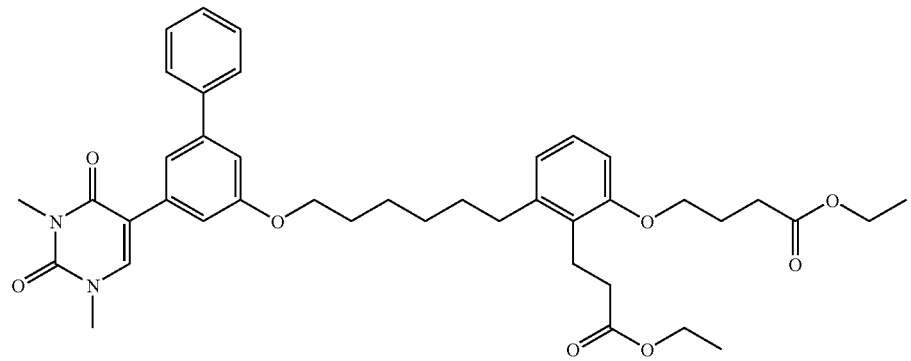

A similar procedure as described in Example 1, step 2 was used, starting from 4-[3-{6-[3-bromo-5-(1,3-dimethyl-2,4-dioxo-1,2,3,4-tetrahydro-pyrimidin-5-yl)-phenoxy]-hexyl}-(2-(2-ethoxycarbonyl-ethyl)-phenoxy)-butyric acid ethyl ester (27 mg, 0.04 mmol) and phenylboronic acid (23 mg, 0.19 mmol) to obtain 4-[3-{6-[5-(1,3-dimethyl-2,4-dioxo-1,2,3,4-tetrahydro-pyrimidin-5-yl)-biphenyl-3-yloxy]-hexyl}-(2-(2-ethoxycarbonyl-ethyl)-phenoxy)-butyric acid ethyl ester (8 mg, 30%) as a light yellow oil: ES(+)-LRMS m/e calculated for $C_{41}H_{50}N_2O_8$ (M+H)$^+$ 699.6, found 699.4.

Step 2: Preparation of 4-(2-(2-carboxy-ethyl)-3-{6-[5-(1,3-dimethyl-2,4-dioxo-1,2,3,4-tetrahydro-pyrimidin-5-yl)-biphenyl-3-yloxy]-hexyl}-phenoxy)-butyric acid

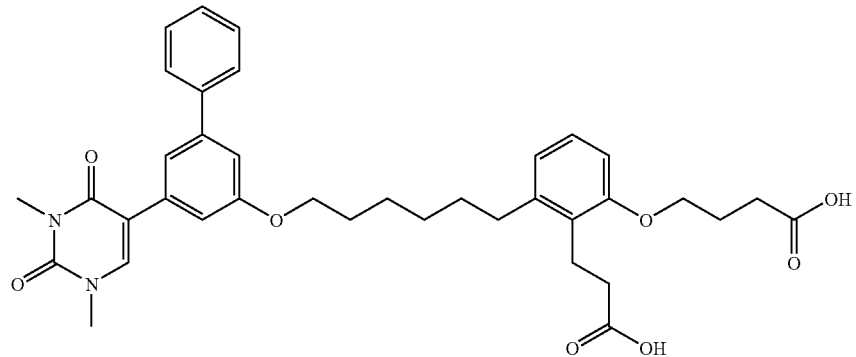

A similar procedure as described in Example 1, step 3 was used, starting from 4-[3-{6-[5-(1,3-dimethyl-2,4-dioxo-1,2,3,4-tetrahydro-pyrimidin-5-yl)-biphenyl-3-yloxy]-hexyl}-(2-(2-ethoxycarbonyl-ethyl)-phenoxy)-butyric acid ethyl ester (6.2 mg, 0.008 mmol) and 1.0 N aqueous sodium hydroxide (1 mL) to afford 4-(2-(2-carboxy-ethyl)-3-{6-[5-(1,3-dimethyl-2,4-dioxo-1,2,3,4-tetrahydro-pyrimidin-5-yl)-biphenyl-3-yloxy]-hexyl}-phenoxy)-butyric acid (5.2 mg, 91%) as an amorphous white solid: ES(+)-HRMS m/e calculated for $C_{37}H_{42}N_2O_8$ (M+Na)$^+$ 665.2833, found 665.2831.

Example 32

4-(2-(2-Carboxy-ethyl)-3-{6-[5-(1,3,6-trimethyl-2,4-dioxo-1,2,3,4-tetrahydro-pyrimidin-5-yl)-biphenyl-3-yloxy]-hexyl}-phenoxy)-butyric acid

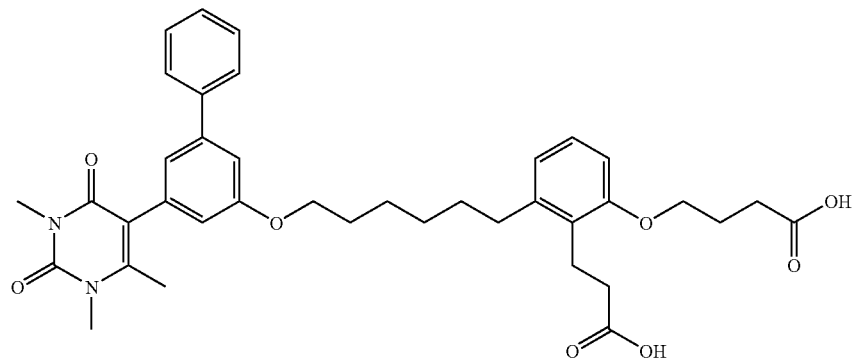

Step 1: Preparation of 4-[3-{6-[3-bromo-5-(1,3,6-trimethyl-2,4-dioxo-1,2,3,4-tetrahydro-pyrimidin-5-yl)-phenoxy]-hexyl}-(2-(2-ethoxycarbonyl-ethyl)-phenoxy)-butyric acid ethyl ester

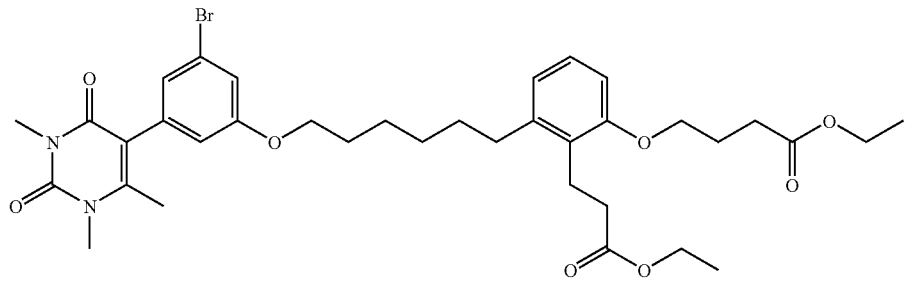

A similar procedure as described in Example 28, step 1 was used, starting from 5-iodo-1,3,6-trimethyl uracil (2.24 g, 8.0 mmol), zinc dust (1.96 g, 30 mmol), and 4-{3-[6-(3,5-dibromo-phenoxy)-hexyl]-2-(2-ethoxycarbonyl-ethyl)-phenoxy}-butyric acid ethyl ester (3.2 g, 5.0 mmol) to obtain 4-[3-{6-[3-bromo-5-(1,3,6-trimethyl-2,4-dioxo-1,2,3,4-tetrahydro-pyrimidin-5-yl)-phenoxy]-hexyl}-(2-(2-ethoxycarbonyl-ethyl)-phenoxy)-butyric acid ethyl ester (510 mg, 14%) as a light yellow oil: ES(+)-HRMS m/e calculated for $C_{36}H_{47}BrN_2O_8$ $(M+H)^+$ 715.2589, found 715.2581.

Step 2: Preparation of 4-2-(2-ethoxycarbonyl-ethyl)-[3-{6-[5-(1,3,6-trimethyl-2,4-dioxo-1,2,3,4-tetrahydro-pyrimidin-5-yl)-biphenyl-3-yloxy]-hexyl}-phenoxy)-butyric acid ethyl ester

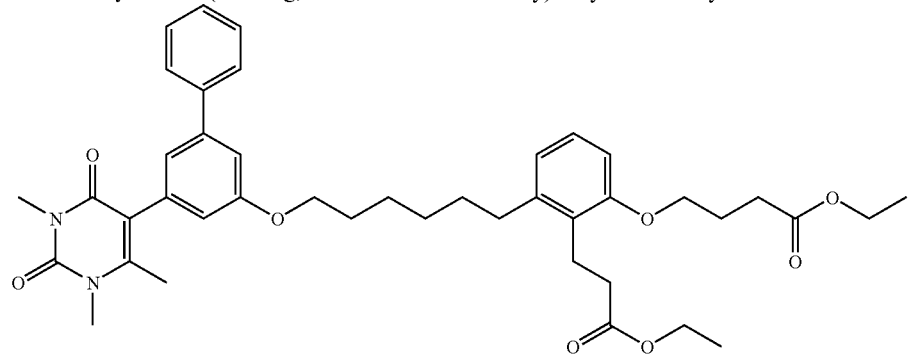

A similar procedure as described in Example 1, step 2 was used, starting from 4-[3-{6-[3-bromo-5-(1,3,6-trimethyl-2,4-dioxo-1,2,3,4-tetrahydro-pyrimidin-5-yl)-phenoxy]-hexyl}-(2-(2-ethoxycarbonyl-ethyl)-phenoxy)-butyric acid ethyl ester (113 mg, 0.16 mmol) and phenylboronic acid (96 mg, 0.78 mmol) to obtain 4-2-(2-ethoxycarbonyl-ethyl)-[3-{6-[5-(1,3,6-trimethyl-2,4-dioxo-1,2,3,4-tetrahydro-pyrimidin-5-yl)-biphenyl-3-yloxy]-hexyl}-phenoxy)-butyric acid ethyl ester (45 mg, 40%) as a light yellow oil: ES(+)-HRMS m/e calculated for $C_{42}H_{52}N_2O_8$ $(M+H)^+$ 713.3797, found 713.3784.

Step 3: Preparation of 4-(2-(2-carboxy-ethyl)-3-{6-[5-(1,3,6-trimethyl-2,4-dioxo-1,2,3,4-tetrahydro-pyrimidin-5-yl)-biphenyl-3-yloxy]-hexyl}-phenoxy)-butyric acid

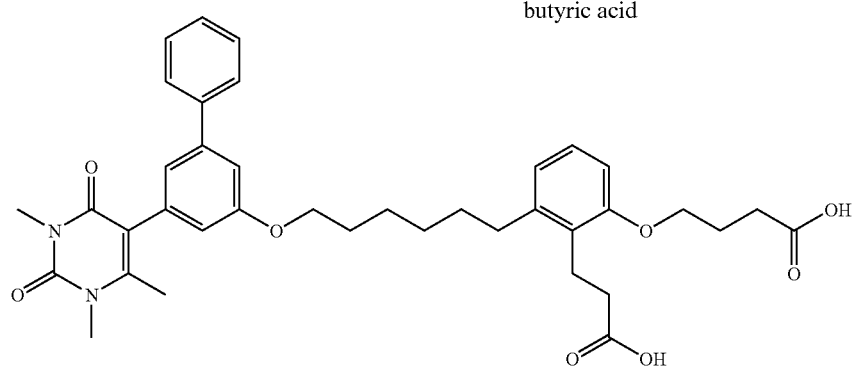

A similar procedure as described in Example 1, step 3 was used, starting from 4-2-(2-ethoxycarbonyl-ethyl)-[3-{6-[5-(1,3,6-trimethyl-2,4-dioxo-1,2,3,4-tetrahydro-pyrimidin-5-yl)-biphenyl-3-yloxy]-hexyl}-phenoxy)-butyric acid ethyl ester (39 mg, 0.05 mmol) and 1.0 N aqueous sodium hydroxide (2 mL) to afford 4-(2-(2-carboxy-ethyl)-3-{6-[5-(1,3,6-trimethyl-2,4-dioxo-1,2,3,4-tetrahydro-pyrimidin-5-yl)-biphenyl-3-yloxy]-hexyl}-phenoxy)-butyric acid (30 mg, 86%) as an amorphous white solid: ES(+)-HRMS m/e calculated for $C_{38}H_{44}N_2O_8$ (M+Na)$^+$ 679.2990, found 679.2990.

Preparation of Preferred Nitrogen-Linked Compounds

Step 1: 3,5-diiodonitrobenzene

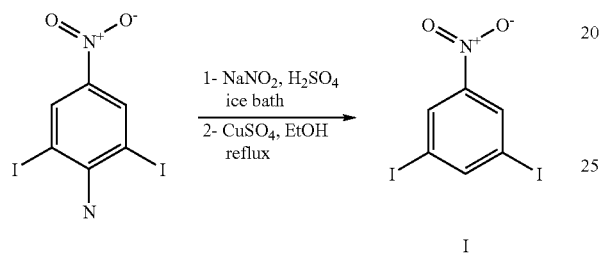

To an iced-cooled solution of concentrated $H_2SO_4$ (95-98%, 100 mL) was added in small portions 2,6-diiodo-4-nitroaniline (25 g, 64.1 mmol). After complete dissolution of the aniline, $NaNO_2$ (9.7 g, 141 mmol) was added at 0° C. and stirred for 2 h at this temperature. Then, the viscous black solution was poured into ice (500 g) and any solid material was filtered off. The brown filtrate obtained was carefully poured into a refluxed solution of $CuSO_4.5H_2O$ (1.0 g, 6.4 mmol) in EtOH (300 mL) and stirred at reflux for 2 h to reduce the diazonium salt. After cooling to room temperature, 3,5-diiodonitrobenzene precipitated from the reaction mixture. After filtration, the product was then recrystallized with hot EtOH to give 15.92 g (67%) of fine brown needles. HR-MS-EI(+): calculated for $C_6H_3I_2NO_2$ [M] 374.8253, found 374.8354.

Step 2: 3,5-diiodoaniline

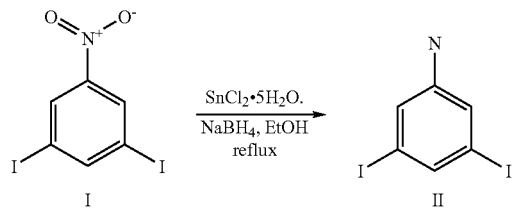

To a suspension of 3,5-diiodonitrobenzene (10 g, 26.7 mmol) in anhydrous EtOH (100 mL) was added $SnCl_2.2H_2O$ (30 g, 133.6 mmol). The reaction mixture was brought to boil and a solution of $NaBH_4$ (508 mg, 13.4 mmol) in EtOH (50 mL) was added slowly then stirred at reflux for 1 h. After the reaction was cooled down to 0° C., the mixture was neutralized with a solution of 3M NaOH (200 mL). The aniline derivative was extracted with chloroform, dried over $Na_2SO_4$ and evaporated under reduced pressure to afford 6.4 g of 3,5-diiodoaniline 11(70%) as a white solid. HR-ES(+): calculated for $C_6H_5I_2N$ [M] 345.8584, found 345.8583.

Step 3: N-tert-butoxycarbonyl-3,5-diiodoaniline

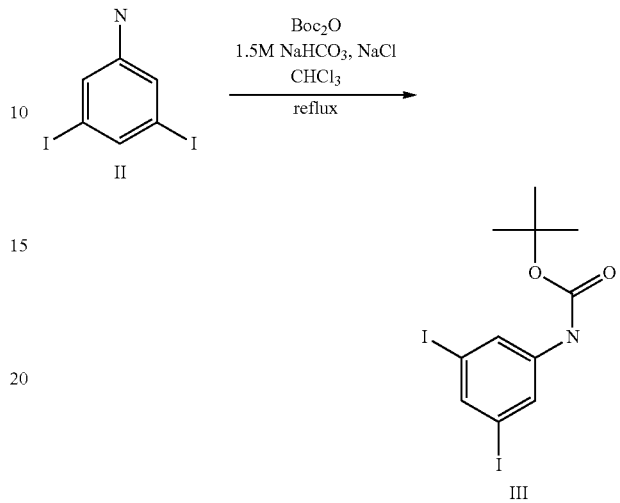

To a solution of 3,5-diiodoaniline (5 g, 14.5 mmol) in chloroform (60 mL) were added a solution of 1.5 M $NaHCO_3$ (6.3 g in 50 ml $H_2O$), NaCl (4.3 g, 74 mmol) and di-tert-butyl dicarbonate (7.9 g, 36.3 mmol). The reaction mixture was refluxed for 48 h. After the reaction mixture was cooled down at room temperature, the crude product was extracted with chloroform and water. The organic phase was washed with brine, dried over $Na_2SO_4$ and evaporated under reduced pressure. Purification using Isco chromatography (Hexanes/EtOAc:95:5) afforded the desired Boc-protected aniline contaminated with $BOC_2O$. Recrystallization was achieved by first solubilizing the crude material with EtOH (50 mL) then by adding $H_2O$ (10 mL) and afforded the pure N-tert-butoxycarbonyl-3,5-diiodoaniline (3.9 g, 61%) as a white solid. HR-MS-EI(+): calculated for $C_{11}H_{13}I_2NO_2$ [M] 444.9036, found 444.9045.

Step 4: 4-[3-{6-[tert-Butoxycarbonyl-(3,5-diiodo-phenyl)-amino]-hexyl}-2-(2-ethoxycarbonyl-ethyl)-phenoxy]-butyric acid ethyl ester

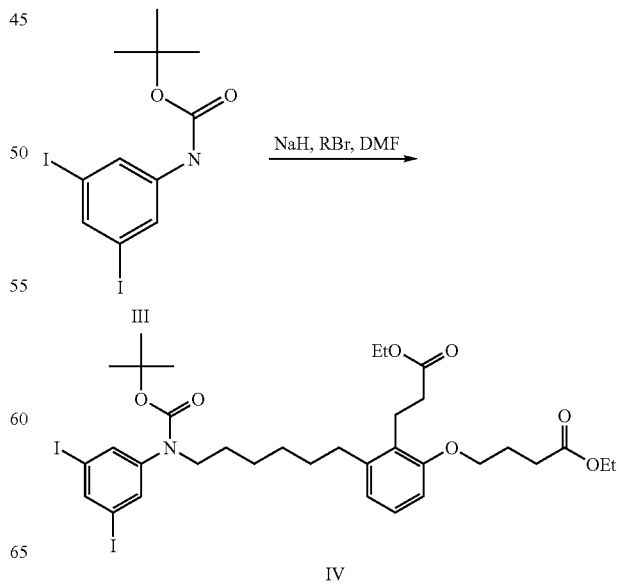

To a mixture of the 4-[3-(6-bromo-hexyl)-2-(2-ethoxycarbonyl-ethyl)-phenoxy]-butyric acid ethyl ester (3.6 g, 7.6 mmol), N-tert-butoxycarbonyl-3,5-diiodoaniline (2.8 g, 6.3 mmol) in DMF (60 mL) was added NaH (60% dispersion in mineral oil), (504 mg, 12.6 mmol). The reaction mixture was stirred at room temperature for 24 h. The reaction mixture was diluted with EtOAc (120 mL), then washed with brine. The organic phase was dried over $Na_2SO_4$ and evaporated under reduced pressure. Purification by Isco chromatography (Gradient of 20 minutes from hexanes to Hexanes/EtOAc 80%) afforded the title compound (3.3 g, 60%) as a light yellow oil. HR-ES(+): calculated for $C_{34}H_{47}N_1O_7I_2$ $(M+Na)^+$ 858.1334, found 858.1325.

Step 5: 4-[3-{6-[tert-Butoxycarbonyl-(3,5-diiodo-phenyl)-amino]-hexyl}-2-(2-carboxy-ethyl)-phenoxy]-butyric acid

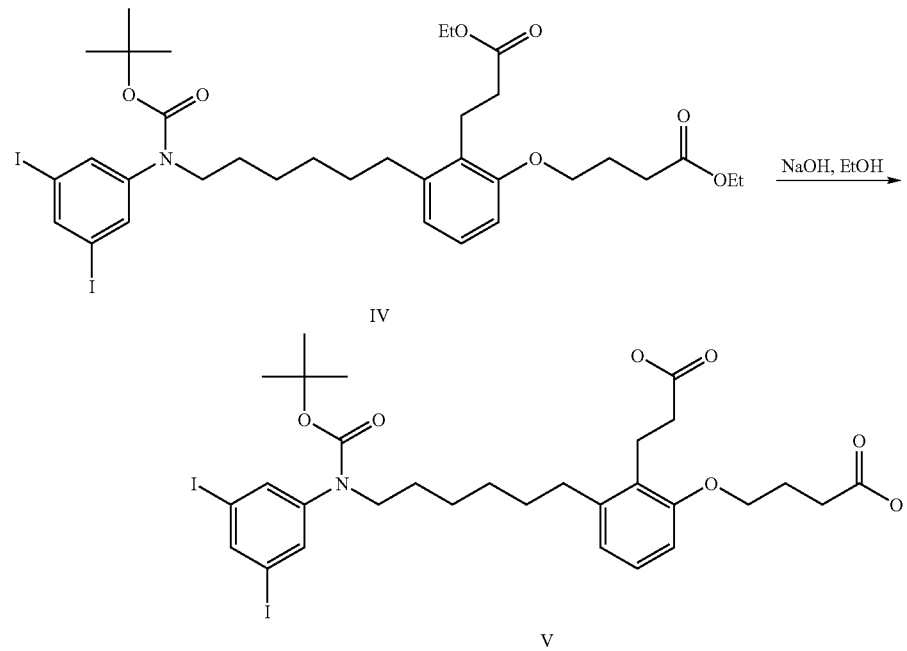

To a solution of compound IV (2.7 g, 3.2 mmol) in EtOH (70 mL) was added NaOH (1.5 g, 30.6 mmol). The reaction mixture was heated at 60° C. and stirred at this temperature for 12 h. When the reaction was completed, a white solid precipitated in the reaction mixture. After cooling to room temperature, a solution of HCl 10% (50 mL) is added to dissolve the salt formed. The solution is then extracted with EtOAc (100 mL), the organic phase dried over $Na_2SO_4$ and evaporated under reduced pressure to afford the desired diacid (2.2 g, 88%) as a light yellow oil. HR-ES (+): calculated for $C_{30}H_{39}N_1O_7I_2$ $(M+Na)^+$ 802.0708, found 802.0701 m/z.

Step 6: Synthesis of Compounds VIa-g

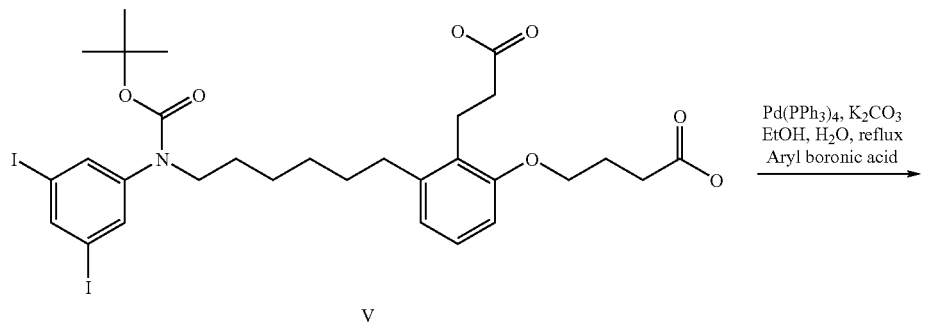

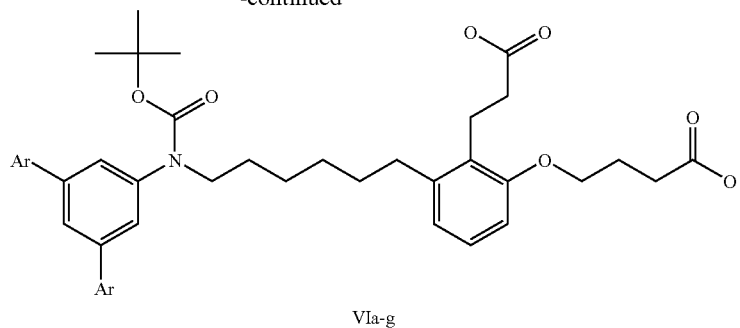

VIa-g

To a solution of 4-[3-{6-[tert-butoxycarbonyl-(3,5-diiodo-phenyl)-amino]-hexyl}-2-(2-carboxy-ethyl)-phenoxy]-butyric acid (100 mg, 0.13 mmol) in EtOH (4 mL)/H$_2$O (1 mL) were added boronic acid (0.51 mmol), potassium carbonate (71 mg, 0.51 mmol) and Pd(PPh$_3$)$_4$ (7 mg, 0.0064 mmol). The mixture was heated at 78° C. for 4 h and then cooled to room temperature. A solution of HCl 10% was added (5 mL). The resulting solution was then extracted with EtOAc (10 mL).

The organic phase was dried over Na$_2$SO$_4$ and concentrated under reduced pressure. Purification by HPLC afforded the desired 3,5-diaryl aniline analog.

Compound VIa: 4-[3-[6-(tert-Butoxycarbonyl-[1,1';3',1"]terphenyl-5'-yl-amino)-hexyl]-2-(2-carboxy-ethyl)-phenoxy]-butyric acid

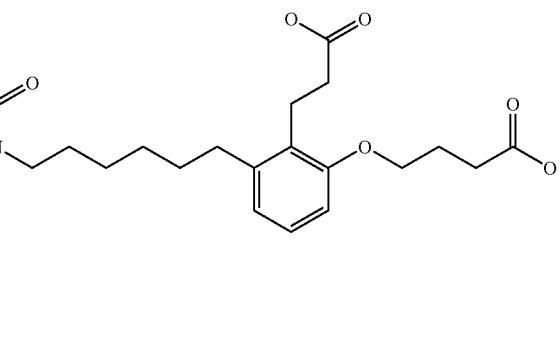

The title compound was prepared by following procedures in step 6 with 2-phenylboronic acid. HR-ES (+): calculated for C$_{42}$H$_{49}$N$_1$O$_7$ (M+Na)$^+$ 702.3401, found 702.3396 m/z.

Compound VIb: 4-[3-{6-[tert-Butoxycarbonyl-(3,5-di-thiophen-3-yl-phenyl)-amino]-hexyl}-2-(2-carboxy-ethyl)-phenoxy]-butyric acid

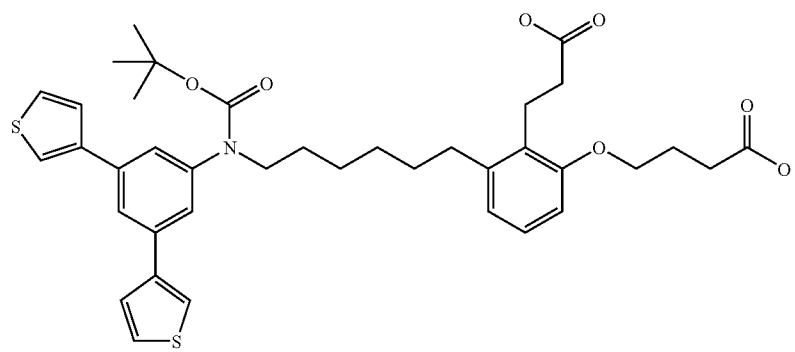

The title compound was prepared by following procedures in step 6 with 3-thiopheneboronic acid.

LCMS: calculated for $C_{38}H_{45}NO_7S_2$ $(M+Na)^+$ 714 found 713.8

Compound VIc: 4-[3-{6-[(3,5-Bis-benzo[1,3]dioxol-5-yl-phenyl)-tert-butoxycarbonyl-amino]-hexyl}-2-(2-carboxy-ethyl)-phenoxy]-butyric acid

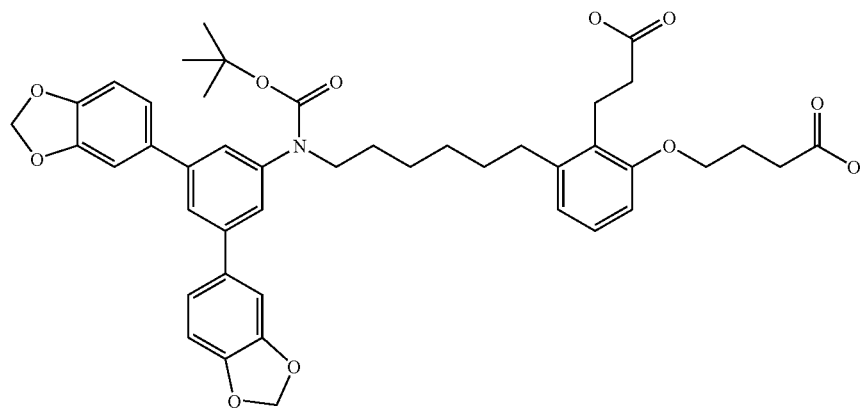

The title compound was prepared by following procedures in step 6 with benzo[1,3]dioxol-5-yl-boronic acid.

LCMS: calculated for $C_{44}H_{49}NO_{11}$ $(M+Na)^+$ 790 found 790.6

Compound VId: 4-[3-{6-[tert-Butoxycarbonyl-(4,4"-dichloro-[1,1';3',1"]terphenyl-5'-yl)-amino]-hexyl}-2-(2-carboxy-ethyl)-phenoxy]-butyric acid

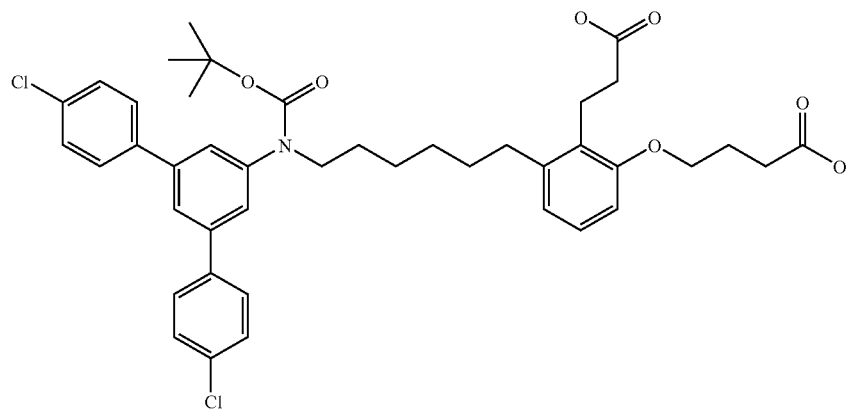

The title compound was prepared by following procedures in step 6 with 4-chlorophenylboronic acid.

LCMS: calculated for $C_{42}H_{47}C_{l2}NO_7$ $(M+H)^+$ (—BOC) 648, found 648.2 m/z.

Compound VIe: 4-[3-{6-[tert-Butoxycarbonyl-(3,3"-difluoro-[1,1';3',1"]terphenyl-5'-yl)-amino]-hexyl}-2-(2-carboxy-ethyl)-phenoxy]-butyric acid

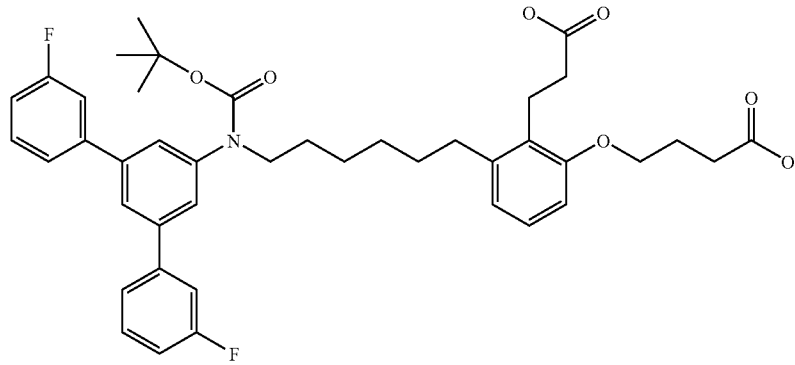

The title compound was prepared by following procedures in step 6 with 3-fluorophenylboronic acid.
LCMS: calculated for $C_{42}H_{47}F_2NO_7$ $(M+H)^+$ (—BOC) 616, found 616.2 m/z.

Compound VIf: 4-[3-{6-[(4,4"-Bis-trifluoromethoxy-[1,1';3',1"]terphenyl-5'-yl)-tert-butoxycarbonyl-amino]-hexyl}-2-(2-carboxy-ethyl)-phenoxy]-butyric acid

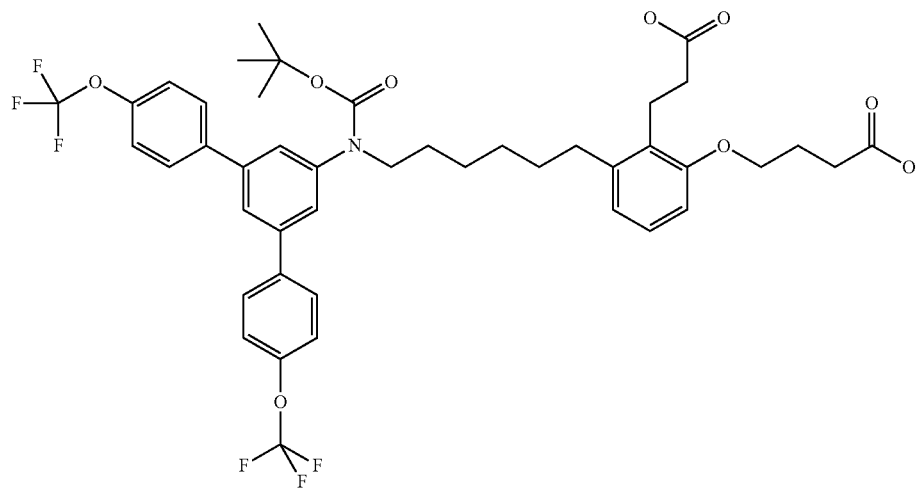

The title compound was prepared by following procedures in step 6 with 4-trifluoromethoxyphenylboronic acid.
LCMS: calculated for $C_{44}H_{47}F_6NO_9$ $(M+H)^+$ (—BOC) 748, found 748.4 m/z.

Compound VIg: 4-[3-(6-{[3,5-Bis-(2,3-dihydro-benzo[1,4]dioxin-6-yl)-phenyl]-tert-butoxycarbonyl-amino}-hexyl)-2-(2-carboxy-ethyl)-phenoxy]-butyric acid

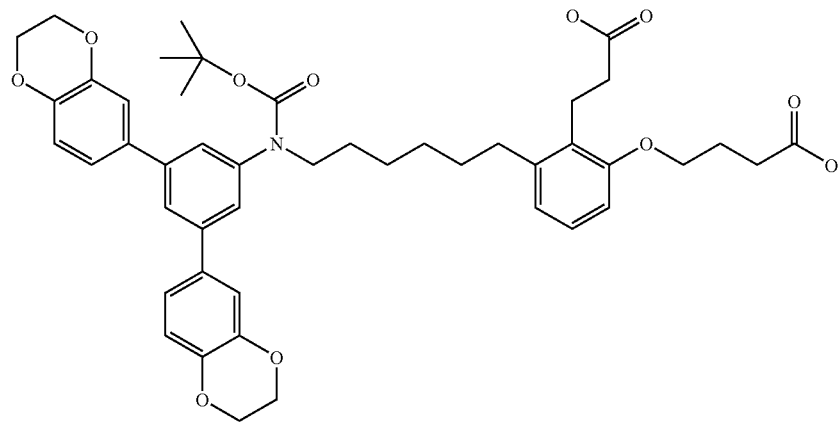

The title compound was prepared by following procedures in step 6 with 1,4-benzodioxane-6-boronic acid.

LCMS: calculated for $C_{46}H_{53}NO_{11}$ $(M+H)^+$ (—BOC) 696, found 696.0 m/z.

Step 7: Synthesis of Most Preferred Compounds

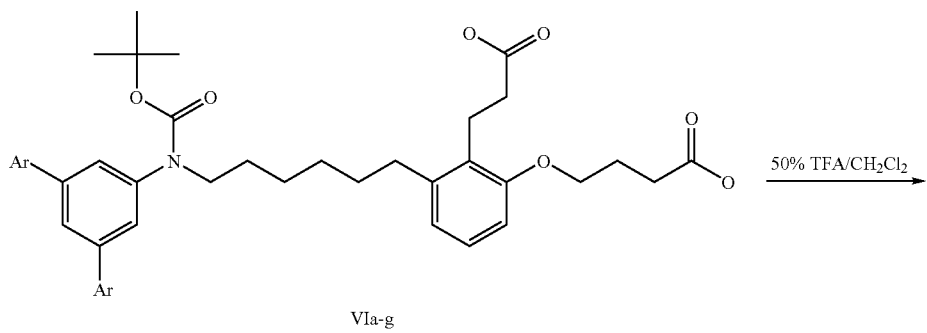

VIa-g

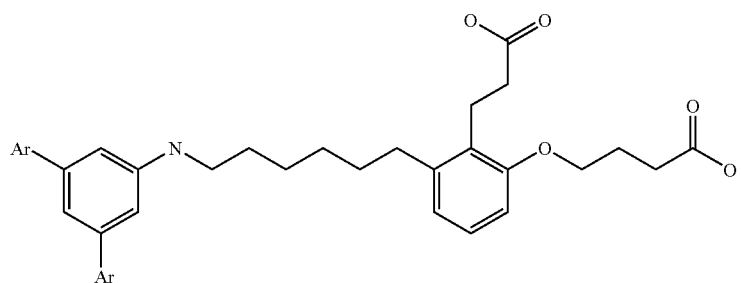

Examples 34-40

Removal of the Boc protecting group was achieved by treating compounds VIa-g with a solution of 50% TFA/$CH_2Cl_2$ (4 mL) and allowing the reaction mixture stir at room temperature for 2 h. The reaction mixture was then evaporated under reduced pressure. The compounds were isolated by preparative HPLC

Example 34

4-{2-(2-Carboxy-ethyl)-3-[6-([1,1";3',1"]terphenyl-5'-ylamino)-hexyl]-phenoxy}-butyric acid

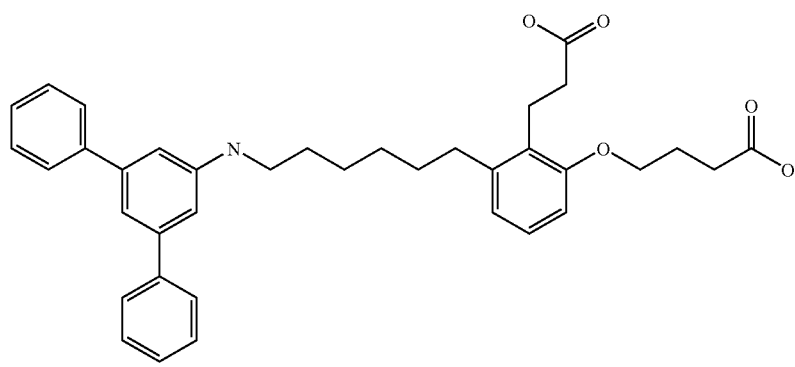

The title compound was prepared by following procedures in step 7 with 4-[3-[6-(tert-Butoxycarbonyl-[1,1';3',1"]terphenyl-5'-yl-amino)-hexyl]-2-(2-carboxy-ethyl)-phenoxy]-butyric acid (compound VIa).

ES(+)-HRMS m/e calcd for $C_{37}H_{41}NO_5$ $(M+H)^+$ 580.3058, found 580.3053.

Example 35

4-{2-(2-Carboxy-ethyl)-3-[6-(3,5-di-thiophen-3-yl-phenylamino)-hexyl]-phenoxy}-butyric acid

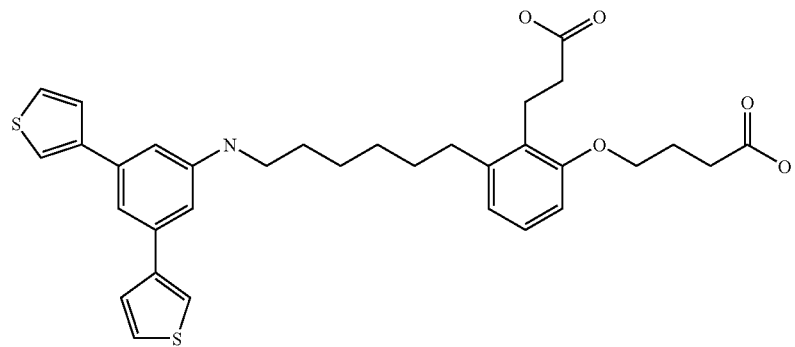

The title compound was prepared by following procedures in step 7 with 4-[3-{6-[tert-Butoxycarbonyl-(3,5-di-thiophen-3-yl-phenyl)-amino]-hexyl}-2-(2-carboxy-ethyl)-phenoxy]-butyric acid (compound VIb).

ES(+)-HRMS m/e calcd for $C_{33}H_{37}NO_5S_2$ $(M+H)^+$ 592.2186, found 592.2184.

Example 36

4-[3-[6-(3,5-Bis-benzo[1,3]dioxol-5-yl-phenylamino)-hexyl]-2-(2-carboxy-ethyl)-phenoxy]-butyric acid

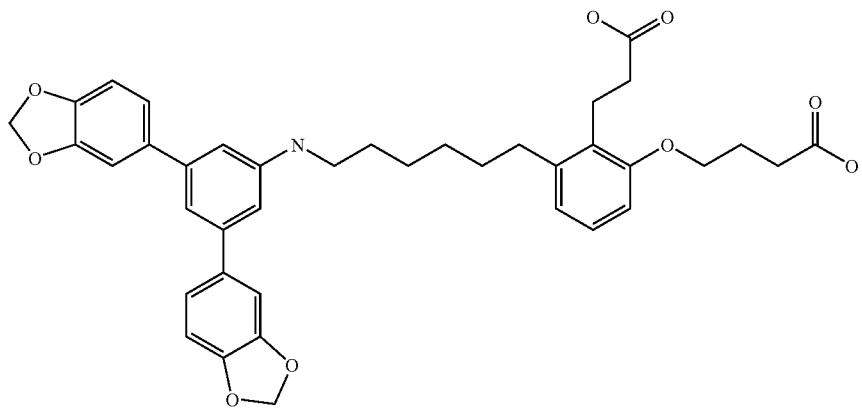

The title compound was prepared by following procedures in step 7 with 4-[3-{6-[(3,5-Bis-benzo[1,3]dioxol-5-yl-phenyl)-tert-butoxycarbonyl-amino]-hexyl}-2-(2-carboxy-ethyl)-phenoxy]-butyric acid (compound VIc).

ES(+)-HRMS m/e calcd for $C_{39}H_{41}NO_9$ (M+H)$^+$ 668.2854, found 668.2848.

Example 37

4-{2-(2-Carboxy-ethyl)-3-[6-(4,4''-dichloro-[1,1';3',1'']terphenyl-5'-ylamino)-hexyl]-phenoxy}-butyric acid

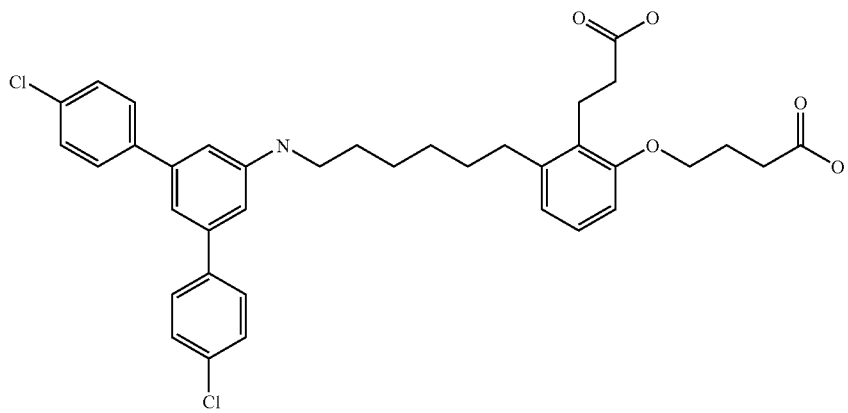

The title compound was prepared by following procedures in step 7 with 4-[3-{6-[tert-Butoxycarbonyl-(4,4''-dichloro-[1,1';3',1'']terphenyl-5'-yl)-amino]-hexyl}-2-(2-carboxy-ethyl)-phenoxy]-butyric acid (compound VId).

ES(+)-HRMS m/e calcd for $C_{37}H_{39}Cl_2NO_5$ (M+H)$^+$ 648.2278, found 648.2280.

Example 38

4-{2-(2-Carboxy-ethyl)-3-[6-(3,3''-difluoro-[1,1';3',1'']terphenyl-5'-ylamino)-hexyl]-phenoxy}-butyric acid

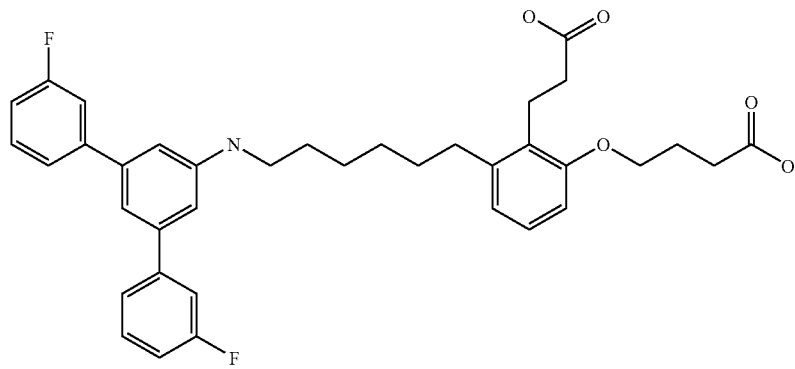

The title compound was prepared by following procedures in step 7 with 4-[3-{6-[tert-Butoxycarbonyl-(3,3''-difluoro-[1,1';3',1'']terphenyl-5'-yl)-amino]-hexyl}-2-(2-carboxy-ethyl)-phenoxy]-butyric acid (compound VIe).

ES(+)-HRMS m/e calcd for $C_{37}H_{39}F_2NO_5$ $(M+H)^+$ 616.2869, found 616.2869.

Example 39

4-[3-[6-(4,4''-Bis-trifluoromethoxy-[1,1';3',1'']terphenyl-5'-ylamino)-hexyl]-2-(2-carboxy-ethyl)-phenoxy]-butyric acid

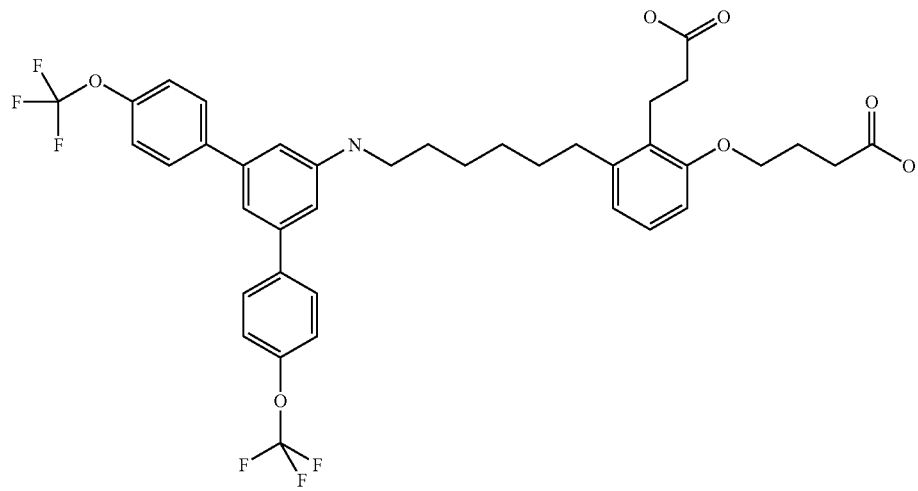

The title compound was prepared by following procedures in step 7 with 4-[3-{6-[(4,4''-Bis-trifluoromethoxy-[1,1';3',1'']terphenyl-5'-yl)-tert-butoxycarbonyl-amino]-hexyl}-2-(2-carboxy-ethyl)-phenoxy]-butyric acid (compound VIf).

ES(+)-HRMS m/e calcd for $C_{39}H_{39}F_6NO_7$ $(M+H)^+$ 748.2704, found 748.2698.

Example 40

4-[3-{6-[3,5-Bis-(2,3-dihydro-benzo[1,4]dioxin-6-yl)-phenylamino]-hexyl}-2-(2-carboxy-ethyl)-phenoxy]-butyric acid

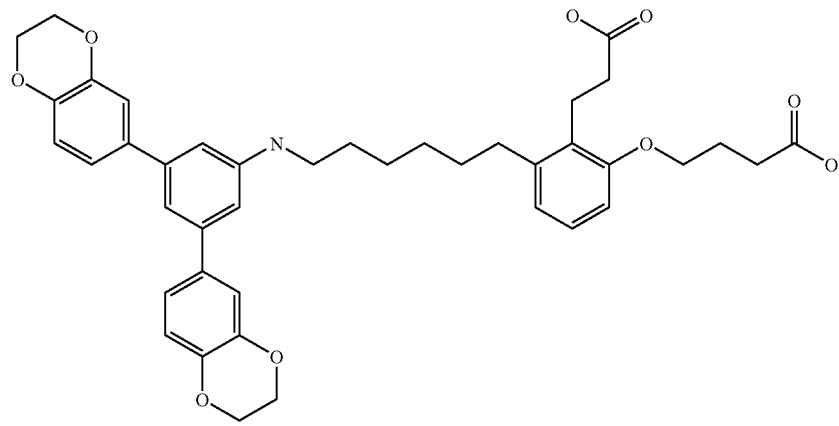

The title compound was prepared by following procedures in step 7 with 4-[3-(6-{[3,5-Bis-(2,3-dihydro-benzo[1,4]dioxin-6-yl)-phenyl]-tert-butoxycarbonyl-amino}-hexyl)-2-(2-carboxy-ethyl)-phenoxy]-butyric acid (compound VIg).

ES(+)-HRMS m/e calcd for $C_{39}H_{39}F_6NO_7$ (M+H)$^+$ 696.3167, found 696.3164.

Preparation of Preferred 3, 5-Diaryl N-Methyl-Aniline Compounds

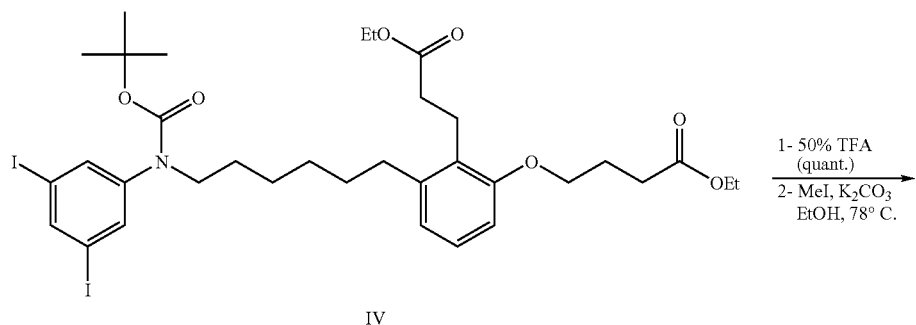

IV

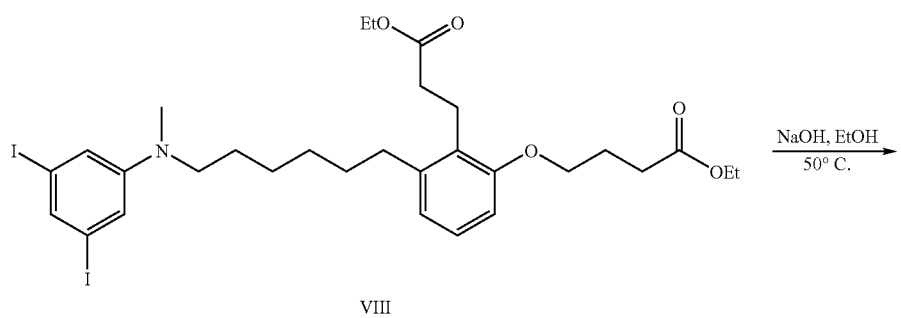

VIII

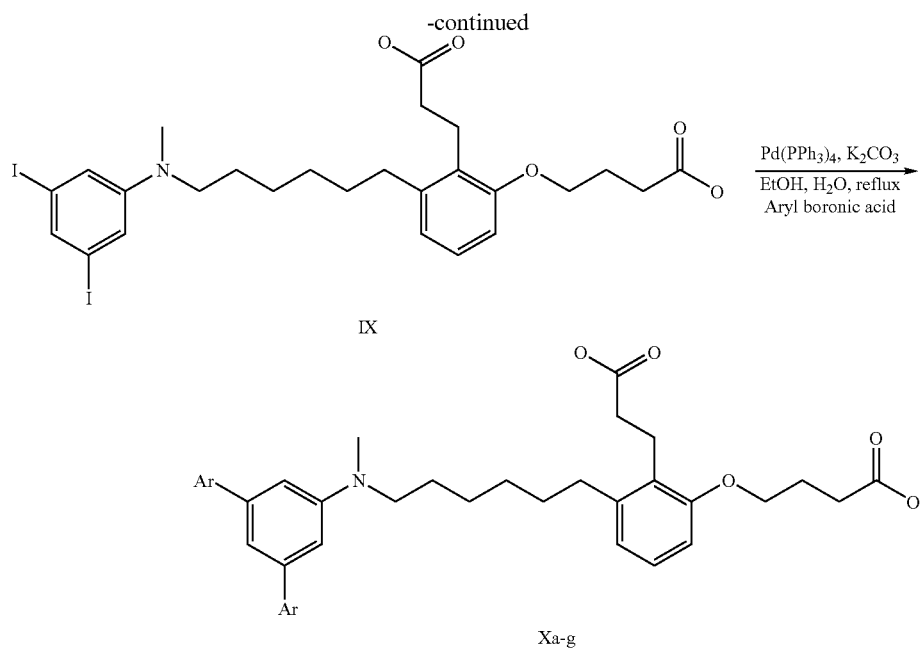

IX

Xa-g

Step 1: Preparation of Compound VIII: 4-[3-{6-[(3,5-Diiodo-phenyl)-methyl-amino]-hexyl}-2-(2-ethoxycarbonyl-ethyl)-phenoxy]-butyric acid ethyl ester

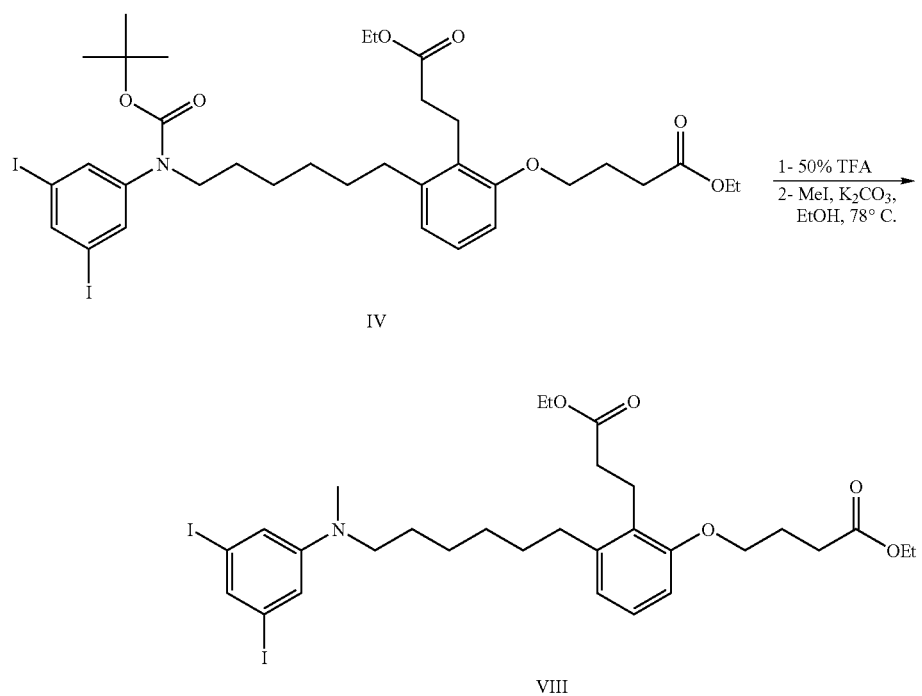

IV

VIII

Removal of the Boc protecting group was achieved by treating compound IV (2.0 g, 2.4 mmol) with a solution of 50% TFA/CH$_2$Cl$_2$ (30 mL) and allowing the reaction mixture stir at room temperature for 3 h. The reaction mixture was then evaporated under reduced pressure. The crude material was then used in the next step without further purification. To the crude material was then added 50 mL ethanol, iodomethane (1.5 mL, 24 mmol) and anhydrous potassium carbonate (3.3 g, 24 mmol). After stirring under gentle reflux for 36 h, the mixture was allowed to cool down, then filtered.

The residue was diluted with ethyl acetate and washed with water. The organic phase was dried over Na$_2$SO$_4$ and concentrated under reduced pressure. Purification by ISCO chromatography (gradient during 20 minutes from Hexane to 20% EtOAc-Hexane) afforded 1.2 g (65%) of the title compound as a light yellow oil.

LCMS: calculated for C$_{30}$H$_{41}$I$_2$NO$_5$ (M+H)$^+$ 750., found 750.0 m/z.

H$^1$ NMR (CDCl$_3$): δ7.28 (s, 1H), 7.15 (t, 1H), 6.90 (s, 2H), 6.80 (d, 1H), 6.75 (d, 1H), 4.22-4.19 (m, 4H), 4.05-3.99 (m, 2H), 3.26-3.22 (m, 2H), 3.05-2.99 (m, 2H), 2.82 (s, 3H), 2.66-2.40 (m, 6H), 2.20-2.11 (m, 2H), 1.65-1.42 (m, 4H), 1.41-1.21 (m, 10H).

Step 2: Preparation of compound IX: 4-(2-(2-Carboxy-ethyl)-3-{6-[(3,5-diiodo-phenyl)-methyl-amino]-hexyl}-phenoxy)-butyric acid

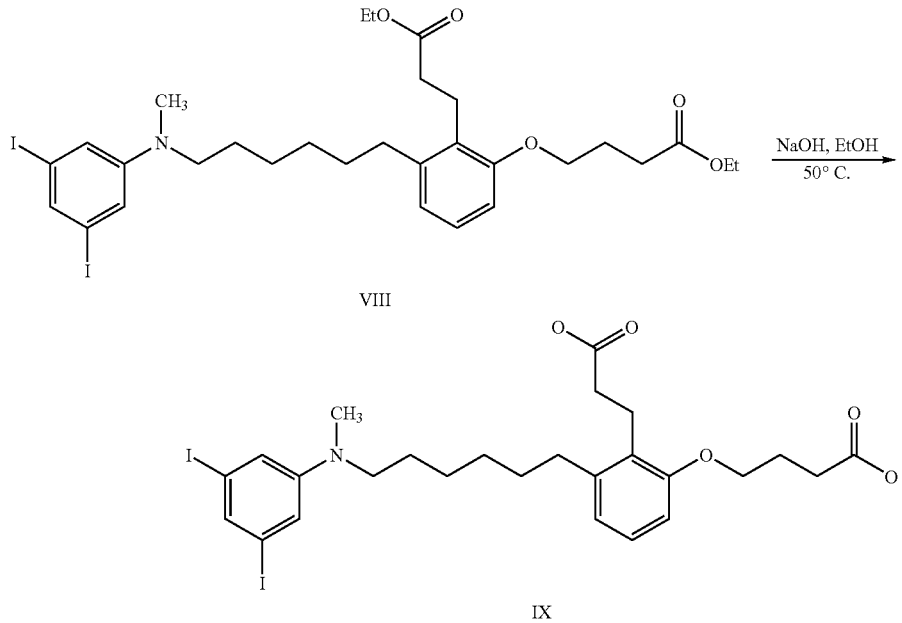

To a solution of compound VIII (0.9 g, 1.2 mmol) in EtOH (40 mL) was added NaOH (0.48 g, 12 mmol). The reaction mixture was heated at 50° C. and stirred at this temperature for 2 h. When the reaction was completed, a white solid precipitated in the reaction mixture. After cooling to room temperature, a solution of HCl 10% was added to dissolve the salt formed. The solution is then extracted with EtOAc (100 mL), the organic phase dried over Na$_2$SO$_4$ and evaporated under reduced pressure to afford the desired di-acid (0.8 g, 88%) as a light yellow oil. LCMS: calculated for C$_{26}$H$_{33}$I$_2$NO$_5$ (M+H)$^+$ 694, found 694.1 m/z. H$^1$ NMR (CDCl$_3$): □9.00-8.00 (bs, 2H), 7.93 (s, 1H), 7.75 (s, 2H), 7.09 (t, 1H), 6.74 (d, 1H), 6.67 (d, 1H), 3.99 (t, 2H), 3.25 (t, 2H), 3.11 (s, 3H), 2.99-2.92 (m, 2H), 2.62-2.41 (m, 6H), 2.22-2.14 (m, 2H), 1.65-1.41 (m, 4H), 1.39-1.23 (m, 4H).

Step 3: Synthesis of Most Preferred Compounds of Examples 41-47

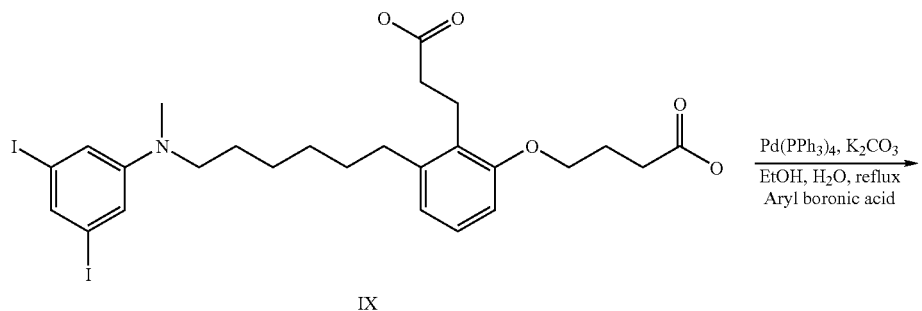

-continued

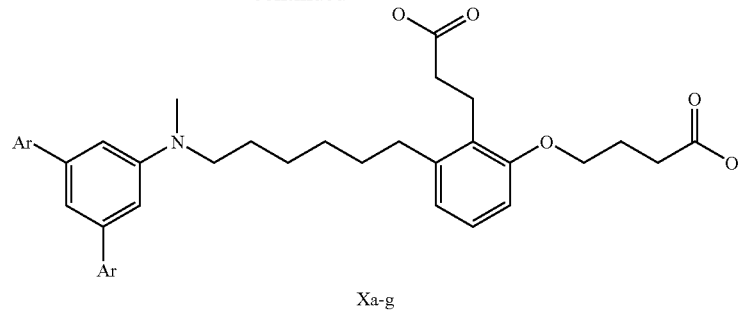

Xa-g

To a solution of compound IX (100 mg, 0.14 mmol) in EtOH (4 mL) and H$_2$O (1 mL) were added boronic acid (0.58 mmol), potassium carbonate (80 mg, 0.58 mmol) and Pd(PPh$_3$)$_4$ (8 mg, 0.007 mmol). The mixture was heated at 78° C. for 4 h and then cooled to room temperature. A solution of HCl 10% was added (5 mL). The resulting solution was then extracted with EtOAc (10 mL). The organic phase was dried over Na$_2$SO$_4$ and concentrated under reduced pressure. Purification by Isco chromatography (gradient of 20 minutes from EtOAc to EtOAc/MeOH 90%) afforded the desired 3,5-diaryl N—Me aniline analog.

Example 41

4-{2-(2-Carboxy-ethyl)-3-[6-(methyl-[1,1';3',1"]terphenyl-5'-yl-amino)-hexyl]-phenoxy}-butyric acid

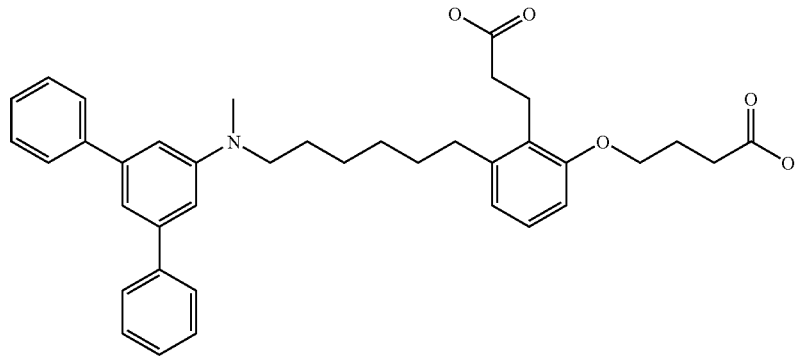

The title compound was prepared by following procedures in step 3 with 2-phenylboronic acid. HR-ES (+): calculated for C$_{38}$H$_{43}$NO$_5$ (M+H)$^+$ 594.3214, found 594.3212 m/z.

Example 42

4-[3-{6-[(3,5-Bis-benzo[1,3]dioxol-5-y-phenyl)-methyl-amino]-hexyl}-2-(2-carboxy-ethyl)-phenoxy]-butyric acid

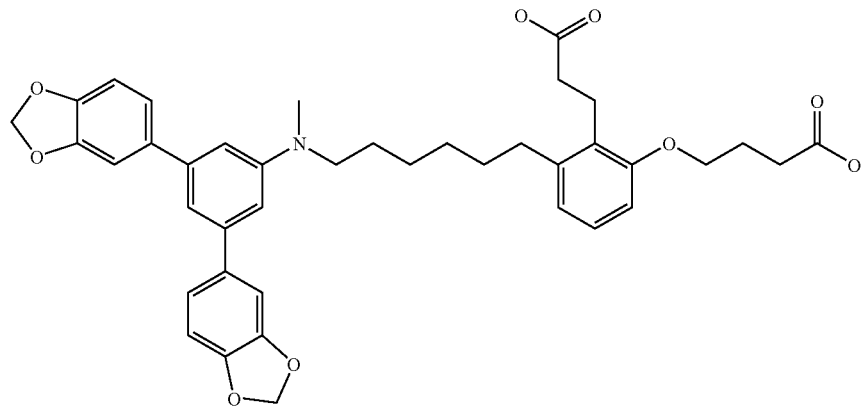

The title compound was prepared by following procedures in step 3 with benzo[1,3]dioxol-5-yl-boronic acid. HR-ES (+): calculated for $C_{40}H_{43}NO_9$ (M+H)$^+$ 682.3011, found 682.3015 m/z.

Example 43

4-(2-(2-Carboxy-ethyl)-3-{6-[(3,5-di-thiophen-3-yl-phenyl)-methyl-amino]-hexyl}-phenoxy)-butyric acid

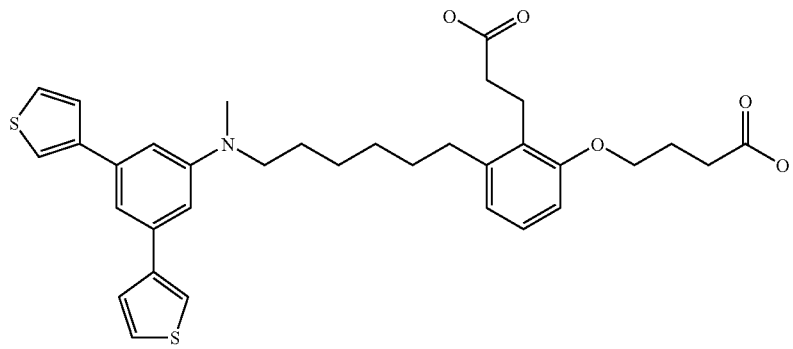

The title compound was prepared by following procedures in step 3 with 3-thiopheneboronic acid. HR-ES (+): calculated for $C_{34}H_{39}NO_5S_2$ (M+H)$^+$ 606.2343, found 606.2344 m/z.

Example 44

4-($^2$-(2-Carboxy-ethyl)-3-{6-[(2,2"-difluoro-[1,1';3',1"]terphenyl-5'-yl)-methyl-amino]-hexyl}-phenoxy)-butyric acid

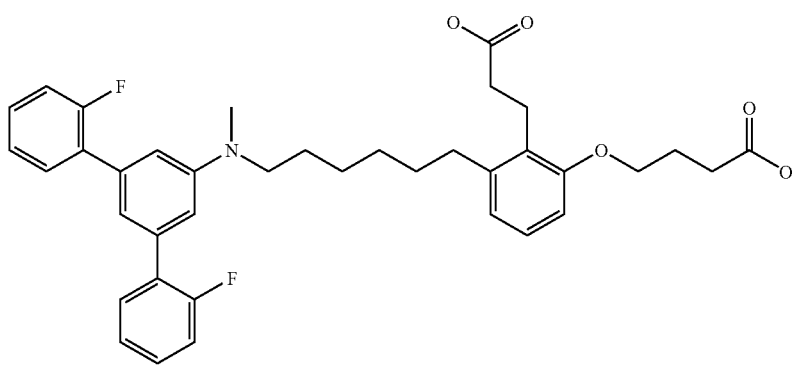

The title compound was prepared by following procedures in step 3 with 2-fluorophenylboronic acid.

LCMS: calculated for $C_{38}H_{41}F_2NO_5$ (M+H)$^+$ 630.75, found 630.2 m/z.

Example 45

4-(2-(2-Carboxy-ethyl)-3-{6-[(3,3"-difluoro-[1,1';3',1"]terphenyl-5'-yl)-methyl-amino]-hexyl}-phenoxy)-butyric acid

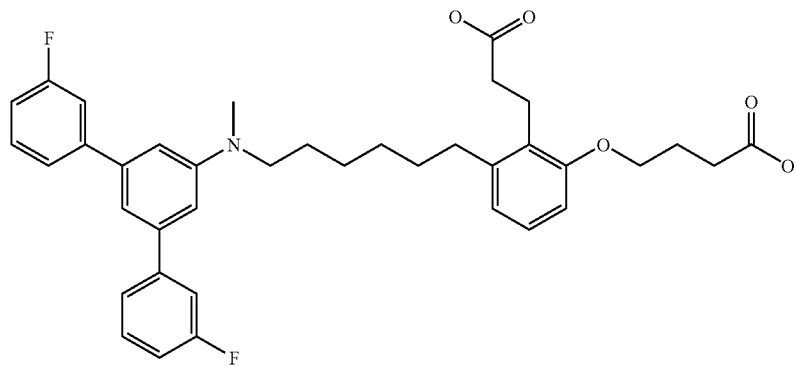

The title compound was prepared by following procedures in step 3 with 2-phenylboronic acid. HR-ES (+): calculated for $C_{38}H_{41}F_2NO_5$ (M+H)$^+$ 630.3026, found 630.3029 m/z.

Example 46

4-(2-(2-Carboxy-ethyl)-3-{6-[(4,4"-difluoro-[1,1';3',1"]terphenyl-5'-yl)-methyl-amino]-hexyl}-phenoxy)-butyric acid

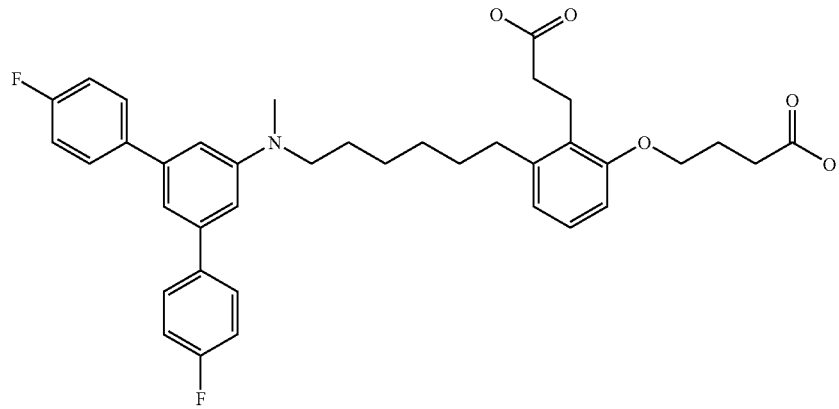

The title compound was prepared by following procedures in step 3 with 2-phenylboronic acid. HR-ES (+): calculated for $C_{38}H_{41}F_2NO_5$ (M+H)$^+$ 630.3026, found 630.3028 m/z.

Example 47
4-[3-(6-{[3,5-Bis-(2,3-dihydro-benzo[1,4]dioxin-6-yl)-phenyl]-methyl-amino}-hexyl)-2-(2-carboxy-ethyl)-phenoxy]-butyric acid
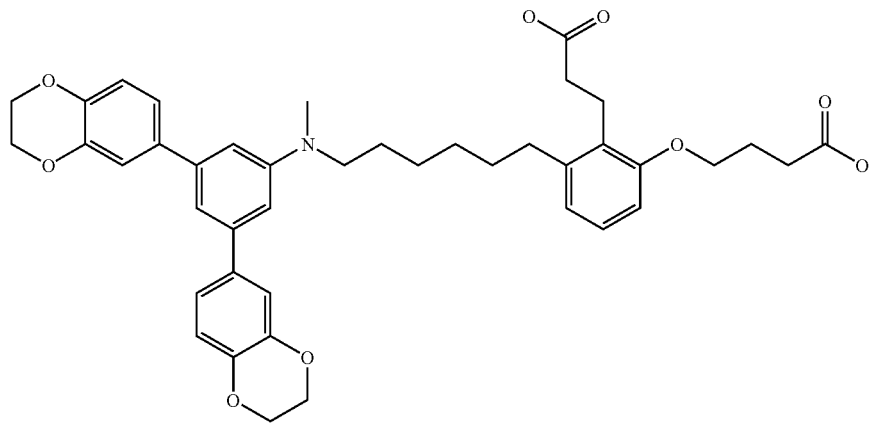
The title compound was prepared by following procedures in step 3 with 1,4-benzodioxane-6-boronic acid. HR-ES (+): calculated for $C_{42}H_4NO_9$ (M+H)$^+$ 710.3324, found 710.3323 m/z.
Preparation of Preferred 3,5-Diaryl 3,5-Diaryl C-Linked Compounds
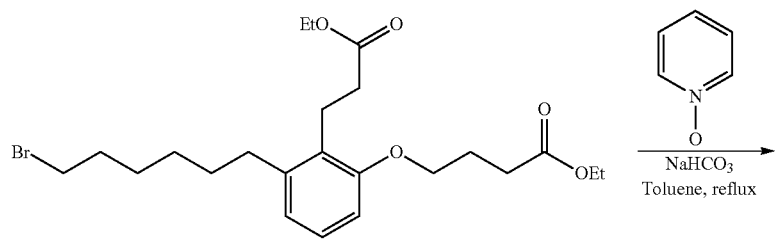
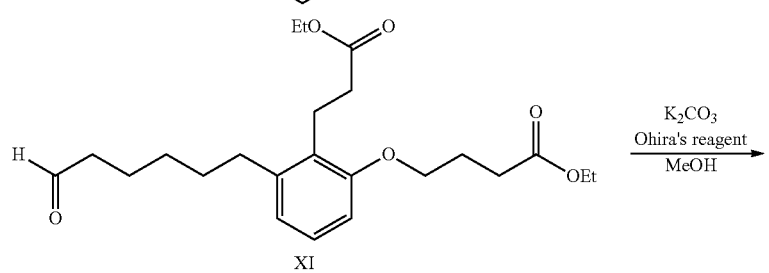
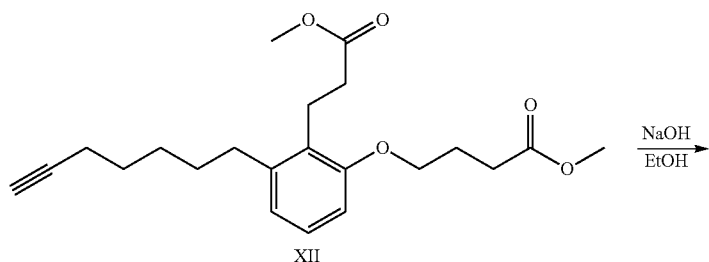

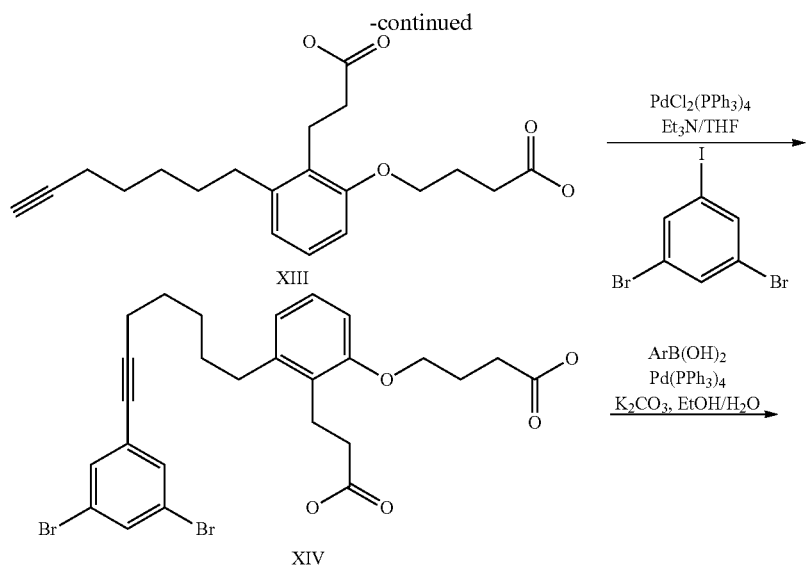
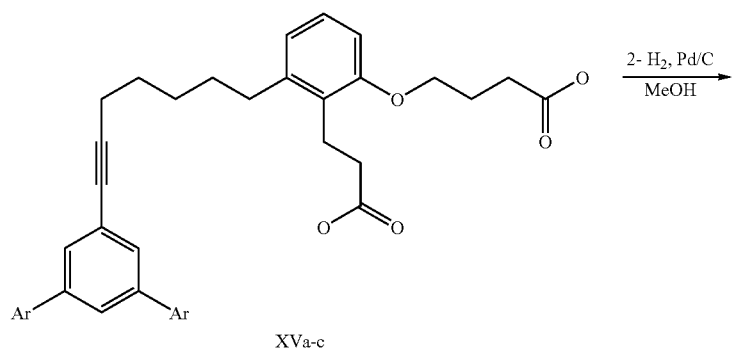
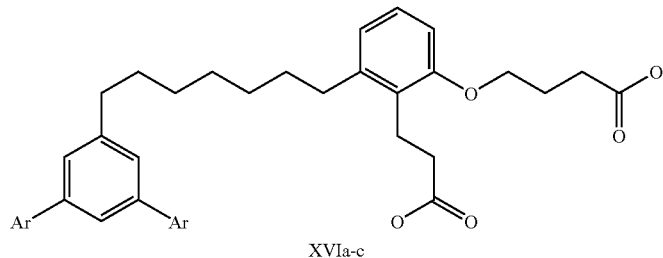
Step 1: Preparation of Compound XI: 4-[2-(2-Ethoxycarbonyl-ethyl)-3-(6-oxo-hexyl)-phenoxy]-butyric acid ethyl ester
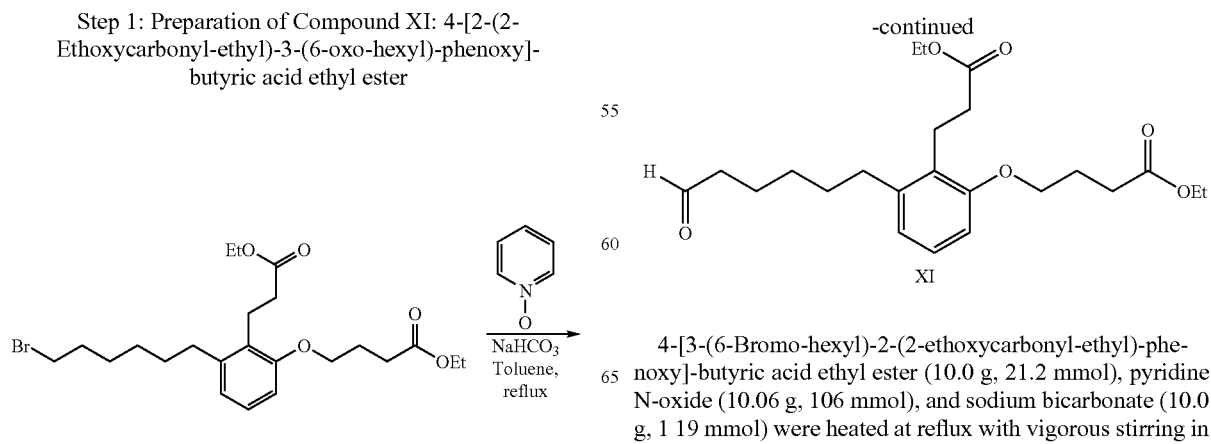
4-[3-(6-Bromo-hexyl)-2-(2-ethoxycarbonyl-ethyl)-phenoxy]-butyric acid ethyl ester (10.0 g, 21.2 mmol), pyridine N-oxide (10.06 g, 106 mmol), and sodium bicarbonate (10.0 g, 1 19 mmol) were heated at reflux with vigorous stirring in toluene (100 mL) for 24 hr. The mixture was cooled down and filtered. The filtrate was then evaporated under vacuo and the crude material was purified by column chromatography using 30% EtOAc-Hexane as eluant to give the title compound (7.0 g, 81%) as an oil. HR-MS-EI(+): calculated for $C_{23}H_{34}O_6$ [M] 406.2350, found 406.2355.

Step 2: Preparation of Compound XII: 4-[3-Hept-6-ynyl-2-(2-methoxycarbonyl-ethyl)-phenoxy]-butyric acid methyl ester

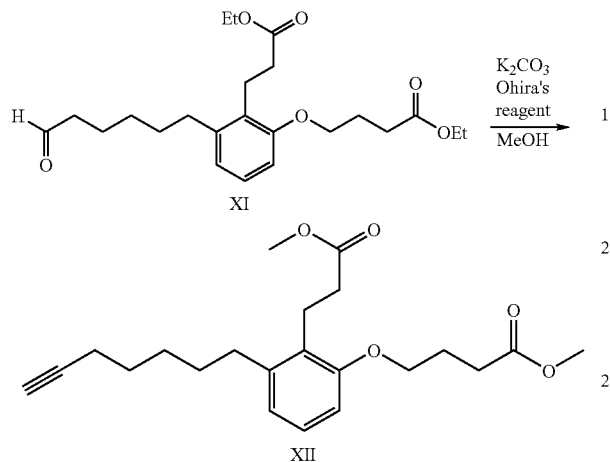

To a 0° C. solution of 4-[2-(2-Ethoxycarbonyl-ethyl)-3-(6-oxo-hexyl)-phenoxy]-butyric acid ethyl ester (7.0 g, 17.24 mmol) and potassium carbonate (7.14 g, 51.72 mmol) in MeOH (200 mL), the Ohira's reagent (ref. cited in *Synlett*, 1996, 521) (6.3 g, 32.8 mmol) in MeOH (50 mL) was added slowly. The cooling bath was removed upon the end of addition and the reaction mixture stirred at room temperature for 5 hr. The reaction was then extracted with EtOAc and brine. The combined organic layers were dried over sodium sulfate then evaporated under vacuo. The crude material was purified by column chromatography using 50% EtOAc-Hexane as eluant to give the title compound (4.6 g, 71%) as a light yellow oil. HR-ES(+): calculated for $C_{22}H_{30}O_5$ $(M+Na)^{1+}$ 397.1985, found 397.1985.

Step 3: Preparation of Compound XIII: 4-[2-(2-Carboxy-ethyl)-3-hept-6-ynyl-phenoxy]-butyric acid

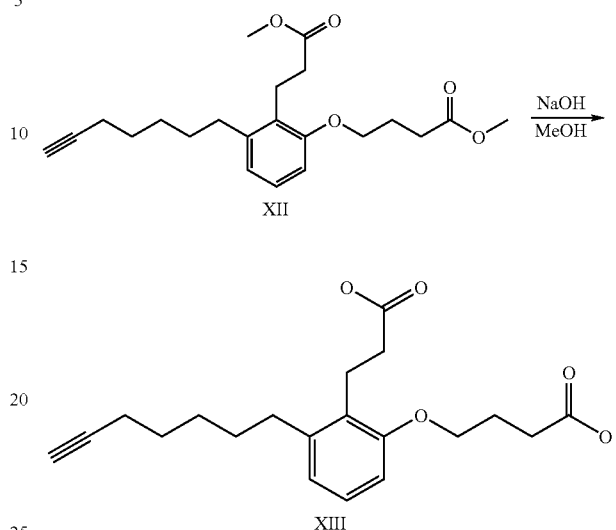

To a solution of 4-[3-hept-6-ynyl-2-(2-methoxycarbonyl-ethyl)-phenoxy]-butyric acid methyl ester (4.6 g, 12.39 mmol) in EtOH (100 mL) was added NaOH (4.96 g, 123.9 mmol) and 20 mL of water. The reaction mixture was heated at 50° C. and stirred at this temperature for 5 h. After cooling to room temperature, a solution of HCl 10% was added. The solution was then extracted with EtOAc (100 mL), the organic phase dried over $Na_2SO_4$ and evaporated under reduced pressure to afford the desired diacid (4.0 g, 93%) as a light yellow oil. HR-ES(+): calculated for $C_{20}H_{26}O_5$ $(M+Na)^{1+}$ 369.1672, found 369.1673.

Step 4: Preparation of Compound XIV: 4-{2-(2-Carboxy-ethyl)-3-[7-(3,5-dibromo-phenyl)-hept-6-ynyl]-phenoxy}-butyric acid

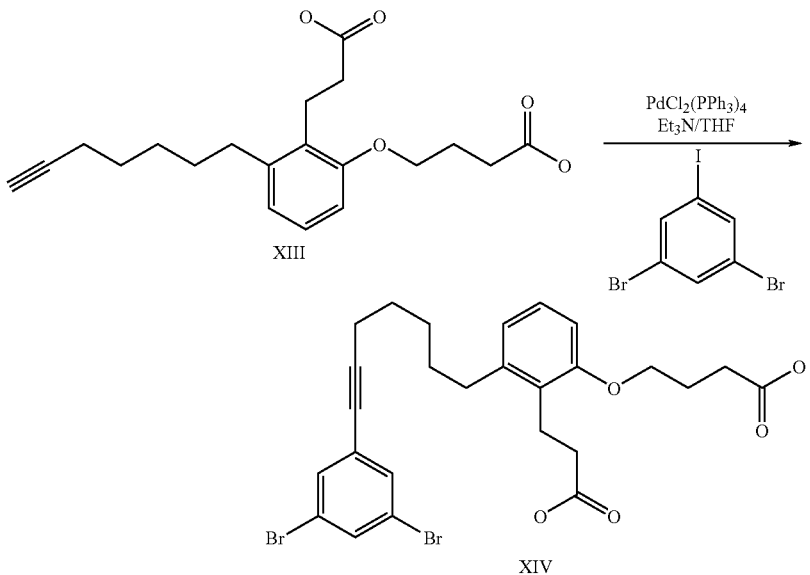

To a solution of 4-[2-(2-Carboxy-ethyl)-3-hept-6-ynyl-phenoxy]-butyric acid (250 mg, 0.72 mmol), 3,5-dibromoiodobenzene (preparation in *J. Org. Chem.* 2003, 68, 8750) (261 mg, 0.72 mmol), CuI (7 mg, 0.036 mmol) in THF (5 mL) and Et$_3$N (5 mL) was added bis-(triphenylphosphine) palladium(II) dichloride (25 mg, 0.036 mmol). The reaction mixture was heated at 60° C. for 3 h. Then the reaction mixture was cooled down, a few drop of TFA was added and the resulting mixture was evaporated under vacuo. The crude material was purified by column chromatography using a gradient from EtOAc to 20% MeOH-EtOAc as eluant to give the title compound (240 mg, 60%) as a oil. HR-MS-EI(+): calculated for C$_{26}$H$_{28}$O$_5$Br$_2$(M+Na) 601.0195, found 601.0193.

Step 5: Synthesis of Compounds of Examples 48-50

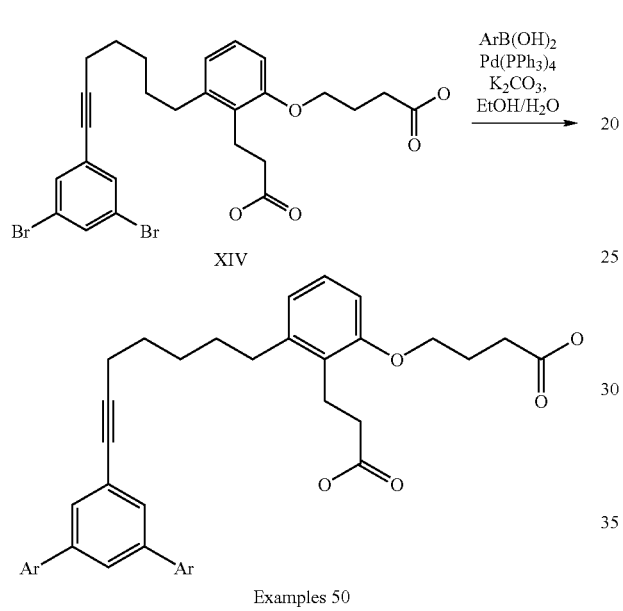

To a solution of compound XIV (110 mg, 0.19 mmol) in EtOH (4 mL)/H$_2$O (1 mL) were added boronic acid (0.76 mmol), potassium carbonate (105 mg, 0.76 mmol) and Pd(PPh$_3$)$_4$ (11 mg, 0.0095 mmol). The mixture was heated at 78° C. for 4 h and then cooled to room temperature. A solution of HCl 10% was added (5 mL). The resulting solution was then extracted with EtOAc (10 mL). The organic phase was dried over Na$_2$SO$_4$ and concentrated under reduced pressure. Purification by preparative HPLC (gradient 50% Acetonitrile-water to 100% water ) afforded the desired compound.

Example 48

4-[2-(2-Carboxy-ethyl)-3-(7-[1,1';3',1"]terphenyl-5'-yl-hept-6-ynyl)-phenoxy]-butyric acid

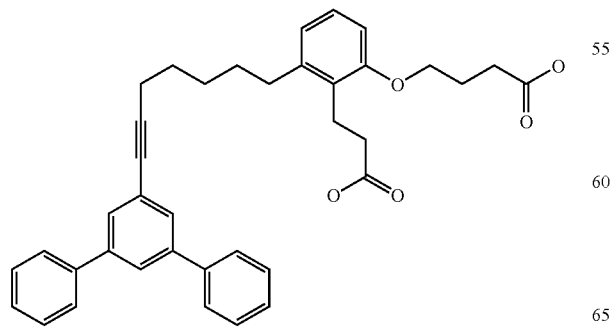

The title compound was prepared by following procedures in step 5 with phenylboronic acid. HR-ES(+): calculated for C$_{38}$H$_{38}$O$_5$ (M+Na)$^+$ 597.2611, found 597.2606.

Example 49

4-[3-[7-(3,5-Bis-benzo[1,3]dioxol-5-yl-phenyl)-hept-6-ynyl]-2-(2-carboxy-ethyl)-phenoxy]-butyric acid

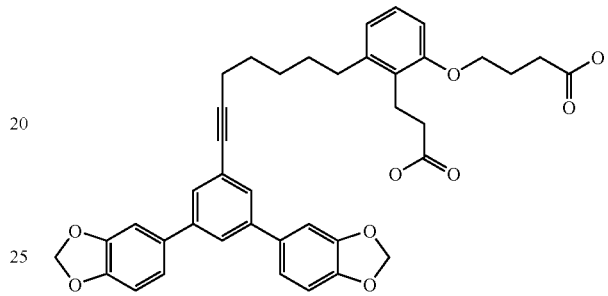

The title compound was prepared by following procedures in step 5 with 3,4-benzo[1,3]dioxol-5-yl-boronic acid. HR-ES(+): calculated for C$_{40}$H$_{38}$O$_9$ (M+Na)$^+$ 685.2408, found 685.2412.

Example 50

4-{2-(2-Carboxy-ethyl)-3-[7-(3,5-di-thiophen-3-yl-phenyl)-hept-6-ynyl]-phenoxy}-butyric acid

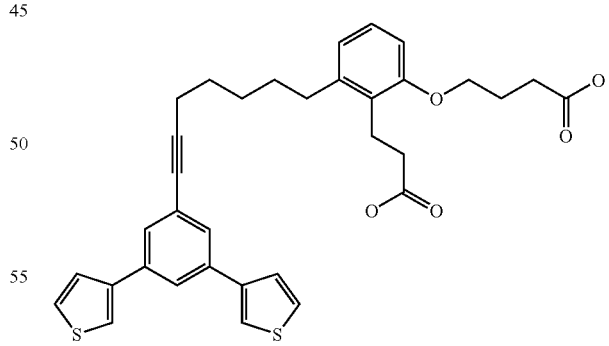

The title compound was prepared by following procedures in step 5 with 3-thiopheneboronic acid.

LCMS: calculated for C$_{34}$H$_{34}$O$_5$S$_2$ (M+Na)$^+$ 609.76, found 609.2 m/z.

Step 6: Synthesis of compounds of Examples 51-53

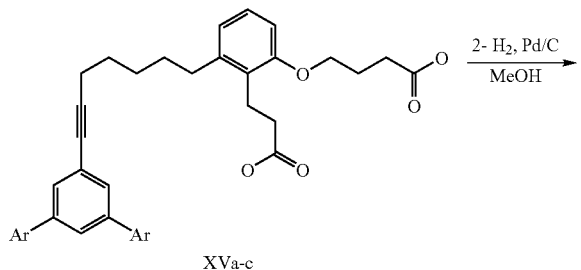

XVa-c

General Procedure:

To a solution of compound XVa-c (0.12 mmol) in MeOH (6 mL) was added 10% Pd/C (10 mg). In some cases some EtOAc was added to help the dissolution of the alkyne. The mixture was stirred for 4 h under hydrogen atmosphere at room temperature. The resulting suspension was filtered through celite and was evaporated under vacuo to afford the corresponding hydrogenated compound.

Example 51

4-[2-(2-Carboxy-ethyl)-3-(7-[1,1';3',1"]terphenyl-5'-yl-heptyl)-phenoxy]-butyric acid

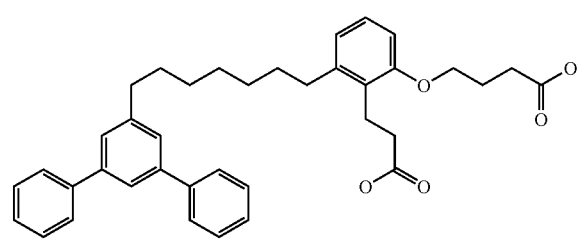

The title compound was prepared by following procedures in step 6 with 4-[2-(2-Carboxy-ethyl)-3-(7-[1,1';3',1"]terphenyl-5"-yl-hept-6-ynyl)-phenoxy]-butyric acid (Example 48). HR-ES(+): calculated for $C_{38}H_{42}O_5$ $(M+Na)^+$ 601.2924, found 601.2925.

Example 52

4-[3-[7-(3,5-Bis-benzo[1,3]dioxol-5-yl-phenyl)-heptyl]-2-(2-carboxy-ethyl)-phenoxy]-butyric acid

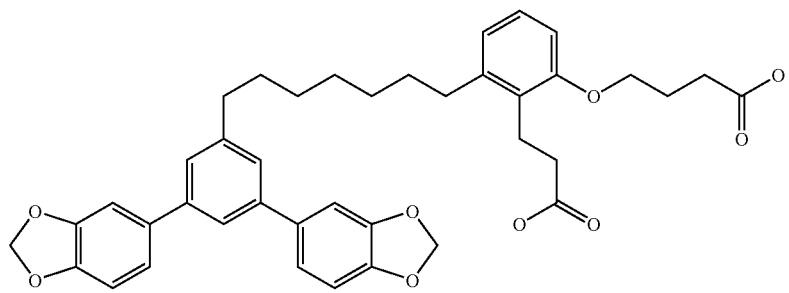

The title compound was prepared by following procedures in step 6 with 4-[3-[7-(3,5-Bis-benzo[1,3]dioxol-5-yl-phenyl)-hept-6-ynyl]-2-(2-carboxy-ethyl)-phenoxy]-butyric acid (Example 49). HR-ES(+): calculated for $C_{40}H_{42}O_9$ $(M+Na)^+$ 689.2721, found 689.2721.

Example 53

4-{2-(2-Carboxy-ethyl)-3-[7-(3,5-di-thiophen-3-yl-phenyl)-heptyl]-phenoxy}-butyric acid

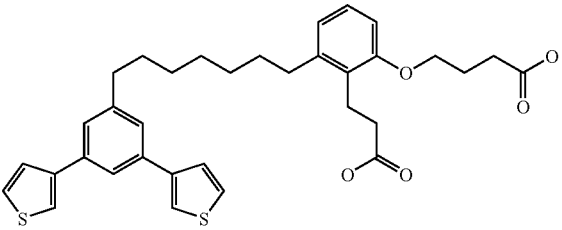

The title compound was prepared by following procedures in step 6 with 4-{2-(2-Carboxy-ethyl)-3-[7-(3,5-di-thiophen-3-yl-phenyl)-hept-6-ynyl]-phenoxy}-butyric acid (Example 50). HR-ES(+): calculated for $C_{34}H_{38}O_5S_2$ $(M+Na)^+$ 613.2053, found 613.2054.

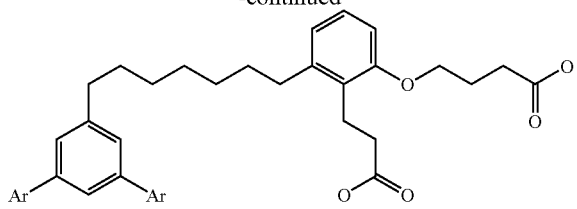

Examples 51-53

Alternative Method for Preparing Symmetric and Asymmetric Bis-Arylphenol Intermediates and Their Use in Preparation of Preferred Compounds
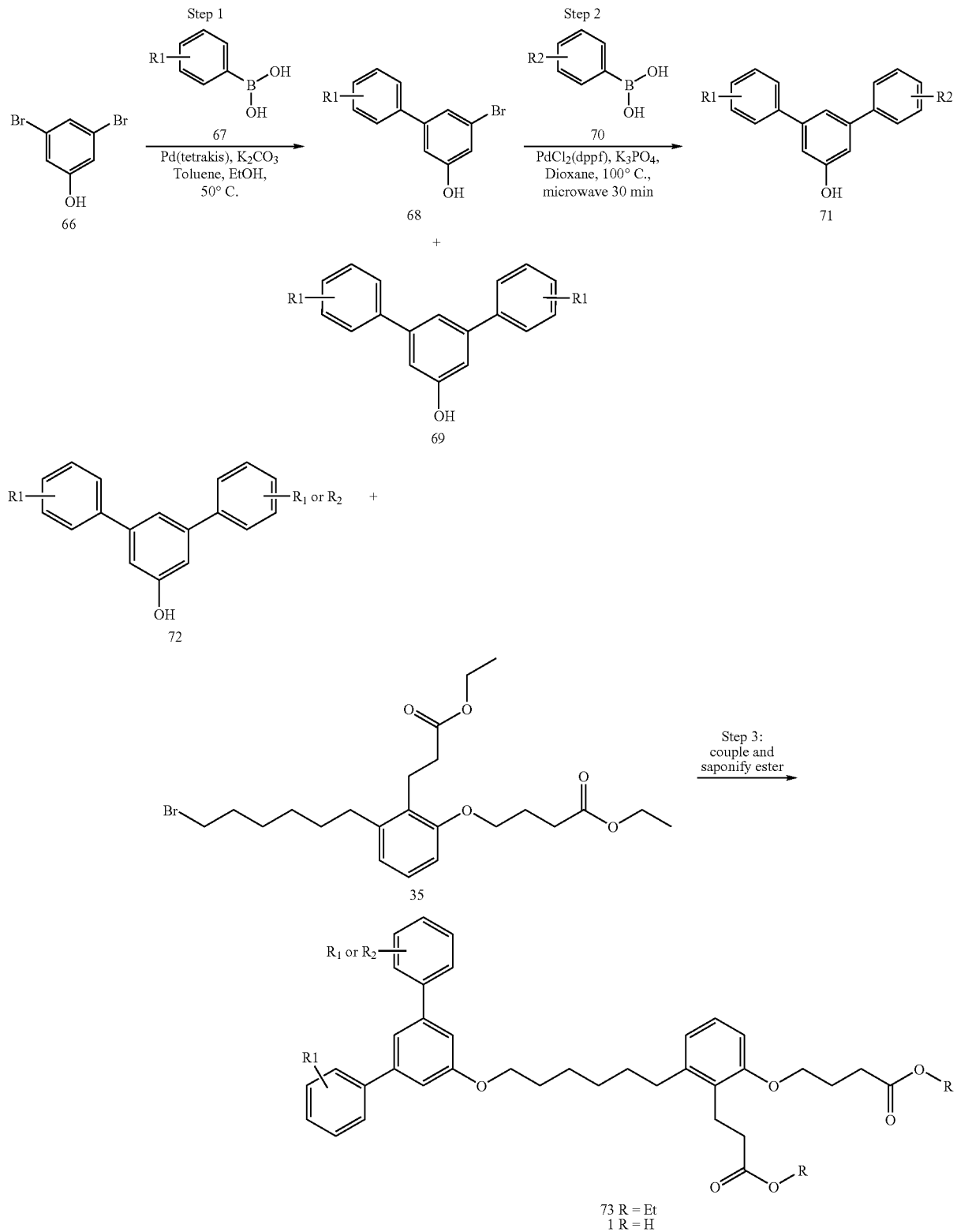

Step 1: To a solution of 3,5-dibromophenol (66) and R1-boronic acid (67) (1 equivalent) in 2:1 toluene:ethanol (3 volumes) at room temperature under nitrogen was added potassium carbonate (2 equivalents) and palladium (0) tetrakis(triphenylphosphine) (0.1 equivalents). The reaction mixture was heated to 50° C. and allowed to stir for 16 hours (reaction progress monitored by LCMS). The solvent was removed under reduced pressure, and the crude product purified by column chromatography (eluting with 9:1 heptane:ethyl acetate). In this manner, it was possible to collect separately both the 5-bromo-R1'-biphenyl-3-ol (68) and symmetric 3-,5-bis-aryl (69) products.

Step 2: To a solution of 5-bromo-R1'-biphenyl-3-ol (68) and R2-boronic acid (70) (1.5 equivalents) in dioxane (2 volumes) at room temperature under nitrogen was added tripotassium phosphate (2 equivalents) and 1,1'-bis(diphenylphosphino)ferrocene palladium (II) dichloride (0.1 equivalents). The reaction mixture was treated under microwave conditions (100° C.; 250 W; 250 psi) for 30 minutes. The solvent was then removed under reduced pressure, and the crude product purified by column chromatography (eluting with 9:1 heptane:ethyl acetate). In this manner, the asymmetric 3-,5-bis-aryl (71) product was obtained.

Step 3: Phenol 69 or 71 was dissolved in (2 mL per 1 mmol of phenol) of a acetone and DMF mixture (2:1) and then compound 35 (1 eq.) was added, followed by addition of $K_2CO_3$ (10 eq.). The resulting suspension was stirred at 75° C. for 2 days. The insoluble material was filtered out and the filtrate was diluted with ethyl acetate and washed with water and then brine. The organic layer was dried over anhydrous sodium sulfate and concentrated under reduced pressure. The crude material was purified on a silica gel column using ethyl acetate and hexanes to afford compound 73.

Step 4: Compound 73 was suspended in a mixture of ethanol and 2M sodium hydroxide solution (1 volume with respect to the volume of ethanol) and stirred at 55° C. over during 2 days. Then the reaction mixture was neutralized with 1N hydrochloric acid and extracted into ethyl acetate. The organic layer was dried over anhydrous sodium sulfate and concentrated under reduced pressure. Crude material was purified by HPLC (post-synthetic group) to afford final compound 1.

Example 54

4-[3-[6-(3,5"-Difluoro-2"-methoxy-[1,1';3',1"]terphenyl-5'-yloxy)-hexyl]-2-(2-ethoxycarbonyl-ethyl)-phenoxy]-butyric acid ethyl ester Example 54 was synthesized in 4 steps from 3-,5-dibromophenol. 2-Methoxy-5-fluorophenyl boronic acid was reacted as described above, step 1. In this manner was isolated 5-bromo-5'-fluoro-2'-methoxy-biphenyl-3-ol, which was then reacted with 3-fluorophenyl boronic reacted as described above, Step 2. In this manner, 3,5"-difluoro-2"-methoxy-[1,1';3',1"]terphenyl-5'-ol was obtained.

This bis-aryl phenol, 3,5"-difluoro-2"-methoxy-[1,1';3',1"]terphenyl-5'-ol, was coupled to 4-[3-(6-bromo-hexyl)-2-(2-ethoxycarbonyl-ethyl)-phenoxy]-butyric acid ethyl ester (1.0 eq) in presence of potassium carbonate (2.0 eq) were added N,N-dimethylformamide (5 mL) and acetone (10 mL) at room temperature as described above in Step 3. The resulting suspension was heated for 2 days. Then, the reaction mixture was cooled to room temperature and diluted with water (20 mL). The organic compound was extracted into ethyl acetate (3×20 mL) and the combined organic extracts were washed with water and brine solution. The organic layers were dried over anhydrous magnesium sulfate and filtration of the drying agent and concentration of the solvent gave the crude product which was purified by using an ISCO silica gel column, eluting with 0-20% ethyl acetate in hexanes to afford 4-{2-(2-carboxy-ethyl)-3-[6-(3,5"-difluoro-2"-methoxy-[1,1 ';3',1"]terphenyl-5'-yloxy)-hexyl]-phenoxy}-butyric acid di-ethyl ester: ES(+)-HRMS m/e calculated for $C_{38}H_{40}O_7F_2$ (M+Na)$^+$ 669.2634, found 669.2637.

Step 4: Preparation of 4-{2-(2-Carboxy-ethyl)-3-[6-(3,5"-difluoro-2"-methoxy-[1,1';3',1"]terphenyl-5'-yloxy)-hexyl]-phenoxy}-butyric acid To a solution of the 4-{2-(2-Carboxy-ethyl)-3-[6-(3,5"-difluoro-2"-methoxy-[1,1';3',1"]terphenyl-5'-yloxy)-hexyl]-phenoxy}-butyric acid di-ethyl ester (506 mg) in ethanol (2.5 mL) was added aqueous 2.0 N sodium hydroxide (2.5 mL) at room temperature. The resulting suspension was heated to 50-55° C. and the mixture was stirred for 48 h. Then, the reaction mixture was acidified with 1.0 N hydrochloric acid and the precipitated white organic compound was extracted into ethyl acetate (2×10 mL). The combined ethyl acetate extracts were washed with brine solution (100 mL) and the organic layers were dried over anhydrous sodium sulfate. Filtration and removal of the solvent afforded the crude product which was purified by preparative HPLC to yield 417 grams of the desired product. Example 54 was characterized by low resolution mass spectrometry where signals corresponding to the following were observed: ES(+)=647, ES(−)=645. Example 54 was also characterized by high resolution mass spectrometry where signals corresponding to the following were observed: m/e calculated for $C_{38}H_{40}F_2O_7$ 646.274211; found compatible with (M+Na)$^{1+}$=669.2637.

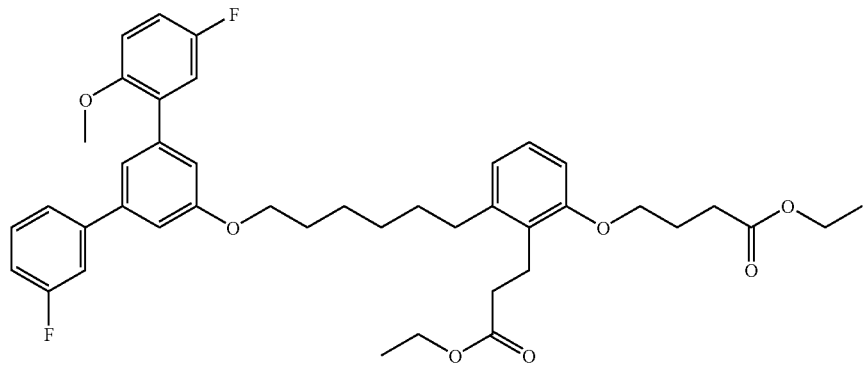

Example 55

4-[3-[6-(3,5-Bis-benzo[1,3]dioxol-5-yl-phenoxy)-hexyl]-2-(2-carboxy-ethyl)-phenoxy]-butyric acid

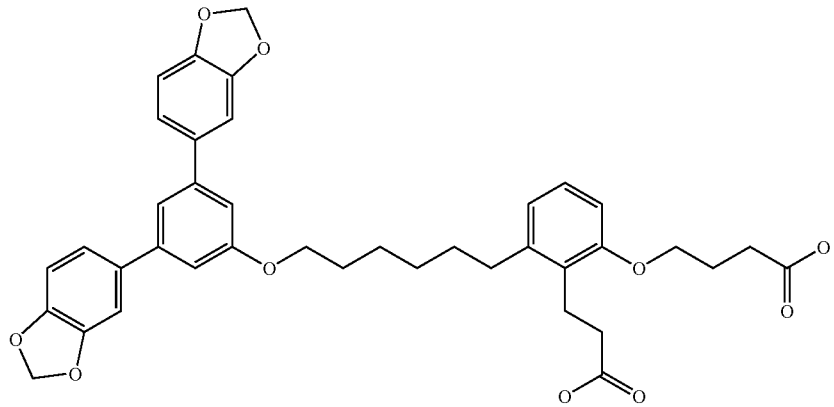

Example 55 was prepared in a similar manner as that described for Example 54. The symmetric bis-arylation product 3,5-bis-benzo[1,3]dioxol-5-yl-phenol obtained from Step one in which 3,5-dibromophenol was reacted with benzo[1,3]dioxol-5-yl-boronic acid. This symmetric bis-arylation product was reacted according to Steps 3 and 4 to obtain Example 55 4-[3-[6-(3,5-Bis-benzo[1,3]dioxol-5-yl-phenoxy)-hexyl]-2-(2-carboxy-ethyl)-phenoxy]-butyric acid.

ES(+)-HRMS m/e calculated for C39H40O10 (M+Na)$^{1+}$ 691.2513, found 691.2513.

Example 56

4-{2-(2-Carboxy-ethyl)-3-[6-(3,5-di-thiophen-3-yl-phenoxy)-hexyl]-phenoxy}-butyric acid

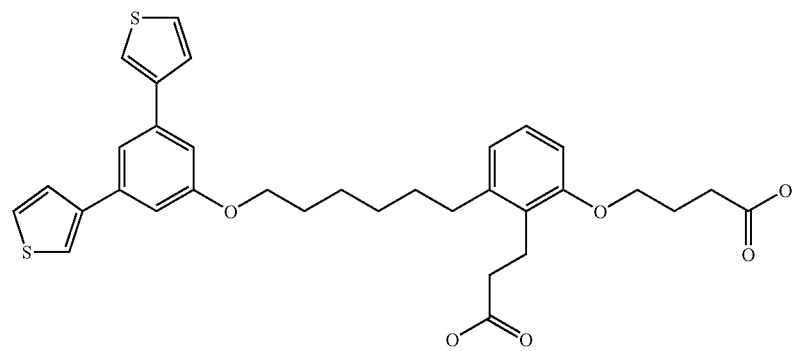

Example 56 was prepared in a similar manner as that described for Example 54. The symmetric bis-arylation product 3,5-bis-benzo[1,3]dioxol-5-yl-phenol obtained from Step one in which 3,5-dibromophenol was reacted with thiophen-3-ylboronic acid. This symmetric bis-arylation product was reacted according to Steps 3 and 4 to obtain Example 56 4-{2-(2-Carboxy-ethyl)-3-[6-(3,5-di-thiophen-3-yl-phenoxy)-hexyl]-phenoxy}-butyric acid. Example 56 was characterized by low resolution mass spectrometry where signals corresponding to the following were observed: ES(+)=592+Na, ES(−)=591. Example 56 was also characterized by high resolution mass spectrometry where signals corresponding to the following were observed: m/e calculated for $C_{33}H_{36}O_6S_2$ 592.195334; found compatible with (M+Na)$^{1+}$=615.1843.

Example 57

4-{2-(2-Carboxy-ethyl)-3-[6-(4"-dimethylamino-3-fluoro-[1,1';3',1"]terphenyl-5'-yloxy)-hexyl]-phenoxy}-butyric acid

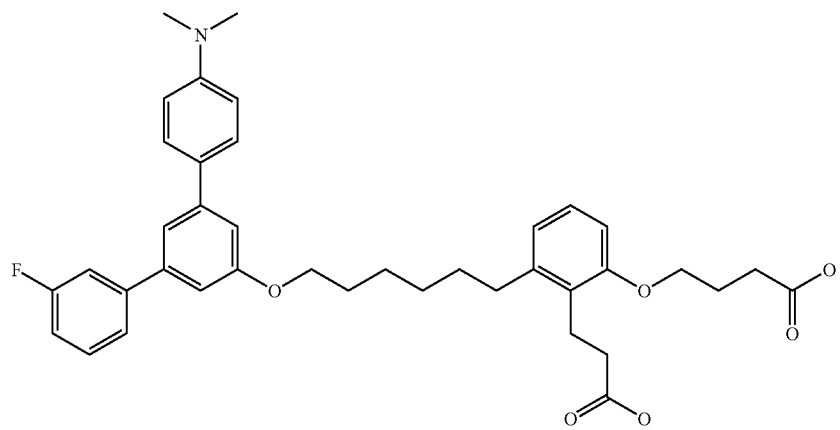

Step 1 Preparation of 5-bromo-4'-dimethylamino-biphenyl-3-ol

Step 2 Preparation of 4-[3-[6-(5-bromo-4'-dimethylamino-biphenyl-3-yloxy)-hexyl]-2-(2-carboxy-ethyl)-phenoxy]-butyric acid

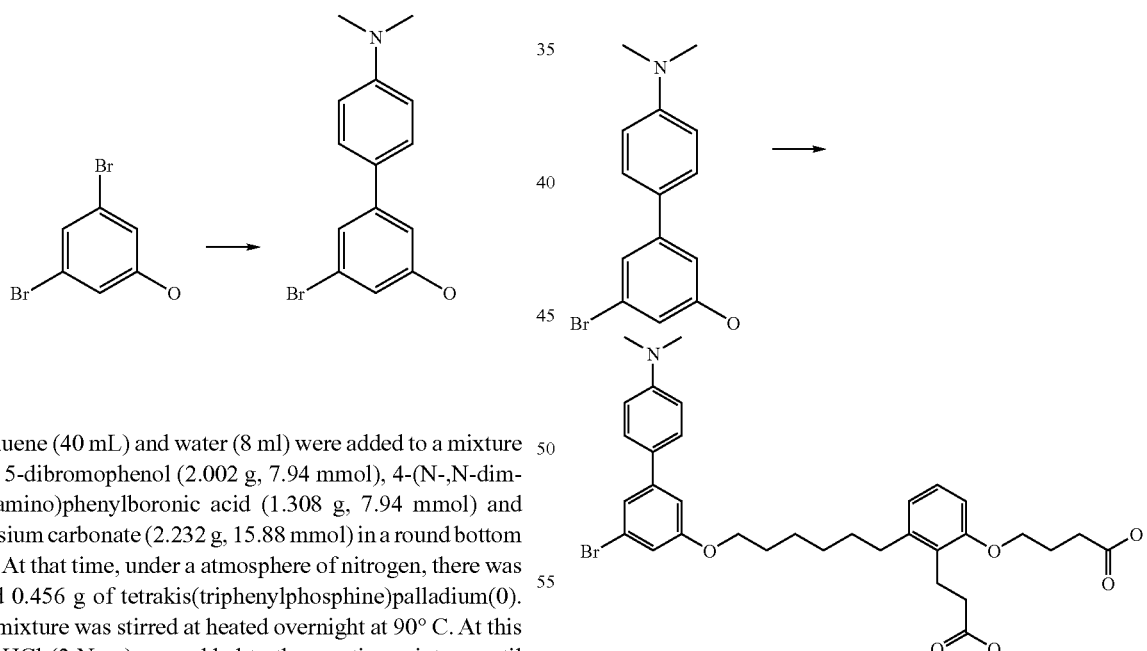

Toluene (40 mL) and water (8 ml) were added to a mixture of 3-, 5-dibromophenol (2.002 g, 7.94 mmol), 4-(N-,N-dimethylamino)phenylboronic acid (1.308 g, 7.94 mmol) and potassium carbonate (2.232 g, 15.88 mmol) in a round bottom flask. At that time, under a atmosphere of nitrogen, there was added 0.456 g of tetrakis(triphenylphosphine)palladium(0). This mixture was stirred at heated overnight at 90° C. At this time, HCl (2 N aq) was added to the reaction mixture until pH=~6 and the subsequent two phases were separated; the aqueous phase was extracted and washed three time with ethyl acetate. The combined organic phases were dried with $MgSO_4$, filtered and washed with ethyl acetate. The filtrate was concentrated in vacuo to provide an oil. The oil was purified by silica gel flash column chromatography eluted with dichloromethane. In this manner, 0.65 grams (28%) of 5-bromo-4'-dimethylamino-biphenyl-3-ol was obtained.

In a round bottom vial charged with 100 mg (0.342 mmol) of 5-bromo-4'-dimethylamino-biphenyl-3-ol, 160 mg (0.342 mmol) of 4-[3-(6-bromo-hexyl)-2-(2-ethoxycarbonyl-ethyl)-phenoxy]-butyric acid ethyl ester, potassium carbonate (94 mg, 0.684 mmol) and 10 mL of DMA were sequentially added. This mixture was heated overnight at 90° C. HPLC analysis of the reaction mixture at this time, indicated the formation of the di-ester intermediate. At this time, 1 mL of 1

N NaOH aq. was added and the reaction mixture was heated again at 90° C. overnight. At this time, the reaction was diluted with water and acidified with 2 N HCl until pH=~7 was achieved. The aqueous phase was thrice extracted with ethyl acetate. The combined organic phases were dried with MgSO$_4$, filtered and washed with ethyl acetate. The filtrate was concentrated in vacuo to provide an oil (91 mg, 42%).

This intermediate was used in subsequent steps without further purification.

Step 3 Preparation of 4-{2-(2-Carboxy-ethyl)-3-[6-(4"-dimethylamino-3-fluoro-[1,1';3',1"]terphenyl-5'-yloxy)-hexyl]-phenoxy}-butyric acid

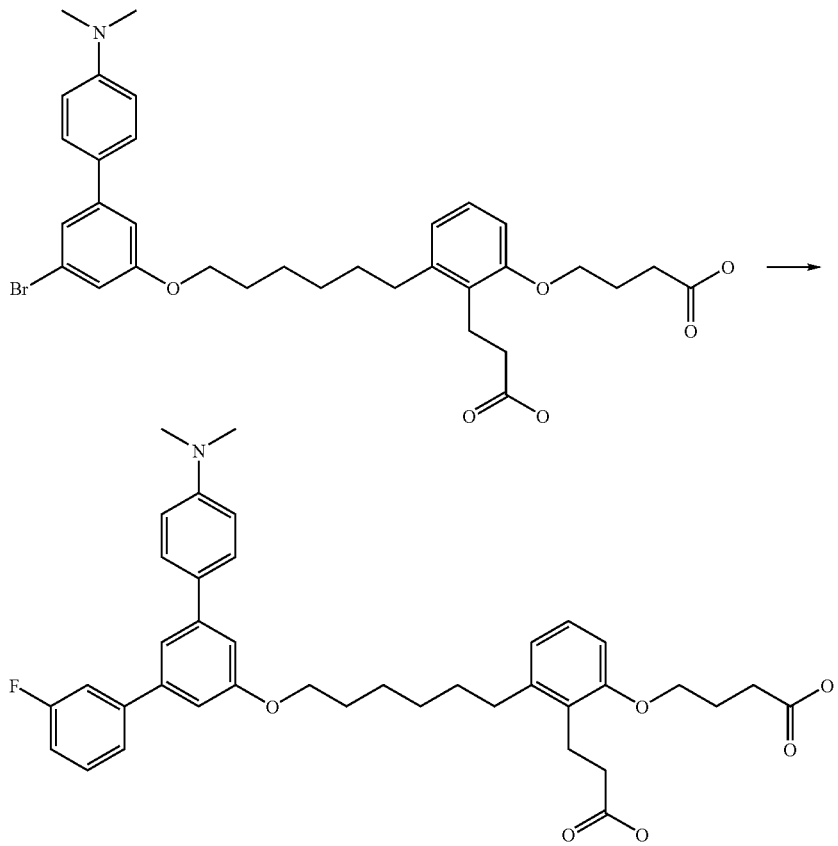

In a reaction vessel charged with 4 mL of toluene and 1 mL of water, was added 45 mg (0.072 mmol) of 4-[3-[6-(5-bromo-4'-dimethylamino-biphenyl-3-yloxy)-hexyl]-2-(2-carboxy-ethyl)-phenoxy]-butyric acid, 3-fluorophenylboronic acid (20 mg, 0.144 mmol), and potassium phosphate (35.9 mg, 0.144 mmol). This mixture was put under an atmosphere of nitrogen and 4.16 mg of tetrakis(triphenylphosphine)palladium(0) was added. This mixture was stirred and was heated overnight at 90° C. At this time, analysis of an aliquot by LC-MS, indicated the formation of the desired product. To the reaction mixture was added 2N HCl to effect pH=~6. The aqueous phase was thrice extracted with ethyl acetate. The combined organic phases were dried with MgSO$_4$, filtered and washed with ethyl acetate. The filtrate was concentrated in vacuo to provide a solid which was purified by preparative HPLC to provide 46 mg of product. Example 57 was characterized by low resolution mass spectrometry where signals corresponding to the following were observed: ES(+)=598+Na, ES(−)=597. Example 57 was also characterized by high resolution mass spectrometry where signals corresponding to the following were observed: m/e calculated for C$_{37}$H$_{39}$FO$_6$ 598.273068; found compatible with (M+Na)$^{1+}$=621.2624.

Example 58

4-{2-(2-Carboxy-ethyl)-3-[6-(4"-dimethylamino-3-methyl-[1,1';3',1"]terphenyl-5'-yloxy)-hexyl]-phenoxy}-butyric acid

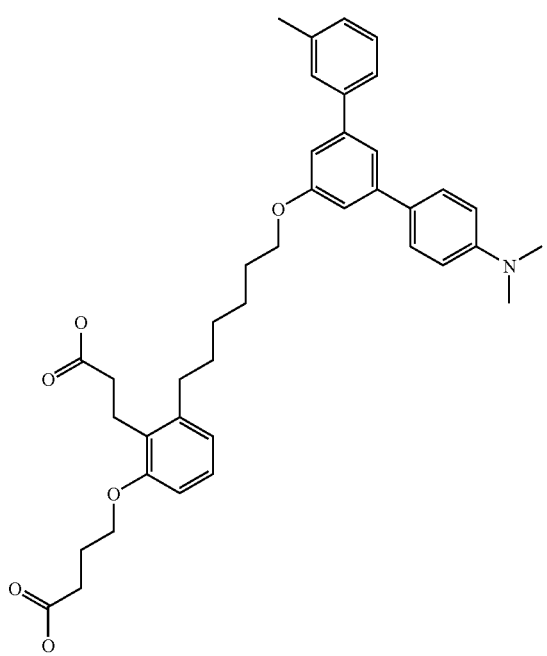

4-{2-(2-Carboxy-ethyl)-3-[6-(4"-dimethylamino-3-methyl-[1,1';3',1"]terphenyl-5'-yloxy)-hexyl]-phenoxy}-butyric acid was prepared as in a similar manner as that described for Example 57, except that 3-methylphenylboronic acid was substituted for 3-fluorophenylboronic acid in step 3. Example 58 was characterized by low resolution mass spectrometry where signals corresponding to the following were observed: ES(+)=638, ES(−)=636. Example 58 was also characterized by high resolution mass spectrometry where signals corresponding to the following were observed: m/e calculated for $C_{40}H_{47}NO_6$ 637.340339; found compatible with $(M+H)^{1+}$=638.3472.

Example 59

4-{2-(2-Carboxy-ethyl)-3-[6-(4"-dimethylamino-3-ethoxy-[1,1';3',1"]terphenyl-5'-yloxy)-hexyl]-phenoxy}-butyric acid

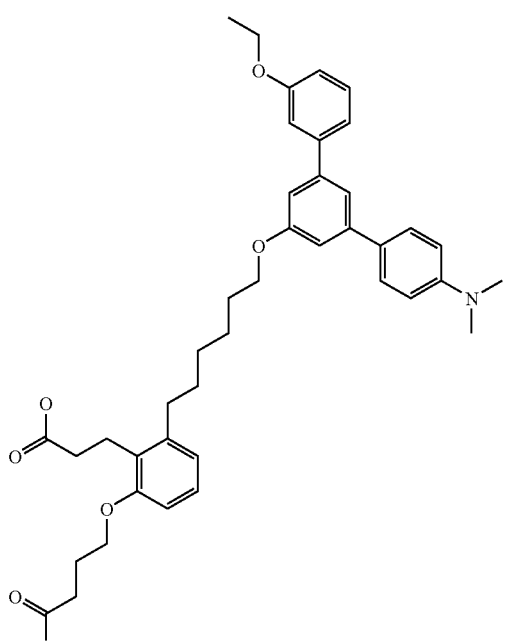

4-{2-(2-Carboxy-ethyl)-3-[6-(4"-dimethylamino-3-ethoxy-[1,1';3',1"]terphenyl-5'-yloxy)-hexyl]-phenoxy}-butyric acid was prepared as in a similar manner as that described for Example 57, except that 3-ethoxyphenylboronic acid was substituted for 3-fluorophenylboronic acid in step 3. Example 59 was characterized by low resolution mass spectrometry where signals corresponding to the following were observed: ES(+)=668, ES(−)=666. Example 59 was also characterized by high resolution mass spectrometry where signals corresponding to the following were observed: m/e calculated for $C_{41}H_{49}NO_7$ 667.350904; found compatible with $(M+H)^{1+}$=668.3577.

Example 60

4-{2-(2-Carboxy-ethyl)-3-[6-(4-dimethylamino-4''-methoxy-[1,1';3',1'']terphenyl-5'-yloxy)-hexyl]-phenoxy}-butyric acid

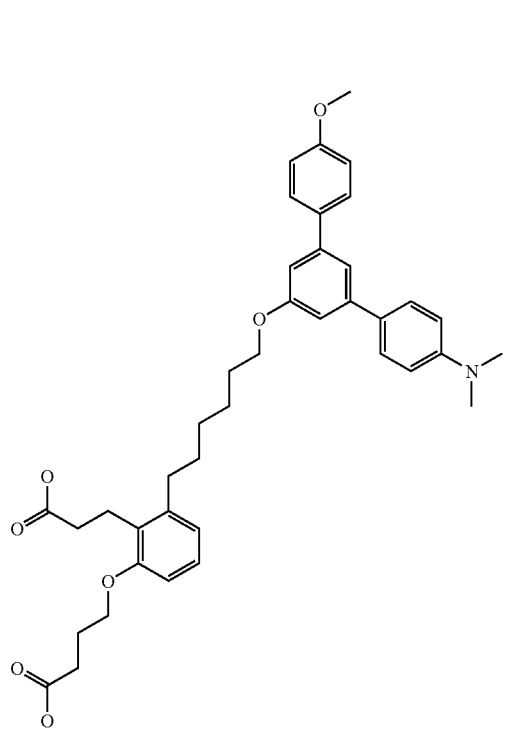

4-{2-(2-Carboxy-ethyl)-3-[6-(4-dimethylamino-4''-methoxy-[1,1';3',1'']terphenyl-5'-yloxy)-hexyl]-phenoxy}-butyric acid was prepared as in a similar manner as that described for Example 57, except that 4-methoxyphenylboronic acid was substituted for 3-fluorophenylboronic acid in step 3. Example 60 was characterized by low resolution mass spectrometry where signals corresponding to the following were observed: ES(+)=654, ES(−)=652. Example 60 was also characterized by high resolution mass spectrometry where signals corresponding to the following were observed: m/e calculated for $C_{40}H_{47}NO_7$ 653.335254; found compatible with $(M+H)^{1+}$=654.3426.

Example 61

4-{2-(2-Carboxy-ethyl)-3-[6-(4''-chloro-4-dimethylamino-[1,1';3',1'']terphenyl-5'-yloxy)-hexyl]-phenoxy}-butyric acid

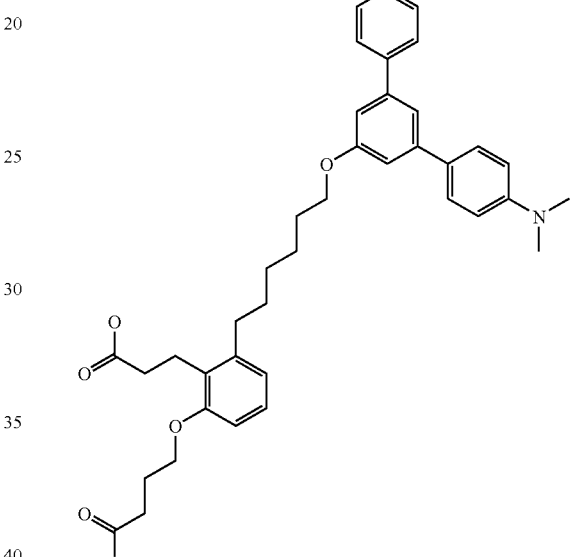

4-{2-(2-Carboxy-ethyl)-3-[6-(4''-chloro-4-dimethylamino-[1,1';3',1'']terphenyl-5'-yloxy)-hexyl]-phenoxy}-butyric acid was prepared as in a similar manner as that described for Example 57, except that 4-chlorophenylboronic acid was substituted for 3-fluorophenylboronic acid in step 3. Example 61 was characterized by low resolution mass spectrometry where signals corresponding to the following were observed: ES(+)=658, ES(−)=656. Example 61 was also characterized by high resolution mass spectrometry where signals corresponding to the following were observed: m/e calculated for $C_{39}H_{44}ClNO_6$ 657.285717; found compatible with $(M+H)^{1+}$=658.2936.

Example 62

4-[3-[6-(5-Benzo[1,3]dioxol-5-yl-4'-dimethylamino-biphenyl-3-yloxy)-hexyl]-2-(2-carboxy-ethyl)-phenoxy]-butyric acid

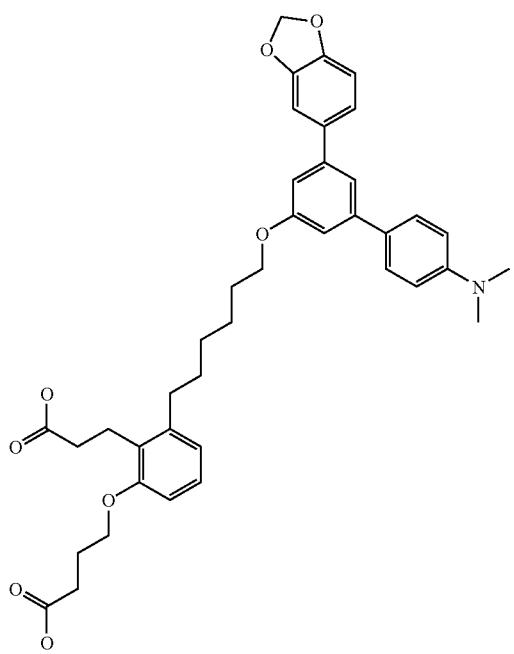

4-[3-[6-(5-Benzo[1,3]dioxol-5-yl-4'-dimethylamino-biphenyl-3-yloxy)-hexyl]-2-(2-carboxy-ethyl)-phenoxy]-butyric acid was prepared as in a similar manner as that described for Example 57, except that benzo[1,3]dioxol-5-yl-boronic acid was substituted for 3-fluorophenylboronic acid in step 3. Example 62 was characterized by low resolution mass spectrometry where signals corresponding to the following were observed: ES(+)=668, ES(−)=666. Example 62 was also characterized by high resolution mass spectrometry where signals corresponding to the following were observed: m/e calculated for $C_{40}H_{45}NO_8$ 667.314519; found compatible with $(M+H)^{1+}$=668.3214.

Example 63

4-{2-(2-Carboxy-ethyl)-3-[6-(4-chloro-4''-dimethylamino-3-fluoro-[1,1';3',1'']terphenyl-5'-yloxy)-hexyl]-phenoxy}-butyric acid

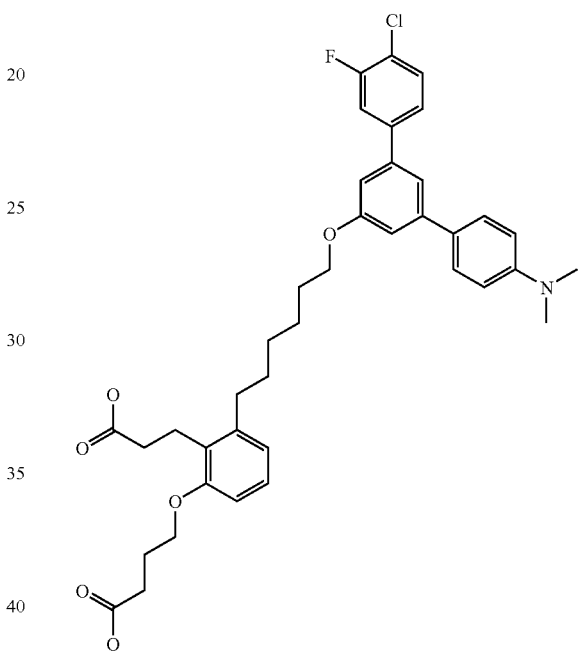

4-{2-(2-Carboxy-ethyl)-3-[6-(4-chloro-4''-dimethylamino-3-fluoro-[1,1';3',1'']terphenyl-5'-yloxy)-hexyl]-phenoxy}-butyric acid was prepared as in a similar manner as that described for Example 57, except that 4-chloro-3-fluorophenylboronic acid was substituted for 3-fluorophenylboronic acid in step 3. Example 63 was characterized by low resolution mass spectrometry where signals corresponding to the following were observed: ES(+)=676. Example 63 was also characterized by high resolution mass spectrometry where signals corresponding to the following were observed: m/e calculated for $C_{39}H_{43}ClFNO_6$ 675.276295; found compatible with $(M+H)^{1+}$=676.2833.

Example 64

4-{2-(2-Carboxy-ethyl)-3-[6-(2-chloro-4''-dimethylamino-[1,1';3',1'']terphenyl-5'-yloxy)-hexyl]-phenoxy}-butyric acid

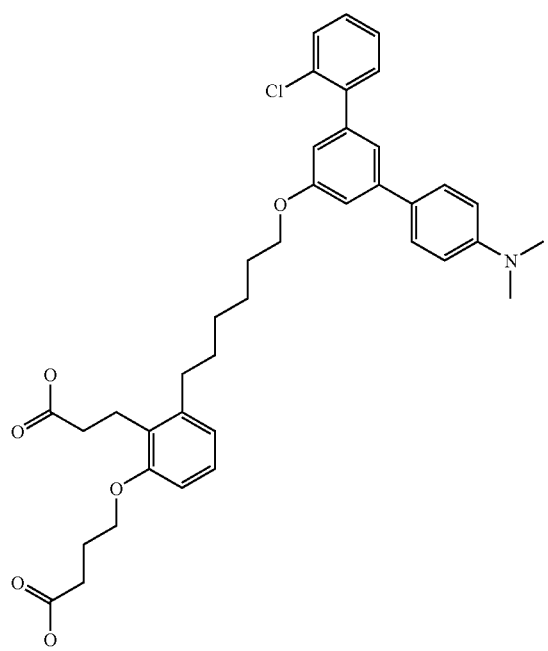

4-{2-(2-Carboxy-ethyl)-3-[6-(2-chloro-4''-dimethylamino-[1,1';3',1'']terphenyl-5'-yloxy)-hexyl]-phenoxy}-butyric acid was prepared as in a similar manner as that described for Example 57, except that 2-chlorophenylboronic acid was substituted for 3-fluorophenylboronic acid in step 3. Example 64 was characterized by low resolution mass spectrometry where signals corresponding to the following were observed: ES(+)=658, ES(−)=656. Example 64 was also characterized by high resolution mass spectrometry where signals corresponding to the following were observed: m/e calculated for $C_{39}H_{44}ClNO_6$ 657.285717; found compatible with $(M+H)^{1+}$=658.2930.

Example 65

4-{2-(2-Carboxy-ethyl)-3-[6-(4''-dimethylamino-4-fluoro-3-methyl-[1,1';3',1'']terphenyl-5'-yloxy)-hexyl]-phenoxy}-butyric acid

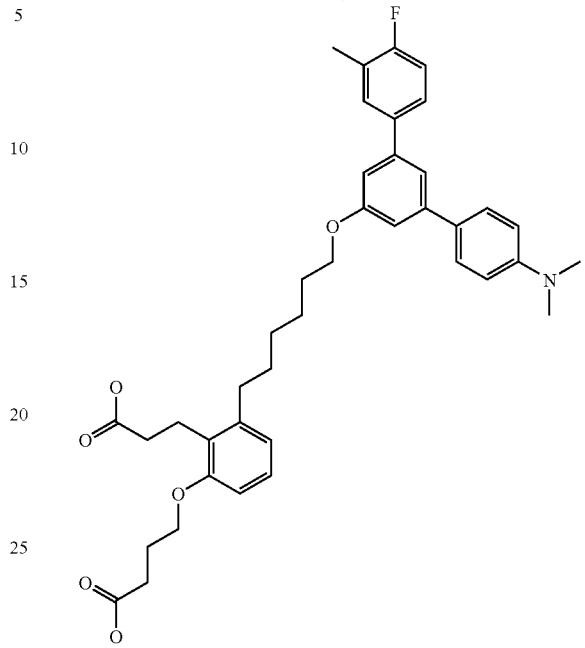

4-{2-(2-Carboxy-ethyl)-3-[6-(4''-dimethyl amino-4-fluoro-3-methyl-[1,1';3',1'']terphenyl-5'-yloxy)-hexyl]-phenoxy}-butyric acid was prepared as in a similar manner as that described for Example 57, except that 4-fluoro-3-methylphenylboronic acid was substituted for 3-fluorophenylboronic acid in step 3. Upon purification by HPLC, the compound was characterized by LC-MS. For the expected mass calculated for $C_{40}H_{46}FO_6$, 655.3309, 678.45 $(M+Na)^{1+}$ was detected for this sample having a purity of 75%.

Example 66

4-{2-(2-Carboxy-ethyl)-3-[6-(4''-dimethylamino-2-fluoro-[1,1';3',1'']terphenyl-5'-yloxy)-hexyl]-phenoxy}-butyric acid

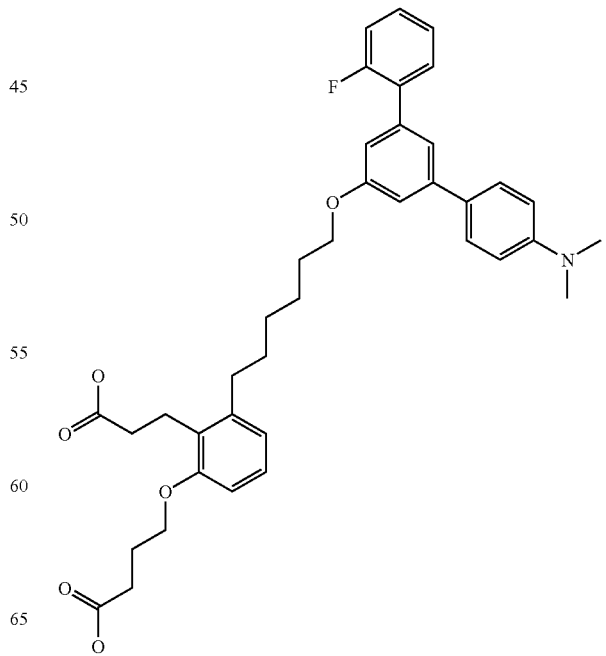

4-{2-(2-Carboxy-ethyl)-3-[6-(4"-dimethyl amino-2-fluoro-[1,1';3',1"]terphenyl-5'-yloxy)-hexyl]-phenoxy}-butyric acid was prepared as in a similar manner as that described for Example 57, except that 2-fluorophenylboronic acid was substituted for 3-fluorophenylboronic acid in step 3 Example 66 was characterized by low resolution mass spectrometry where signals corresponding to the following were observed: ES(+)=642. Example 66 was also characterized by high resolution mass spectrometry where signals corresponding to the following were observed: m/e calculated for C39H44F NO6 641.315267; found compatible with (M+H)$^{1+}$=642.3222.

Example 67

4-{2-(2-Carboxy-ethyl)-3-[6-(3-ethoxy-[1,1';3',1"]terphenyl-5'-yloxy)-hexyl]-phenoxy}-butyric acid

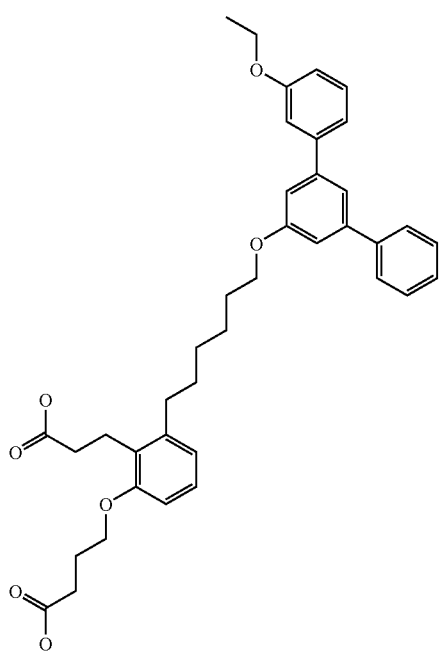

Step 1 Preparation of 5-bromo-biphenyl-3-ol

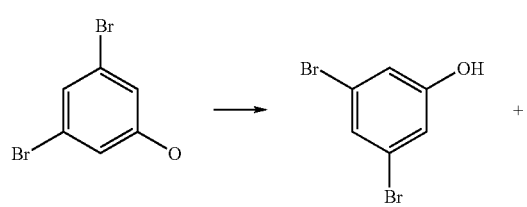

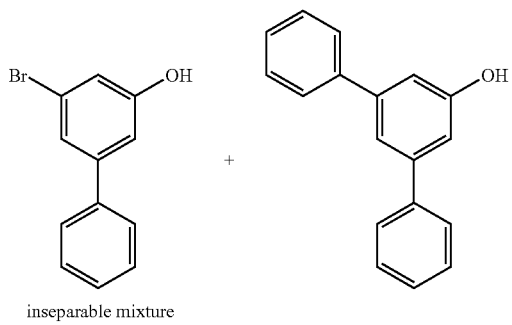

inseparable mixture

Toluene (400 mL) and water (20 mL) were added to a mixture of 3-,5-dibromophenol (5.088 g, 19.85 mmol), phenylboronic acid (2.42 g, 19.85 mmol) and potassium carbonate (5.48 g, 39.7 mmol) in a round bottom flask. This was followed by addition of 1.149 g of tetrakis(triphenylphosphine)palladium(0) under a atmosphere of nitrogen. This mixture was stirred at heated overnight at 90° C. At this time, HCl (2 N aq) was added to the reaction mixture until pH=~2 and the subsequent two phases were separated; the aqueous phase was extracted and washed three time with ethyl acetate. The combined organic phases were dried with MgSO$_4$, filtered and washed with ethyl acetate. The filtrate was concentrated in vacuo to provide an orange oil. Analysis of the oil by LC/MS indicated a mixture of desired product, starting material and the bis-phenyl coupling product The mixture was carried on to the next aryl boronic acid coupling step 2.

Step 2 Preparation of 5-aryl-biphenyl-3-ol

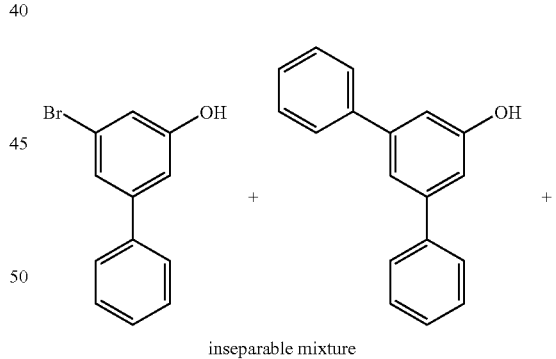

inseparable mixture

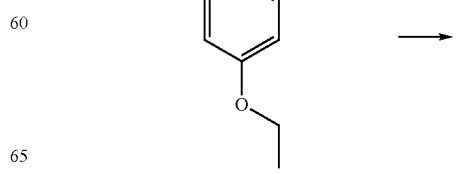

-continued

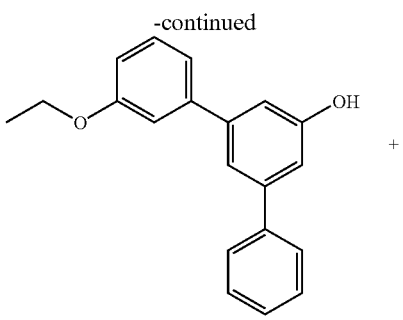

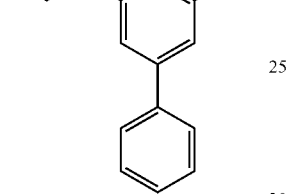

A reaction vial was charged with starting material (0.17 g). The starting material contained in addition to 5-bromo-biphenyl-3-ol, [1,1';3',1"]terphenyl-5'-ol. It was estimated that the 5-bromo-biphenyl-3-ol was present in 0.68 mmol quantity. To this mixture was added 3-ethoxyphenylboronic acid (350 mg) followed by tripotassium phosphate (342 mg) and 39 mg of tetrakis(triphenylphosphine)palladium(0). To this mixture was added 8 mL of toluene and 2 mL of water. A dark orange suspension was obtained and heated overnight to 90° C. At this time, the reaction was allowed to cool to room temperature and stirred for another 2 days. At this time, the mixture was acidified by addition of 2 M HCl to pH=~2. The product was extracted into ethyl acetate (2×5 mL EtOAc). The combined organic phases were dried with MgSO₄, filtered and washed with ethyl acetate. The filtrate was concentrated in vacuo to provide an brown oil. The crude product was purified by column chromatography eluted with a gradient of dichloromethane/hexane (2:8) to 100% dichloromethane. The 3-5-diphenylphenol product from Step 1 was eluted first; the desired 3-ethoxy-[1,1';3',1"]terphenyl-5'-ol was eluted next (60 mg, 0.20 mmol). This product was characterized by LC-MS where (M+H)⁺=291.

Step 3 Preparation of 4-{2-(2-carboxy-ethyl)-3-[6-(3-ethoxy-[1,1';3',1"]terphenyl-5'-yloxy)-hexyl]-phenoxy}-butyric acid 3-Ethoxy-[1,1';3',1"]terphenyl-5'-ol was reacted according to Step 3 of Example 57 to yield after HPLC purification 4-{2-(2-carboxy-ethyl)-3-[6-(3-ethoxy-[1,1';3',1"]terphenyl-5'-yloxy)-hexyl]-phenoxy}-butyric acid. Example 67 was characterized by low resolution mass spectrometry where signals corresponding to the following were observed: ES(+)=624+Na, ES(−)=623. Example 67 was also characterized by high resolution mass spectrometry where signals corresponding to the following were observed: m/e calculated for $C_{39}H_{44}O_7$ 624.308705; found compatible with $(M+Na)^{1+}$=647.2980.

Example 68

4-[3-[6-(5-Benzo[1,3]dioxol-5-yl-biphenyl-3-yloxy)-hexyl]-2-(2-carboxy-ethyl)-phenoxy]-butyric acid

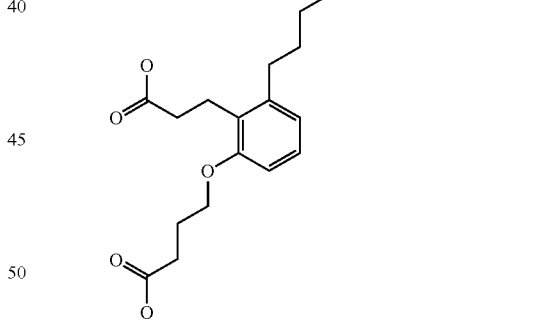

4-[3-[6-(5-Benzo[1,3]dioxol-5-yl-biphenyl-3-yloxy)-hexyl]-2-(2-carboxy-ethyl)-phenoxy]-butyric acid was prepared as in a similar manner as that described for Example 67, except that benzo[1,3]dioxol-5-yl-boronic acid was substituted for 3-ethoxyphenylboronic acid in step 2. Example 68 was characterized by low resolution mass spectrometry where signals corresponding to the following were observed: calculated for $C_{38}H_{40}O_8$, 624.2723; found 624.3 and 647.52 $(M+Na)^{1+}$; the compound was shown to have a purity of 84%.

183

Example 69

4-{2-(2-Carboxy-ethyl)-3-[6-(3-methyl-[1,1';3',1"]terphenyl-5'-yloxy)-hexyl]-phenoxy}-butyric acid

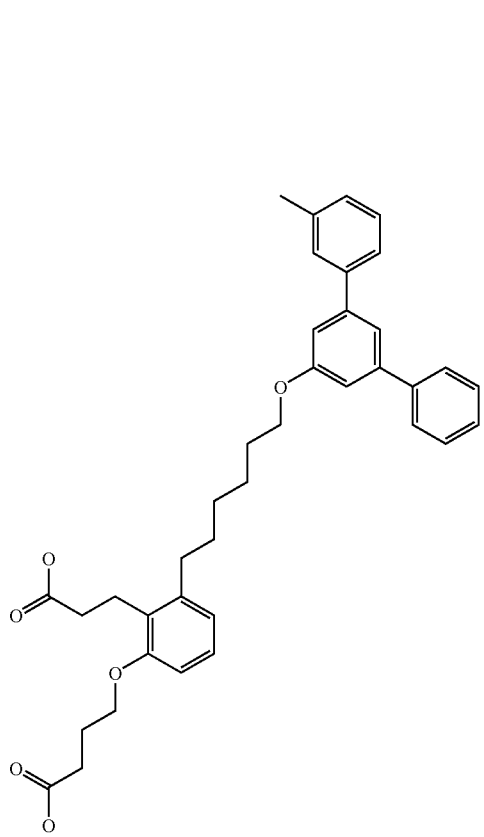

4-{2-(2-Carboxy-ethyl)-3-[6-(3-methyl-[1,1';3',1"]terphenyl-5'-yloxy)-hexyl]-phenoxy}-butyric acid was prepared as in a similar manner as that described for Example 67, except that 3-methylphenylboronic acid was substituted for 3-fluorophenylboronic acid in step 3. Example 69 was characterized by low resolution mass spectrometry where signals corresponding to the following were observed: ES(+)=594, ES(−)=593. Example 69, having an expected mass of 594.29814, was also characterized by high resolution mass spectrometry where signals corresponding to the following were observed: Compatible with $(M+Na)^{1+}$=617.2875.

184

Example 70

4-{2-(2-Carboxy-ethyl)-3-[6-(4-trifluoromethoxy-[1,1';3',1"]terphenyl-5'-yloxy)-hexyl]-yloxy)-hexyl]-phenoxy}-butyric acid

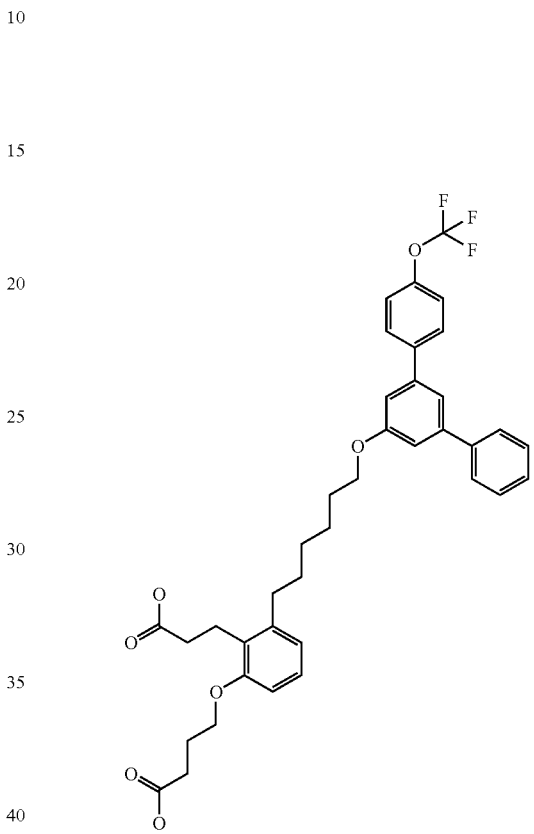

4-{2-(2-Carboxy-ethyl)-3-[6-(4-trifluoromethoxy-[1,1';3',1"]terphenyl-5'-yloxy)-hexyl]-phenoxy}-butyric acid was prepared as in a similar manner as that described for Example 67, except that 4-trifluoromethoxyphenylboronic acid was substituted for 3-ethoxyphenylboronic acid in step 2. Example 70 was characterized by low resolution mass spectrometry where signals corresponding to the following were observed: ES(+)=664+Na, ES(−)=663. Example 70 was also characterized by high resolution mass spectrometry where signals corresponding to the following were observed: m/e calculated for $C_{38}H_{39}F_3O_7$ 664.264789; found compatible with $(M+Na)^{1+}$=687.2536.

Example 71
4-{2-(2-Carboxy-ethyl)-3-[6-(3-chloro-4-fluoro-[1,1';3',1"]terphenyl-5'-yloxy)-hexyl]-phenoxy}-butyric acid

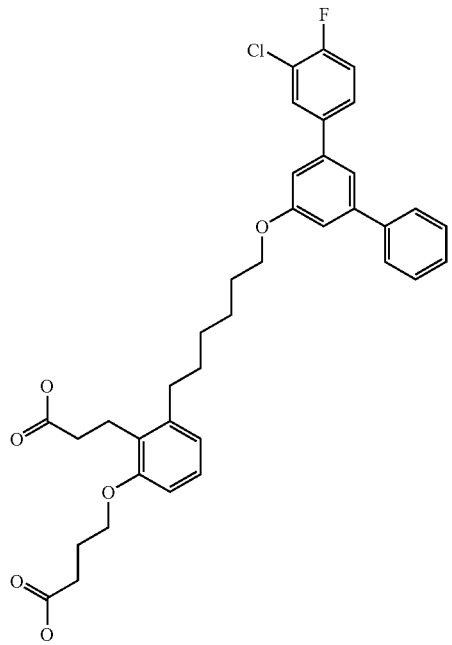

4-{2-(2-Carboxy-ethyl)-3-[6-(3-chloro-4-fluoro-[1,1';3',1"]terphenyl-5'-yloxy)-hexyl]-phenoxy}-butyric acid was prepared as in a similar manner as that described for Example 67, except that 3-chloro-4-fluorophenylboronic acid was substituted for 3-ethoxyphenylboronic acid in step 2. Example 71 was characterized by low resolution mass spectrometry where signals corresponding to the following were observed: ES(+)=632+Na, ES(−)=631. Example 71 was also characterized by high resolution mass spectrometry where signals corresponding to the following were observed: m/e calculated for $C_{37}H_{38}ClFO_6$ 632.234096; found compatible with $(M+Na)^{1+}$=655.2232.

Example 72
4-{2-(2-Carboxy-ethyl)-3-[6-(2-chloro-[1,1';3',1"]terphenyl-5'-yloxy)-hexyl]-phenoxy}-butyric acid

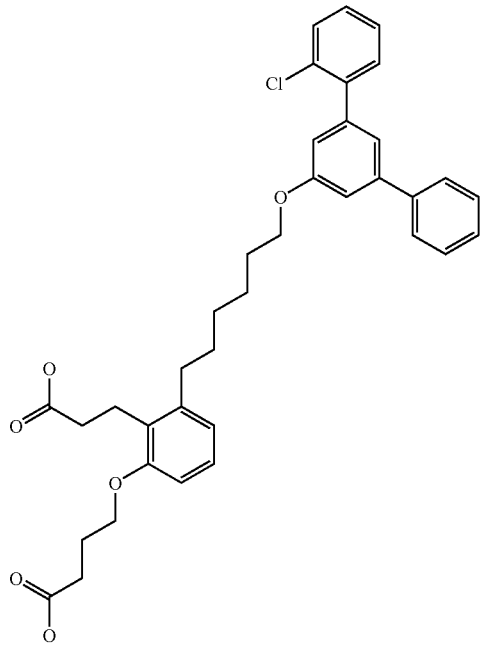

4-{2-(2-Carboxy-ethyl)-3-[6-(2-chloro-[1,1';3',1"]terphenyl-5'-yloxy)-hexyl]-phenoxy}-butyric acid was prepared as in a similar manner as that described for Example 67, except that 2-chlorophenylboronic acid was substituted for 3-ethoxyphenylboronic acid in step 2. Upon purification by HPLC, the compound was characterized by LC-MS. For the expected mass calculated for $C_{37}H_{39}ClO_6$, 614.2435, 637.47 $(M+Na)^{1+}$ was detected for this sample having a purity of 80%.

Example 73

4-{2-(2-Carboxy-ethyl)-3-[6-(5-quinolin-5-yl-biphenyl-3-yloxy)-hexyl]-phenoxy}-butyric acid

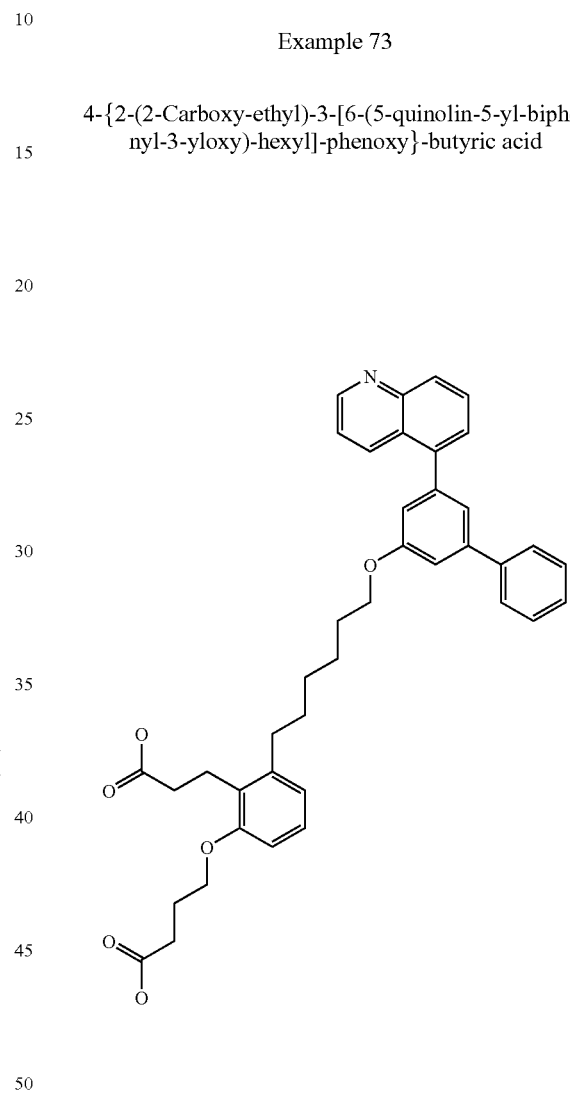

4-{2-(2-Carboxy-ethyl)-3-[6-(5-quinolin-5-yl-biphenyl-3-yloxy)-hexyl]-phenoxy}-butyric acid was prepared as in a similar manner as that described for Example 67, except that 5-quinolinylboronic acid was substituted for 3-ethoxyphenylboronic acid in step 2. Example 73 was characterized by low resolution mass spectrometry where signals corresponding to the following were observed: ES(+)=632, ES(−)=630. Example 73 was also characterized by high resolution mass spectrometry where signals corresponding to the following were observed: m/e calculated for $C_{40}H_{41}O_6$ 631.293389; found compatible with $(M+H)^{1+}$=632.3003.

Example 74

4-(2-(2-Carboxy-ethyl)-3-{6-[5-(1-methyl-1H-indol-5-yl)-biphenyl-3-yloxy]-hexyl}-phenoxy)-butyric acid

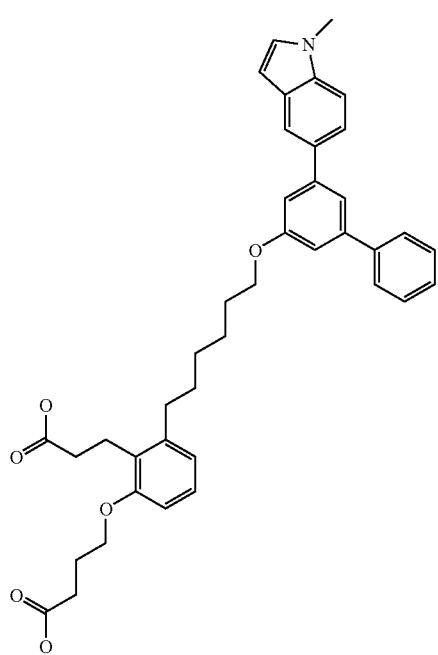

4-(2-(2-Carboxy-ethyl)-3-{6-[5-(1-methyl-1H-indol-5-yl)-biphenyl-3-yloxy]-hexyl}-phenoxy)-butyric acid was prepared as in a similar manner as that described for Example 67, except that 5-(1-methyl-1H-indole)-boronic acid was substituted for 3-ethoxyphenylboronic acid in step 2. Example 74 was characterized by low resolution mass spectrometry where signals corresponding to the following were observed: ES(+)=633+, ES(−)=632. Example 74, having an expected mass of 633.309039, was also characterized by high resolution mass spectrometry where signals corresponding to the following were observed: Compatible with (M+Na)$^{1+}$=656.2985.

Example 75

4-{2-(2-Carboxy-ethyl)-3-[6-(3-fluoro-[1,1';3',1"]terphenyl-5'-yloxy)-hexyl]-phenoxy}-butyric acid

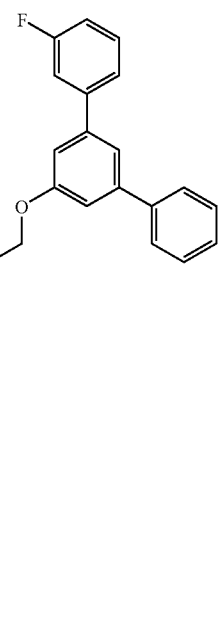

4-{2-(2-Carboxy-ethyl)-3-[6-(3-fluoro-[1,1';3',1"]terphenyl-5'-yloxy)-phenoxy}-butyric acid was prepared as in a similar manner as that described for Example 67, except that 3-fluorophenylboronic acid was substituted for 3-ethoxyphenylboronic acid in step 2. Example 75 was characterized by low resolution mass spectrometry where signals corresponding to the following were observed: ES(+)=633+, ES(−)=632. Example 75, having an expected mass of 633.309039, was also characterized by high resolution mass spectrometry where signals corresponding to the following were observed: Compatible with (M+Na)$^{1+}$=656.2985.

Example 76

4-{2-(2-Carboxy-ethyl)-3-[6-(4"-methoxy-3-methyl-[1,1';3',1"]terphenyl-5'-yloxy)-hexyl]-phenoxy}-butyric acid

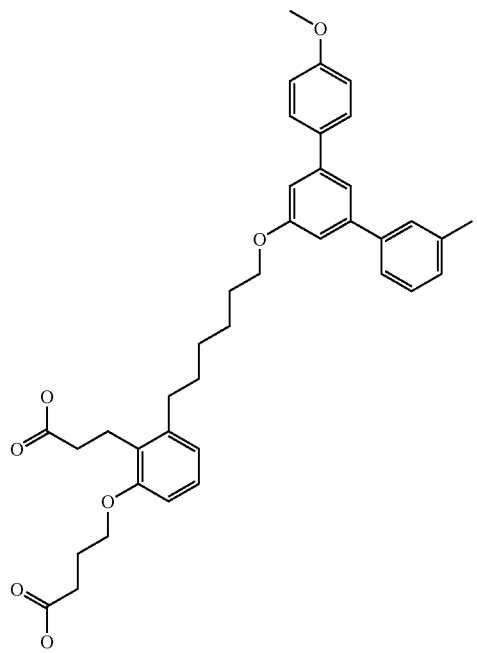

Example 77

4-{2-(2-Carboxy-ethyl)-3-[6-(4-fluoro-4"-methoxy-3-methyl-[1,1';3',1"]terphenyl-5'-yloxy)-hexyl]-phenoxy}-butyric acid

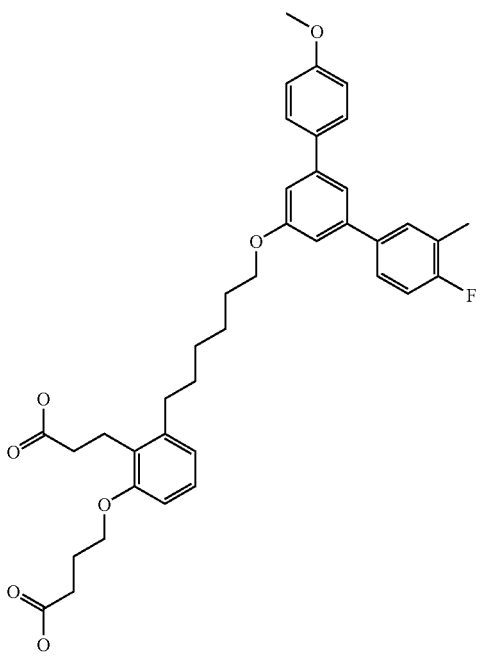

4-{2-(2-Carboxy-ethyl)-3-[6-(4"-methoxy-3-methyl-[1,1';3',1"]terphenyl-5'-yloxy)-hexyl]-phenoxy}-butyric acid was synthesized in a manner similar to Example 67 except that in Step 1, 4-methoxyphenylboronic acid was used as the first boronic acid coupling reagent. In Step 2, 3-methylphenylboronic acid was used as the second boronic acid coupling reagent. Coupling of the bis-arylphenol was conducted in a manner as described for Example 57, Step 3. Upon purification by HPLC, the compound was characterized by LC-MS. For the expected mass of 624.308705, 647.42 (M+Na)$^+$ was observed; the compound was shown to have a purity of 100%. Example 76 was characterized by low resolution mass spectrometry where signals corresponding to the following were observed: ES(+)=624+Na, ES(−)=623. Example 76 was also characterized by high resolution mass spectrometry where signals corresponding to the following were observed: m/e calculated for $C_{39}H_{44}O_7$ 624.308705; found compatible with (M+Na)$^{1+}$=647.2977.

4-{2-(2-Carboxy-ethyl)-3-[6-(4-fluoro-4"-methoxy-3-methyl-[1,1';3',1"]terphenyl-5'-yloxy)-hexyl]-phenoxy}-butyric acid was synthesized in a manner similar to Example 67 except that in Step 1, 4-methoxyphenylboronic acid was used as the first boronic acid coupling reagent. In Step 2, 2-fluoro-3-methylphenylboronic acid was used as the second boronic acid coupling reagent. Coupling of the bis-arylphenol was conducted in a manner as described for Example 57, Step 3. Upon purification by HPLC, the compound was characterized by LC-MS. For the expected mass of 642.299283, 665.40 (M+Na)$^+$ was observed; the compound was shown to have a purity of 100%. Example 77 was characterized by low resolution mass spectrometry where signals corresponding to the following were observed: ES(+)=643, ES(−)=641. Example 76 was also characterized by high resolution mass spectrometry where signals corresponding to the following were observed: m/e calculated for $C_{39}H_{43}FO_7$ 642.299283; found compatible with (M+Na)$^{1+}$=665.2886.

Example 78

4-{2-(2-Carboxy-ethyl)-3-[6-(2-fluoro-4"-methoxy-[1,1';3',1"]terphenyl-5'-yloxy)-hexyl]-phenoxy}-butyric acid

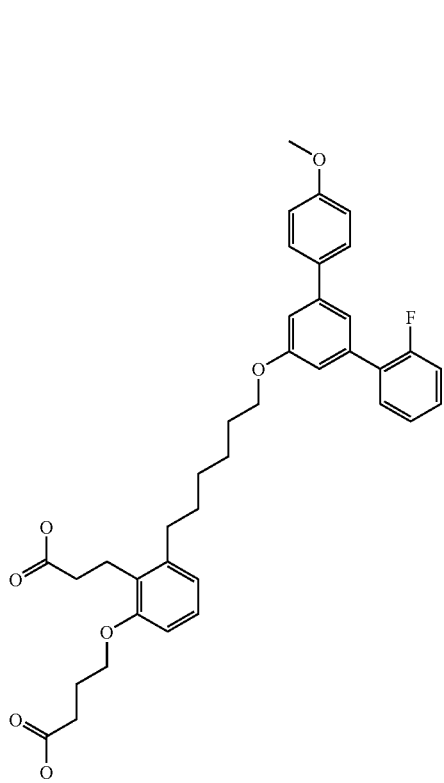

4-{2-(2-Carboxy-ethyl)-3-[6-(2-fluoro-4"-methoxy-[1,1';3',1"]terphenyl-5'-yloxy)-hexyl]-phenoxy}-butyric acid was synthesized in a manner similar to Example 67 except that in Step 1, 4-methoxyphenylboronic acid was used as the first boronic acid coupling reagent. In Step 2, 2-fluorophenylboronic acid was used as the second boronic acid coupling reagent. Coupling of the bis-arylphenol was conducted in a manner as described for Example 57, Step 3. Upon purification by HPLC, the compound was characterized by LC-MS. For the expected mass of 628.283633, 651.40 (M+Na)$^+$ was observed; the compound was shown to have a purity of 100%. Example 78 was characterized by low resolution mass spectrometry where signals corresponding to the following were observed: ES(+)=628+Na+H2O. Example 78 was also characterized by high resolution mass spectrometry where signals corresponding to the following were observed: m/e calculated for $C_{38}H_{41}FO_7$ 628.283633; found compatible with (M+Na)$^{1+}$=651.2732

Example 79

4-{2-(2-Carboxy-ethyl)-3-[6-(4"-methoxy-4-trifluoromethoxy-[1,1';3',1"]terphenyl-5'-yloxy)-hexyl]-phenoxy}-butyric acid

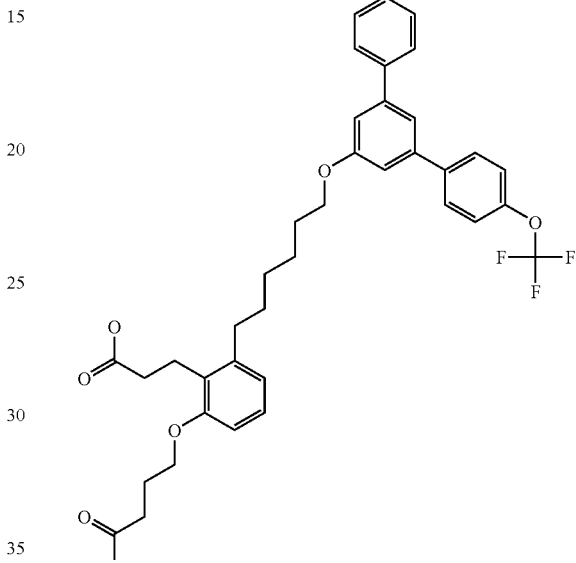

4-{2-(2-Carboxy-ethyl)-3-[6-(4"-methoxy-4-trifluoromethoxy-[1,1';3',1"]terphenyl-5'-yloxy)-hexyl]-phenoxy}-butyric acid was synthesized in a manner similar to Example 67 except that in Step 1, 4-methoxyphenylboronic acid was used as the first boronic acid coupling reagent. In Step 2, 4-trifluoromethoxy-phenylboronic acid was used as the second boronic acid coupling reagent. Coupling of the bis-arylphenol was conducted in a manner as described for Example 57, Step 3. Upon purification by HPLC, the compound was characterized by LC-MS. For the expected mass of 694.275354, 693.47 (M+H)$^+$ was observed; the compound was shown to have a purity of 100%. Example 79 was characterized by low resolution mass spectrometry where signals corresponding to the following were observed: ES(+)=694+Na, ES(−)=693. Example 79 was also characterized by high resolution mass spectrometry where signals corresponding to the following were observed: m/e calculated for $C_{39}H_{41}F_3O_8$ 694.275354; found compatible with (M+Na)$^{1+}$=717.2652.

Example 80

4-{2-(2-Carboxy-ethyl)-3-[6-(4-fluoro-4"-methoxy-3-methyl-[1,1';3',1"]terphenyl-5'-yloxy)-hexyl]-phenoxy}-butyric acid

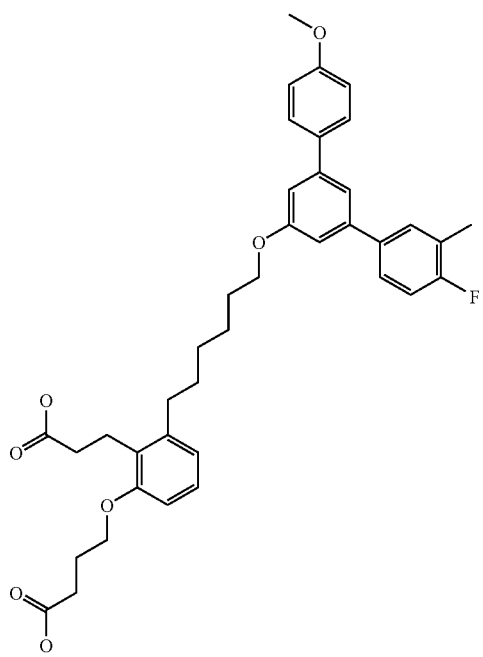

4-{2-(2-Carboxy-ethyl)-3-[6-(4-fluoro-4"-methoxy-3-methyl-[1,1';3',1"]terphenyl-5'-yloxy)-hexyl]-phenoxy}-butyric acid was synthesized in a manner similar to Example 67 except that in Step 1, 4-methoxyphenylboronic acid was used as the first boronic acid coupling reagent. In Step 2, 4-fluoro-3-methylphenylboronic acid was used as the second boronic acid coupling reagent. Coupling of the bis-arylphenol was conducted in a manner as described for Example 57, Step 3. Upon purification by HPLC, the compound was characterized by LC-MS. For the expected mass of 642.299283, 665.40 (M+Na)$^+$ was observed; the compound was shown to have a purity of 100%. Example 80 was characterized by low resolution mass spectrometry where signals corresponding to the following were observed: ES(+)=643, ES(−)=641. Example 80 was also characterized by high resolution mass spectrometry where signals corresponding to the following were observed: m/e calculated for $C_{39}H_{43}FO_7$ 642.299283; found compatible with (M+Na)$^{1+}$=665.2886.

Example 81

4-{2-(2-Carboxy-ethyl)-3-[6-(4"-methoxy-2-trifluoromethyl-[1,1';3',1"]terphenyl-5'-yloxy)-hexyl]-phenoxy}-butyric acid

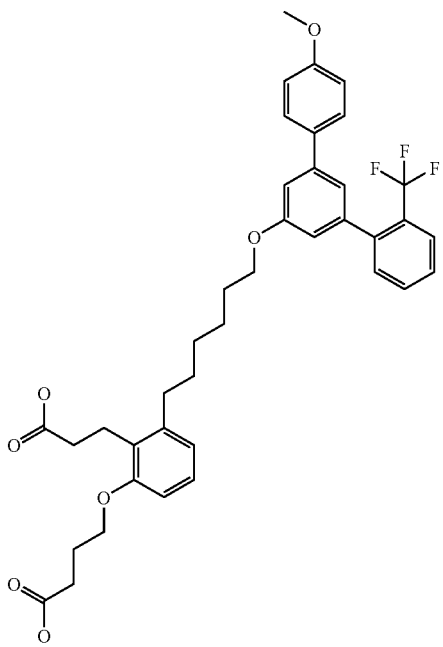

4-{2-(2-Carboxy-ethyl)-3-[6-(4"-methoxy-2-trifluoromethyl-[1,1';3',1"]terphenyl-5'-yloxy)-hexyl]-phenoxy}-butyric acid was synthesized in a manner similar to Example 67 except that in Step 1, 4-methoxyphenylboronic acid was used as the first boronic acid coupling reagent. In Step 2, 2-methoxy-4-fluorophenylboronic acid was used as the second boronic acid coupling reagent. Coupling of the bis-arylphenol was conducted in a manner as described for Example 57, Step 3. Upon purification by HPLC, the compound was characterized by LC-MS. For the expected mass of 678.280439, 701.39 (M+Na)$^+$ was observed; the compound was shown to have a purity of 100%. Example 81 was characterized by low resolution mass spectrometry where signals corresponding to the following were observed: ES(+)=678, ES(−)=677. Example 81 was characterized by low resolution mass spectrometry where signals corresponding to the following were observed: ES(+)=678+Na, ES(−)=677. Example 81 was also characterized by high resolution mass spectrometry where signals corresponding to the following were observed: m/e calculated for $C_{39}H_{41}F_3O_7$ 678.280439; found compatible with (M+Na)$^{1+}$=701.2696.

Example 82

4-{2-(2-Carboxy-ethyl)-3-[6-(4''-fluoro-4-methoxy-[1,1';3',1'']terphenyl-5'-yloxy)-hexyl]-phenoxy}-butyric acid

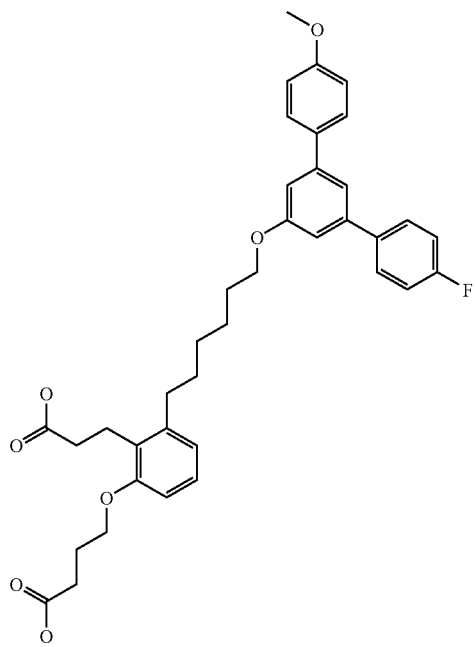

Example 83

4-{2-(2-Carboxy-ethyl)-3-[6-(5'-fluoro-2'-methoxy-5-thiophen-3-yl-biphenyl-3-yloxy)-hexyl]-phenoxy}-butyric acid

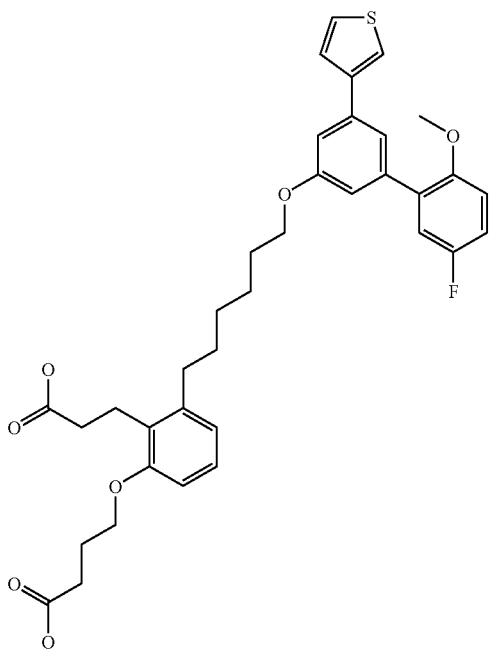

4-{2-(2-Carboxy-ethyl)-3-[6-(4''-fluoro-4-methoxy-[1,1'; 3',1'']terphenyl-5'-yloxy)-hexyl]-phenoxy}-butyric acid was synthesized in a manner similar to Example 67 except that in Step 1, 4-fluorophenylboronic acid was used as the first boronic acid coupling reagent. In Step 2, 2-trifluoromethylphenylboronic acid was used as the second boronic acid coupling reagent. Coupling of the bis-arylphenol was conducted in a manner as described for Example 57, Step 3. Upon purification by HPLC, the compound was characterized by LC-MS. For the expected mass of 628.283633, 651.41 $(M+Na)^+$ was observed; the compound was shown to have a purity of 100%. Example 82 was characterized by low resolution mass spectrometry where signals corresponding to the following were observed: ES(+)=646, ES(−)=645. Example 82 was characterized by low resolution mass spectrometry where signals corresponding to the following were observed: ES(+)=628+Na, ES(−)=627. Example 82 was also characterized by high resolution mass spectrometry where signals corresponding to the following were observed: m/e calculated for C38H41 FO7 628.283633; found compatible with $(M+Na)^{1+}$=651.2734.

4-{2-(2-Carboxy-ethyl)-3-[6-(5'-fluoro-2'-methoxy-5-thiophen-3-yl-biphenyl-3-yloxy)-hexyl]-phenoxy}-butyric acid was synthesized in a manner similar to Example 67 except that in Step 1, thiophen-3-ylboronic acid was used as the first boronic acid coupling reagent. In Step 2, 2-methoxy-4-fluorophenylboronic acid was used as the second boronic acid coupling reagent. Coupling of the bis-arylphenol was conducted in a manner as described for Example 57, Step 3. Upon purification by HPLC, the compound was characterized by LC-MS. For the expected mass of 634.240055, 657.38 $(M+Na)^+$ was observed; the compound was shown to have a purity of 100%. Example 83 was characterized by low resolution mass spectrometry where signals corresponding to the following were observed: ES(+)=634, ES(−)=633. Example 83 was characterized by low resolution mass spectrometry where signals corresponding to the following were observed: ES(+)=634+Na, ES(−)=633. Example 83 was also characterized by high resolution mass spectrometry where signals corresponding to the following were observed: m/e calculated for $C_{36}H_{39}FO_7$ S 634.240055; found compatible with $(M+Na)^{1+}$=657.2293.

Example 84

4-[3-[6-(5-Benzo[1,3]dioxol-5-yl-4'-methoxy-biphenyl-3-yloxy)-hexyl]-2-(2-carboxy-ethyl)-phenoxy]-butyric acid

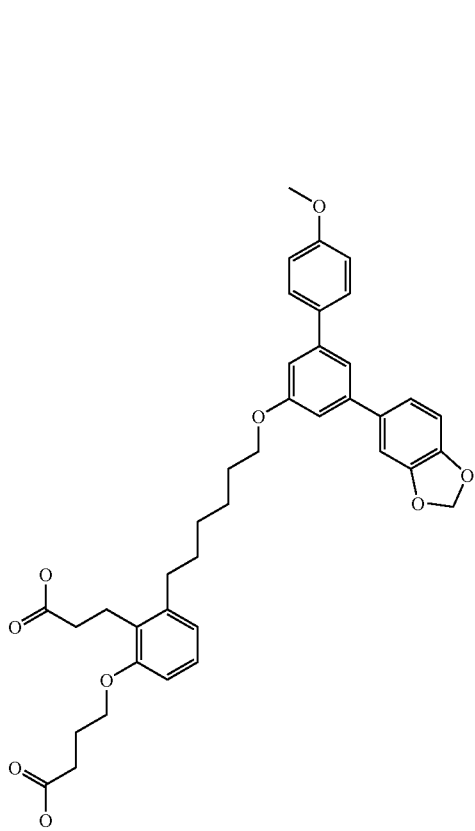

4-[3-[6-(5-Benzo[1,3]dioxol-5-yl-4'-methoxy-biphenyl-3-yloxy)-hexyl]-2-(2-carboxy-ethyl)-phenoxy]-butyric acid was synthesized in a manner similar to Example 67 except that in Step 1, benzo[1,3]dioxol-5-yl-boronic acid was used as the first boronic acid coupling reagent. In Step 2, 4-fluoro-3-methylphenylboronic acid was used as the second boronic acid coupling reagent. Coupling of the bis-arylphenol was conducted in a manner as described for Example 57, Step 3. Upon purification by HPLC, the compound was characterized by LC-MS. For the expected mass of 654.282885 for $C_{39}H_{42}O_9$, 677.45 $(M+Na)^{1+}$ was observed; the compound was shown to have a purity of 100%.

Example 85

4-[3-[6-(5-Benzo[1,3]dioxol-5-yl-4'-fluoro-3'-methyl-biphenyl-3-yloxy)-hexyl]-2-(2-carboxy-ethyl)-phenoxy]-butyric acid

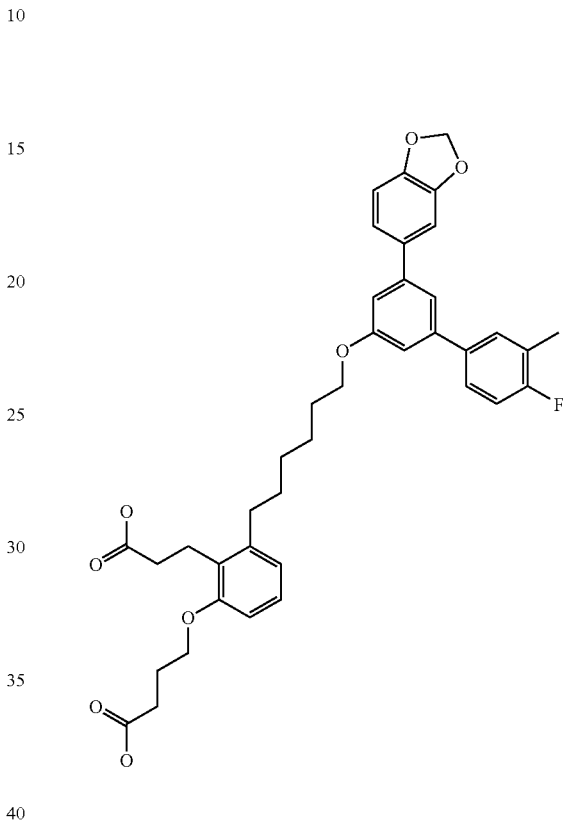

4-[3-[6-(5-Benzo[1,3]dioxol-5-yl-4'-fluoro-3'-methyl-biphenyl-3-yloxy)-hexyl]-2-(2-carboxy-ethyl)-phenoxy]-butyric acid was synthesized in a manner similar to Example 67 except that in Step 1, benzo[1,3]dioxol-5-yl-boronic acid was used as the first boronic acid coupling reagent. In Step 2, 3-methyl-4-fluorophenylboronic acid was used as the second boronic acid coupling reagent. Coupling of the bis-arylphenol was conducted in a manner as described for Example 57, Step 3. Upon purification by HPLC, the compound was characterized by LC-MS. For the expected mass of 656.278548, 679.47 $(M+Na)^+$ was observed; the compound was shown to have a purity of 100%. Example 85 was characterized by low resolution mass spectrometry where signals corresponding to the following were observed: ES(+)=656+Na, ES(−)=655. Example 85 was also characterized by high resolution mass spectrometry where signals corresponding to the following were observed: m/e calculated for $C_{39}H_{41}FO_8$ 656.278548; found compatible with $(M+Na)^{1+}$=679.2682.

Example 86

4-[3-[6-(5-Benzo[1,3]dioxol-5-yl-3'-methyl-biphenyl-3-yloxy)-hexyl]-2-(2-carboxy-ethyl)-phenoxy]-butyric acid

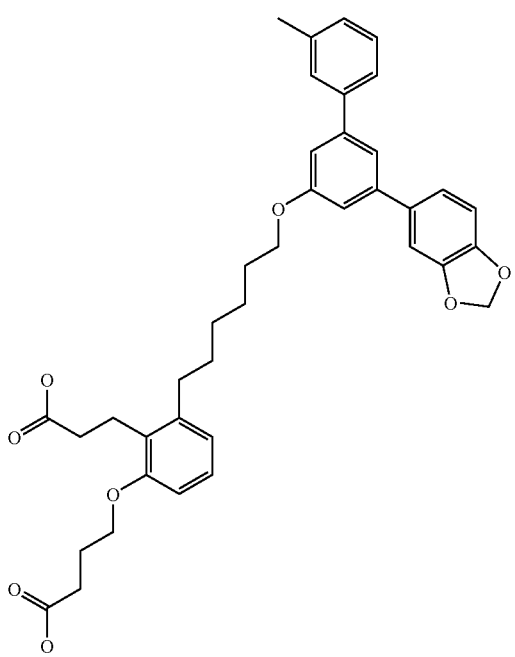

Example 87

4-[3-[6-(5-Benzo[1,3]dioxol-5-yl-2'-fluoro-biphenyl-3-yloxy)-hexyl]-2-(2-carboxy-ethyl)-phenoxy]-butyric acid

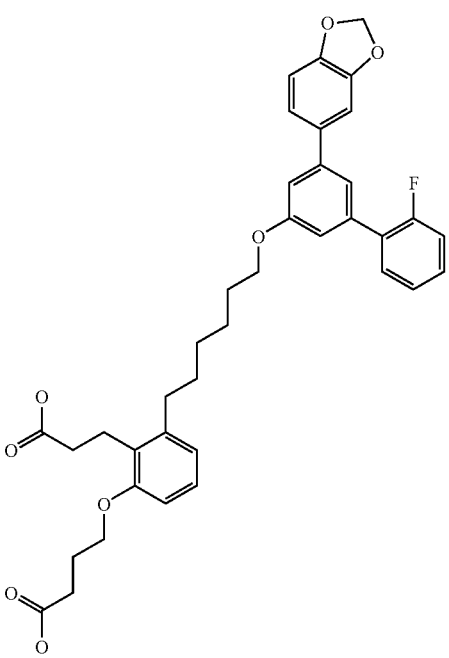

4-[3-[6-(5-Benzo[1,3]dioxol-5-yl-3'-methyl-biphenyl-3-yloxy)-hexyl]-2-(2-carboxy-ethyl)-phenoxy]-butyric acid was synthesized in a manner similar to Example 67 except that in Step 1, benzo[1,3]dioxol-5-yl-boronic acid was used as the first boronic acid coupling reagent. In Step 2, 3-methylphenylboronic acid was used as the second boronic acid coupling reagent. Coupling of the bis-arylphenol was conducted in a manner as described for Example 57, Step 3. Upon purification by HPLC, the compound was characterized by LC-MS. For the expected mass of 638.28797, 661.46 (M+Na)$^+$ was observed; the compound was shown to have a purity of 100%. Example 86 was characterized by low resolution mass spectrometry where signals corresponding to the following were observed: ES(+)=638+Na, ES(−)=637. Example 86 was also characterized by high resolution mass spectrometry where signals corresponding to the following were observed: m/e calculated for $C_{39}H_{42}O_8$ 638.28797; found compatible with (M+Na)$^{1+}$=661.2775.

4-[3-[6-(5-Benzo[1,3]dioxol-5-yl-2'-fluoro-biphenyl-3-yloxy)-hexyl]-2-(2-carboxy-ethyl)-phenoxy]-butyric acid was synthesized in a manner similar to Example 67 except that in Step 1, benzo[1,3]dioxol-5-yl-boronic acid was used as the first boronic acid coupling reagent. In Step 2, 2-fluoromethylphenylboronic acid was used as the second boronic acid coupling reagent. Coupling of the bis-arylphenol was conducted in a manner as described for Example 57, Step 3. Upon purification by HPLC, the compound was characterized by LC-MS. For the expected mass of 642.262898, 665.46 (M+Na)$^+$ was observed; the compound was shown to have a purity of 100%. Example 87 was characterized by low resolution mass spectrometry where signals corresponding to the following were observed: ES(+)=642+Na, ES(−)=641. Example 87 was also characterized by high resolution mass spectrometry where signals corresponding to the following were observed: m/e calculated for $C_{38}H_{39}FO_8$ 642.262898; found compatible with (M+Na)$^{1+}$=665.2524.

Example 88

4-{2-(2-Carboxy-ethyl)-3-[6-(4,4''-dimethoxy-[1,1'; 3',1'']terphenyl-5'-yloxy)-hexyl]-phenoxy}-butyric acid

Example 89

4-[3-[6-(4,4''-Bis-trifluoromethoxy-[1,1';3',1'']terphenyl-5'-yloxy)-hexyl]-2-(2-carboxy-ethyl)-phenoxy]-butyric acid

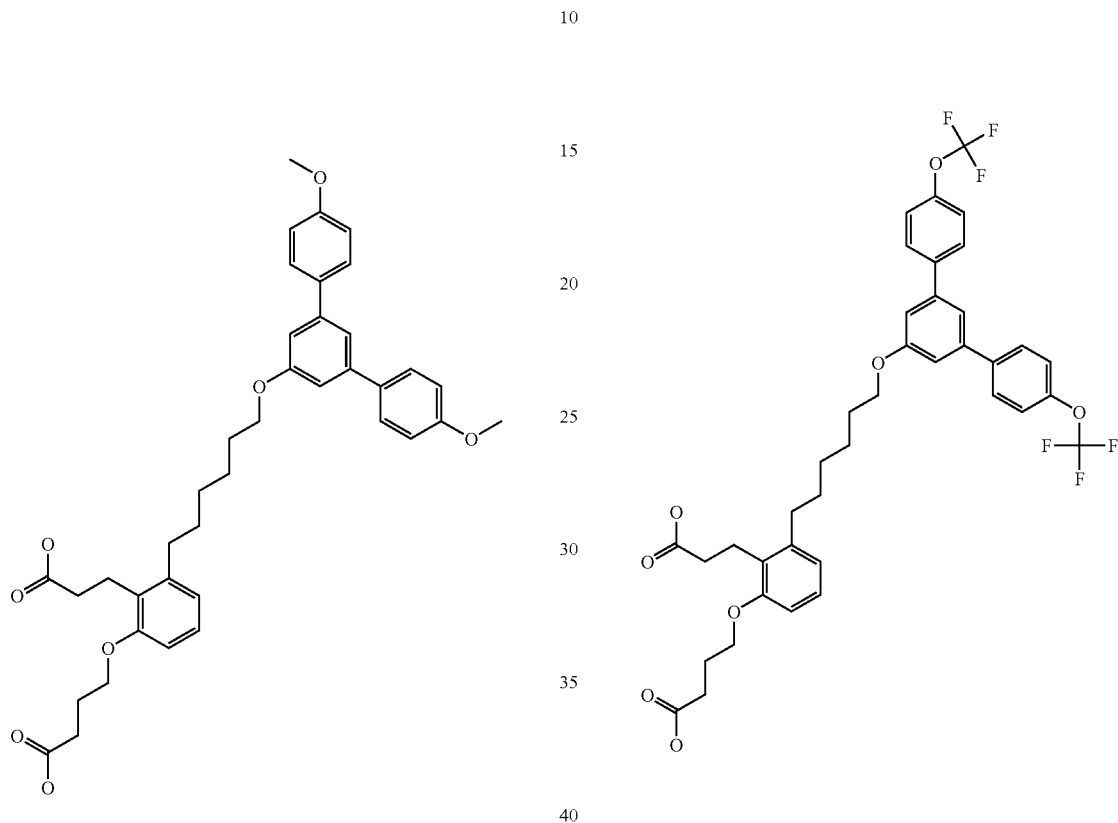

4-{2-(2-Carboxy-ethyl)-3-[6-(4,4''-dimethoxy-[1,1';3',1''] terphenyl-5'-yloxyl)-hexyl]-phenoxy}-butyric acid was synthesized in a manner similar to Example 67 except that in Step 1, 4-methoxyphenylboronic acid was used as the first boronic acid coupling reagent, and the symmetric coupling reagent Coupling of the bis-arylphenol was conducted in a manner as described for Example 57, Step 3. Upon purification by HPLC, the compound was characterized by LC-MS. For the expected mass of 640.30362, 663.53 (M+Na)⁺ was observed; the compound was shown to have a purity of 100%. Example 88 was characterized by low resolution mass spectrometry where signals corresponding to the following were observed: ES(+)=640+Na, ES(−)=639. Example 88 was also characterized by high resolution mass spectrometry where signals corresponding to the following were observed: m/e calculated for $C_{39}H_{44}O_8$ 640.30362; found compatible with (M+Na)$^{1+}$=663.2928.

4-[3-[6-(4,4''-Bis-trifluoromethoxy-[1,1';3',1'']terphenyl-5'-yloxy)-hexyl]-2-(2-carboxy-ethyl)-phenoxy]-butyric acid was synthesized in a manner similar to Example 67 except that in Step 1, 4-trifluoromethoxyphenylboronic acid was used as the first boronic acid coupling reagent, and the symmetric coupling product, 4,4''-bis-trifluoromethoxy-[1,1';3', 1'']terphenyl-5'-ol was obtained and carried forward to Step 3 as described un Example 57. Upon purification by HPLC, the compound was characterized by LC-MS. For the expected mass of 748.247088, 747.52 (M−H)⁻ was observed; the compound was shown to have a purity of 100%. Example 89 was characterized by low resolution mass spectrometry where signals corresponding to the following were observed: ES(+)=748+Na, ES(−)=747. Example 89 was also characterized by high resolution mass spectrometry where signals corresponding to the following were observed: m/e calculated for $C_{39}H_{38}F_6O_8$ 748.247088; found compatible with (M+Na)$^{1+}$=771.2362.

203
Example 90

4-{2-(2-Carboxy-ethyl)-3-[6-(4,4''-difluoro-[1,1';3',1'']terphenyl-5'-yloxy)-hexyl]-phenoxy}-butyric acid

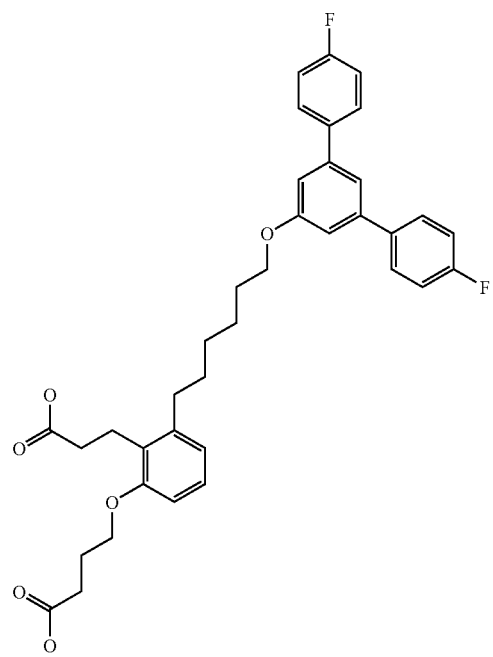

204
Example 91

4-[3-[6-(4,4''-Bis-trifluoromethoxy-[1,1';3',1'']terphenyl-5'-yloxy)-hexyl]-2-(2-carboxy-ethyl)-phenoxy]-butyric acid

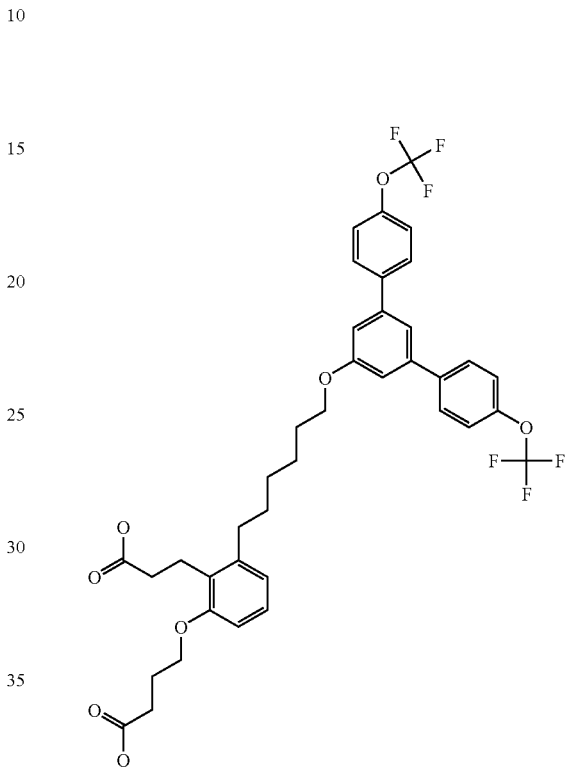

4-{2-(2-Carboxy-ethyl)-3-[6-(4,4''-difluoro-[1,1';3',1''] terphenyl-5'-yloxy)-hexyl]-phenoxy}-butyric acid was synthesized in a manner similar to Example 67 except that in Step 1, 4-fluoromethoxyphenylboronic acid was used as the first boronic acid coupling reagent, and the symmetric coupling product, 4,4''-difluoro-[1,1';3',1'']terphenyl-5'-ol was obtained and carried forward to Step 3 as described un Example 57. Coupling of the bis-arylphenol was conducted in a manner as described for Example 57, Step 3. Upon purification by HPLC, the compound was characterized by LC-MS. For the expected mass of 616.263646, 639.49 (M+Na)$^+$ was observed; the compound was shown to have a purity of 100%. Example 90 was characterized by low resolution mass spectrometry where signals corresponding to the following were observed: ES(+)=616+Na, ES(−)=615. Example 90 was also characterized by high resolution mass spectrometry where signals corresponding to the following were observed: m/e calculated for $C_{37}H_{38}F_2O_6$ 616.263646; found compatible with (M+Na)$^{1+}$=639.2530.

4-[3-[6-(4,4''-Bis-trifluoromethoxy-[1,1';3',1'']terphenyl-5'-yloxy)-hexyl]-2-(2-carboxy-ethyl)-phenoxy]-butyric acid was synthesized in a manner similar to Example 67 except that in Step 1, 4-trifluoromethoxyphenylboronic acid was used as the first boronic acid coupling reagent and the symmetric coupling product, 4,4''-bis-trifluoromethoxy-[1,1';3',1'']terphenyl-5'-ol was obtained and carried forward to Step 3 as described in Example 57. Upon purification by HPLC, the compound was characterized by LC-MS. For the expected mass of 748.247088, 747.52 (M−H)$^{−1}$ was observed; the compound was shown to have a purity of 100%. Example 91 was characterized by low resolution mass spectrometry where signals corresponding to the following were observed: ES(+)=748+Na, ES(−)=747. Example 91 was also characterized by high resolution mass spectrometry where signals corresponding to the following were observed: m/e calculated for $C_{39}H_{38}F_6O_8$ 748.247088; found compatible with (M+Na)$^{1+}$=771.2362.

Example 92

4-{2-(2-Carboxy-ethyl)-3-[6-(4"-dimethylamino-4-fluoro-[1,1';3',1"]terphenyl-5'-yloxy)-hexyl]-phenoxy}-butyric acid

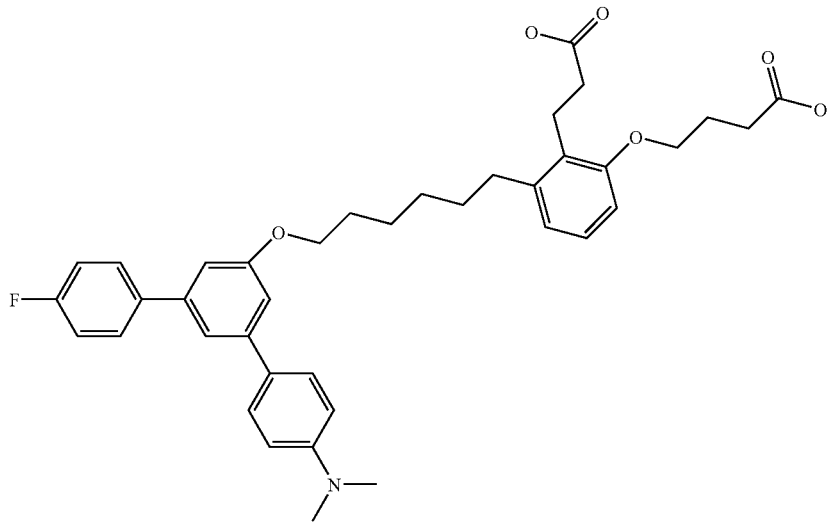

4-{2-(2-Carboxy-ethyl)-3-[6-(4"-dimethyl amino-4-fluoro-[1,1';3',1"]terphenyl-5'-yloxy)-hexyl]-phenoxy}-butyric acid was synthesized in a manner similar to Example 67 except that in Step 1, 4-(phenyl)-dimethyl-amine boronic acid was used as the first boronic acid coupling reagent. In Step 2, 4-fluorophenylboronic acid was used as the second boronic acid coupling reagent. Coupling of the bis-arylphenol was conducted in a manner as described for Example 57, Step 3. Upon purification by HPLC, the compound was characterized by LC-MS. For the expected mass of 641.315267, 642.55 (M+H)$^+$ was observed; the compound was shown to have a purity of 100%. Example 92 was characterized by low resolution mass spectrometry where signals corresponding to the following were observed: ES(+)=642. Example 92 was also characterized by high resolution mass spectrometry where signals corresponding to the following were observed: m/e calculated for $C_{39}H_{44}FNO_6$ 641.315267; found compatible with (M+H)$^{1+}$=642.3222.

Example 93

4-{2-(2-Carboxy-ethyl)-3-[6-(4'-dimethylamino-5-thiophen-3-yl-biphenyl-3-yloxy)-hexyl]-phenoxy}-butyric acid

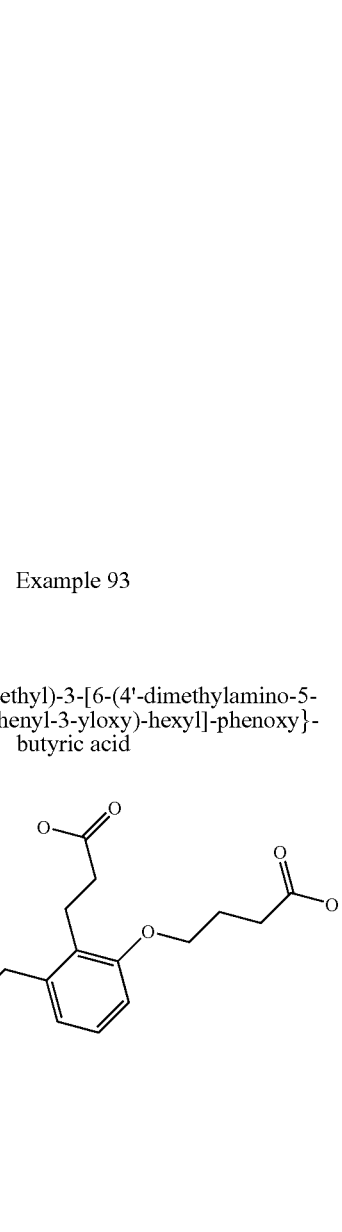

4-{2-(2-Carboxy-ethyl)-3-[6-(4'-dimethylamino-5-thiophen-3-yl-biphenyl-3-yloxy)-hexyl]-phenoxy}-butyric acid was synthesized in a manner similar to Example 67 except that in Step 1, 4-(phenyl)-dimethyl-amine boronic acid was used as the first boronic acid coupling reagent. In Step 2, thiophen-3-ylboronic acid was used as the second boronic acid coupling reagent. Coupling of the bis-arylphenol was conducted in a manner as described for Example 57, Step 3. Upon purification by HPLC, the compound was characterized by LC-MS. For the expected mass of 629.281111, 630.54 (M+H)$^+$ was observed; the compound was shown to

Example 94

4-{2-(2-Carboxy-ethyl)-3-[6-(4-fluoro-3-methyl-[1,1';3',1"]terphenyl-5'-yloxy)-hexyl]-phenoxy}-butyric acid

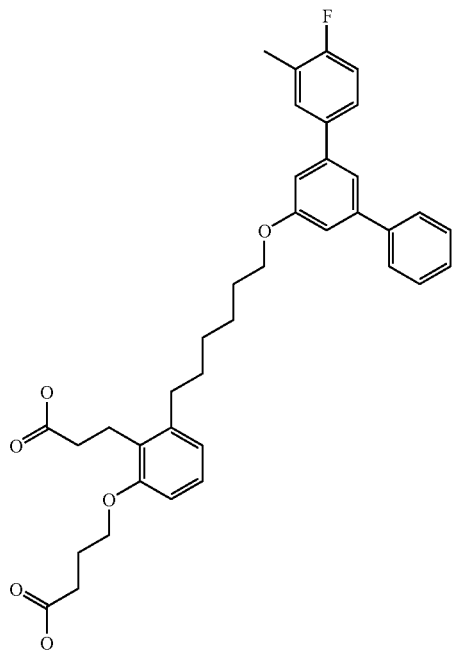

4-{2-(2-Carboxy-ethyl)-3-[6-(4-fluoro-3-methyl-[1,1';3',1"]terphenyl-5'-yloxy)-hexyl]-phenoxy}-butyric acid was synthesized in a manner similar to Example 67 except that in Step 1, phenylboronic acid was used as the first boronic acid coupling reagent. In Step 2, 4-fluoro-3-methylphenylboronic acid was used as the second boronic acid coupling reagent. Coupling of the bis-arylphenol was conducted in a manner as described for Example 57, Step 3. Upon purification by HPLC, the compound was characterized by LC-MS. Example 94 was characterized by low resolution mass spectrometry where signals corresponding to the following were observed: ES(+)=612 ES(−)=611. Example 94 was characterized by low resolution mass spectrometry where signals corresponding to the following were observed: ES(+)=612+Na, ES(−)=611. Example 94 was also characterized by high resolution mass spectrometry where signals corresponding to the following were observed: m/e calculated for $C_{38}H_{41}FO_6$ 612.288718; found compatible with $(M+Na)^{1+}$=635.2780.

Example 95

Assay of Compounds for Inhibition of $LTB_4$ Activity $Ca^{2+}$ Flux Assay for LTB4 Antagonist Assay Cell Culture Conditions:

Human leukemia HL-60 cells endogenously expressing BLT1 and BLT2 receptors were cultured in RPMI-1640 medium supplemented with 20% fetal bovine serum, 2 mM glutamine, 100 U/ml penicillin and 100 ug/ml streptomycin. Seventy two hours prior to experiment cells are counted using ViaCount reagent, centrifuged and resuspended at $2.0\times10^5$ cells /ml density with the complete growth media containing 1 μM Retinoic Acid (Sigma).

Dye Loading and Assay:

On a day of the experiment loading buffer (Calcium-3 Assay Kit, Molecular Devices) was prepared by dissolving the contents of one vial (Express Kit) into 500 ml Hank's Balanced Salt Solution containing 20 mM HEPES and 5 mM probenecid. Equal volume of the loading buffer was mixed with the replacement buffer (Hank's Balanced Salt Solution containing 20 mM HEPES, 0.05% BSA and 5 mM probenecid). Retinoic Acid induced HL-60 cells were counted using ViaCount reagent, centrifuged and resuspended at $2.0\times10^6$ cells /ml density with the loading buffer/replacement buffer, dispensed into 384 well black/clear microplates (Falcon)(25 μl/well) and placed in a 37° C./5% $CO_2$ incubator for 1 hour.

During the incubation, test compounds were prepared at 6× the desired concentration in HBSS/20 mM HEPES/0.05% BSA as well as LTB4 (Biomol) was prepared at 2.2× concentration in HBSS/20 mM HEPES/0.5% BSA buffer.

After the incubation, both the cell and compound plates were brought to the FLIPR and 5 μl of the diluted compounds were transferred to the cell plates by the FLIPR. Plates were then incubated for 30min at room temperature. After the ½ hour incubation, plates were returned to the FLIPR and 25 μl of 2.2× LTB4 was added to the cell plates. During the assay, fluorescence readings were taken simultaneously from all 384 wells of the cell plate every 1.5 seconds. Five readings were taken to establish a stable baseline, then 25 μl (LTB4) of sample was rapidly and simultaneously added to each well of the cell plate. The fluorescence was continuously monitored before, during and after sample addition for a total elapsed time of 100 seconds. Responses (increase in peak fluorescence) in each well following agonist addition was determined. The initial fluorescence reading from each well, prior to ligand stimulation, was used a zero baseline value for the data from that well. The responses are expressed as % inhibition of the neutral control (neutral control: wells that received buffer plus DMSO but no test compound).

Assay Results

| Example 1 | 4-{2-(2-Carboxy-ethyl)-3-[6-(3,5-di-pyridin-4-yl-phenoxy)-hexyl]-phenoxy}-butyric acid | IC50 = 0.07 nM |
|---|---|---|
| Example 12 | 4-[3-[6-(3-Benzo[1,3]dioxol-5-yl-5-thiophen-3-yl-phenoxy)-hexyl]-2-(2-carboxy-ethyl)-phenoxy]-butyric acid | IC50 = 0.21 nM |
| Example 13 | 4-{2-(2-Carboxy-ethyl)-3-[6-(5-thiophen-3-yl-biphenyl-3-yloxy)-hexyl]-phenoxy}-butyric acid | IC50 = 0.36 nM |
| Example 14 | 4-{2-(2-Carboxy-ethyl)-3-[6-(3-pyridin-4-yl-5-thiophen-3-yl-phenoxy)-hexyl]-phenoxy}-butyric acid | IC50 = 0.2 nM |

-continued

| Example | | IC50 |
|---|---|---|
| Example 15 | 4-(2-(2-Carboxy-ethyl)-3-{6-[3-(2-chloro-pyridin-4-yl)-5-thiophen-3-yl-phenoxy]-hexyl}-phenoxy)-butyric acid | IC50 = 0.57 nM |
| Example 16 | 4-{2-(2-Carboxy-ethyl)-3-[6-(3-pyrimidin-5-yl-5-thiophen-3-yl-phenoxy)-hexyl]-phenoxy}-butyric acid | IC50 = 0.39 nM |
| Example 17 | 4-[3-[6-(5-Benzo[1,3]dioxol-5-yl-3'-fluoro-biphenyl-3-yloxy)-hexyl]-2-(2-carboxy-ethyl)-phenoxy]-butyric acid | IC50 = 1.19 nM |
| Example 18 | 4-{2-(2-Carboxy-ethyl)-3-[6-(3'-fluoro-5-pyridin-4-yl-biphenyl-3-yloxy)-hexyl]-phenoxy}-butyric acid | IC50 = 0.18 nM |
| Example 2 | 4-{2-(2-Carboxy-ethyl)-3-[6-([1,1';3',1'']terphenyl-5'-yloxy)-hexyl]-phenoxy}-butyric acid | IC50 = 0.21 nM |
| Example 20 | 4-[3-[6-(3-Benzo[1,3]dioxol-5-yl-5-pyridin-4-yl-phenoxy)-hexyl]-2-(2-carboxy-ethyl)-phenoxy]-butyric acid | IC50 = 0.21 nM |
| Example 21 | 4-[3-[6-(3-Benzo[1,3]dioxol-5-yl-5-pyrimidin-5-yl-phenoxy)-hexyl]-2-(2-carboxy-ethyl)-phenoxy]-butyric acid | IC50 = 0.43 nM |
| Example 24 | 4-(2-(2-Carboxy-ethyl)-3-{6-[3-(2,3-dihydro-benzo[1,4]dioxin-6-yl)-5-pyridin-4-yl-phenoxy]-hexyl}-phenoxy)-butyric acid | IC50 = 0.23 nM |
| Example 26 | 4-{2-(2-Carboxy-ethyl)-3-[6-(3,5-di-pyridin-2-yl-phenoxy)-hexyl]-phenoxy}-butyric acid | IC50 = 0.97 nM |
| Example 28 | 4-(2-(2-Carboxy-ethyl)-3-{6-[3-(1,6-dimethyl-2-oxo-4-trifluoromethyl-1,2-dihydro-pyridin-3-yl)-5-thiophen-3-yl-phenoxy]-hexyl}-phenoxy)-butyric acid | IC50 = 99.44 nM |
| Example 3 | 4-[3-{6-[3,5-Bis-(2-fluoro-pyridin-4-yl)-phenoxy]-hexyl}-2-(2-carboxy-ethyl)-phenoxy]-butyric acid | IC50 = 0.17 nM |
| Example 35 | 4-{2-(2-Carboxy-ethyl)-3-[6-(3,5-di-thiophen-3-yl-phenylamino)-hexyl]-phenoxy}-butyric acid | IC50 = 99.07 nM |
| Example 4 | 4-{2-(2-Carboxy-ethyl)-3-[6-(3,5-di-pyridin-3-yl-phenoxy)-hexyl]-phenoxy}-butyric acid | IC50 = 0.64 nM |
| Example 48 | 4-[2-(2-Carboxy-ethyl)-3-(7-[1,1';3',1'']terphenyl-5'-yl-hept-6-ynyl)-phenoxy]-butyric acid | IC50 = 2.69 nM |
| Example 52 | 4-[3-[7-(3,5-Bis-benzo[1,3]dioxol-5-yl-phenyl)-heptyl]-2-(2-carboxy-ethyl)-phenoxy]-butyric acid | IC50 = 42.52 nM |
| Example 56 | 4-{2-(2-Carboxy-ethyl)-3-[6-(3,5-di-thiophen-3-yl-phenoxy)-hexyl]-phenoxy}-butyric acid | IC50 = 0.58 nM |
| Example 63 | 4-{2-(2-Carboxy-ethyl)-3-[6-(4-chloro-4''-dimethylamino-3-fluoro-[1,1';3',1'']terphenyl-5'-yloxy)-hexyl]-phenoxy}-butyric acid | IC50 = 59.77 nM |
| Example 65 | 4-{2-(2-Carboxy-ethyl)-3-[6-(4''-dimethylamino-4-fluoro-3-methyl-[1,1';3',1'']terphenyl-5'-yloxy)-hexyl]-phenoxy}-butyric acid | IC50 = 0.47 nM |
| Example 7 | 4-{2-(2-Carboxy-ethyl)-3-[6-([1,1';3',1'']terphenyl-5'-ylsulfanyl)-hexyl]-phenoxy}-butyric acid | IC50 = 74.98 nM |
| Example 70 | 4-[3-[6-(5-Benzo[1,3]dioxol-5-yl-biphenyl-3-yloxy)-hexyl]-2-(2-carboxy-ethyl)-phenoxy]-butyric acid | IC50 = 0.58 nM |
| Example 88 | 4-[3-[6-(5-Benzo[1,3]dioxol-5-yl-2'-fluoro-biphenyl-3-yloxy)-hexyl]-2-(2-carboxy-ethyl)-phenoxy]-butyric acid | IC50 = 0.61 nM |
| Example 97 | 4-{2-(2-Carboxy-ethyl)-3-[6-(2-fluoro-[1,1';3',1'']terphenyl-5'-yloxy)-hexyl]-phenoxy}-butyric acid | IC50 = 0.25 nM |

It is to be understood that the invention is not limited to the particular embodiments of the invention described above, as variations of the particular embodiments may be made and still fall within the scope of the appended claims.

What is claimed is:

1. A compound of formula (I):

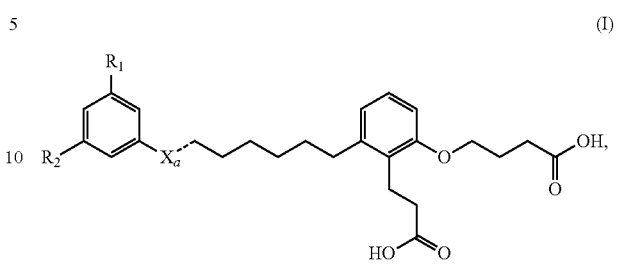

wherein:
$R_1$ and $R_2$, independently of each other, are
halogen,
benzo[1,3]dioxole, unsubstituted or mono- or bi-substituted with halogen,
2,3-dihydro-benzo[1,4]dioxine, unsubstituted or mono- or bi-substituted with halogen,
3,4-dihydro-2H-benzo[b][1,4]dioxepine, unsubstituted or mono- or bi-substituted with halogen
monocyclic 5- or 6-membered aryl or monocyclic 5- or 6-membered heteroaryl, unsubstituted or substituted with one to four substituents selected from the group consisting of halogen, lower alkyl, haloloweralkyl, carboxy, alkoxy, hydroxy, aminoloweralkyl and —OCF$_3$;
bicyclic 8- to 12-membered heteroaryl, unsubstituted or substituted with one to four substituents selected from the group consisting of halogen, lower alkyl, haloloweralkyl, carboxy, alkoxy, hydroxy, aminoloweralkyl and —OCF$_3$;
X is O, C, S, or N, unsubstituted or substituted with lower alkyl; and
a is a single bond or an alkynyl bond,
and pharmaceutically acceptable salts thereof.

2. The compound according to claim 1, wherein:
$R_1$ and $R_2$, independently of each other, are benzo[1,3]dioxole, 2,3-dihydro-benzo[1,4]dioxine or 3,4-dihydro-2H-benzo[b][1,4]dioxepine; and
X is O, C, S, or N, unsubstituted or substituted with lower alkyl,
and pharmaceutically acceptable salts thereof.

3. The compound according to claim 1, wherein:
$R_1$ and $R_2$, independently of each other, are bicyclic 8- to 12-membered heteroaryl, unsubstituted or substituted with one to four substituents selected from the group consisting of halogen, lower alkyl, haloloweralkyl, carboxy, alkoxy, hydroxy, aminoloweralkyl and —OCF$_3$; and
X is O, C, S, or N, unsubstituted or substituted with lower alkyl,
and pharmaceutically acceptable salts thereof.

4. The compound according to claim 1, wherein:
$R_1$ is benzo[1,3]dioxole, 2,3-dihydro-benzo[1,4]dioxine or 3,4-dihydro-2H-benzo[b][1,4]dioxepine;
$R_2$ is monocyclic 5- or 6-membered aryl or monocyclic 5- or 6-membered heteroaryl, unsubstituted or substituted with one to four substituents selected from the group consisting of halogen, lower alkyl, haloloweralkyl, carboxy, alkoxy, hydroxy, aminoloweralkyl and —OCF$_3$; and X is O, C, S, or N, unsubstituted or substituted with lower alkyl, and pharmaceutically acceptable salts thereof.

5. The compound according to claim 1, wherein:

$R_1$ is benzo[1,3]dioxole, 2,3-dihydro-benzo[1,4]dioxine or 3,4-dihydro-2H-benzo[b][1,4]dioxepine;

$R_2$ is bicyclic 8- to 12-membered heteroaryl, unsubstituted or substituted with one to four substituents selected from the group consisting of halogen, lower alkyl, haloloweralkyl, carboxy, alkoxy, hydroxy, aminoloweralkyl and —$OCF_3$; and X is O, C, S, or N, unsubstituted or substituted with lower alkyl, and pharmaceutically acceptable salts thereof.

6. The compound according to claim 1, wherein $R_1$ and/or $R_2$ is benzo[1,3]dioxole, 2,3-dihydro-benzo[1,4]dioxine or 3,4-dihydro-2H-benzo[b][1,4]dioxepine.

7. The compound according to claim 1, wherein said bicyclic 8- to 12-membered heteroaryl is 5-indolyl or 5-quinolinyl.

8. The compound according to claim 1, wherein:

$R_1$ and $R_2$, independently of each other, are monocyclic 5- or 6-membered aryl, unsubstituted or substituted with one to four substituents selected from the group consisting of halogen, lower alkyl, haloloweralkyl, carboxy, alkoxy, hydroxy, aminoloweralkyl and —$OCF_3$; and X is O, C, S, or N, unsubstituted or substituted with lower alkyl, and pharmaceutically acceptable salts thereof.

9. The compound according to claim 1, wherein:

$R_1$ and $R_2$, independently of each other, are monocyclic 5- or 6-membered heteroaryl, unsubstituted or substituted with one to four substituents selected from the group consisting of halogen, lower alkyl, haloloweralkyl, carboxy, alkoxy, hydroxy, aminoloweralkyl and —$OCF_3$; and X is O, C, S, or N, unsubstituted or substituted with lower alkyl, and pharmaceutically acceptable salts thereof.

10. The compound according to claim 1, wherein:

$R_1$ is monocyclic 5- or 6-membered aryl, unsubstituted or substituted with one to four substituents selected from the group consisting of halogen, lower alkyl, haloloweralkyl, carboxy, alkoxy, hydroxy, aminoloweralkyl and —$OCF_3$;

$R_2$ or monocyclic 5- or 6-membered heteroaryl, unsubstituted or substituted with one to four substituents selected from the group consisting of halogen, lower alkyl, haloloweralkyl, carboxy, alkoxy, hydroxy, aminoloweralkyl and —$OCF_3$; and X is O, C, S, or N, unsubstituted or substituted with lower alkyl, and pharmaceutically acceptable salts thereof.

11. The compound according to claim 1, wherein:

$R_1$ is monocyclic 5- or 6-membered heteroaryl, unsubstituted or substituted with one to four substituents selected from the group consisting of halogen, lower alkyl, haloloweralkyl, carboxy, alkoxy, hydroxy, aminoloweralkyl and —$OCF_3$;

$R_2$ is monocyclic 5- or 6-membered aryl, unsubstituted or substituted with one to four substituents selected from the group consisting of halogen, lower alkyl, haloloweralkyl, carboxy, alkoxy, hydroxy, aminoloweralkyl and —$OCF_3$; and X is O, C, S, or N, unsubstituted or substituted with lower alkyl, and pharmaceutically acceptable salts thereof.

12. The compound according to claim 1, wherein $R_1$ and/or $R_2$ is phenyl.

13. The compound according to claim 1, wherein $R_1$ and/or $R_2$ is pyridine, pyrimidine or thiophene.

14. The compound according to claim 1, wherein X is O or N.

15. The compound according to claim 1, wherein said compound is:

4-{2-(2-Carboxy-ethyl)-3-[6-(3,5-di-pyridin-4-yl-phenoxy)-hexyl]-phenoxy}-butyric acid, 4-[3-{6-[3,5-Bis-(2-fluoro-pyridin-4-yl)-phenoxy]-hexyl}-2-(2-carboxy-ethyl)-phenoxy]-butyric acid, 4-{2-(2-Carboxy-ethyl)-3-[6-(3'-fluoro-5-pyridin-4-yl-biphenyl-3-yloxy)-hexyl]-phenoxy}-butyric acid, 4-{2-(2-Carboxy-ethyl)-3-[6-(3-pyridin-4-yl-5-thiophen-3-yl-phenoxy)-hexyl]-phenoxy}-butyric acid, 4-{2-(2-Carboxy-ethyl)-3-[6-([1,1';3',1"]terphenyl-5'-yloxy)-hexyl]-phenoxy}-butyric acid, 4-[3-[6-(3-Benzo[1,3]dioxol-5-yl-5-thiophen-3-yl-phenoxy)-hexyl]-2-(2-carboxy-ethyl)-phenoxy]-butyric acid, 4-[3-[6-(3-Benzo[1,3]dioxol -5-yl-5-pyridin-4-yl-phenoxy)-hexyl]-2-(2-carboxy-ethyl)-phenoxy]-butyric acid, 4-(2-(2-Carboxy-ethyl)-3-{6-[3-(2,3-dihydro-benzo[1,4]dioxin-6-yl)-5-pyridin-4-yl-phenoxy]-hexyl}-phenoxy)-butyric acid, 4-{2-(2-Carboxy-ethyl)-3-[6-(2-fluoro-[1,1';3',1"]terphenyl-5'-yloxy)-hexyl]-phenoxy}-butyric acid, 4-{2-(2-Carboxy-ethyl)-3-[6-(5-thiophen-3-yl-biphenyl-3-yloxy)-hexyl]-phenoxy}-butyric acid, 4-{2-(2-Carboxy-ethyl)-3-[6-(3-pyrimidin-5-yl-5-thiophen-3-yl-phenoxy)-hexyl]-phenoxy}-butyric acid, 4-[3-[6-(3-Benzo[1,3]dioxol-5-yl-5-pyrimidin-5-yl-phenoxy)-hexyl]-2-(2-carboxy-ethyl)-phenoxy]-butyric acid, 4-{2-(2-Carboxy-ethyl)-3-[6-(4"-dimethylamino-4-fluoro-3-methyl-[1,1';3',1"]terphenyl-5'-yloxy)-hexyl]-phenoxy}-butyric acid, 4-(2-(2-Carboxy-ethyl)-3-{6-[3-(2-chloro-pyridin-4-yl)-5-thiophen-3-yl-phenoxy]-hexyl}-phenoxy)-butyric acid, 4-{2-(2-Carboxy-ethyl)-3-[6-(3,5-di-thiophen-3-yl-phenoxy)-hexyl]-phenoxy}-butyric acid, 4-[3-[6-(5-Benzo[1,3]dioxol-5-yl-biphenyl-3-yloxy)-hexyl]-2-(2-carboxy-ethyl)-phenoxy]-butyric acid, 4-[3-[6-(5-Benzo[1,3]dioxol-5-yl-2"-fluoro-biphenyl-3-yloxy)-hexyl]-2-(2-carboxy-ethyl)-phenoxy]-butyric acid, 4-{2-(2-Carboxy-ethyl)-3-[6-(3,5-di-pyridin-3-yl-phenoxy)-hexyl]-phenoxy}-butyric acid, 4-{2-(2-Carboxy-ethyl)-3-[6-(3,5-di-pyridin-2-yl-phenoxy)-hexyl]-phenoxy}-butyric acid, 4-[3-[6-(5-Benzo[1,3]dioxol-5-yl-3'-fluoro-biphenyl-3-yloxy)-hexyl]-2-(2-carboxy-ethyl)-phenoxy]-butyric acid, or 4-[3-[7-(3,5-Bis-benzo[1,3]dioxol-5-yl-phenyl)-heptyl]-2-(2-carboxy-ethyl)-phenoxy]-butyric acid.

16. A pharmaceutical composition, comprising a therapeutically effective amount of a compound according to claim 1 or a pharmaceutically acceptable salt thereof and a pharmaceutically acceptable carrier.

* * * * *